(12) United States Patent
Belema et al.

(10) Patent No.: US 7,906,655 B2
(45) Date of Patent: Mar. 15, 2011

(54) HEPATITIS C VIRUS INHIBITORS

(75) Inventors: Makonen Belema, North Haven, CT (US); Andrew C. Good, Wallingford, CT (US); Jason Goodrich, Wallingford, CT (US); Ramesh Kakarla, South Glastonbury, CT (US); Guo Li, Wallingford, CT (US); Omar D. Lopez, Wallingford, CT (US); Van N. Nguyen, Meriden, CT (US); Jayne Kapur, Houston, TX (US); Yuping Qiu, Princeton Junction, NJ (US); Jeffrey Lee Romine, Meriden, CT (US); Denis R. St. Laurent, Newington, CT (US); Michael Serrano-Wu, Belmont, MA (US); Lawrence B. Snyder, Killingworth, CT (US); Fukang Yang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/536,362

(22) Filed: Aug. 5, 2009

(65) Prior Publication Data

US 2010/0068176 A1     Mar. 18, 2010

Related U.S. Application Data

(60) Provisional application No. 61/087,078, filed on Aug. 7, 2008.

(51) Int. Cl.
| | |
|---|---|
| C07D 403/14 | (2006.01) |
| C07D 217/08 | (2006.01) |
| C07D 211/32 | (2006.01) |
| C07D 239/04 | (2006.01) |
| C07D 413/14 | (2006.01) |
| A61K 31/47 | (2006.01) |
| A61K 31/497 | (2006.01) |
| A61K 31/445 | (2006.01) |
| A61K 31/5355 | (2006.01) |
| A01N 43/60 | (2006.01) |

(52) U.S. Cl. ............... 548/311.7; 546/149; 546/199; 544/370; 544/139; 514/309; 514/254.06; 514/322; 514/394; 514/234.5

(58) Field of Classification Search ............... 548/311.7; 546/146, 199; 544/370, 139; 514/309, 254.06, 514/322, 394, 234.5
See application file for complete search history.

(56) References Cited

U.S. PATENT DOCUMENTS

| | | | |
|---|---|---|---|
| 5,654,451 A | 8/1997 | Kari | |
| 2010/0022557 A1* | 1/2010 | Martin et al. | 514/254.06 |
| 2010/0160402 A1* | 6/2010 | Huang et al. | 514/394 |

FOREIGN PATENT DOCUMENTS

| | | |
|---|---|---|
| WO | WO 94/15909 | 7/1994 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/077186 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/133753 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |

OTHER PUBLICATIONS

Katritzky et al., J. Polym. Sci. Polym. Chem. Ed, vol. 27, 1781-1790 (1989).*
U.S. Appl. No. 12/569,466, filed Sep. 29, 2009, Belema et al.

* cited by examiner

Primary Examiner — Kamal A Saeed
Assistant Examiner — Nyeemah Grazier
(74) Attorney, Agent, or Firm — Pamela A. Mingo

(57) ABSTRACT

The present disclosure relates to compounds, compositions and methods for the treatment of Hepatitis C virus (HCV) infection. Also disclosed are pharmaceutical compositions containing such compounds and methods for using these compounds in the treatment of HCV infection.

28 Claims, No Drawings

HEPATITIS C VIRUS INHIBITORS

CROSS-REFERENCE TO RELATED APPLICATIONS

This application claims the benefit of U.S. Provisional Application Ser. No. 61/087,078 filed Aug. 7, 2008.

FIELD OF THE INVENTION

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. The current standard of care for HCV, which employs a combination of pegylated-interferon and ribavirin, has a non-optimal success rate in achieving sustained viral response and causes numerous side effects. Thus, there is a clear and long-felt need to develop effective therapies to address this undermet medical need.

HCV is a positive-stranded RNA virus. Based on a comparison of the deduced amino acid sequence and the extensive similarity in the 5 untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., World Patent Application WO-2006093867, Sep. 8, 2006.

In a first aspect the present disclosure provides a compound of Formula (I)

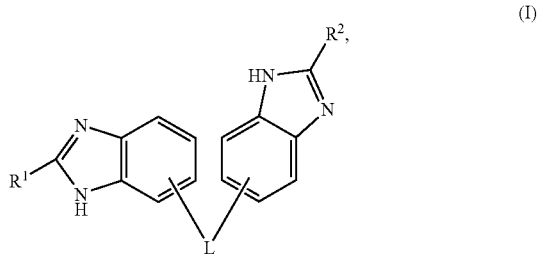

or a pharmaceutically acceptable salt thereof, wherein

L is a bond or is selected from

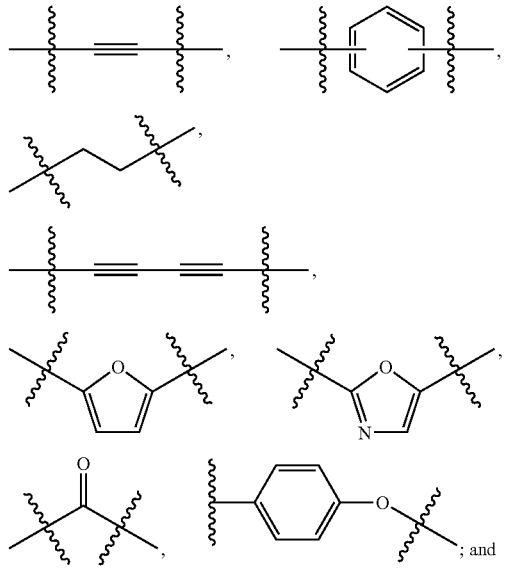

-continued

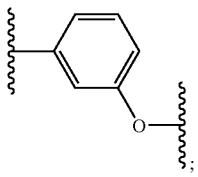

R¹ and R² are independently selected from

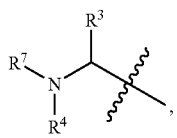 , 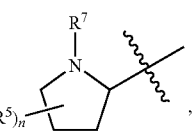 ,

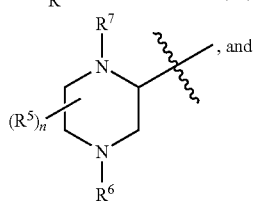 , and 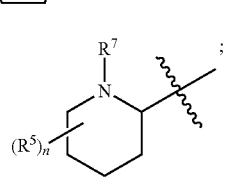 ;

wherein
n is 0, 1, 2, or 3;
R³ is selected from alkoxyalkyl, alkoxycarbonylalkyl, alkyl, alkylsulfanylalkyl, carboxyalkyl, and (NR$^a$R$^b$)carbonylalkyl;
R⁴ is selected from hydrogen and alkyl;
each R⁵ is independently selected from alkoxy, alkyl, hydroxy, —NR$^a$R$^b$, and oxo, wherein the alkyl can optionally form a fused three- to six-membered ring with an adjacent carbon atom, wherein the three- to six-membered ring is optionally substituted with one or two alkyl groups;
R⁶ and R⁷ are independently selected from hydrogen and R⁸—C(O)—;
each R⁸ is independently selected from alkoxy, alkyl, aryl, arylalkoxy, arylalkyl, arylcarbonyl, aryloxyalkyl, cycloalkyl, (cycloalkyl)alkyl, heterocyclyl, heterocyclylalkyl, —NR$^c$R$^d$, (NR$^c$R$^d$)alkenyl, and (NR$^c$R$^d$)alkyl.

In a first embodiment of the first aspect the present disclosure provides a compound of Formula (I), or a pharmaceutically acceptable salt thereof, wherein L is selected from

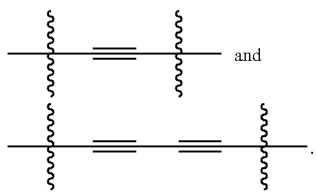

In a second embodiment of the first aspect the present disclosure provides a compound of Formula (I), or a pharmaceutically acceptable salt thereof, wherein L is selected from

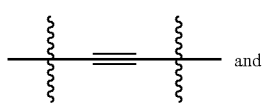 and

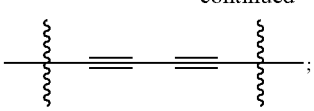 ;

and
R¹ and R² are each

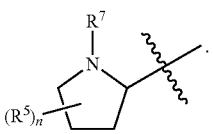

In a third embodiment of the first aspect the present disclosure provides a compound of Formula (I), or a pharmaceutically acceptable salt thereof, wherein L is selected from

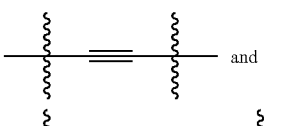 and

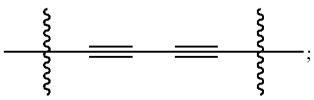 ;

and
R¹ and R² are each

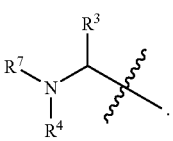

In a fourth embodiment of the first aspect the present disclosure provides a compound of Formula (I), or a pharmaceutically acceptable salt thereof wherein L is

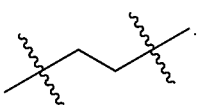

In a fifth embodiment of the first aspect the present disclosure provides a compound of Formula (I), or a pharmaceutically acceptable salt thereof, wherein L is

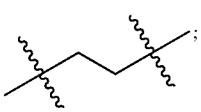 ;

and
R¹ and R² are each

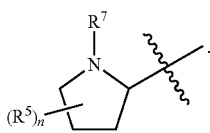

In a sixth embodiment of the first aspect the present disclosure provides a compound of Formula (I), or a pharmaceutically acceptable salt thereof, wherein L is

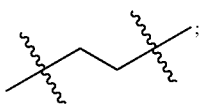

and
R¹ and R² are each

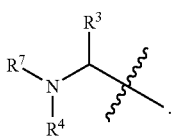

In a seventh embodiment of the first aspect the present disclosure provides a compound of Formula (I), or a pharmaceutically acceptable salt thereof, wherein L is

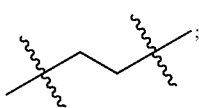

and
R¹ and R² are each

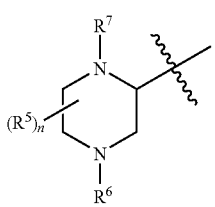

In an eighth embodiment of the first aspect the present disclosure provides a compound of Formula (I), or a pharmaceutically acceptable salt thereof, wherein L is

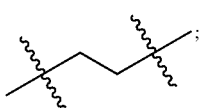

and
R¹ and R² are each

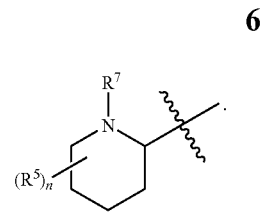

In a ninth embodiment of the first aspect the present disclosure provides a compound of Formula (I), or a pharmaceutically acceptable salt thereof, wherein L is selected from

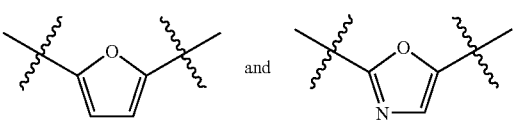

In a tenth embodiment of the first aspect the present disclosure provides a compound of Formula (I), or a pharmaceutically acceptable salt thereof, wherein L is selected from

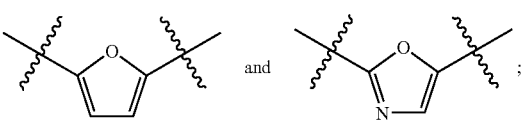

and
R¹ and R² are independently selected from

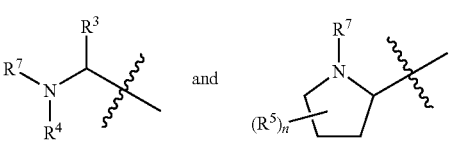

In an eleventh embodiment of the first aspect the present disclosure provides a compound of Formula (I), or a pharmaceutically acceptable salt thereof, wherein L is selected from a bond,

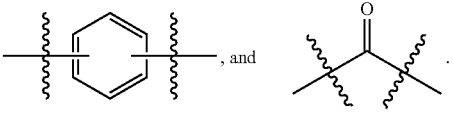

In a twelfth embodiment of the first aspect the present disclosure provides a compound of Formula (I), or a pharmaceutically acceptable salt thereof, wherein L is selected from a bond,

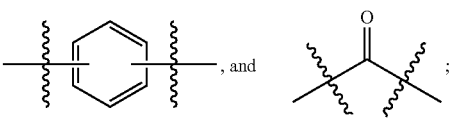

and
R¹ and R² are independently selected from

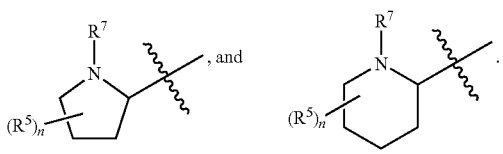

In a thirteenth embodiment of the first aspect the present disclosure provides a compound of Formula (I), or a pharmaceutically acceptable salt thereof, wherein L is selected from

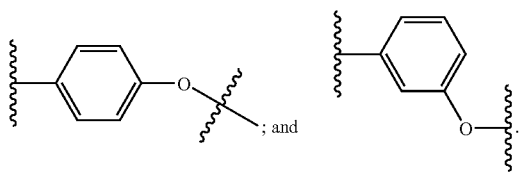

In a fourteenth embodiment of the first aspect the present disclosure provides a compound of Formula (I), or a pharmaceutically acceptable salt thereof, wherein L is selected from

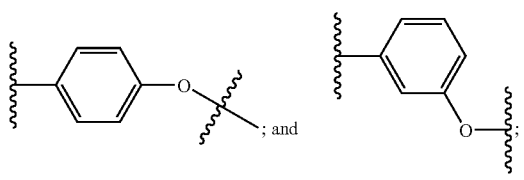

and
$R^1$ and $R^2$ are each

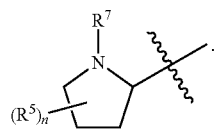

In a second aspect the present disclosure provides a composition comprising a compound of Formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastiod interferon tau.

In a fourth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCM egress, HCM NS5A protein, and IMPDH for the treatment of an HCV infection.

In a third aspect the present disclosure provides a method of treating an HCV infection in a patient, comprising administering to the patient a therapeutically effective amount of a compound of Formula (I), or a pharmaceutically acceptable salt thereof. In a first embodiment of the third aspect the method further comprises administering at least one additional compound having anti-HCV activity prior to, after or simultaneously with the compound of Formula (I), or a pharmaceutically acceptable salt thereof. In a second embodiment of the third aspect at least one of the so additional compounds is an interferon or a ribavirin. In a third embodiment of the third aspect the interferon is selected from interferon alpha 2B, pegylated interferon alpha, consensus interferon, interferon alpha 2A, and lymphoblastiod interferon tau.

In a fourth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when N is 2, each of the two $R^5$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms. In the compounds of the present disclosure, when n is 1, 2, or 3 and at least one $R^5$ is alkyl, each alkyl can optionally form a fused three- to six-membered ring with an adjacent carbon atom to provide one of the structures shown below:

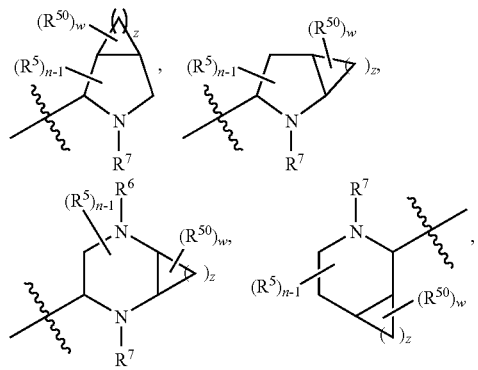

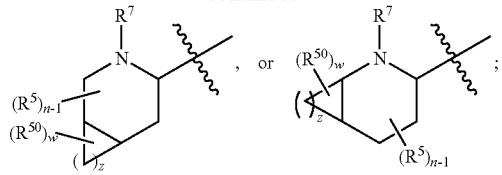

where z is 1, 2, 3, or 4, w is 0, 1, or 2, and $R^{50}$ is alkyl. When w is 2, the two $R^{50}$ alkyl groups may be the same or different.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfanylalkyl," as used herein, refers to an alkyl group substituted with one, two, or three alkysulfanyl groups.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$)alkyl, oxo, and —$P(O)(OR')_2$, wherein each R' is independently hydrogen or alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl halo, haloalkoxy, haloalkyl, hydroxy, —NR$^x$R$^y$, and oxo.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The terms "Cap" and "cap", as used herein, refer to the group which is placed on the nitrogen atom of the pyrrolidine ring (or its acyclic analogs) in the compounds of formula (I). It should be understood that "Cap" or "cap" can also refer to the reagent which is a precursor to the final "cap" in compounds of formula (I) and is used as one of the starting materials in the reaction to append a group on the pyrrolidine (or its acyclic analogs) nitrogen that results in the final product, a compound which contains the functionalized pyrrolidine that will be present in the compound of formula (I).

The term "carbonyl," as used herein, refers to —C(O)—.

The term "carboxy," as used herein, refers to —CO$_2$H.

The term "carboxyalkyl," as used herein, refers to an alkyl group substituted with one, two, or three carboxy groups.

The term "cyano," as used herein, refers to —CN.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present disclosure can be attached to the parent molecular moiety through a carbon atom or a nitrogen atom in the group. Examples of heterocyclyl groups include, but are not limited to, 7-azabicyclo[2.2.1]heptane, benzisoxazolyl, benzothiazolyl, benzothienyl, furyl, imidazolyl, indolinyl, indolyl, isoquinolinyl, isothiazolyl, isoxazolyl, morpholinyl, oxazolidine, oxazolyl, piperazinyl, piperidinyl, pyrazolyl, pyridinyl, pyrimidinyl, pyrrolidinyl, pyrrolopyridinyl, pyrrolyl, quinolinyl, tetrahydrofuryl, thiazolyl, thienyl, thiomorpholinyl, and triazolyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —$NR^cR^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^xR^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkoxycarbonyl, alkyl, alkylcarbonyl, and formyl; or, $R^a$ and $R^b$, together with the nitrogen atom to which they are attached, form a 5- or 6-membered ring optionally containing one additional heteroatom selected from nitrogen, oxygen, and sulfur.

The term "($NR^aR^b$)carbonyl" as used herein refers to an —$NR^aR^b$ group attached to the parent molecular moiety through a carbonyl group.

The term "($NR^aR^b$)carbonylalkyl," as used herein, refers to an alkyl group substituted with one, two, or three ($NR^aR^b$) carbonyl groups.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^xR^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "($NR^cR^d$)alkenyl," as used herein, refers to an alkenyl group substituted with one, two, or three —$NR^cR^d$ groups.

The term "($NR^cR^d$)alkyl," as used herein, refers to an alkyl group substituted with one, two, or three —$NR^cR^d$ groups. The alkyl part of the ($NR^cR^d$)alkyl is further optionally substituted with one or two additional groups selected from alkoxy, alkoxyalkylcarbonyl, alkoxycarbonyl, alkylsulfanyl, arylalkoxycarbonyl, arylalkoxyalkylcarbonyl, carboxy, cycloalkyl, heterocyclyl, heterocyclylcarbonyl, hydroxy, ($NR^eR^f$)carbonyl, and trialkylsilyloxy; wherein the heterocyclyl is further optionally substituted with one, two, three, four, or five substituents independently selected from alkoxy, alkyl, cyano, halo, haloalkoxy, haloalkyl, and nitro.

The term "($NR^cR^d$)carbonyl," as used herein, refers to an —$NR^cR^d$ group attached to the parent molecular moiety through a carbonyl group.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cycloalkyl)alkyl, unsubstituted heterocyclyl, unsubstituted heterocyclylalkyl, ($NR^xR^y$)alkyl, and ($NR^xR^y$)carbonyl.

The term "($NR^eR^f$)alkyl," as used herein, refers to an alkyl group substituted with one, two, or three —$NR^eR^f$ groups.

The term "($NR^eR^f$)alkylcarbonyl," as used herein, refers to an ($NR^eR^f$)alkyl group attached to the parent molecular moiety through a carbonyl group.

The term "($NR^eR^f$)carbonyl," as used herein, refers to an —$NR^eR^f$ group attached to the parent molecular moiety through a carbonyl group.

The term "($NR^eR^f$)sulfonyl," as used herein, refers to an —$NR^eR^f$ group attached to the parent molecular moiety through a sulfonyl group.

The term "—$NR^xR^y$," as used herein, refers to two groups, $R^x$ and $R^y$, which are attached to the parent molecular moiety through a nitrogen atom. $R^x$ and $R^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{x'}R^{y'}$)carbonyl, wherein $R^{x'}$ and $R^{y'}$ are independently selected from hydrogen and alkyl.

The term "($NR^xR^y$)alkyl," as used herein, refers to an alkyl group substituted with one, two, or three —$NR^xR^y$ groups.

The term "($NR^xR^y$)carbonyl," as used herein, refers to an —$NR^xR^y$ group attached to the parent molecular moiety through a carbonyl group.

The term "oxo," as used herein, refers to =O.

The term "sulfonyl," as used herein, refers to —$SO_2$—.

The term "trialkylsilyl," as used herein, refers to —$SiR_3$, wherein each R is an alkyl group. The three alkyl groups may be the same or different.

The term "trialkylsilyloxy," as used herein, refers to a trialkylsilyl group attached to the parent molecular moiety through an oxygen atom.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure also includes compounds of formula (I) wherein one or more of the atoms, e.g., C or H, are replaced by the corresponding radioactive isotopes of that atom (e.g., C replaced by $^{14}$C or H replaced by $^{3}$H), or a stable isotope of that atom (e.g., C replaced by $^{13}$C or H replaced by $^{2}$H). Such compounds may have a variety of potential uses, e.g., as standards and reagents in determining the ability of a potential pharmaceutical to bind to neurotransmitter proteins. In addition, in the case of stable isotopes, such compounds may have the potential to favorably is modify the biological properties, e.g. pharmacological and/or pharmacokinetic properties, of compounds of formula (I). The details concerning the selection of suitable sites for incorporating radioactive isotopes into the compounds, and the techniques for incorporating the radioactive isotopes into the compounds, are known to those skilled in the art.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Debio-025 | | | Debiopharm |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |

TABLE 1-continued

| Brand Name | Physiological Class | Type of Inhibitor or Target | Source Company |
|---|---|---|---|
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |

TABLE 1-continued

| Brand Name | Physiological Class | Type of Inhibitor or Target | Source Company |
|---|---|---|---|
| GS-9190 | Antiviral | NS5B Polymerase Inhibitor | Gilead |
| Peg-interferon lamda | Antiviral | Interferon | ZymoGenetics/Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: TFA for trifluoroacetic acid; EDCI for 1-(3-dimethylaminopropyl)-3-ethylcarbodiimide hydrochloride; h or hr for hours; EtOAc for ethyl acetate; DMSO for dimethylsulfoxide; $PPh_3$ for triphenylphosphine; DMF for N,N-dimethylformamide; MeOH for methanol; HATU for O-(7-azabenzotriazol-1-yl)-N,N,N',N'-tetramethyluronium hexafluorophosphate; $iPr_2EtN$, DIEA, or DIPEA for diisopropylethylamine; Cbz for carbobenzyloxy; TEA or $NEt_3$ for triethylamine; ACN for acetonitrile; AcOH for acetic acid; Boc or BOC for tert-butoxycarbonyl; DMAP for 4-dimethylaminopyridine; THF for tetrahydrofuran; TBAF for tetrabutylammonium fluoride; Me for methyl; Et for ethyl; t-Bu for tert-butyl; min for minutes; dba for dibenzylideneacetone; rt or RT for room temperature or retention time (context will dictate); HMDS for hexamethyldisilazide; DIBAL for diisobutyl aluminum hydride; TBDMS for t-butyldimethylsilyl; TBDPS for t-butyldimethylsilyl; and iPr for isopropyl.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

EXAMPLES

Purity assessment and low resolution mass analysis were conducted on a Shimadzu LC system coupled with Waters Micromass ZQ MS system. It should be noted that retention times may vary slightly between machines. Unless noted otherwise, the LC conditions employed in determining the retention time (RT) were:

| M-Cond. 1 | |
|---|---|
| Column = | XTERRA C18 S7 (3.0 × 50 mm) |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| M-Cond. 1a | |
| Column = | Phenomenex-Luna S5 (3.0 × 50 mm) |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| M-Cond. 1b | |
| Column = | Phenomenex-Luna S10 (3.0 × 50 mm) |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| M-Cond. 2 | |
| Column = | XTERRA C18 S7 (3.0 × 50 mm) |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| M-Cond. 3 | |
| Column = | PHENOMENEX-LUNA S10 (3.0 × 50 mm) |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| F-Cond. 1 | |
| Column = | XTERRA C18 S7 (3.0 × 50 mm) |
| Start % B = | 0 |
| Final % B = | 100 |
| Gradient time = | 2 min |

-continued

| | |
|---|---|
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

G-Cond. 1

| | |
|---|---|
| Column = | PHENOMENEX 4.6 × 30 mm 10 u |
| Start % B = | 0 |
| Final % B = | 100 |
| Gradient time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

G-Cond. 2

| | |
|---|---|
| Column = | XTERRA 4.6 × 30 mm S5 Column |
| Start % B = | 0 |
| Final % B = | 100 |
| Gradient time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

OL-Cond. 1

| | |
|---|---|
| Column = | XTERRA C18 S5 (4.6 × 50 mm) |
| Start % B = | 0 |
| Final % B = | 100 |
| Gradient time = | 4 min |
| Stop time = | 5 min |
| Flow Rate = | 4 mL/min |
| Wavelength = | 220 nm |
| Solvent A = | 0.2% H$_3$PO$_4$ in 10% methanol/90% H$_2$O |
| Solvent B = | 0.2% H$_3$PO$_4$ in 90% methanol/10% H$_2$O |

OL-Cond. 1a

| | |
|---|---|
| Column = | XTERRA C18 S5 (4.6 × 50 mm) |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.2% H$_3$PO$_4$ in 10% methanol/90% H$_2$O |
| Solvent B = | 0.2% H$_3$PO$_4$ in 90% methanol/10% H$_2$O |

D-Cond. 1

| | |
|---|---|
| Column = | Phenomenex-Luna S10 (3.0 × 50 mm) |
| Start % B = | 0 |
| Final % B = | 100 |
| Gradient time = | 3 min |
| Stop time = | 3 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

D-Cond. 2

| | |
|---|---|
| Column = | Phenomenex-Luna S10 (4.6 × 50 mm) |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

D-Cond. 1a

| | |
|---|---|
| Column = | XTERRA S7 (3.0 × 50 mm) |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

D-Cond. 1b

| | |
|---|---|
| Column = | XTERRA S5 (3.3 × 50 mm) |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

D-Cond. 1c

| | |
|---|---|
| Column = | Waters Polarity; 2.1 × 150 mm |
| Start % B = | 4 |
| Final % B = | 100 |
| Gradient time = | 15 min |
| Stop time = | 18 min |
| Flow Rate = | 0.35 mL/min |
| Wavelength = | 220 nm |
| Solvent A = | 5 mM NH$_4$OAc (pH = 5), 2% ACN, 98% H$_2$O |
| Solvent B = | 5 mM NH$_4$OAc (pH = 5), 90% ACN, 10% H$_2$O |

JG-Cond. 1

| | |
|---|---|
| Column = | XTERRA MS C18 S7 (3.0 × 50 mm) |
| Start % B = | 0 |
| Final % B = | 100 |
| Gradient time = | 3 min |
| Stop time = | 4 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

JG-Cond. 2

| | |
|---|---|
| Column = | Phenomenex Luna C18 (4.6 × 50 mm) |
| Start % B = | 0 |
| Final % B = | 100 |
| Gradient time = | 4 min |
| Stop time = | 5 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

J-Cond. 2

| | |
|---|---|
| Column = | Phenomenex-Luna S10 (3.0 × 50 mm) |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

J-Cond. 3

| | |
|---|---|
| Column = | XTERRA C18 S7 (3.0 × 50 mm) |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Example M1

5,5'-(1,2-ethynediyl)bis(2-((2S)-1-((2R)-2-phenyl-propanoyl)-2-pyrrolidinyl)-1H-benzimidazole)

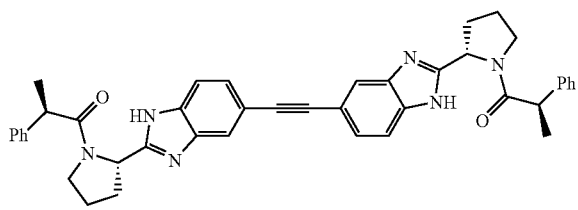

Example M1

Step a

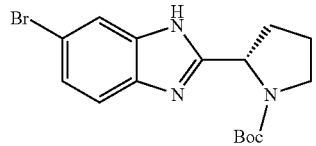

EDCI.HCl (2.348 g, 12.25 mmol) was added to a mixture of 4-bromobenzene-1,2-diamine (2.078 g, 11.11 mmol), N-Boc-L-proline (2.311 g, 10.74 mmol) and 1-hydroxybenzotriazole (1.742 g, 12.89 mmol) in $CH_2Cl_2$ (40 mL), and stirred at ambient conditions for 19 h. The mixture was then diluted with $CH_2Cl_2$, washed with water (2×), dried (brine; $MgSO_4$), filtered, and concentrated in vacuo to provide a brown foam. Acetic acid (40 mL) was added to the foam, and the mixture was heated at 65° C. for 90 min. The volatile component was removed in vacuo, and the residue was dissolved in EtOAc and washed carefully with saturated $NaHCO_3$ solution (2×), and the organic phase was dried (brine; $MgSO_4$), filtered, and concentrated in vacuo. The resultant crude material was submitted to flash chromatography (silica gel; EtOAc) to provide benzimidazole M1a as a tan foam (2.5 g). $^1H$ NMR (DMSO-$d_6$, δ=2.5 ppm, 400 MHz): 12.49-12.33 (four br s, 1H), 7.71 (d, J=2, 0.54H), 7.60 (app br s, 0.46H), 7.50 (d, J=8.6, 0.45H), 7.40 (d, J=8.4, 0.55H), 7.26 (m, 1H), 4.96-4.87 (m, 1H), 3.64-3.51 (m, 1H), 3.44-3.38 (m, 1H), 2.38-2.21 (m, 1H), 1.99-1.85 (m, 3H), 1.39 (s, 3.7H), 1.06 (s, 5.3H). LC/MS: Anal. Calcd. for $[M+H]^+$ $C_{16}H_{21}{}^{81}BrN_3O_2$; 368.03. found: 368.18.

Example M1

Step b

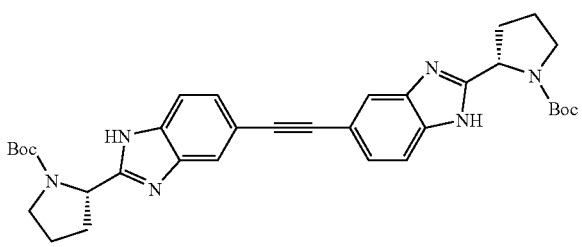

$Pd(Ph_3P)_4$ (0.482 g, 0.417 mmol) was added to a mixture of bromide M1a (3.061 g, 8.358 mmol) and bis(trimethyltin) acetylene (1.768 g, 5.028 mmol) in DMF (40 mL), and the mixture was flushed with nitrogen and heated at 80° C. for 14 h. The volatile component was removed in vacuo, and a silica gel mesh was prepared directly from the resultant residue and submitted to flash chromatography (silica gel; 50-100% EtOAc/hexanes) to provide alkyne M1b as an oil which solidified to a tan solid upon standing (2.1 g; the sample contained DMF and EtOAc). $^1H$ NMR (DMSO-$d_6$, δ=2.5 ppm, 400 MHz): 12.48-12.36 (four br s, 2H), 7.74-7.46 (m, 4H), 7.35-7.30 (m, 2H), 4.99-4.89 (m, 2H), 3.63-3.55 (m, 2H), 3.45-3.39 (m, 2H), 2.41-2.23 (m, 2H), 2.05-1.87 (m, 6H), 1.40 (s, 7.6H), 1.07 (S, 10.4H). LC/MS: Anal. Calcd. for $[M+H]^+$ $C_{34}H_{41}N_6O_4$: 597.32. found: 597.49.

Example M1

Step c

A solution of alkyne M1b (1.60 g, 2.68 mmol) in 20% TFA/$CH_2Cl_2$ (15 mL) was stirred at room temperature until the deprotection was complete (~8.5 h). The volatile component was removed in vacuo and the resultant residue was free-based with SCX (MeOH wash; 2.0 M $NH_3$/MeOH elution) to provide pyrrolidine M1c as a tan foam, containing minor unidentified impurities (1.0 g). The sample was used in the next step without further purification. $^1H$ NMR (DMSO-$d_6$, δ=2.5 ppm, 400 MHz): 7.64 (br s, 2H), 7.48 (d, J=8.0, 2H), 7.30 (dd, J=8.2, 1.6, 2H), 4.37 (dd, J=7.9, 6.2, 2H), 2.95 (app t, J=6.8, 4H), 2.20-2.11 (m, 2H), 1.99-1.91 (m, 2H), 1.79-1.72 (m, 4H). LC/MS: Anal. Calcd. for $[M+H]^+$ $C_{24}H_{25}N_6$: 397.21. found: 397.29.

Example M1

HATU (41.4 mg, 0.109 mmol) was added to a mixture of pyrrolidine M1c (19.0 mg, 0.0479 mmol), (R)-2-phenylpropanoic acid (17.7 mg, 0.118 mmol) and DIEA (40 µL, 0.229 mmol) in DMF (1.5 mL), and the mixture was stirred for 3 h. The volatile component was removed in vacuo and the residue was purified with a reverse phase HPLC (MeOH/$H_2O$/TFA) to provide the TFA salt of Example M1 as an off-white solid (16.4 mg). $^1H$ NMR (DMSO-$d_6$, δ=2.5 ppm, 500 MHz): 7.91 (s, 1.6H), 7.74-7.24 (m, 13.1H), 6.77-6.71 (m, 1.3H), 5.63 (m, 0.3H), 5.23 (dd, J=8.4, 2.7, 1.7H), 4.05-3.94 (m, 3.5H), 3.86-3.51 (m, 0.9H), 3.27-3.21 (m, 1.6H), 2.29-1.83 (m, 8H), 1.32-1.28 (m, 6H). LC (M-Cond. 1); RT=1.30 min; >95% homogeneity index. LC/MS: Anal. Calcd. for $[M+H]^+$ $C_{42}H_{41}N_6O_2$: 661.33. found; 661.21.

Examples M2 to M26.6

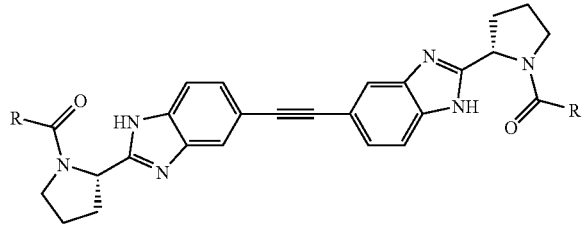

All the examples in the table below, except Example M26.4, were prepared from intermediate M1c and appropriate acids by employing either HATU- or EDCI-coupling condition. Example M26.4 was prepared from pyrrolidine M1c by reacting it with CbzCl in the presence of $Et_3N$. In all cases, purifications were conducted with a reverse phase HPLC (solvent systems: $H_2O$/MeOH/TFA, $H_2O$/ACN/TFA or $H_2O$/ACN/$NH_4$OAc), and final products were isolated as either TFA or AcOH salts. In some instances, the corresponding free-base form was obtained by employing an SCX free-basing protocol described in the preparation of pyrrolidine M1c. The coupling partners (i.e., $RCO_2$) were either prepared in house or obtained from commercial sources. Consult the cap synthesis section for a listing of the acid coupling partners prepared in house.

| Example | Compound Name | Coupling protocol | (Form status of final product) | RT (LC-Cond.); % homogeneity index; MS data |
|---|---|---|---|---|
| M2 | 5,5'-(1,2-ethynediyl)bis(2-((2S)-1-propionyl-2-pyrrolidinyl)-1H-benzimidazole | EDCI | (TFA) | 1.36 min (M-Cond. 2); >95%; LC/MS: Anal. Calcd. for $[M + H]^+$ $C_{30}H_{33}N_6O_2$: 509.27; found: 509.35. HRMS: Anal. Calcd. for $[M + H]^+$ $C_{30}H_{33}N_6O_2$: 509.2665; found 509.2665 |
| M3 | 5,5'-(1,2-ethynediyl)bis(2-((2S)-1-isobutyryl-2-pyrrolidinyl)-1H-benzimidazole) | EDCI | (TFA) | 1.50 min (M-Cond. 2); >95%; LC/MS: Anal. Calcd. for $[M + H]^+$ $C_{32}H_{37}N_6O_2$: 537.30; found: 537.37. HRMS: Anal. Calcd. for $[M + H]^+$ $C_{32}H_{37}N_6O_2$: 537.2978; found 537.2964 |
| M4 | 2-((2S)-1-(cyclopropylcarbonyl)-2-pyrrolidinyl)-5-((2-((2S)-1-(cyclopropylcarbonyl)-2-pyrrolidinyl)-1H-benzimidazol-6-yl)ethynyl)-1H-benzimidazole | EDCI | (TFA) | 1.44 min (M-Cond. 2); >95%; LC/MS Anal. Calcd. for $[M + H]^+$ $C_{32}H_{33}N_6O_2$: 533.27; found: 533.35. HRMS: Anal. Calcd. for $[M + H]^+$ $C_{32}H_{33}N_6O_2$: 533.2665; found 533.2644 |

-continued

| Example | Compound Name | Coupling protocol | (Form status of final product) | RT (LC-Cond.); % homogeneity index; MS data |
|---|---|---|---|---|
| M5 | 5,5'-(1,2-ethynediyl)bis(2-((2S)-1-((2R)-tetrahydro-2-furanylcarbonyl)-2-pyrrolidinyl)-1H-benzimidazole) | EDCI | 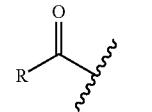<br>(TFA) | 1.35 min (M-Cond. 2); >95%; LC/MS: Anal. Calcd. for [M + H]$^+$ C$_{34}$H$_{37}$N$_6$O$_4$: 593.29; found: 593.41. HRMS: Anal. Calcd. for [M + H]$^+$ C$_{34}$H$_{37}$N$_6$O$_4$: 593.2876; found 593.2861 |
| M6 | 2-((2S)-1-benzoyl-2-pyrrolidinyl)-5-((2-((2S)-1-benzoyl-2-pyrrolidinyl)-1H-benzimidazol-6-yl)ethynyl)-1H-benzimidazole | EDCI | 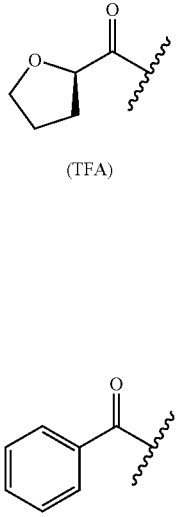 | 1.71 min (M-Cond. 2); 95%; LC/MS: Anal. Calcd. for [M + H]$^+$ C$_{38}$H$_{33}$N$_6$O$_2$: 605.27; found: 605.36. HRMS: Anal. Calcd. for [M + H]$^+$ C$_{38}$H$_{33}$N$_6$O$_2$: 605.2665; found 605.2637 |
| M7 | 5,5'-(1,2-ethynediyl)bis(2-((2S)-1-(2-pyridinylacetyl)-2-pyrrolidinyl)-1H-benzimidazole) | EDCI, Et$_3$N | 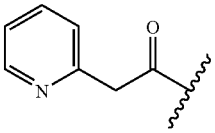<br>(TFA) | 1.19 min (M-Cond. 2); >95%; LC/MS: Anal. Calcd. for [M + H]$^+$ C$_{38}$H$_{35}$N$_8$O$_2$: 635.29; found: 635.36. HRMS: Anal. Calcd. for [M + H]$^+$ C$_{38}$H$_{35}$N$_8$O$_2$: 635.2883; found 635.2867 |
| M8 | 2-((2S)-1-(cyclopropylacetyl)-2-pyrrolidinyl)-5-((2-((2S)-1-(cyclopropylacetyl)-2-pyrrolidinyl)-1H-benzimidazol-6-yl)ethynyl)-1H-benzimidazole | EDCI | 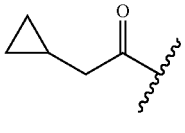<br>(TFA) | 1.53 min (M-Cond. 2); >95%; LC/MS: Anal. Calcd. for [M + H]$^+$ C$_{34}$H$_{37}$N$_6$O$_2$: 561.30; found: 561.41. HRMS: Anal. Calcd. for [M + H]$^+$ C$_{34}$H$_{37}$N$_6$O$_2$: 561.2978; found 561.2993 |

-continued

| Example | Compound Name | Coupling protocol | (Form status of final product) | RT (LC-Cond.); % homogeneity index; MS data |
|---|---|---|---|---|
| M9 | 2-((2S)-1-(cyclobutylcarbonyl)-2-pyrrolidinyl)-5-((2-((2S)-1-(cyclobutylcarbonyl)-2-pyrrolidinyl)-1H-benzimidazol-6-yl)ethynyl)-1H-benzimidazole | EDCI | 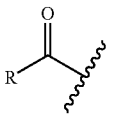 (TFA) | 1.64 min (M-Cond. 2); >95%; LC/MS: Anal. Calcd. for [M + H]+ $C_{34}H_{37}N_6O_2$: 561.30; found: 561.41. HRMS: Anal. Calcd. for [M + H]+ $C_{34}H_{37}N_6O_2$: 561.2978; found 561.2988 |
| M10 | 5,5'-(1,2-ethynediyl)bis(2-((2S)-1-(2-thienylcarbonyl)-2-pyrrolidinyl)-1H-benzimidazole) | EDCI | 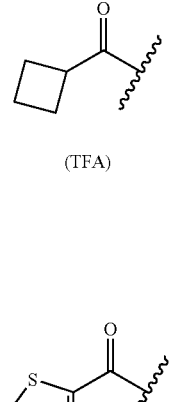 (TFA) | 1.69 min (M-Cond. 2); >95%; LC/MS: Anal. Calcd. for [M + H]+ $C_{34}H_{29}N_6O_2S_2$: 617.18; found: 617.31. HRMS: Anal. Calcd. for [M + H]+ $C_{34}H_{29}N_6O_2S_2$: 617.1793; found: 617.1805 |
| M11 | 5,5'-(1,2-ethynediyl)bis(2-((2S)-1-(3-pyridinylacetyl)-2-pyrrolidinyl)-1H-benzimidazole) | EDCI, Et$_3$N | 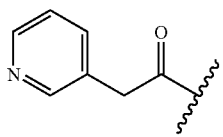 (TFA) | 1.14 min (M-Cond. 2); >95%; LC/MS: Anal. Calcd. for [M + H]+ $C_{38}H_{35}N_8O_2$: 635.29; found: 635.43. HRMS: Anal. Calcd. for [M + H]+ $C_{38}H_{35}N_8O_2$: 635.2883; found: 635.2888 |
| M12 | 5,5'-(1,2-ethynediyl)bis(2-((2S)-1-((1-methyl-1H-pyrrol-2-yl)carbonyl)-2-pyrrolidinyl)-1H-benzimidazole) | EDCI | 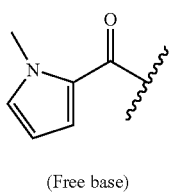 (Free base) | 1.72 min (M-Cond. 2); >95%; LC/MS: Anal. Calcd. for [M + H]+ $C_{36}H_{35}N_8O_2$: 611.29; found: 611.37. |
| M13 | 5,5'-(1,2-ethynediyl)bis(2-((2S)-1-(3-furoyl)-2-pyrrolidinyl)-1H-benzimidazole) | EDCI | 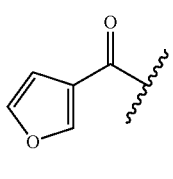 (TFA) | 1.50 min (M-Cond. 2); >95%; LC/MS: Anal. Calcd. for [M + H]+ $C_{34}H_{29}N_6O_4$: 585.22; found: 585.35. HRMS: Anal. Calcd. for [M + H]+ $C_{34}H_{29}N_6O_4$: 585.2250; found: 585.2245 |

-continued

| Example | Compound Name | Coupling protocol | (Form status of final product) | RT (LC-Cond.); % homogeneity index; MS data |
|---------|---------------|-------------------|-------------------------------|---------------------------------------------|
| M14 | 5,5'-(1,2-ethynediyl)bis(2-((2S)-1-(tetrahydro-3-furanylcarbonyl)-2-pyrrolidinyl)-1H-benzimidazole) | EDCI | 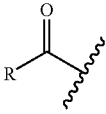 (Free base; mixture of diastereomers) | 1.33 min (M-Cond. 2); >95%; LC/MS: Anal. Calcd. for $[M + H]^+$ $C_{34}H_{37}N_6O_4$: 593.29; found: 593.39. HRMS: Anal. Calcd. for $[M + H]^+$ $C_{34}H_{37}N_6O_4$: 593.2876; found: 593.2875 |
| M15 | (1R,1'R)-2,2'-(1,2-ethynediylbis(1H-benzimidazole-5,2-diyl(2S)-2,1-pyrrolidinediyl))bis(2-oxo-1-phenylethanol) | HATU, DIEA |  (TFA salt) | 1.04 min (M-Cond. 1); 95%; LC/MS: Anal. Calcd. for $[M + H]^+$ $C_{40}H_{37}N_6O_4$: 665.29; found: 665.18. |
| M16 | (2S,2'S)-1,1'-(1,2-ethynediylbis(1H-benzimidazole-5,2-diyl(2S)-2,1-pyrrolidinediyl))bis(1-oxo-2-phenyl-2-propanol | HATU, DIEA | 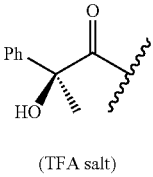 (TFA salt) | 1.25 min (M-Cond. 1); >95%; LC/MS: Anal. Calcd. for $[M + H]^+$ $C_{42}H_{41}N_6O_4$: 693.32; found: 693.20. |
| M17 | 2,2'-(1,2-ethynediylbis(1H-benzimidazole-5,2-diyl(2S)-2,1-pyrrolidinediylcarbonyl))bis(7-methoxyquinoline) | HATU, DIEA | 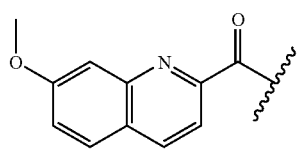 (Free base) | 1.40 min (M-Cond. 1); >95%; LC/MS: Anal. Calcd. for $[M + H]^+$ $C_{46}H_{39}N_8O_4$: 767.31; found: 767.24. |

-continued

| Example | Compound Name | Coupling protocol | (Form status of final product) | RT (LC-Cond.); % homogeneity index; MS data |
|---|---|---|---|---|
| M18 | 3-chloro-1-(((2S)-2-(5-((2-((2S)-1-((3-chloro-5-methoxy-1-isoquinolinyl)carbonyl)-2-pyrrolidinyl)-1H-benzimidazol-6-yl)ethynyl)-1H-benzimidazol-2-yl)-1-pyrrolidinyl)carbonyl)-5-methoxyisoquinoline | HATU, DIEA | (Free base) | 1.04 min (M-Cond. 1); >95%; LC/MS: Anal. Calcd. for [M + H]$^+$ C$_{46}$H$_{37}$Cl$_2$N$_8$O$_4$: 835.23; found: 835.21. |
| M19 | (1R)-2-((2S)-2-(5-((2-((2S)-1-((2R)-2-(dimethylamino)-2-phenylacetyl)-2-pyrrolidinyl)-1H-benzimidazol-6-yl)ethynyl)-1H-benzimidazol-2-yl)-1-pyrrolidinyl)-N,N-dimethyl-2-oxo-1-phenylethanamine | HATU, DIEA | (Free base) | 0.99 min (M-Cond. 1); >95%; LC/MS: Anal. Calcd. for [M + H]$^+$ C$_{44}$H$_{47}$N$_8$O$_2$: 719.38; found: 719.25. |
| M20 | N,N'-(1,2-ethynediylbis(1H-benzimidazole-5,2-diyl(2S)-2,1-pyrrolidinediyl((1R)-2-oxo-1-phenyl-2,1-ethanediyl)))diformamide | HATU, DIEA | (TFA) | 1.18 min (M-Cond. 1a); >95%; LC/MS: Anal. Calcd. for [M + H]$^+$ C$_{42}$H$_{39}$N$_8$O$_4$: 719.31; found: 719.21. |
| M21 | N-((1R)-2-((2S)-2-(5-((2-((2S)-1-((2R)-2-acetamido-2-phenylacetyl)-2-pyrrolidinyl)-1H-benzimidazol-6-yl)ethynyl)-1H-benzimidazol-2-yl)-1-pyrrolidinyl)-2-oxo-1-phenylethyl)acetamide | HATU, DIEA | (TFA) | 1.25 min (M-Cond. 1a); 90%; LC/MS: Anal. Calcd. for [M + H]$^+$ C$_{44}$H$_{43}$N$_8$O$_4$: 747.34; found: 747.25. |
| M22 | 5,5'-(1,2-ethynediyl)bis(2-((2S)-1-((2R)-2-(4-morpholinyl)-2-phenylacetyl)-2-pyrrolidinyl)-1H-benzimidazole) | HATU, DIEA | (Free base) | 1.15 min (M-Cond. 1a); >95%; LC/MS: Anal. Calcd. for [M + H]$^+$ C$_{48}$H$_{51}$N$_8$O$_4$: 803.40; found: 803.38. |

-continued

R group structure: R-C(=O)- (attached via wavy bond)

| Example | Compound Name | Coupling protocol | (Form status of final product) | RT (LC-Cond.); % homogeneity index; MS data |
|---------|---------------|-------------------|--------------------------------|---------------------------------------------|
| M23 | dimethyl (1,2-ethynediylbis(1H-benzimidazole-5,2-diyl(2S)-2,1-pyrrolidinediyl((1R)-2-oxo-1-phenyl-2,1-ethanediyl)))biscarbamate | HATU, DIEA | methyl carbamate-NH-CH(Ph)-C(=O)- (TFA) | 1.67 min (M-Cond. 1a); >95%; LC/MS: Anal. Calcd. for $[M + H]^+$ $C_{44}H_{43}N_8O_6$: 779.33; found: 779.47. |
| M24 | methyl ((1S)-1-(((2S)-2-(5-((2-((2S)-1-((2S)-2-((methoxycarbonyl)amino)-3-methylbutanoyl)-2-pyrrolidinyl)-1H-benzimidazol-5-yl)ethynyl)-1H-benzimidazol-2-yl)-1-pyrrolidinyl)carbonyl)-2-methylpropyl)carbamate | HATU, DIEA | methyl carbamate-NH-CH(iPr)-C(=O)- (TFA) | 2.00 min (M-Cond. 3); >95%; LC/MS: Anal. Calcd. for $[M + H]^+$ $C_{38}H_{47}N_8O_6$: 711.36; found: 711.35. HRMS: Anal. Calcd. for $[M + H]^+$ $C_{38}H_{47}N_8O_6$: 711.3619; found: 711.3605. $^1$H NMR (DMSO-$d_6$, δ = 2.5 ppm, 500 MHz): 7.94/7.91 (two s, 2 H), 7.76-7.71 (m, 2 H), 7.60 (d, J = 8.5, 2 H), 7.34 (d, J = 8.5, 1.81 H), 7.22 (d, J = 8.9, 0.19 H), 5.62 (app d, J = 7.9, 0.17 H), 5.23 (dd, J = 8.2, 5.4, 1.83 H), 4.13 (app t, J = 8.1, 1.76 H), 3.95-3.50 (m, 4.24), 3.55/3.15 (two s, 6 H), 2.44-1.81 (m, 10 H), 0.90/0.86/0.84/0.80 (four d, J = 7.0, 7.0, 6.7, 6.7 respectively, 12 H). |
| M25 | methyl ((1S)-2-((2S)-2-(5-((2-((2S)-1-(N-(methoxycarbonyl)-L-alanyl)-2-pyrrolidinyl)-1H-benzimidazol-5-yl)ethynyl)-1H-benzimidazol-2-yl)-1-pyrrolidinyl)-1-methyl-2-oxoethyl)carbamate | HATU, DIEA | methyl carbamate-NH-CH(CH3)-C(=O)- (TFA) | 1.76 min (M-Cond. 3); >95%; LC/MS: Anal. Calcd. for $[M + H]^+$ $C_{34}H_{39}N_8O_6$: 655.30; found: 655.32. HRMS: Anal. Calcd. for $[M + H]^+$ $C_{34}H_{39}N_8O_6$: 655.2993; found: 655.2993 |

-continued

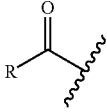

| Example | Compound Name | Coupling protocol | (Form status of final product) | RT (LC-Cond.); % homogeneity index; MS data |
|---|---|---|---|---|
| M26 | methyl ((1R)-2-((2S)-2-(5-((2-((2S)-1-(N-(methoxycarbonyl)-D-alanyl)-2-pyrrolidinyl)-1H-benzimidazol-5-yl)ethynyl)-1H-benzimidazol-2-yl)-1-pyrrolidinyl)-1-methyl-2-oxoethyl)carbamate | HATU, DIEA | 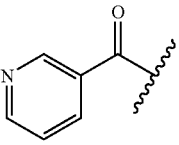<br>(AcOH) | 1.70 min (M-Cond. 3); >95%; LC/MS: Anal. Calcd. for [M + H]$^+$ C$_{34}$H$_{39}$N$_8$O$_6$: 655.30; found: 655.26. |
| M26.1 | N,N'-(1,2-ethynediyl)bis(2-((2S)-1-(3-pyridinylcarbonyl)-2-pyrrolidinyl)-1H-benzimidazole) | EDCI | 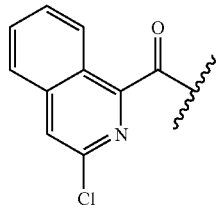<br>(TFA) | 1.28 min (M-Cond. 2); >95%; LC/MS: Anal. Calcd. for [M + H]$^+$ C$_{36}$H$_{31}$N$_8$O$_2$: 607.26; found: 607.38. HRMS: Anal. Calcd. for [M + H]$^+$ C$_{36}$H$_{31}$N$_8$O$_2$: 607.2570; found: 607.2569 |
| M26.2 | 3-chloro-1-(((2S)-2-(5-((2-((2S)-1-((3-chloro-1-isoquinolinyl)carbonyl)-2-pyrrolidinyl)-1H-benzimidazol-6-yl)ethynyl)-1H-benzimidazol-2-yl)-1-pyrrolidinyl)carbonyl) isoquinoline | EDCI | 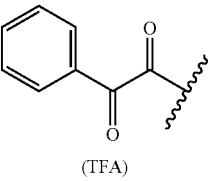<br>(TFA) | 2.15 min (M-Cond. 2); >95%; LC/MS: Anal. Calcd. for [M + H]$^+$ C$_{44}$H$_{33}$Cl$_2$N$_8$O$_2$: 775.21; found: 775.09 |
| M26.3 | 2,2'-(1,2-ethynediylbis(1H-benzimidazole-5,2-diyl(2S)-2,1-pyrrolidinediyl))bis(2-oxo-1-phenylethanone) | EDCI | 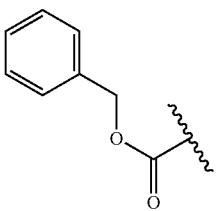<br>(TFA) | 2.12 min (M-Cond. 2); >95%; LC/MS: Anal. Calcd. for [M + H]$^+$ C$_{40}$H$_{33}$N$_6$O$_4$: 661.26; found: 661.07. |
| M26.4 | benzyl (2S)-2-(5-((2-((2S)-1-((benzyloxy)carbonyl)-2-pyrrolidinyl)-1H-benzimidazol-6-yl)ethynyl)-1H-benzimidazol-2-yl)-1-pyrrolidinecarboxylate | — |  | 2.01 min (M-Cond. 2); >95%; LC/MS: Anal. Calcd. for [M + H]$^+$ C$_{40}$H$_{37}$N$_6$O$_4$: 665.29; found: 665.36. |

-continued

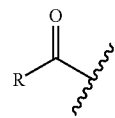

| Example | Compound Name | Coupling protocol | (Form status of final product) | RT (LC-Cond.); % homogeneity index; MS data |
|---|---|---|---|---|
| M26.5 | 5,5'-(1,2-ethynediyl)bis(2-((2S)-1-((2S)-tetrahydro-2-furanylcarbonyl)-2-pyrrolidinyl)-1H-benzimidazole | EDCI | (TFA) | 1.44 min (M-Cond. 2); >95%; LC/MS: Anal. Calcd. for [M + H]$^+$ $C_{34}H_{37}N_6O_4$: 593.29; found: 593.40. HRMS: Anal. Calcd. for [M + H]$^+$ $C_{34}H_{37}N_6O_4$: 593.2876; found 593.2875 |
| M26.6 | 5,5'-(1,2-ethynediyl)bis(2-((2S)-1-(2-furoyl)-2-pyrrolidinyl)-1H-benzimidazole) | EDCI | (TFA) | 1.49 min (M-Cond. 2); >95%; LC/MS: Anal. Calcd. for [M + H]$^+$ $C_{34}H_{29}N_6O_4$: 585.22; found: 585.34. HRMS: Anal. Calcd. for [M + H]$^+$ $C_{34}H_{29}N_6O_4$: 585.2250; found: 585.2257 |

Examples M27-M31

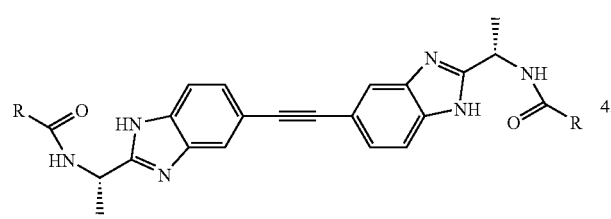

Examples M27-M31 were prepared according to the procedure described for the synthesis of Example 1 with the exception that (L)-Boc-alanine was used instead of the (L)-Boc-proline for the first step and that appropriate acids were employed for the final step.

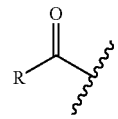

| Example | Compound Name | Coupling protocol; | (Form status of final product) | RT (LC-Cond.); % homogeneity index; MS data |
|---|---|---|---|---|
| M27 | (2R,2'R)-N,N'-(1,2-ethynediylbis(1H-benzimidazole-5,2-diyl(1S)-1,1-ethanediyl))bis(2-hydroxy-2-phenylacetamide | HATU, DIEA | (TFA salt) | 1.59 min (M-Cond. 1b); >95%; LC/MS: Anal. Calcd. for [M + H]$^+$ $C_{36}H_{33}N_6O_4$: 613.26; found: 613.08. |

-continued

| Example | Compound Name | Coupling protocol; | (Form status of final product) | RT (LC-Cond.); % homogeneity index; MS data |
|---------|---------------|--------------------|---------------------------------|---------------------------------------------|
| M28 | (2S,2'S)-N,N'-(1,2-ethynediylbis(1H-benzimidazole-5,2-diyl(1S)-1,1-ethanediyl))bis(2-hydroxy-2-phenylpropanamide | HATU, DIEA | (TFA salt) | 1.74 min (M-Cond. 1b); >95%; LC/MS: Anal. Calcd. for [M + H]$^+$ $C_{38}H_{37}N_6O_4$: 641.29; found: 640.99 |
| M29 | (2R)-2-(dimethylamino)-N-((1S)-1-(5-((2-((1S)-1-(((2R)-2-(dimethylamino)-2-phenylacetyl)amino)ethyl)-1H-benzimidazol-6-yl)ethynyl)-1H-benzimidazol-2-yl)ethyl)-2-phenylacetamide | HATU, DIEA; | (Free base) | 1.42 min (M-Cond. 1b); >95%; LC/MS: Anal. Calcd. for [M + H]$^+$ $C_{40}H_{43}N_8O_2$: 667.35; found: 667.09. |
| M30 | (2R)-2-acetamido-N-((1S)-1-(5-((2-((1S)-1-(((2R)-2-acetamido-2-phenylacetyl)amino)ethyl)-1H-benzimidazol-6-yl)ethynyl)-1H-benzimidazol-2-yl)ethyl)-2-phenylacetamide | HATU, DIEA; | (TFA salt) | 1.56 min (M-Cond. 1b); >95%; LC/MS: Anal. Calcd. for [M + H]$^+$ $C_{40}H_{39}N_8O_4$: 695.31; found: 695.06. |
| M31 | dimethyl (1,2-ethynediylbis(1H-benzimidazole-5,2-diyl(1S)-1,1-ethanediylimino((1R)-2-oxo-1-phenyl-2,1-ethanediyl))) biscarbamate | HATU, DIEA; | (Free base) | 1.69 min (M-Cond. 1b); >95%; LC/MS: Anal. Calcd. for [M + H]$^+$ $C_{40}H_{39}N_8O_6$: 727.30; found: 727.06 |

Example M32-M36

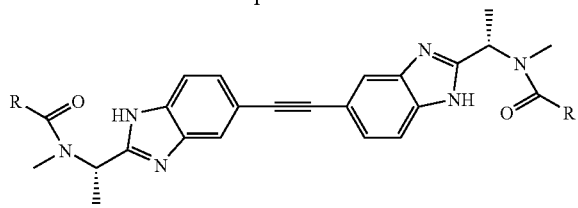

Examples M32-M36 were prepared according to the procedure described for Example 1 with the exception that (L)-Boc-N-methylalanine was used instead of the (L)-Boc-proline for the first step and that appropriate acids were employed for the final step.

| Example | Compound Name | Coupling protocol | (Form status of final product) R-C(O)- | RT (LC-Cond.); % homogeneity index; MS data |
|---|---|---|---|---|
| M32 | N,N'-(1,2-ethynediylbis(1H-benzimidazole-5,2-diyl(1S)-1,1-ethanediyl))bis(N-methyl-2-phenylacetamide | HATU, DIEA | Ph-CH2-C(O)- (TFA salt) | 1.71 min (M-Cond. 1b); >95%; LC/MS: Anal. Calcd. for [M + H]$^+$ $C_{38}H_{37}N_6O_2$: 609.30; found: 609.43. |
| M33 | (2R,2'R)-N,N'-(1,2-ethynediylbis(1H-benzimidazole-5,2-diyl(1S)-1,1-ethanediyl))bis(2-hydroxy-N-methyl-2-phenylacetamide | HATU, DIEA | Ph-CH(OH)-C(O)- (TFA salt) | 1.61 min (M-Cond. 1b); >95%; LC/MS: Anal. Calcd. for [M + H]$^+$ $C_{38}H_{37}N_6O_4$: 641.29; found: 641.44 |
| M34 | (2S,2'S)-N,N'-(1,2-ethynediylbis(1H-benzimidazole-5,2-diyl(1S)-1,1-ethanediyl))bis(2-hydroxy-N-methyl-2-phenylpropanamide | HATU, DIEA | Ph-C(OH)(CH3)-C(O)- (TFA salt) | 1.83 min (M-Cond. 1b); >95%; LC/MS: Anal. Calcd. for [M + H]$^+$ $C_{40}H_{41}N_6O_4$: 669.32; found: 669.51 |
| M35 | (2R)-2-(dimethylamino)-N-((1S)-1-(5-((2-((1S)-1-(((2R)-2-(dimethylamino)-2-phenylacetyl)methyl)amino)ethyl)-1H-benzimidazol-6-yl)ethynyl)-1H-benzimidazol-2-yl)ethyl)-N-methyl-2-phenylacetamide | HATU, DIEA | Me2N-CH(Ph)-C(O)- (Free base) | 1.45 min (M-Cond. 1b); >95%; LC/MS: Anal. Calcd. for [M + H]$^+$ $C_{42}H_{47}N_8O_2$: 695.38; found: 695.56 |
| M36 | dimethyl (1,2-ethynediylbis(1H-benzimidazole-5,2-diyl(1S)-1,1-ethanediyl(methylimino)((1R)-2-oxo-1-phenyl-2,1-ethanediyl)))biscarbamate | HATU, DIEA | MeO-C(O)-NH-CH(Ph)-C(O)- (TFA) | 1.75 min (M-Cond. 1b); >95%; LC/MS: Anal. Calcd. for [M + H]$^+$ $C_{42}H_{43}N_8O_6$: 755.33; found: 755.54 |

Example M37

5,5'-(1,2-ethynediyl)bis(2-((2S)-1-(phenylacetyl)-2-pyrrolidinyl)-1H-benzimidazole)

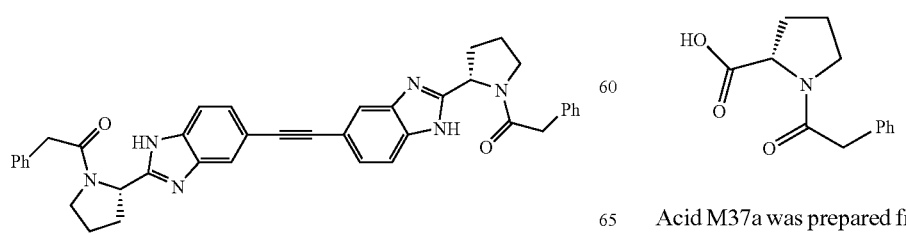

Example M37

Step a

Acid M37a was prepared from (L)-proline according to the procedure described in Gudasheva, et al. *Eur. J. Med. Chem. Chim. Ther.* 1996, 31, 151.

Example M37

Step b

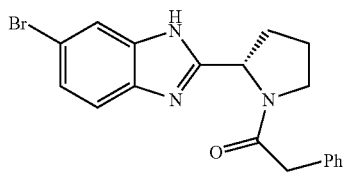

Bromide M37b was prepared from acid M37a and 4-bromobenzene-1,2-diamine according to the procedure described for the synthesis of intermediate M1a. $^1$H NMR (CDCl$_3$, δ=7.24 ppm, 500 MHz): 10.71/10.68 (overlapping br s, 1H), 7.85 (s, 0.48H), 7.56 (d, J=8.6, 0.52H), 7.50 (s, 0.52H), 7.35-7.22 (m, 6.48H), 5.38 (app br d, J=8.1, 1H), 3.73 (d, J=15.7, 1H), 3.67 (d, J=15.6, 1H), 3.64-3.51 (m, 2H), 3.12-3.04 (m, 1H), 2.41-2.28 (m, 1H), 2.20-2.08 (m, 2H). LC/MS: Anal. Calcd. for [M+H]$^+$ C$_{19}$H$_{19}$$^{81}$BrN$_3$O: 386.07. found: 386.10.

Example M37

Example M37 was prepared from bromide M37b according to the procedure described for the synthesis of alkyne M1b. The crude material was purified with a combination of flash chromatography (70-100% EtOAc/hexnes followed by 5.0-7.5% MeOH/EtOAc) and a reverse phase HPLC (MeOH/H$_2$O/TFA) to provide the TFA salt of Example M37 as an off-white solid. $^1$H NMR (DMSO-d$_6$, δ=2.5 ppm, 500 MHz). 7.92 (s, 1.65H), 7.82-7.81 (m, 0.35H), 7.75-7.72 (m, 1.67H), 7.64-7.58 (m, 1.96H), 7.50-7.48 (m, 0.33H), 7.31-7.20 (m, 8.52H), 7.17-7.09 (m, 0.87H), 7.03-7.01 (m, 0.61H), 5.52-5.48 (m, 0.36H), 5.27 (dd, J=8.4, 3.2, 1.64H), 3.93-3.88 (m, 1.63H), 3.83-3.49 (m, 6.37H), 2.44-2.32 (m, 2H), 2.19-2.01/ 1.95-1.82 (m, 6H). LC (M-Cond. 1): RT=1.28 min; >95% homogeneity index. LC/MS: Anal. Calcd. for [M+H]$^+$ C$_{40}$H$_{37}$N$_6$O$_2$: 633.30. found: 633.31. HRMS: Anal. Calcd. for [M+H]$^+$ C$_{40}$H$_{37}$N$_6$O$_2$: 633.2978. found: 633.2974.

Example M37.1

(3R,5S,3'R,5'S)-5,5'-(1,2-ethynediylbis(1H-benzimidazole-5,2-diyl))bis(1-(phenylacetyl)-3-pyrrolidinol)

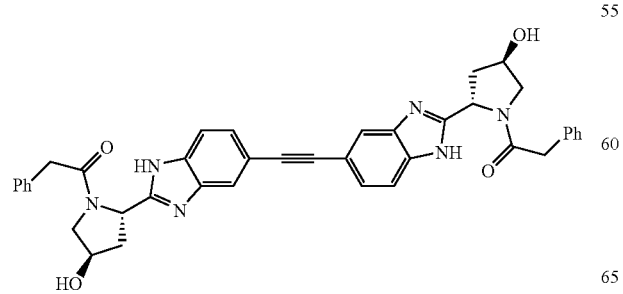

Example M37.1

Step a

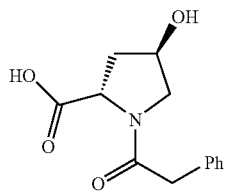

Acid M37.1a was prepared from N-Boc-4-(R)-hydroxy-L-proline according to the procedure described in acid M37a.

Example M37.1

Step b

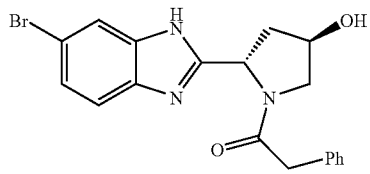

Bromide M37.1b was prepared from acid M37.1a and 4-bromobenzene-1,2-diamine according to the procedure described for the synthesis of intermediate M1a. LC (D-Cond. 1a): 1.42 min; LC/MS: Anal. Calcd. for [M+H]$^+$ C$_{19}$H$_{19}$BrN$_3$O$_2$: 400.07. found: 400.07. HRMS: Anal. Calcd. for [M+H]$^+$ C$_{19}$H$_{19}$BrN$_3$O$_2$: 400.0661. found 400.0667.

Example M37.1

Example M37.1 was prepared from bromide M37.1b according to the procedure described for the synthesis of alkyne M1b. LC (D-Cond. 1b): 1.93 min; LC/MS: Anal. Calcd. for [M+H]$^+$ C$_{40}$H$_{37}$N$_6$O$_4$: 665.29. found: 665.42. HRMS: Anal. Calcd. for [M+H]$^+$ C$_{40}$H$_{37}$N$_6$O$_4$: 665.2876. found 665.2882.

Example M37.2

(3'S,5'S,3''''S,5''''S)-5',5''-(1,2-ethynediylbis(1H-benzimidazole-5,2-diyl))bis(1'-(phenylacetyl)-1,3'-bipyrrolidine)

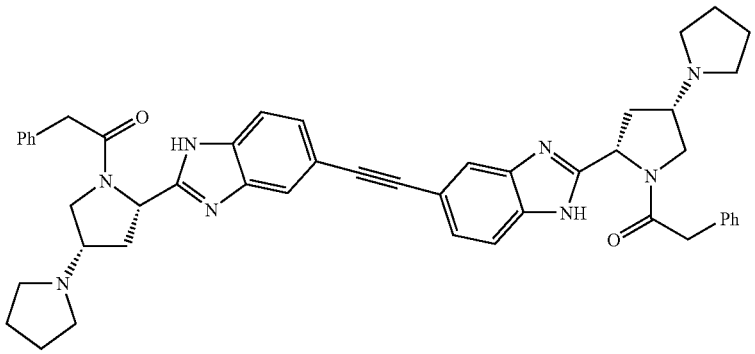

Example M37.2 Step a

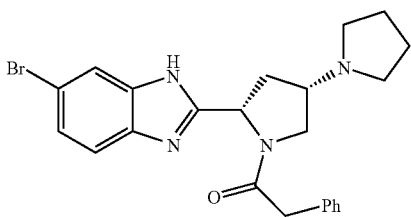

Mesyl chloride (0.097 mL, 1.25 mmol) was added to a cold (0° C.) solution of M37.1b (0.50 g, 1.25 mmol) and triethylamine (0.174 mL) in dry dichloromethane (5 mL) under nitrogen. The mixture was stirred for 1 h at 0° C., and additional mesyl chloride (0.194 mL, 2.50 mmol) and triethylamine (0.350 mL, 2.50 mmol) were added to consume unreacted starting material. The reaction mixture was diluted with dichloromethane (10 mL) and washed with water, brine, dried $Na_2SO_4$), filtered, and concentrated. The residue was applied to a 40M Biotage silica gel column and subjected to gradient elution 30%-80% B (1800 mL); B=EtOAc and A=hexanes to provide mesylate product (0.52 g) isolated as a yellow foam which was taken up in neat pyrrolidine (0.50 mL). The reaction mixture was heated to 80° C. for 3 h, cooled, diluted with methanol, filtered, and subjected to prep. HPLC. Gradient: 30%-85% B gradient on XTERRA (S5, 30×100 mm) over 14 min to give the TFA salt of M37.2a 140 mg as a tan foam. LC (D-Cond. 1a): 1.64 min; LC/MS: Anal. Calcd. for [M+H]+ $C_{23}H_{26}BrN_4O$: 453.13. found: 453.12.

Example M37.2

Example M37.2 was prepared from bromide M37.2a according to the procedure described for the synthesis of alkyne M1b. LC (D-Cond. 1a): 1.75 min; LC/MS: Anal. Calcd. for [M+H]+ $C_{48}H_{51}N_8O_2$: 771.41. found: 771.41. HRMS: Anal. Calcd. for [M+H]+ $C_{48}H_{51}N_8O_2$: 771.4135. found 771.4158.

Example M37.3

5,5'-(1,2-ethynediyl)bis(2-((2S,4S)-4-(4-morpholinyl)-1-(phenylacetyl)-2-pyrrolidinyl)-1H-benzimidazole)

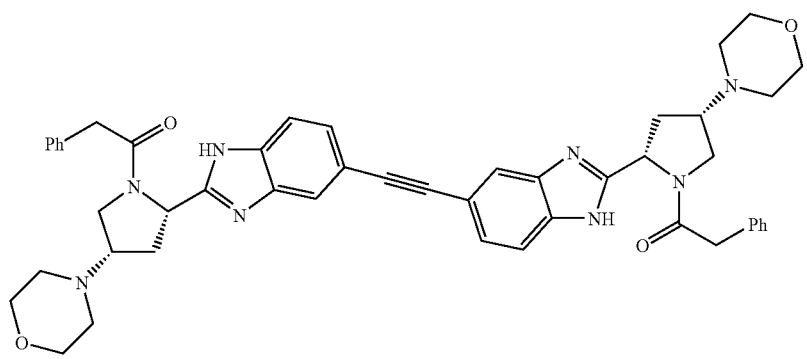

Example M37.3

Step a

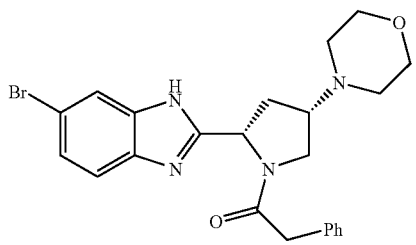

Bromide M37.3a was prepared from acid M37.1b and morpholine according to the procedure described for the synthesis of intermediate M37.2a. LC (D-Cond. 1a): 1.61 min; LC/MS: Anal. Calcd. for [M+H]$^+$ C$_{23}$H$_{26}$BrN$_4$O$_2$: 469.12. found: 469.08. HRMS: Anal. Calcd. for [M+H]$^+$ C$_{23}$H$_{26}$BrN$_4$O$_2$: 469.1239. found 469.1230.

Example M37.3

Example M37.3 was prepared from bromide M37.3a according to the procedure described for the synthesis of alkyne M1b. LC (D-Cond. 1a): 1.69 min; LC/MS: Anal. Calcd. for [M+H]$^+$ C$_{48}$H$_{51}$N$_8$O$_4$: 803.40. found: 803.49. HRMS: Anal. Calcd. for [M+H]$^+$ C$_{48}$H$_{51}$N$_5$O$_4$: 803.4033. found 803.4031.

Example M38

5,5'-(1,2-ethanediyl)bis(2-((2S)-1-phenylacetyl)-2-pyrrolidinyl)-1H-benzimidazole)

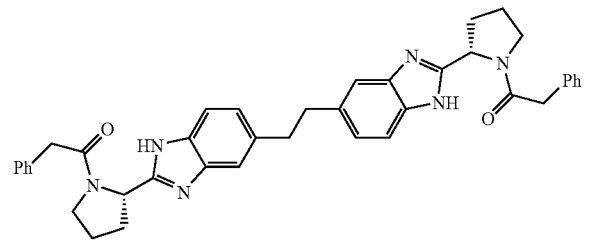

A mixture of TFA salt of Example M37 (26.1 mg, 0.03 mmol) and 10% Pd/C (12.1 mg) in MeOH (3 mL) was stirred under a balloon of hydrogen for 135 min. The reaction mixture was filtered through a pad of diatomaceous earth (Celite®), and the filtrate was concentrated in vacuo to provide the TFA salt of Example M38 as a white solid. $^1$H NMR (DMSO-d$_6$, δ=2.5 ppm, 500 MHz): 7.64-6.99 (m, 16H), 5.50 (m, 0.22H), 5.25 (m, 1.78H), 3.93-3.47 (m, 8H), 3.15-3.07 (m, 4H), 2.44-2.34 (m, 2H), 2.18-1.88 (m, 6H). LC (M-Cond. 1): RT=1.19 min; >95% homogeneity index. LC/MS: Anal. Calcd. for [M+H]$^+$ C$_{40}$H$_{41}$N$_6$O$_2$: 637.33. found: 637.33. HRMS: Anal. Calcd. for [M+H]$^+$ C$_{40}$H$_{41}$N$_6$O$_2$: 637.3291. found: 637.3272.

Example M39

2,2'-bis((2S)-1-(phenylacetyl)-2-pyrrolidinyl)-1H,1'H-5,5'-bibenzimidazole

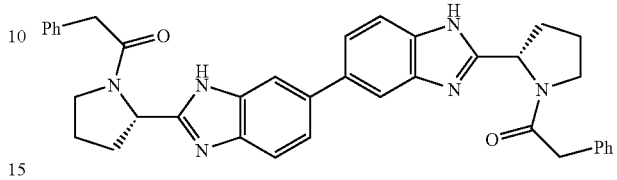

The TFA salt of Example M39 was prepared from 3,3'-diaminobenzidine and acid M37a according to the procedure described for the preparation of benzimidazole M1a with the following exceptions: the acylation was conducted in DMF; CH$_2$Cl$_2$ was used for the second work-up step, instead of EtOAc; and, the final product was purified with a combination of flash chromatography (0-4% MeOH/CH$_2$Cl$_2$) and reverse phase HPLC (MeOH/H$_2$O/TFA). $^1$H NMR (DMSO-d$_6$, δ=2.5 ppm, 400 MHz): 7.97 (s, 1.75H), 7.88-7.64 (m, 4.25H), 7.31-7.05 (m, 10H), 5.52 (br m, 0.27H), 5.31 (dd, J=8.6, 3.5, 1.73H), 3.96-3.50 (m, 8H), 2.47-2.37 (m, 2H), 2.19-1.84 (m, 6H). LC (M-Cond. 1): RT=1.17 min; >95% homogeneity index. LC/MS: Anal. Calcd. for [M+H]$^+$ C$_{38}$H$_{37}$N$_6$O$_2$: 609.30. found: 609.38. HRMS: Anal Calcd. for [M+H]$^+$ C$_{38}$H$_{37}$N$_6$O$_2$: 609.2978. found: 609.2984.

Example M40 dibenzyl(2S,2'S)-2,2'-(1H,1'H-5,5'-bibenzimidazole-2,2'-diyl)di(1-pyrrolidinecarboxylate)

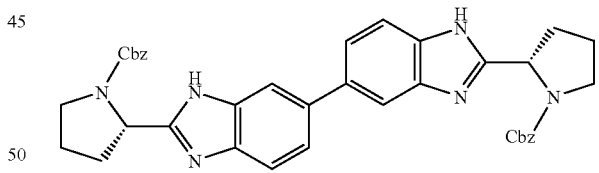

The TFA salt of Example M40 was prepared from 3,3'-diaminobenzidine and (L)-Cbz-Proline according to the procedure described for the synthesis of Example M39. $^1$H NMR (DMSO-d$_6$, δ=2.5 ppm, 400 MHz). 7.95/7.89 (two s, 2H), 7.83-7.76 (m, 4H), 7.40-7.32 (m, 5H), 7.10 (m, 1H), 7.01 (app t, J=7.5, 2H), 6.90 (d, J=7.3, 2H), 3.76-3.69 (m, 2H), 3.60-3.51 (m, 2H), ~2.50-2.40 (m, 2H; partially overlapped with solvent signal), 2.19-1.96 (m, 6H). LC (M-Cond. 1): RT=1.17 min; >95% homogeneity index. LC/MS: Anal. Calcd. for [M+H]$^+$ C$_{38}$H$_{37}$N$_6$O$_4$: 641.29. found: 641.37. HRMS: Anal. Calcd. for [M+H]$^+$ C$_{38}$H$_{37}$N$_6$O$_4$: 641.2876. found: 641.2882.

Example M41

2-((2S)-1-(cyclopropylcarbonyl)-2-pyrrolidinyl)-5-(2-(2-((2S)-1-(cyclopropylcarbonyl)-2-pyrrolidinyl)-1H-benzimidazol-6-yl)ethyl)-1H-benzimidazole

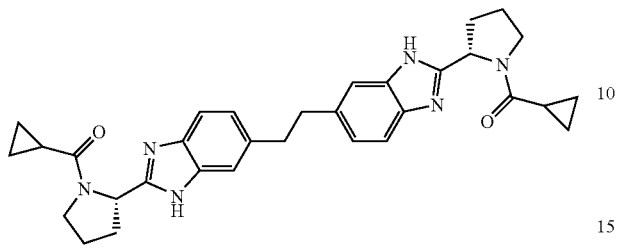

Example M41

Step a

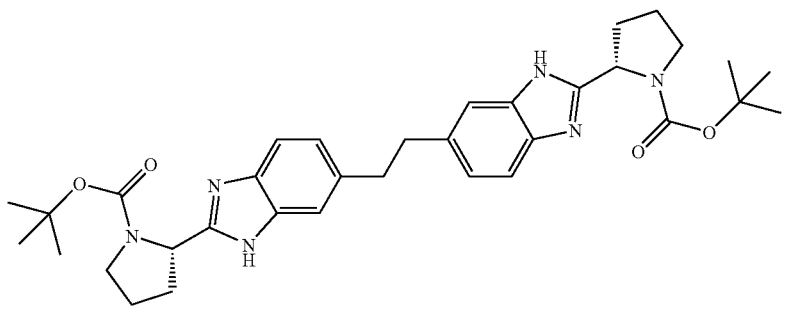

Acetic acid (11 pipet drops) was added to a mixture of the alkyne M1b (1.10 g, 1.84 mmol) and 10% Pd/C (260 mg) in MeOH (25 ml), and stirred at room temperature and under 50 psi hydrogen until the reaction was complete by LC/MS analysis. The reaction mixture was filtered through a pad of diatomaceous earth (Celite®), and concentrated in vacuo to provide carbamate M41a as a tan foam (905.8 mg), which was used in a subsequent step without further purification. LC/MS: Anal. Calcd. for $[M+H]^+$ $C_{34}H_{45}N_6O_4$: 601.35. found: 601.45.

Example M41

Step b

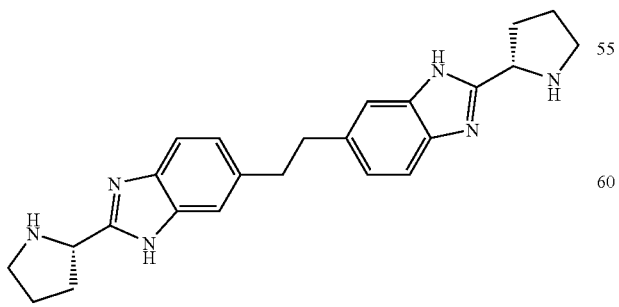

A solution of carbamate M41a (904.2 mg, 1.50 mmol) in 20% TFA/CH$_2$Cl$_2$ (10 ml) was stirred at room temperature for 15 h. The volatile component was removed in vacuo, and the residue was free-based with a SCX cartridge (10 g; MeOH wash; 2N NH$_3$/MeOH elution) to provide pyrrolidine M41b as a tan foam (511.8 mg), which was used as such in a subsequent step. LC/MS: Anal. Calcd. for $[M+H]^+$ $C_{24}H_{29}N_6$: 401.25. found: 401.32.

Example M41

EDCI (40.1 mg, 0.209 mmol) was added to CH$_2$Cl$_2$ (2 mL) solution of cyclopropanecarboxylic acid (17.6 mg, 0.204 mmol) and pyrrolidine M41b (29.1 mg, 0.0726 mml), and the reaction mixture was stirred for ~20 hr. The volatile component was removed in vacuo, and the residue was treated with 2.0 N NH$_3$/MeOH (2 mL) and stirred for 1 hr. The volatile component was removed in vacuo, and the residue was purified with a reverse phase HPLC (MeOH/H$_2$O/TFA) to provide the TFA salt of Example M41 as an off-white solid (17.9 mg). LC (M-Cond. 2): 1.39 min; >95%; LC/MS; Anal. Calcd. for $[M+H]^+$ $C_{32}H_{37}N_6O_2$: 537.30. found: 537.39. HRMS: Anal. Calcd. for $[M+H]^+$ $C_{32}H_{37}N_6O_2$: 537.2978. found: 537.2982.

Example M42 to M45.2

The TFA salts of Example M42 to M45.2 were prepared from pyrrolidine M41b and commercially available acids according to the procedure described for the preparation of Example M41.

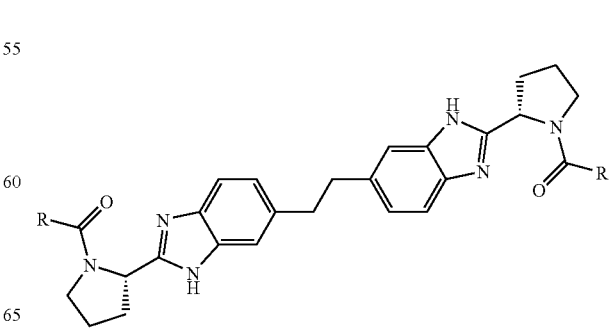

| Example | Compound Name | Coupling protocol | R (acyl group) | RT (LC-Cond.); % homogeneity index; MS data |
|---|---|---|---|---|
| M42 | 5,5'-(1,2-ethanediyl)bis(2-((2S)-1-((2R)-tetrahydro-2-furanylcarbonyl)-2-pyrrolidinyl)-1H-benzimidazole) | EDCI | tetrahydrofuran-2-yl C(=O)- | 1.32 min (M-Cond. 2); >95%; LC/MS: Anal. Calcd. for [M + H]$^+$ C$_{34}$H$_{41}$N$_6$O$_4$: 597.32; found: 597.37. HRMS: Anal. Calcd. for [M + H]$^+$ C$_{34}$H$_{41}$N$_6$O$_4$: 597.3189; found 597.3194 |
| M43 | 5,5'-(1,2-ethanediyl)bis(2-((2S)-1-(2-pyridinylacetyl)-2-pyrrolidinyl)-1H-benzimidazole) | EDCI, Et$_3$N | (2-pyridyl)CH$_2$C(=O)- | 1.18 min (M-Cond. 2); >95%; LC/MS: Anal. Calcd. for [M + H]$^+$ C$_{38}$H$_{39}$N$_8$O$_2$: 639.32; found: 639.37. HRMS: Anal. Calcd. for [M + H]$^+$ C$_{38}$H$_{39}$N$_8$O$_2$: 639.3196; found 639.3200 |
| M44 | 2-((2S)-1-(cyclopropylacetyl)-2-pyrrolidinyl)-5-(2-(2-((2S)-1-(cyclopropylacetyl)-2-pyrrolidinyl)-1H-benzimidazol-6-yl)ethyl)-1H-benzimidazole | EDCI | cyclopropyl-CH$_2$-C(=O)- | 1.54 min (M-Cond. 2); >95%; LC/MS: Anal. Calcd. for [M + H]$^+$ C$_{34}$H$_{41}$N$_6$O$_2$: 565.33; found: 565.43. HRMS: Anal. Calcd. for [M + H]$^+$ C$_{34}$H$_{41}$N$_6$O$_2$: 565.3291; found 565.3295 |
| M45 | 2-((2S)-1-(cyclobutylcarbonyl)-2-pyrrolidinyl)-5-(2-(2-((2S)-1-(cyclobutylcarbonyl)-2-pyrrolidinyl)-1H-benzimidazol-6-yl)ethyl)-1H-benzimidazole | EDCI | cyclobutyl-C(=O)- | 1.59 min (M-Cond. 2); >95%; LC/MS: Anal. Calcd. for [M + H]$^+$ C$_{34}$H$_{41}$N$_6$O$_2$: 565.33; found: 565.41. HRMS: Anal. Calcd. for [M + H]$^+$ C$_{34}$H$_{41}$N$_6$O$_2$: 565.3291; found 565.3303 |
| M45.1 | 5,5'-(1,2-ethanediyl)bis(2-((2S)-1-(2-thienylcarbonyl)-2-pyrrolidinyl)-1H-benzimidazole) | EDCI | (2-thienyl)C(=O)- | 1.59 min (M-Cond. 2); >95%; LC/MS: Anal. Calcd. for [M + H]$^+$ C$_{34}$H$_{33}$N$_6$O$_2$S$_2$: 621.21; found: 621.27. HRMS: Anal. Calcd. for [M + H]$^+$ C$_{34}$H$_{33}$N$_6$O$_2$S$_2$: 621.2106; found 621.2099 |
| M45.2 | 5,5'-(1,2-ethanediyl)bis(2-((2S)-1-(3-pyridinylacetyl)-2-pyrrolidinyl)-1H-benzimidazole) | EDCI, Et$_3$N | (3-pyridyl)CH$_2$C(=O)- | 1.18 min (M-Cond. 2); >95%; LC/MS: Anal. Calcd. for [M + H]$^+$ C$_{38}$H$_{39}$N$_8$O$_2$: 639.32; found: 639.37. HRMS: Anal. Calcd. for [M + H]$^+$ C$_{38}$H$_{39}$N$_8$O$_2$: 639.3196; found 639.3217 |

Example M46 methyl((1S)-1-(((1R,3S,5R)-3-(6-(4-(2-((1R,3S,5R)-2-((2S)-2-((methoxycarbonyl)amino)-3-methylbutanoyl)-2-azabicyclo[3.1.0]hex-3-yl)-1H-benzimidazol-6-yl)phenyl)-1H-benzimidazol-2-yl)-2-azabicyclo[3.1.0]hex-2-yl)carbonyl)-2-methylpropyl) carbamate

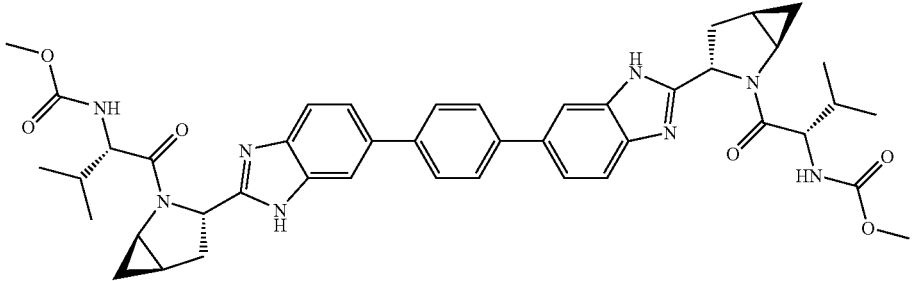

Example M46

Step a

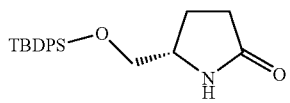

To a solution of (S)-5-(hydroxymethyl)pyrrolidin-2-one (10 g, 87 mmol) in $CH_2Cl_2$ (50 mL) was added tert-butylchlorodiphenylsilane (25.6 g, 93 mmol), $Et_3N$ (12.1 mL, 87 mmol) and DMAP (1.06 g, 8.7 mmol). The mixture was stirred at room temperature until the starting pyrrolidinone was completely consumed, and then it was diluted with $CH_2Cl_2$ (50 mL) and washed with water (50 mL). The organic layer was dried ($Na_2SO_4$), filtered, and evaporated in vacuo, and the crude material was submitted to flash chromatography (silica gel; 30 to 100% of EtOAc/hexanes) to afford ether M46a as a colorless oil (22.7 g, 74% yield). $^1$H-NMR (400 MHz, DMSO-$d_6$, $\delta$=2.5 ppm) 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.87-1.81 (m, 1H), 1.00 (s, 9H). LC/MS (M+H)$^+$=354.58.

Example M46

Step b

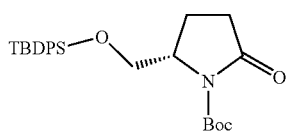

Di-tert-butyl dicarbonate (38.5 g, 177 mmol) was added in portions as a solid over 10 min to a $CH_2Cl_2$ (200 mL) solution of silyl ether M46a (31.2 g, 88.3 mmol), $Et_3N$ (8.93 g, 88 mmol), and DMAP (1.08 g, 8.83 mmol) and stirred for 18 h at 24° C. Most of the volatile material was removed in vacuo and the crude material was taken up in 20% EtOAc/Hexanes and applied to a 2 L funnel containing 1.3 L of silica gel and then eluted with 3 L of 20% EtOAc/hex and 2 L of 50% EtOAc). Upon concentration of the desired fractions in a rotary evaporator, a white slurry of solid formed which was filtered, washed with hexanes and dried in vacuo to afford carbamate M46b as a white solid (32.65 g, 82% yield). $^1$H-NMR (400 MHz, DMSO-$d_6$, $\delta$=2.5 ppm) 7.61-7.59 (m, 2H), 7.56-7.54 (m, 2H), 7.50-7.38 (m, 6H), 4.18 (m, 1H), 3.90 (dd, J=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H). LC/MS (M-Boc+H)$^+$=354.58.

Example M46

Step c

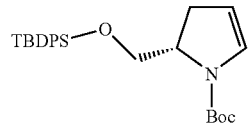

A three-necked flask equipped with a thermometer and a nitrogen inlet was charged with carbamate M46b (10.05 g, 22.16 mmol) and toluene (36 mL), and lowered into −55° C. cooling bath. When the internal temperature of the mixture reached −50° C., lithium triethylborohydride (23 mL of 1.0 M/THF, 23.00 mmol) was added dropwise over 30 min and the mixture stirred for 35 min while maintaining the internal temperature between −50° C. and −45° C. Hunig's base (16.5 mL, 94 mmol) was added dropwise over 10 min. Then, DMAP (34 mg, 0.278 mmol) was added in one batch, followed by the addition of trifluoroacetic anhydride (3.6 mL, 25.5 mmol) over 15 min, while maintaining the internal temperature between −50° C. and −45° C. The bath was removed 10 min later, and the reaction mixture was stirred for 14 h while allowing it to rise to ambient temperature. It was diluted with toluene (15 mL), cooled with an ice-water bath, and treated slowly with water (55 mL) over 5 min. The phases were separated and the organic layer washed with water (50 mL, 2×) and concentrated in vacuo. The crude material was purified by flash chromatography (silica gel; 5% EtOAc/hexanes) to afford dihydropyrrole M46c as a colorless viscous oil (7.947 g, 82% yield). Rt=2.41 min under the following HPLC conditions: Solvent gradient from 100% A:0% B to 0% A:100% B (A=0.1% TFA in 1:9 MeOH/$H_2O$; B=0.1% TFA in 9:1 MeOH/$H_2O$) over 2 min and hold for 1 min; detection@220 nm; Phenomenex-Luna 3.0×50 mm S10 column. $^1$H-NMR (400 MHz, DMSO-$d_6$, $\delta$=2.5 ppm) 7.62-7.58 (m, 4H), 7.49-7.40 (m, 6H), 6.47 (br s, 1H), 5.07/5.01 (overlapping br d, 1H), 4.18 (br s, 1H), 3.89 (br s, 0.49H), 3.69 (br s, 1.51H), 2.90-2.58 (br m, 2H), 1.40/1.26 (overlaping br s, 9H), 0.98 (s, 9H). LC/MS; [M+Na]$^+$=460.19.

Example M46

Step d

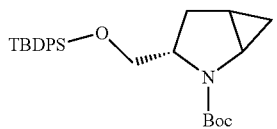

M46d-1: trans-isomer
M46d-2: cis-isomer

Diethylzinc (19 mL of ~1.1 M in toluene, 20.9 mmol) was added dropwise over 15 min to a cooled (−30° C.) toluene (27 mL) solution of dihydropyrrole M46c (3.94 g, 9.0 mmol). Chloroiodomethane (stabilized over copper; 3.0 mL, 41.2 mmol) was added dropwise over 10 min, and stirred while maintaining the bath temperature at −25° C. for 1 h and between −25° C. and −21° C. for 18.5 h. The reaction mixture was opened to the air and quenched by the slow addition of 50% saturated NaHCO$_3$ solution (40 mL), and then removed from the cooling bath and stirred at ambient temperature for 20 min. It was filtered through a filter paper and the white cake was washed with 50 mL of toluene. The organic phase of the filtrate was separated and washed with water (40 mL, 2×), dried (MgSO$_4$) and concentrated in vacuo. The crude material was purified using a Biotage system (350 g silica gel; sample was loaded with 7% EtOAc/hexanes; eluted with 7-20% EtOAc/hexanes) to afford a mixture of methanopyrrolidines M46d-1 and M46d-2 as a colorless viscous oil (3.69 g, 90.7%). [Note: the exact cis/trans-isomer ratio was not determined at this stage]. Rt=2.39 min under the following HPLC conditions: Solvent gradient from 100% A:0% B to 0% A:100% B (A=0.1% TFA in 1:9 MeOH/H$_2$O; B=0.1% TEA in 9:1 MeOH/H$_2$O) over 2 min, and hold for 1 min; detection@220 nm; Phenomenex-Luna 3.0×50 mm S10 column. $^1$H-NMR (400 MHz, DMSO-d$_6$, δ=2.5 ppm) 7.62-7.60 (m, 4H), 7.49-7.40 (m, 6H), 3.77/3.67 (overlapping br s, 3H), 3.11-3.07 (m, 1H), 2.23 (app br s, 1H), 2.05-2.00 (m, 1H), 1.56-1.50 (m, 1H), 1.33 (very broad s, 9H), 1.00 (s, 9H), 0.80 (m, 1H), 0.30 (m, 1H). LC/MS [M+Na]$^+$=474.14.

Example M46

Step e

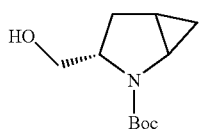

M46e-1: trans-isomer
M46e-2: cis-isomer

TBAF (7.27 mL of 1.0 M in THF, 7.27 mmol) was added dropwise over 5 min to a THF (30 mL) solution of silyl ether M46d-1/-2 (3.13 g, 6.93 mmol) and the mixture was stirred at ambient temperature for 4.75 h. After the addition of saturated NH$_4$Cl solution (5 mL), most of the volatile material was removed in vacuo and the residue partitioned between CH$_2$Cl$_2$ (70 mL) and 50% saturated NH$_4$Cl solution (30 mL). The aqueous phase was extracted with CH$_2$Cl$_2$ (30 mL), and the combined organic phase was dried (MgSO$_4$), filtered, concentrated in vacuo and then exposed to high vacuum overnight. The crude material was purified using a Biotage (silica gel; 40-50% EtOAc/hexanes) to afford a mixture of alcohols M46e-1 and M46e-2, contaminated with traces of a lower R$_f$ spot, as a colorless oil (1.39 g, ~94% yield). [Note: the exact cis/trans isomer ratio was not determined at this stage.] $^1$H-NMR (400 MHz, DMSO-d$_6$, δ=2.5 ppm) 4.70 (t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-1.44 (m, 1H), 1.40 (s, 9H), 0.76-0.71 (m, 1H), 0.26 (m, 1H). LC/MS (M+Na)$^+$=236.20.

Example M46

Step f

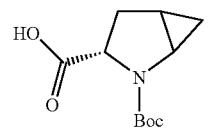

M46f-1: trans-isomer
M46f-2: cis-isomer

A semi-solution of NaIO$_4$ (6.46 g, 30.2 mmol) in H$_2$O (31 mL) was added to a solution of alcohol M46e-1/-2 (2.15 g, 10.08 mmol) in CH$_3$CN (20 mL) and CCl$_4$ (20 mL). RuCl$_3$ (0.044 g, 0.212 mmol) was added immediately and the heterogeneous reaction mixture was stirred vigorously for 75 min. The reaction mixture was diluted with H$_2$O (60 mL) and extracted with CH$_2$Cl$_2$ (50 mL, 3×). The combined organic phase was treated with 1 mL MeOH, allowed to stand for about 5 min, and then filtered through a pad of diatomaceous earth (Celite®). The Celite® was washed with CH$_2$Cl$_2$ (50 mL), and the filtrate was concentrated in vacuo to afford a light charcoal-colored solid. $^1$H-NMR analysis of this crude material indicated a 1.00:0.04:0.18 mole ratio of trans acid M46f-1:cis acid M46f-2:presumed side product, tert-butyl 3-oxo-2-azabicyclo[3.1.0]hexane-2-carboxylate. The crude material was dissolved in EtOAc (~10 mL) with heating and allowed to stand at ambient temperature with seeding. About 15 min into the cooling phase, a rapid crystal formation was observed. About 1 h later, hexanes (~6 mL) was added and the mixture refrigerated is overnight (it did not appear that additional material precipitated out). The mixture was filtered and washed with ice/water-cooled hexanes/EtOAc (2:1 ratio; 20 mL) and dried under high vacuum to afford the first crop of acid M46f-1 (off-white crystals, 1.222 g). The mother liquor was concentrated in vacuo, and the residue dissolved in ~3 mL of EtOAc with heating, allowed to stand at ambient temperature for 1 h, and then 3 mL hexanes was added and stored in a refrigerator for ~15 h. A second crop of acid M46f-1 was retrieved similarly (grey crystals, 0.133 g), for a combined yield of 59%. Acid M46f-1: Rt=1.48 min under the following HPLC conditions: Solvent gradient from 100% A:0% B to 0% A:100% B (A=0.1% TFA in 1:9 MeOH/H$_2$O; B=0.1% TFA in 9:1 MeOH/H$_2$O) over 3 min; detection@220 nm; Phenomenex-Luna 3.0×50 mm S10 column. MP (dec.) for the first crop 147.5-149.5° C. $^1$H-NMR (400 MHz, DMSO-d$_6$, δ=2.5 ppm) 12.46 (s, 1H), 3.88 (app br s, 1H), 3.27 (app br s, 1H;

overlapped with water signal), 2.28 (br m, 1H), 2.07 (app br s, 1H), 1.56 (app s, 1H), 1.40/1.34 (two overlapped s, 9H), 0.71 (m, 1H), 0.45 (m, 1H). $^{13}$C-NMR (100.6 MHz, DMSO-$d_6$, δ=39.21 ppm) 172.96, 172.60, 154.45, 153.68, 78.74, 59.88, 59.58, 36.91, 31.97, 31.17, 27.77, 27.52, 14.86, 14.53, 13.69. LC/MS [M+Na]$^+$=250.22. Anal. Calcd. for $C_{11}H_{17}NO_4$: C, 58.13; H, 7.54; N, 6.16. Found (for first crop): C, 58.24; H, 7.84; N, 6.07. Optical rotation (10 mg/mL in CHCl$_3$): [α]$_D$=−216 and −212 for the first and second crop, respectively.

Example M46

Step g

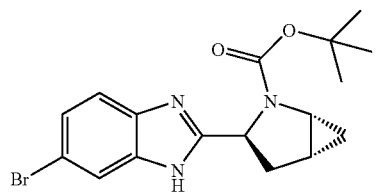

Benzimidazole M46g was prepared from 4-bromobenzene-1,2-diamine and trans-acid M46f-1 according to the procedure described for the synthesis of benzimidazole M1a. $^1$H NMR (DMSO-$d_6$, δ=2.5 ppm, 500 MHz): 12.45/12.39 (two overlapping br s, 1H), 7.72 (d, J=1.5, 0.5H), 7.60 (d, J=1.6, 0.5H), 7.49 (d, J=8.5, 0.5H), 7.40 (d, J=8.6, 0.5H), 7.29 (dd, J=1.9, 8.6, 0.5H), 7.26 (dd, J=1.8, 8.5, 0.5H), 4.91-4.59 (br s, 1H), 3.60-3.34 (br s, 1H), 2.47-2.43 (m, 1H), 2.33-2.14 (m, 1H), 1.73-1.59 (m, 1H), 1.59-1.18 (br s, 4H), 1.18-0.85 (br s, 5H), 0.84-0.74 (m, 1H), 0.69-0.57 (br s, 1H). LC/MS: Anal. Calcd. for [M+H]$^+$ $C_{17}H_{21}BrN_3O_2$: 378.08. found: 378.10.

Example M46

Step h

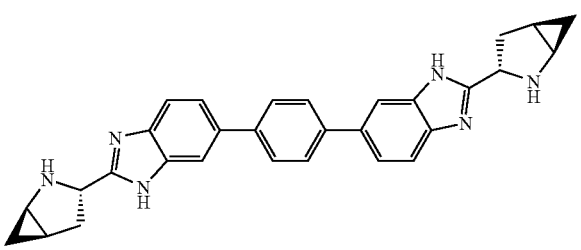

Pd (Ph$_3$P)$_4$ (0.083 g, 0.072 mmol) was added to a mixture of bromide M46g (0.5461 g, 1.444 mmol), 1,4-bis(4,4,5,5-tetramethyl-1,3,2-dioxaborolan-2-yl)benzene (0.238 g, 0.722 mmol) and sodium bicarbonate (0.364 g, 4.33 mmol) in 1,2-dimethoxyethane (5.41 mL) and water (1.805 mL) in a pressure tube. The reaction vessel was flushed with nitrogen, capped and heated at 80° C. for 16.5 h and at 100° C. for 5.5 h. All of the volatile components were removed in vacuo, and the residue was taken up in 20% MeOH/CHCl$_3$ (50 ml) and washed with water (20 ml). The aqueous phase was re-extracted with 20% MeOH/CHCl$_3$ (50 ml), and the combined organic phase was washed with saturated NaHCO$_3$ (aq) (25 ml), dried (MgSO$_4$), filtered, and concentrated in vacuo. The residue was purified by a reverse phase HPLC (MeOH/H$_2$O/TFA) to provide an off-white foam (95 mg).

The off-white foam 95 mg was taken up in 25% TFA/CH$_2$Cl$_2$ (5 ml) and stirred at ~25° C. for 3 h. The volatile component was removed in vacuo, and the residue was free-based with MCX cartridge (1 g; MeOH wash; 2N NH$_3$/MeOH elution) to provide pyrrolidine M46h as a light tan solid (45 mg). $^1$H NMR (DMSO-$d_6$, δ=2.5 ppm, 500 MHz): 12.18 (s, 2H), 7.94-7.43 (m, 10H), 4.18 (app dd, J=7.9, 9.3, 2H), 2.89 (td, J=5.9, 2.8, 2H), 2.30 (app. dd, J=12.1, 7.3, 2H), 2.02-1.96 (m, 2H), 1.51-1.46 (m, 2H), 0.74-0.68 (m, 2H), 0.41-0.38 (m, 2H). LC/MS: Anal. Calcd. for [M+H]$^+$ $C_{30}H_{29}N_6$: 473.25. found: 473.15.

Example M46

Example M46 (TFA salt) was prepared from pyrrolidine M46h and appropriate acid according to the procedure described for the synthesis of Example M1. $^1$H NMR (DMSO-$d_6$, δ=2.5 ppm, 500 MHz): 7.99-7.75 (m, 10H), 7.25 (d, J=5.8, 1.86H), 6.96 (br s, 0.14H), 5.25-5.16 (m, 2H), 4.25-4.41 (m, 2H), 3.82-3.71 (br s, 2H), 3.57 (s, 6H), 2.56-2.39 (m, 4H, overlapped with DMSO), 2.18-2.07 (m, 2H), 2.03-1.94 (m, 2H), 1.11-0.75 (m, 16f). LC (M-Cond. 3): RT=2.4 min. LC/MS: Anal. Calcd. for [M+H]$^+$ $C_{44}H_{51}N_8O_6$: 787.39. found: 787.44.

Example M46.1 & M46.2

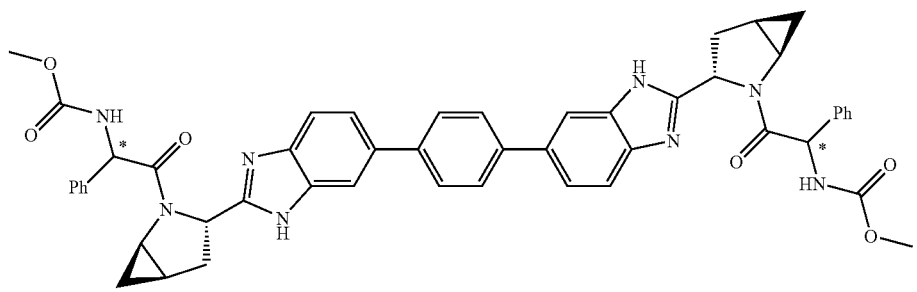

M46.1 (diastereomer-1)
M46.2 (diastereomer-2)

When pyrrolidine M46h was reacted with (R)-2-(methoxycarbonylamino)-2-phenylacetic acid under the condition described for the preparation of Example M1, diastereomers Example M46.1 and M46.2 were isolated as TFA salts.

| Example | Compound Name | R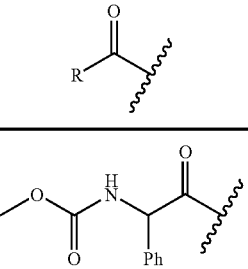 | RT (LC-Cond.); % homogeneity index; MS data |
|---|---|---|---|
| M46.1 (diastereomer-1) | dimethyl (1,4-phenylenebis (1H-benzimidazole-5,2-diyl(1R,3S,5R)-2-azabicyclo [3.1.0] hexane-3,2-diyl(2-oxo-1-phenyl-2,1-ethanediyl)))bis carbamate | 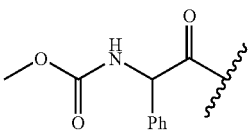 | 1.94 min (M-Cond. 3); >95%; LC/MS: Anal. Calcd. for [M + H]$^+$ C$_{50}$H$_{47}$N$_8$O$_6$: 855.36; found: 855.57. |
| M46.2 (diastereomer-2) | dimethyl (1,4-phenylenebis (1H-benzimidazole-5,2-diyl(1R,3S,5R)-2-azabicyclo [3.1.0] hexane-3,2-diyl(2-oxo-1-phenyl-2,1-ethanediyl)))bis carbamate | 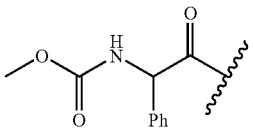 | 1.94 min (M-Cond. 3); >95%; LC/MS: Anal. Calcd. for [M + H]$^+$ C$_{50}$H$_{47}$N$_8$O$_6$: 855.36; found: 855.57. |

Example M46.3

Methyl((1S)-1-(((2S)-2-(5-(4-(2-((2S)-1-((2S)-2-((methoxycarbonyl)amino)-3-methylbutanoyl)-2-piperidinyl)-1H-benzimidazol-5-yl)phenyl)-1H-benzimidazol-2-yl)-1-piperidinyl)carbonyl)-2-methylpropyl)carbamate

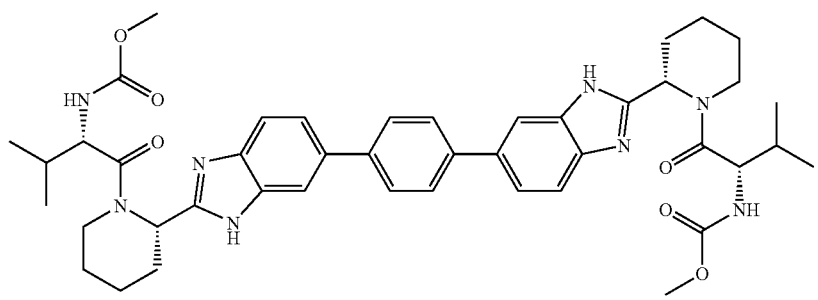

Example M46.3 (TFA salt) was prepared from (S)-1-(tert-butoxycarbonyl)piperidine-2-carboxylic acid according to the procedure described for the preparation of Example M46. LC (M-Cond. 3): RT=2.06 min; >95% homogeneity index. LC/MS: Anal. Calcd. for [M+H]+ $C_{44}H_{55}N_8O_6$: 791.42. found: 791.42.

Example M47

5-((2-((2S)-1-(phenylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole

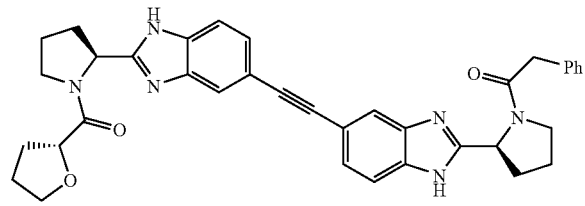

Example M47

Step a

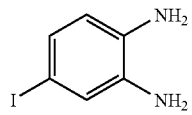

4-Iodo-2-nitroaniline (35.2 g, 0.133 mol) was added in batches via an open funnel over 25 min to a heated (65° C.) mixture of $SnCl_2·2H_2O$ (106.86 g, 0.465 mol) and 12 N HCl (200 ml). An additional 12N HCl (30 ml) was added and the reaction mixture was heated at 65° C. for an additional 1 h, and stirred at room temperature for 1 h. It was placed in a refrigerator for 15 h, and the precipitate was filtered. The resultant solid was transferred into a flask containing water (210 ml), cooled (ice/water), and a solution of NaOH (aq) (35 g in 70 ml of water) was added to it over 10 min with stirring. The cooling bath was removed, and vigorous stirring was continued for 45 min. The mixture was filtered and the solid was washed with water and dried in vacuo to provide iodide M47a as a tan solid (25.4 g). The product was used in the next step without further purification. $^1$H NMR (DMSO-d$_6$, δ=2.5 ppm, 500 MHz): 6.79 (d, J=2, 1H), 6.63 (dd, J=1.9, 8.1, 1H), 6.31 (d, J=8.1, 1H), 4.65 (br s, 2H), 4.59 (br s, 2H). LC/MS: Anal. Calcd. for [M+H]+ $C_6H_8IN_2$: 234.97. found: 234.9.

Example M47

Step b

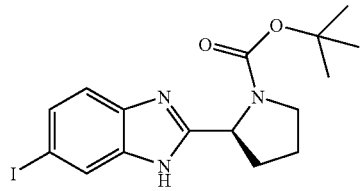

Benzimidazole M47b was prepared from iodide M47a and (L)-Boc-proline according to the procedure described for the synthesis of M1a. $^1$H NMR (DMSO-d$_6$, δ=2.5 ppm, 500 MHz): 12.51-12.22 (m, 1H), 7.90-7.76 (m, 1H), 7.43-7.20 (m, 2H), 4.96-4.87 (m, 1H), 3.64-3.51 (m, 1H), 3.44-3.38 (m, 1H), 2.38-2.20 (m, 1H), 2.05-1.83 (m, 3H), 1.39 (br s, 4H), 1.06 (br s, 5H). LC/MS: Anal. Calcd. for [M+H]+ $C_{16}H_{21}IN_3O_2$; 414.07. found; 414.13.

Example M47

Step c

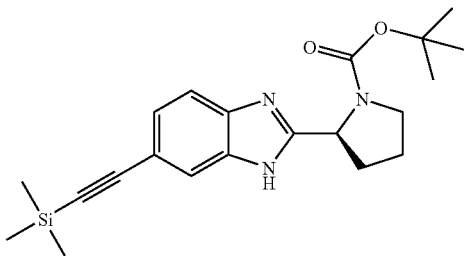

A mixture of CuI (299.6 mg, 48.1 mmol) and Pd(PPh$_3$)$_2$Cl$_2$ (1.29 g, 4.41 mmol) was added to a DMF (200 ml) solution of the iodide M47b (16.0 g, 38.7 mmol), (trimethylsilyl)acetylene (6.8 ml, 48.1 mmol), and triethylamine (16 ml), and the reaction mixture was stirred at ~25° C. for 19.5 h. The volatile component was removed in vacuo and a silica gel mesh was prepared from the residue and submitted to a flash chromatography (silica gel; eluting with 40% ethyl acetate/hexanes) to provide alkyne M47c as a tan foam (13.96 g). $^1$H NMR (DMSO-d$_6$, δ=2.5 ppm, 500 MHz): 12.52-12.38 (m, 1H), 7.62-7.41 (m, 2H), 7.24-7.19 (m, 1H), 5.01-4.85 (m, 1H), 3.64-3.51 (m, 1H), 3.46-3.35 (m, 1H), 2.38-2.21 (m, 1H), 2.07-1.81 (m, 3H), 1.39 (s, 4H), 1.04 (s, 5H), 0.23 (s, 9H). LC/MS: Anal. Calcd. for [M+H]+ $C_{21}H_{30}N_3O_2Si$; 384.21. found: 384.27.

Example M47

Step d

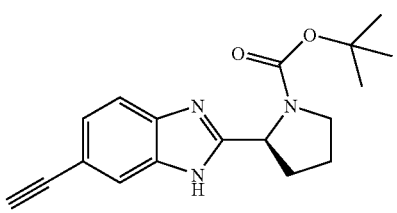

K$_2$CO$_3$ (0.5526 g, 4 mmol) was added to a MeOH (200 ml) solution of alkyne M47c (13.9 g, 36.2 mmol), and the mixture was stirred at room temperature for 17 h. The volatile component was removed in vacuo, and the residue was partitioned between ethyl acetate and saturated NH$_4$Cl (aq) solution, and the organic layer was is separated and washed with brine, dried (MgSO$_4$), filtered, and concentrated in vacuo to provide alkyne M47d as a tan foam (9.3 g). $^1$H NMR (DMSO-d$_6$, δ=2.5 ppm, 500 MHz): 12.58-12.30 (br s, 1H), 7.72-7.36 (two overlapping app br s, 2H), 7.23 (d, J=8.1, 1H), 4.97-4.88 (m, 1H), 4.02 (s, 1H), 3.64-3.52 (m, 1H), 3.44-3.36 (m, 1H), 2.40-2.20 (m, 1H), 2.06-1.81 (m, 3H), 1.39 (s, 4H), 1.05 (s, 5H). LC/MS: Anal. Calcd. for [M+Na]+ $C_{18}H_{21}N_3NaO_2$: 334.15. found: 334.24.

Example M47

Step e

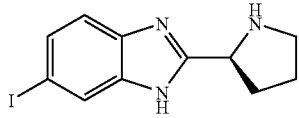

Carbamate M47b was deprotected to provide pyrrolidine M47e according to the procedure described for the preparation of M1c. $^1$H NMR (DMSO-$d_6$, δ=2.5 ppm, 500 MHz): 12.58-11.62 (br s, 1H), 7.80 (s, 1H), 7.39 (dd, J=1.7, 8.4, 1H), 8.30 (d, J=8.2, 1H), 4.35 (dd, J=6.1, 8.0, 1H), 2.93 (t, J=6.6, 2H), 2.17-2.10 (m, 1H), 1.96-1.89 (m, 1H), 1.76-1.71 (m, 2H). LC/MS: Anal. Calcd. for [M+H]$^+$ C$_{11}$H$_{13}$IN$_3$: 314.02. found: 314.09.

Example M47

Step f

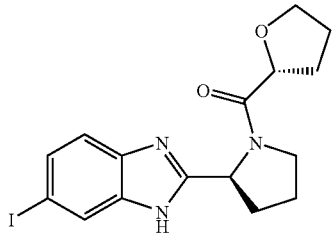

EDCI (0.9637 g, 5.02 mmol) was added to a CH$_2$Cl$_2$ (25 ml) solution of pyrrolidine M47e (1.50 g, 4.79 mmol) and (R)-tetrahydro-2-furoic acid (0.6121 g, 5.27 mmol), and the reaction mixture was stirred at ambient condition for 16 h. The reaction mixture was concentrated to remove about 80% of the solvent, and the residue was directly submitted to a flash chromatography (silica gel; 0-15% MeOH/ethyl acetate) to provide iodide M47f as a tan solid (1.8 g). $^1$H NMR (DMSO-$d_6$, δ=2.5 ppm, 500 MHz): 12.56 (s, 0.18H), 12.48 (s, 0.16H), 12.26 (s, 0.35H), 12.16 (s, 0.31H), 7.94 (d, J=1.2, 0.19H), 7.89 (d, J=0.90, 0.35H), 7.79 (d, J=0.9, 0.46H), 7.47-7.29 (m, 2H), 5.49-5.74 (app d, J=7.9, 0.35H), 5.12 (dt, J=8.2, 2.5, 0.65H), 4.61 (dd, J=5.2, 7.6, 0.65H), 4.23 (dd, J=5.2, 7.4, 0.35H), 3.86-3.71 (m, 2.33H), 3.69-3.46 (m, 1.67H), 2.42-2.31 (m, 0.48H), 2.27-2.16 (m, 0.88H), 2.16-1.72 (m, 5.93H), 1.68-1.57 (m, 0.36H), 1.44-1.33 (m, 0.35H). LC/MS: Anal. Calcd. for [M+H]$^+$ C$_{16}$H$_{19}$N$_3$O$_2$: 412.05. found: 412.10. HRMS: Anal. Calcd. For [M+H]$^+$ C$_{16}$H$_{19}$IN$_3$O$_2$: 412.022. found: 412.0531.

Example M47

Step g

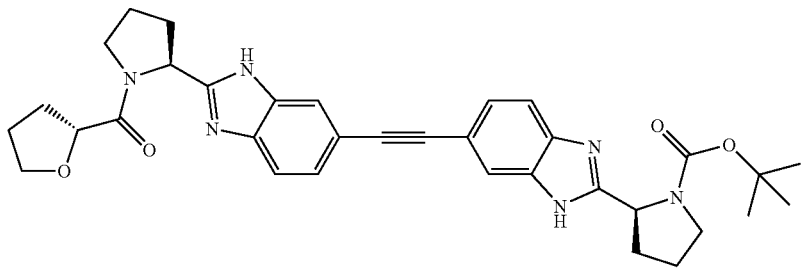

CuI (55.9 mg, 0.294 mmol) and Pd(PPh$_3$)$_4$ (329.8 mg, 0.285 mmol) were added to a DMF (15 ml) solution of iodide M47f (1.1744 g, 2.86 mmol), alkyne M47d (1.1730 g, 3.77 mmol) and Et$_3$N (1.0 mL), and the reaction mixture was flushed with nitrogen and stirred at room temperature for 48 h. The volatile component was removed in vacuo and the residue was submitted to flash chromatography (silica gel; 0-15% MeOH/ethyl acetate) to provide alkyne M47g as a light yellow solid (1.8 g; the presence of residual solvent was observed in $^1$H NMR). $^1$H NMR (DMSO-$d_6$, δ=2.5 ppm, 500 MHz): 12.64-12.27 (br s, 2H), 7.28 (br s, 2H), 7.52 (d, J=8.2, 2H), 7.36-7.32 (m, 2H), 5.51 (dd, J=2.1, 8.2, 0.4H), 5.15 (dd, J=2.8, 8.2, 0.6H), 5.02-4.96 (m, 0.4H), 4.94-4.88 (m, 0.6H), 4.63 (dd, J=5.5, 7.9, 0.6H), 4.27 (dd, J=4.9, 7.8, 0.4H), 3.87-3.72 (m, 2H), 3.70-3.39 (m, 4H), 2.45-1.76 (m, 12H), 1.40 (br s, 4H), 1.07 (br s, 5H). LC/MS: Anal. Calcd. for [M+H]$^+$ C$_{34}$H$_{39}$N$_6$O$_4$: 595.30. found: 595.46.

Example M47

Step h

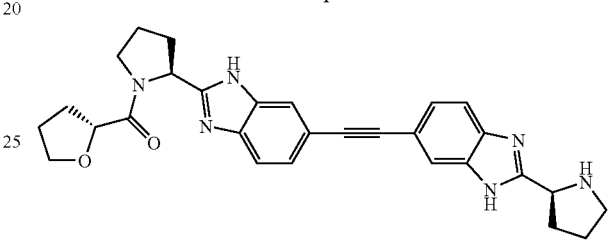

A solution of carbamate M47g (1.7 g, 2.86 mmol) in 20% TFA/CH$_2$Cl$_2$ (20 mL) was stirred at room temperature for 14.5 h. The volatile component was removed in vacuo and the residue was free-based with a SCX cartridge (10 g; MeOH wash; 2 N NH$_3$/MeOH elution) to provide pyrrolidine M47h as a light yellow foam (1.2 g). $^1$H NMR (DMSO-$d_6$, δ=2.5 ppm, 500 MHz): 12.50-12.12 (app br S, 2H), 7.73-7.59 (m, 2H), 7.58-7.46 (m, 2H), 7.36-7.27 (m, 2H), 5.51 (dd, J=1.9, 8.0, 0.4H), 5.15 (dd, J=2.7, 8.2, 0.6H), 4.62 (dd, J=6.7, 7.8, 0.6H), 4.37 (dd, J=7.8, 6.7, 1H), 4.28 (dd, J=4.6, 7.6, 0.4H), 3.90-3.44 (m, 4H), 2.43-1.38 (m, 12H). LC/MS: Anal. Calcd. for [M+H]$^+$ C$_{29}$H$_{31}$N$_6$O$_2$ 495.25. found: 495.31.

Example M47

Example M47 (TFA salt) was prepared from pyrroldine M47h and phenylacetic acid according to the procedure described for the preparation of Example M41. $^1$H NMR (DMSO-$d_6$, δ=2.5 ppm, 500 MHz): 7.91-7.47 (collection of 'm', 6H), 7.31-7.01 (m, 5H), 5.57 (dd, J=8.3, 1.7, 0.22H), 5.49 (dd, J=7.9, 2.2, 0.16H), 5.24 (dd, J=8.5, 3.1, 0.84H), 5.22 (dd, J=8.5, 3.3, 0.78H), 4.65 (dd, J=8.2, 5.3, 0.79H), 4.28 (dd, J=7.4, 5.5, 0.21H), 3.94-3.48 (m, 8H), 2.46-2.30 (m, 2H), 2.20-1.77 (m, 9.54H), 1.71-1.61 (m, 0.25H), 1.55-1.47 (m, 0.21H). LC (M-Cond. 2): RT=1.64 min; >95% homogeneity index. LC/MS: Anal. Calcd. for [M+H]$^+$ C$_{37}$H$_{37}$N$_6$O$_3$: 613.29. found: 613.40.

Example M47.1

(3R,5S,3'R,5'S)-5,5'-(1,2-ethynediylbis(1H-benzimidazole-5,2-diyl))bis(1-((2R)-tetrahydro-2-furanylcarbonyl)-3-pyrrolidinol)

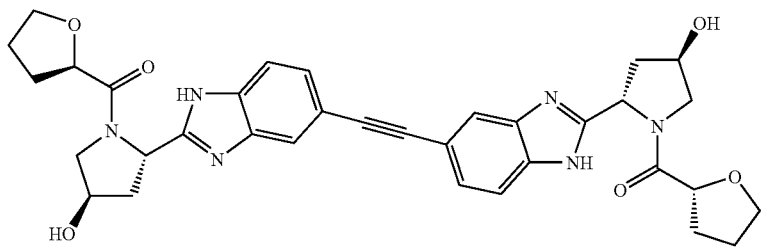

Example M47.1

Step a

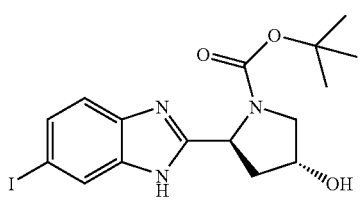

Benzimidazole M47.1a was prepared from iodide M47a and N-Boc-4-(R)-hydroxy-(L)-proline according to the procedure described for the synthesis of M1a. LC (D-Cond. 1a): RT=1.59 min; LC/MS: Anal. Calcd. for [M+H]+ $C_{16}H_{21}IN_3O_3$: 430.06. found: 430.13. HRMS: Anal. Calcd. for [M+H]+ $C_{16}H_{21}IN_3O_3$: 430.0628. found 430.0628.

Example M47.1

Step b

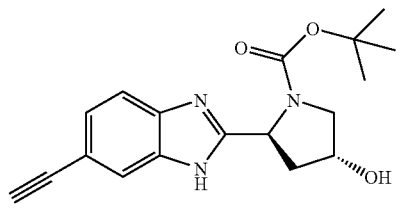

Benzimidazole M47.1b was prepared from iodide M47.1a according to the procedures described for the synthesis of M47d through M47c. LC (D-Cond. 1a): RT=1.41 min; LC/MS: Anal. Calcd. for [M+H]+ $C_{18}H_{22}N_3O_3$: 328.17. found: 328.23. HRMS: Anal. Calcd. for [M+H]+ $C_{18}H_{22}N_3O_3$: 328.1661. found 328.1659.

Example M47.1

Step c

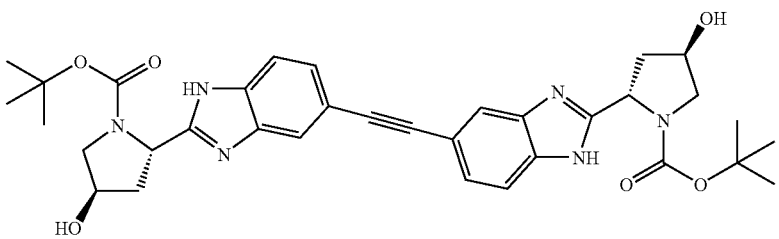

Benzimidazole M47.1c was prepared from iodide M47.1a and alkyne M47.1b according to the procedure described for the synthesis of M47g. LC (D-Cond. 1a): RT=1.80 min; LC/MS: Anal. Calcd. for [M+H]+ $C_{34}H_{41}N_6O_6$; 629.31. found: 629.34.

Example M47.1

Step d

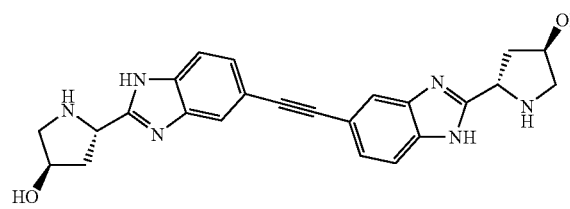

Benzimidazole M47.1d was prepared from iodide M47.1c according to the procedure described for the synthesis of J6.c (vide infra). LC (D-Cond. 1a): RT=1.13 min; LC/MS: Anal. Calcd. for [M+H]+ $C_{24}H_{25}N_6O_2$: 429.20. found: 429.24. HRMS: Anal. Calcd. for [M+H]+ $C_{24}H_{25}N_6O_2$: 429.2039. found 429.2040.

Example M47.1

Example M47.1 was prepared from M47.1d according to the procedure described for the preparation of Example M1. $^1$H NMR (400 MHz, MeOH-$d_4$) δ: 7.78 (s, 2H), 7.74-7.68 (m, 4H), 5.41-5.37 (m, 2H), 4.68-4.63 (m, 4H), 4.01-3.90 (m, 4H), 3.87-3.77 (m, 4H), 2.57-2.52 (m, 2H), 2.32-2.24 (m, 4H), 2.03-1.89 (2m, 6H); LC (D-Cond. 1c): RT=7.18 min; LC/MS: Anal. Calcd. for [M+H]+ $C_{34}H_{37}N_6O_6$: 625.28. found: 625.28. HRMS: Anal. Calcd. for [M+H]+ $C_{34}H_{37}N_6O_6$: 625.2775. found: 625.2786.

Example M47.2

(3S,5S,3'S,5'S)-5,5'-(1,2-ethynediylbis(1H-benzimidazole-5,2-diyl))bis(N-isobutyl-1-((2R)-tetrahydro-2-furanylcarbonyl)-3-pyrrolidinamine)

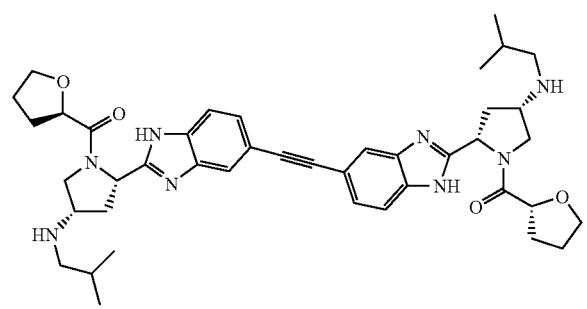

Example M47.2

Step a

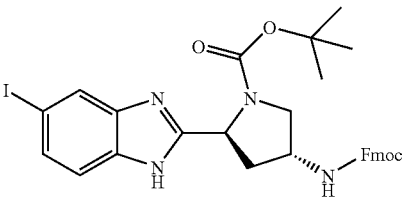

Example M47.2a was prepared from aniline M47a and the commercially available (2S,4R)-tert-butyl 4-(((9H-fluoren-9-yl)methoxy)carbonylamino)-2-(6-iodo-1H-benzo[d]imidazol-2-yl)pyrrolidine-1-carboxylate by employing the procedure described for the synthesis of M1a. LC (D-Cond. 1a): RT=2.45 min; LC/MS; Anal. Calcd. for [M+H]+ $C_{31}H_{32}IN_4O_4$: 651.15. found: 651.07. HRMS: Anal. Calcd. for [M+H]+ $C_{31}H_{32}IN_4O_4$: 651.1468. found 651.1469.

Example M47.2

Step b

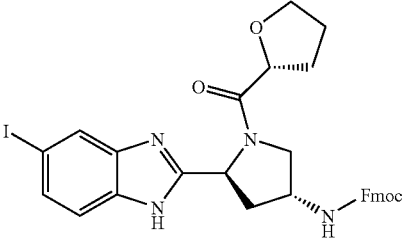

Example M47.2b was prepared from M47.2a by employing the procedure described for J6.c (vide infra) and Example M1. LC (D-Cond. 1a): RT=2.38 min; LC/MS: Anal. Calcd. for [M+H]+ $C_{31}H_{30}IN_4O_4$: 649.13. found: 649.06.

Example M47.2

Step c

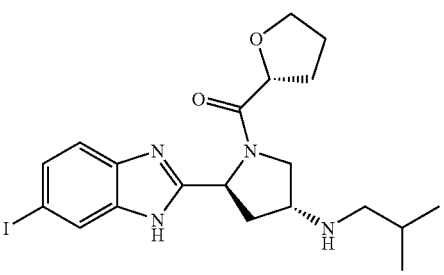

Morpholine (0.5 mL) was added to M47.2b (0.94 g, 1.44 mmol) in a solution of dry DMF (5 mL) under nitrogen and the reaction mixture was stirred for 16 h. A white precipitate was removed by filtration and the filtrate was concentrated in vacuo. The residue was taken up in EtOAc/MeOH and subjected to flash chromatography on SiO₂, elution with 25% MeOH/EtOAc to give 631 mg of a tan colored solid. Sodium cyanoborohydride (29.5 mg, 0.47 mmol) was added in one portion to a stirred solution of the amine (200 mg, 0.47 mmol), isobutyraldehyde (0.043 mL, 0.47 mmol) and acetic acid (3 drops) in dry MeOH (2 mL). The mixture was stirred for 2 h before being diluted with DMF (0.5 mL) and subjected to prep HPLC (30%-100% B over 14 min a XTERRA column (S5, 30×100 mm)). The colorless oil was free-based using an UCT (CHQAX 12m6) cartridge eluting with MeOH to give M47.2c (138.6 mg). LC (D-Cond. 1a): 1.75 min; LC/MS: Anal. Calcd. for [M+H]⁺ $C_{20}H_{28}IN_4O_2$: 483.13. found: 483.16. HRMS: Anal. Calcd. for [M+H]⁺ $C_{20}H_{28}IN_4O_2$: 483.1257. found 483.1278.

Example M47.2

Example M47.2 was prepared from M47.2c according to the procedure described for the preparation of Example M1b. LC (D-Cond. 1a): RT=1.70 min; LC/MS: Anal. Calcd. for [M+H]⁺ $C_{42}H_{55}N_8O_4$: 735.43. found: 735.49. HRMS: Anal. Calcd. for [M+H]⁺ $C_{42}H_{55}N_8O_4$: 735.4346. found 735.4354.

Examples M48-M54.15

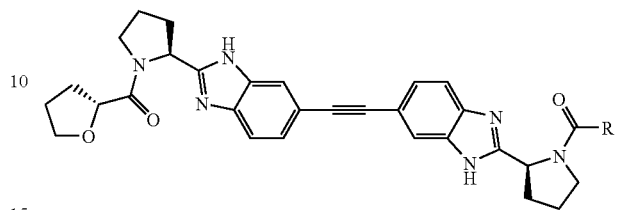

Examples M48-M53 and Examples M54.1-54.15 were prepared from pyrrolidine M47h and appropriate acids, obtained from commercial sources or prepared in house, according to the procedure described for the preparation of Example M41. Example M54 was prepared from pyrrolidine M47h and CbzCl/Et₃N, and purified similarly.

| Example | Compound Name | Coupling protocol | (Form status) | RT (LC-Cond.); % homogeneity index; MS data |
|---|---|---|---|---|
| M48 | 5-((2-((2S)-1-(2-pyridinylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI, Et₃N | (TFA) | 1.35 min (M-Cond. 2); >95%; LC/MS: Anal. Calcd. for [M + H]⁺ $C_{36}H_{36}N_7O_3$: 614.29; found: 614.37. |
| M49 | 5-((2-((2S)-1-(3-pyridinylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI, Et₃N | (TFA) | 1.32 min (M-Cond. 2); >95%; LC/MS: Anal. Calcd. for [M + H]⁺ $C_{36}H_{36}N_7O_3$: 614.29; found: 614.38. |
| M50 | 5-((2-((2S)-1-((2R)-tetrahydro-2-furanylcarbonyl)-2-pyrrolidinyl)-1H-benzimidazol-6-yl)ethynyl)-2-((2S)-1-(2-thienylacetyl)-2-pyrrolidinyl)-1H-benzimidazole | EDCI | (TFA) | 1.60 min (M-Cond. 2); >95%; LC/MS: Anal. Calcd. for [M + H]⁺ $C_{35}H_{35}N_6O_3S$: 619.25; found: 619.35. |

-continued

| Example | Compound Name | Coupling protocol |  (Form status) | RT (LC-Cond.); % homogeneity index; MS data |
|---|---|---|---|---|
| M51 | 5-((2-((2S)-1-(2-furoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 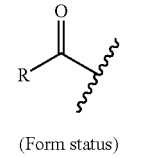 (TFA) | 1.45 min (M-Cond. 2); >95%; LC/MS: Anal. Calcd. for [M + H]$^+$ C$_{34}$H$_{33}$N$_6$O$_4$: 589.26; found: 589.39. |
| M52 | 5-((2-((2S)-1-(cyclopropylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 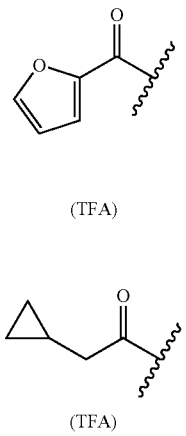 (TFA) | 1.49 min (M-Cond. 2); >95%; LC/MS: Anal. Calcd. for [M + H]$^+$ C$_{34}$H$_{37}$N$_6$O$_3$: 577.29; found: 577.40. |
| M53 | (1R)-N,N-dimethyl-2-oxo-1-phenyl-2-((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)ethanamine | HATU, DIEA | 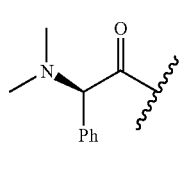 (TFA) | 1.10 min (M-Cond. 1a); >95%; LC/MS: Anal. Calcd. for [M + H]$^+$ C$_{39}$H$_{42}$N$_7$O$_3$: 656.33; found: 656.18. |
| M54 | benzyl (2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinecarboxylate | — | 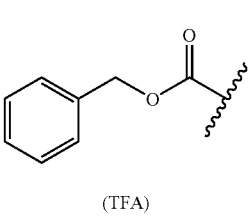 (TFA) | 1.71 min (M-Cond. 2); >95%; LC/MS: Anal. Calcd. for [M + H]$^+$ C$_{37}$H$_{37}$N$_6$O$_4$: 629.29; found: 629.37. |
| M54.1 | 5-((2-((2S)-1-benzoyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 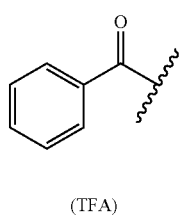 (TFA) | 1.61 min (M-Cond. 2); >95%; LC/MS: Anal. Calcd. for [M + H]$^+$ C$_{36}$H$_{35}$N$_6$O$_3$: 599.28; found: 599.37. |

-continued

| Example | Compound Name | Coupling protocol |  (Form status) | RT (LC-Cond.); % homogeneity index; MS data |
|---|---|---|---|---|
| M54.2 | 5-((2-((2S)-1-(2-ethylbenzoyl)-2-pyrrolidinyl)-1H-benzimidazol-6-yl)ethynyl)-2-((2S)-1-((2R)-tetrahydro-2-furanylcarbonyl)-1H-benzimidazole | EDCI | 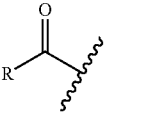 (TFA) | 1.72 min (M-Cond. 2); >95%; LC/MS: Anal. Calcd. for [M + H]$^+$ C$_{38}$H$_{39}$N$_6$O$_3$: 627.31; found: 627.43. |
| M54.3 | 5-((2-((2S)-1-(3-pyridinylcarbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 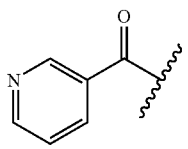 (TFA) | 1.33 min (M-Cond. 2); >95%; LC/MS: Anal. Calcd. for [M + H]$^+$ C$_{35}$H$_{34}$N$_7$O$_3$: 600.27; found: 600.41. |
| M54.4 | 5-((2-((2S)-1-((2R)-tetrahydro-2-furanylcarbonyl)-2-pyrrolidinyl)-1H-benzimidazol-6-yl)ethynyl)-2-((2S)-1-(2-thienylcarbonyl)-2-pyrrolidinyl)-1H-benzimidazole | EDCI | 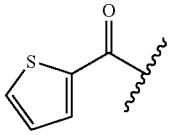 (TFA) | 1.70 min (M-Cond. 2); >95%; LC/MS: Anal. Calcd. for [M + H]$^+$ C$_{34}$H$_{33}$N$_6$O$_3$S: 605.23; found: 605.32. |
| M54.5 | 5-((2-((2S)-1-(3-furoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 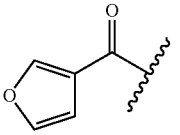 (TFA) | 1.40 min (M-Cond. 2); >95%; LC/MS: Anal. Calcd. for [M + H]$^+$ C$_{34}$H$_{33}$N$_6$O$_4$: 589.26; found: 589.35. |
| M54.6 | 5-((2-((2S)-1-((1-methyl-1H-pyrrol-2-yl)carbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 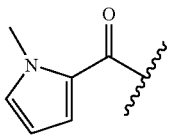 (TFA) | 1.53 min (M-Cond. 2); >95%; LC/MS: Anal. Calcd. for [M + H]$^+$ C$_{35}$H$_{36}$N$_7$O$_3$: 602.29; found: 602.41. |

-continued

| Example | Compound Name | Coupling protocol | (Form status) | RT (LC-Cond.); % homogeneity index; MS data |
|---|---|---|---|---|
| M54.7 | 5-((2-((2S)-1-propionyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 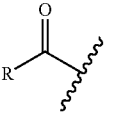 (TFA) | 1.36 min (M-Cond. 2); >95%; LC/MS: Anal. Calcd. for [M + H]$^+$ C$_{32}$H$_{35}$N$_6$O$_3$: 551.28; found: 551.41. |
| M54.8 | 5-((2-((2S)-1-isobutyryl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 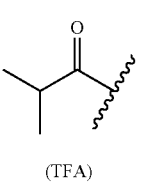 (TFA) | 1.43 min (M-Cond. 2); >95%; LC/MS: Anal. Calcd. for [M + H]$^+$ C$_{33}$H$_{37}$N$_6$O$_3$: 565.29; found: 565.42. |
| M54.9 | 5-((2-((2S)-1-(cyclopropyl-carbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 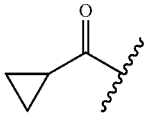 (TFA) | 1.41 min (M-Cond. 2); >95%; LC/MS: Anal. Calcd. for [M + H]$^+$ C$_{33}$H$_{35}$N$_6$O$_3$: 563.28; found: 563.37. |
| M54.10 | 5-((2-((2S)-1-(cyclobutyl-carbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 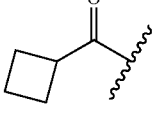 (TFA) | 1.50 min (M-Cond. 2); >95%; LC/MS: Anal. Calcd. for [M + H]$^+$ C$_{34}$H$_{37}$N$_6$O$_3$: 577.29; found: 577.40. |

-continued

| Example | Compound Name | Coupling protocol | (Form status) | RT (LC-Cond.); % homogeneity index; MS data |
|---|---|---|---|---|
| M54.11 | N-methyl-2-(((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)carbonyl)aniline | EDCI | 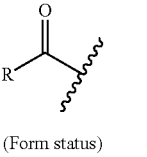 (TFA) | 1.63 min (M-Cond. 2); >95%; LC/MS: Anal. Calcd. for $[M + H]^+$ $C_{37}H_{38}N_7O_3$: 628.30; found: 628.45. |
| M54.12 | 5-((2-((2S)-1-(2-propoxybenzoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 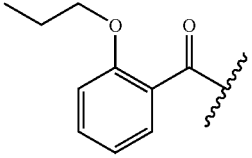 (TFA) | 1.78 min (M-Cond. 2); >95%; LC/MS: Anal. Calcd. for $[M + H]^+$ $C_{39}H_{41}N_6O_4$: 657.32; found: 657.45. |
| M54.13 | N-benzyl-2-(((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)carbonyl)aniline | EDCI | 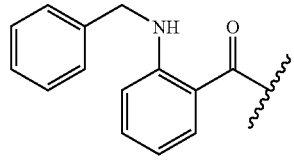 (TFA) | 2.03 min (M-Cond. 2); >95%; LC/MS: Anal. Calcd. for $[M + H]^+$ $C_{43}H_{42}N_7O_3$: 704.33; found: 704.47. |
| M54.14 | 5-((2S-((2S)-1-(2-methoxy-5-methylbenzoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 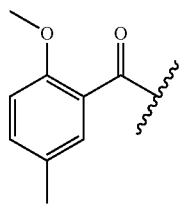 (TFA) | 1.63 min (M-Cond. 2); >95%; LC/MS: Anal. Calcd. for $[M + H]^+$ $C_{38}H_{39}N_6O_4$: 643.30; found: 643.43. |
| M54.15 | 5-((2-((2S)-1-(3-phenoxypropanoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | EDCI | 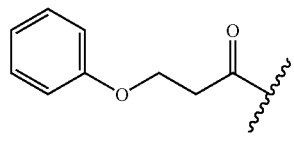 (TFA) | 1.70 min (M-Cond. 2); >95%; LC/MS: Anal. Calcd. for $[M + H]^+$ $C_{38}H_{39}N_6O_4$: 643.30; found: 643.43. |

Examples M54.16-M56

The synthesis of Examples M54.16-M56 as TFA salts is outlined in the scheme below. Intermediate M54.16c, which was prepared starting from iodide M47a and by employing some of the procedures described in the preparation of pyrrolidine M47h, was derivitized with appropriate coupling partners under standard conditions as indicated in the table below.

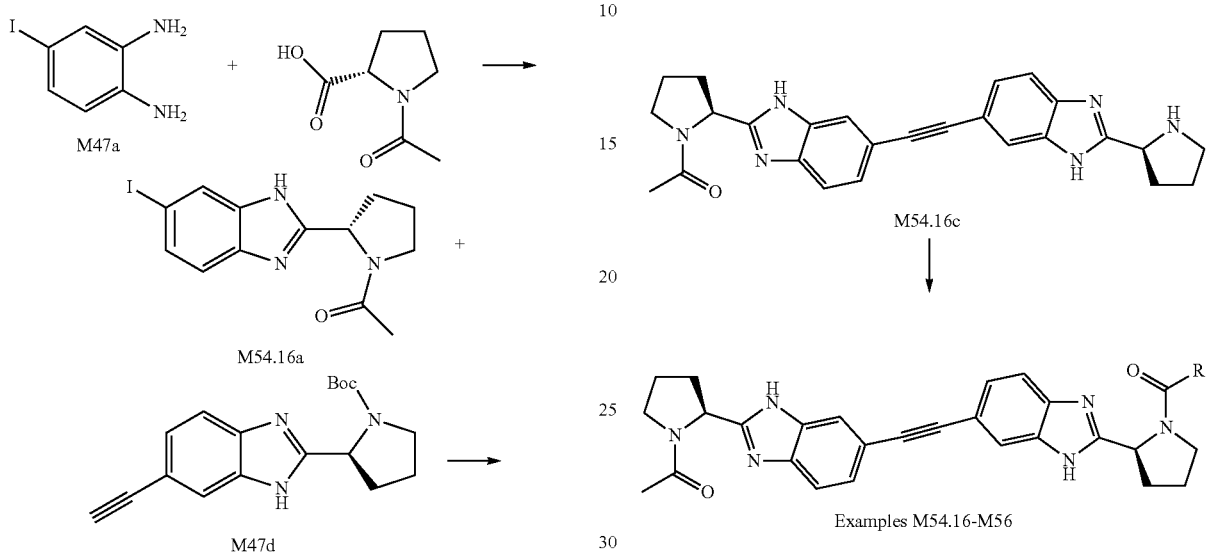

| Example | Compound Name | Coupling protocol | (Form status) | RT (LC-Cond.); % homogeneity index; MS data |
|---|---|---|---|---|
| M54.16 | 5-((2-((2S)-1-acetyl-2-pyrrolidinyl)-1H-benzimidazol-6-yl)ethynyl)-2-((2S)-1-(phenylacetyl)-2-pyrrolidinyl)-1H-benzimidazole | Acid, EDCI, $CH_2Cl_2$ | (TFA) | 1.11 min (M-Cond. 1); >95%; LC/MS: Anal. Calcd. for $[M + H]^+$ $C_{34}H_{33}N_6O_2$: 557.27; found: 557.36. HRMS: Anal. Calcd. for $[M + H]^+$ $C_{34}H_{33}N_6O_2$: 557.2665; found: 557.2668. |
| M54.17 | 5-((2-((2S)-1-acetyl-2-pyrrolidinyl)-1H-benzimidazol-6-yl)ethynyl)-2-((2S)-1-((3-methoxyphenyl)acetyl)-2-pyrrolidinyl)-1H-benzimidazole | Acid, EDCI, $CH_2Cl_2$ | | 1.13 min (M-Cond. 1); >95%; LC/MS: Anal. Calcd. for $[M + H]^+$ $C_{35}H_{35}N_6O_3$: 587.28; found: 587.33. HRMS: Anal. Calcd. for $[M + H]^+$ $C_{35}H_{35}N_6O_3$: 587.2771; found 587.2711. |

-continued

| Example | Compound Name | Coupling protocol | (Form status) | RT (LC-Cond.); % homogeneity index; MS data |
|---|---|---|---|---|
| M54.18 | 5-((2-((2S)-1-acetyl-2-pyrrolidinyl)-1H-benzimidazol-6-yl)ethynyl)-2-((2S)-1-benzoyl-2-pyrrolidinyl)-1H-benzimidazole | Acid, EDCI, $CH_2Cl_2$ | | 1.12 min (M-Cond. 1); >95%; LC/MS: Anal. Calcd. for $[M + H]^+$ $C_{33}H_{31}N_6O_2$: 543.25; found: 543.32. HRMS: Anal. Calcd. for $[M + H]^+$ $C_{33}H_{31}N_6O_2$: 543.2509; found 543.2514. |
| M54.19 | 5-((2-((2S)-1-acetyl-2-pyrrolidinyl)-1H-benzimidazol-6-yl)ethynyl)-2-((2S)-1-(2-ethylbenzoyl)-2-pyrrolidinyl)-1H-benzimidazole | Acid, EDCI, $CH_2Cl_2$ | | 1.20 min (M-Cond. 1); >95%; LC/MS: Anal. Calcd. for $[M + H]^+$ $C_{35}H_{35}N_6O_2$: 571.28; found: 571.31. HRMS: Anal. Calcd. for $[M + H]^+$ $C_{35}H_{35}N_6O_2$: 571.2822; found 571.2812. |
| M54.20 | 5-((2-((2S)-1-acetyl-2-pyrrolidinyl)-1H-benzimidazol-6-yl)ethynyl)-2-((2S)-1-(2-pyridinylacetyl)-2-pyrrolidinyl)-1H-benzimidazole | Acid/HCl, EDCI, $Et_3N$, $CH_2Cl_2$ | | 0.91 min (M-Cond. 1); >95%; LC/MS: Anal. Calcd. for $[M + H]^+$ $C_{33}H_{32}N_7O_2$: 558.26; found 558.33 HRMS: Anal. Calcd. for $[M + H]^+$ $C_{33}H_{32}N_7O_2$: 558.2618; found 558.2618. |
| M54.21 | 5-((2-((2S)-1-acetyl-2-pyrrolidinyl)-1H-benzimidazol-6-yl)ethynyl)-2-((2S)-1-(3-pyridinylacetyl)-2-pyrrolidinyl)-1H-benzimidazole | Acid/HCl, EDCI, $Et_3N$, $CH_2Cl_2$ | | 0.87 min (M-Cond. 1); >95%; LC/MS: Anal. Calcd. for $[M + H]^+$ $C_{33}H_{32}N_7O_2$: 558.26; found: 558.33. HRMS: Anal. Calcd. for $[M + H]^+$ $C_{33}H_{32}N_7O_2$: 558.2618; found 558.2618. |
| M54.22 | 5-((2-((2S)-1-acetyl-2-pyrrolidinyl)-1H-benzimidazol-6-yl)ethynyl)-2-((2S)-1-(3-pyridinylcarbonyl)-2-pyrrolidinyl)-1H-benzimidazole | Acid/EDCI, $CH_2Cl_2$ | | 0.93 min (M-Cond. 1); >95%; LC/MS: Anal. Calcd. for $[M + H]^+$ $C_{32}H_{30}N_7O_2$: 554.25; found: 544.30. HRMS: Anal. Calcd. for $[M + H]^+$ $C_{32}H_{30}N_7O_2$: 544.2461; found: 544.2463. |

-continued

R⌇⌇⌇O⌇⌇⌇ (Form status)

| Example | Compound Name | Coupling protocol | (Form status) | RT (LC-Cond.); % homogeneity index; MS data |
|---|---|---|---|---|
| M54.23 | 5-((2-((2S)-1-acetyl-2-pyrrolidinyl)-1H-benzimidazol-6-yl)ethynyl)-2-((2S)-1-(2-thienylacetyl)-2-pyrrolidinyl)-1H-benzimidazole | Acid, EDCI, $CH_2Cl_2$ | 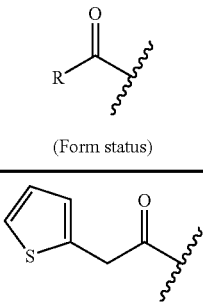 | 1.08 min (M-Cond. 1); >95%; LC/MS: Anal. Calcd. for $[M + H]^+$ $C_{32}H_{31}SN_6O_2$: 563.22; found: 563.30. HRMS: Anal. Calcd. for $[M + H]^+$ $C_{32}H_{31}SN_6O_2$: 563.2229; found: 563.2231 |
| M54.24 | 5-((2-((2S)-1-acetyl-2-pyrrolidinyl)-1H-benzimidazol-6-yl)ethynyl)-2-((2S)-1-(2-thienylcarbonyl)-2-pyrrolidinyl)-1H-benzimidazole | Acid, EDCI, $CH_2Cl_2$ | 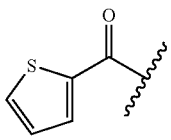 | 1.05 min (M-Cond. 1); >95%; LC/MS: Anal. Calcd. for $[M + H]^+$ $C_{31}H_{29}N_6O_2S$: 549.21; found: 549.27. HRMS: Anal. Calcd. for $[M + H]^+$ $C_{31}H_{29}N_6O_2S$: 549.2073; found 549.2068. |
| M54.25 | 5-((2-((2S)-1-acetyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole | Acid, EDCI, $CH_2Cl_2$ | 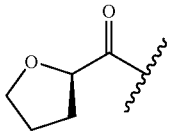 | 0.94 min (M-Cond. 1); >95%; LC/MS: Anal. Calcd. for $[M + H]^+$ $C_{31}H_{33}N_6O_3$: 537.32; found: 537.26. HRMS: Anal. Calcd. for $[M + H]^+$ $C_{31}H_{33}N_6O_3$: 537.2614; found: 537.2607. |
| M54.26 | benzyl (2S)-2-(5-((2-((2S)-1-acetyl-2-pyrrolidinyl)-1H-benzimidazol-5-yl)ethynyl)-1H-benzimidazol-2-yl)-1-pyrrolidine-carboxylate | Cbz-Cl, $Et_3N$, $CH_2Cl_2$ | 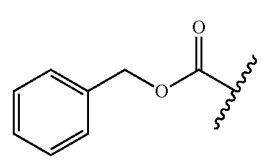 | 1.25 min (M-Cond. 1); >95%; LC/MS: Anal. Calcd. for $[M + H]^+$ $C_{34}H_{33}N_6O_3$: 573.26; found: 573.32 HRMS: Anal. Calcd. for $[M + H]^+$ $C_{34}H_{33}N_6O_3$: 573.2614; found: 573.2607. |
| M54.27 | 5-((2-((2S)-1-acetyl-2-pyrrolidinyl)-1H-benzimidazol-6-yl)ethynyl)-2-((2S)-1-(1-methyl-L-prolyl)-2-pyrrolidinyl)-1H-benzimidazole | EDCI, $CH_2Cl_2$ | 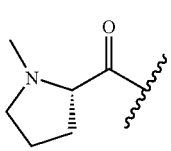 | 0.87 min (M-Cond. 1); >95%; LC/MS: Anal. Calcd. for $[M + H]^+$ $C_{32}H_{36}N7O_2$: 550.29; found: 550.38. HRMS: Anal. Calcd. for $[M + H]^+$ $C_{32}H_{36}N7O_2$: 550.2931; found: 550.2931. |

| Example | Compound Name | Coupling protocol | (Form status) | RT (LC-Cond.); % homogeneity index; MS data |
|---------|---------------|-------------------|---------------|----------------------------------------------|
| M54.28 | 2-((2S)-1-acetyl-2-pyrrolidinyl)-5-((2-((2S)-1-acetyl-2-pyrrolidinyl)-1H-benzimidazol-6-yl)ethynyl)-1H-benzimidazole | Acetic anhydride, Et$_3$N, CH$_2$Cl$_2$ | | 0.92 min (M-Cond. 1); >95%; LC/MS: Anal. Calcd. for [M + H]$^+$ C$_{28}$H$_{29}$N$_6$O$_2$: 481.24; found: 481.28 HRMS: Anal. Calcd. for [M + H]$^+$ C$_{28}$H$_{29}$N$_6$O$_2$: 481.2352; found: 481.2366. |
| M54.29 | 5-((2-((2S)-1-acetyl-2-pyrrolidinyl)-1H-benzimidazol-6-yl)ethynyl)-2-((2S)-1-propionyl-2-pyrrolidinyl)-1H-benzimidazole | Acid, EDCI, CH$_2$Cl$_2$ | | 0.95 min (M-Cond. 1); >95%; LC/MS: Anal. Calcd. for [M + H]$^+$ C$_{29}$H$_{31}$N$_6$O$_2$: 495.25; found: 495.31. HRMS: Anal. Calcd. for [M + H]$^+$ C$_{29}$H$_{31}$N$_6$O$_2$: 495.2509; found: 495.2516. |
| M54.30 | 5-((2-((2S)-1-acetyl-2-pyrrolidinyl)-1H-benzimidazol-6-yl)ethynyl)-2-((2S)-1-(cyclopropyl-carbonyl)-2-pyrrolidinyl)-1H-benzimidazole | Acid, EDCI, CH$_2$Cl$_2$ | | 0.97 min (M-Cond. 1); >95%; LC/MS: Anal. Calcd. for [M + H]$^+$ C$_{30}$H$_{31}$N$_6$O$_2$: 507.25; found: 507.33. HRMS: Anal. Calcd. for [M + H]$^+$ C$_{30}$H$_{31}$N$_6$O$_2$: 507.2509; found: 507.2519. |
| M54.31 | 5-((2-((2S)-1-acetyl-2-pyrrolidinyl)-1H-benzimidazol-6-yl)ethynyl)-2-((2S)-1-(cyclobutyl-carbonyl)-2-pyrrolidinyl)-1H-benzimidazole | Acid, EDCI, CH$_2$Cl$_2$ | | 1.04 min (M-Cond. 1); >95%; LC/MS: Anal. Calcd. for [M + H]$^+$ C$_{31}$H$_{33}$N$_6$O$_2$: 521.27; found: 521.36. HRMS: Anal. Calcd. for [M + H]$^+$ C$_{31}$H$_{33}$N$_6$O$_2$: 521.2665; found: 521.2680. |

-continued

| Example | Compound Name | Coupling protocol | (Form status) | RT (LC-Cond.); % homogeneity index; MS data |
|---|---|---|---|---|
| M54.32 | 5-((2-((2S)-1-acetyl-2-pyrrolidinyl)-1H-benzimidazol-6-yl)ethynyl)-2-((2S)-1-(cyclopropyl-acetyl)-2-pyrrolidinyl)-1H-benzimidazole | Acid, EDCI, $CH_2Cl_2$ | 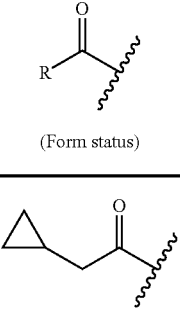 | 1.02 min (M-Cond. 1); >95%; LC/MS: Anal. Calcd. for $[M + H]^+$ $C_{31}H_{33}N_6O_2$: 521.27; found: 521.36. HRMS: Anal. Calcd. for $[M + H]^+$ $C_{31}H_{33}N_6O_2$: 521.2665; found: 521.2674. |
| M54.33 | 5-((2-((2S)-1-acetyl-2-pyrrolidinyl)-1H-benzimidazol-6-yl)ethynyl)-2-((2S)-1-(4-morpholinyl-carbonyl)-2-pyrrolidinyl)-1H-benzimidazole | morpholine-4-carbonyl chloride, $Et_3N$, $CH_2Cl_2$ | 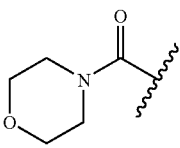 | 0.96 min (M-Cond. 1); >95%; LC/MS: Anal. Calcd. for $[M + H]^+$$C_{31}H_{34}N_7O_3$: 552.27; found: 552.36. HRMS: Anal. Calcd. for $[M + H]^+$ $C_{31}H_{34}N_7O_3$: 552.2723; found: 552.2723. |
| M55 | 5-((2-((2S)-1-acetyl-2-pyrrolidinyl)-1H-benzimidazol-6-yl)ethynyl)-2-((2S)-1-((4-methyl-1-piperazinyl)carbonyl)-2-pyrrolidinyl)-1H-benzimidazole | 4-methyl-piperazine-1-carbonyl chloride, $Et_3N$, $CH_2Cl_2$ | 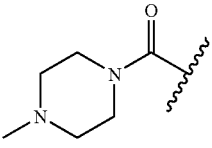 | 0.87 min (M-Cond. 1); >95%; LC/MS: Anal. Calcd. for $[M + H]^+$ $C_{32}H_{37}N_8O_2$: 565.30; found: 565.37. HRMS: Anal. Calcd. for $[M + H]^+$ $C_{32}H_{37}N_8O_2$: 565.3040; found: 565.3056. |
| M56 | (1R)-2-((2S)-2-(5-((2-((2S)-1-acetyl-2-pyrrolidinyl)-1H-benzimidazol-5-yl)ethynyl)-1H-benzimidazol-2-yl)-1-pyrrolidinyl)-N,N-dimethyl-2-oxo-1-phenyl-ethanamine | Acid/HCl salt, HATU, DIEA, DMF | 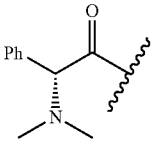 | 1.08 min (M-Cond. 1a); >95%; LC/MS: Anal. Calcd. for $[M + H]^+$ $C_{36}H_{38}N_7O_2$: 600.31; found: 600.13. |

Example M57

5,5'-(1,3-butadiyne-1,4-diyl)bis(2-((2S)-1-(phenylacetyl)-2-pyrrolidinyl)-1H-benzimidazole)

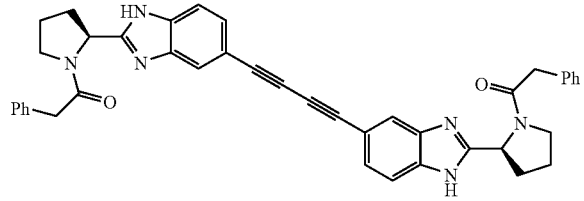

Example M57

Step a

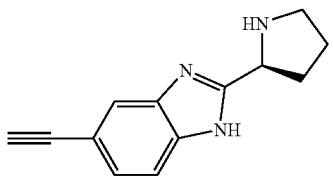

A solution of carbamate M47d (4.0 g, 12.85 mmol) in 30% TFA/CH$_2$Cl$_2$ (30 mL) was stirred at room temperature for 4.3 h. The volatile component was removed in vacuo and the oily residue was free-based with a SCX cartridge (MeOH wash; 2.0 M NH$_3$/MeOH) elution) to provide pyrrolidine M57a as a dull yellow dense solid (2.55 g). $^1$H NMR (DMSO-d$_6$, δ=2.5 ppm, 400 MHz): 7.57 (app s, 1H), 7.44 (d, J=8.0, 1H), 7.21 (d, J=8.2, 1.6, 1H), 4.36 (dd, J=8.1, 5.9, 1H), 3.99 (s, 1H), 2.93 (app t, J=6.8, 2H), 2.18-2.09 (m, 1H), 1.97-1.89 (m, 1H), 1.78-1.69 (m, 2H). LC/MS: Anal. Calcd. for [M+H]$^+$ C$_{13}$H$_{14}$N$_3$: 212.12. found: 212.26.

Example M57

Step b

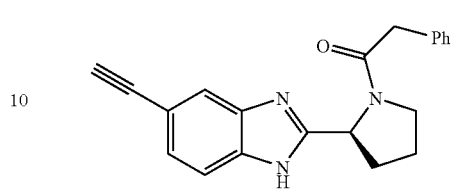

EDCI.HCl (1.29 g, 6.72 mmol) was added to a mixture of the alkyne M57a (1.41 g, 6.67 mmol) and phenylacetic acid (1.01 g, 7.42 mmol) in CH$_2$Cl$_2$ (35 ml), and the mixture was stirred at room temperature for 15.5 h. The volatile component was removed in vacuo, and the residue was submitted to flash chromatography (silica gel; 50-100% EtOAc/hexanes) to provide amide M57b as a light yellow foam (2.1 g). $^1$H NMR (DMSO-d$_6$, δ=2.5 ppm, 500 MHz): 12.67/12.64 (two overlapping s, 0.3H), 12.35/12.31 (two overlapping s, 0.7H), 7.73 (s, 0.13H), 7.65 (s, 0.37H), 7.60-7.43 (m, 1.5H), 7.30-7.11 (m, 5.47H), 7.00 (m, 0.53H), 5.38 (d, J=7.9, 0.3H), 5.16 (br m, 0.7H), ~4.00 (signal overlapping with solvent, 1H), 3.88-3.46 (m, 4H), 2.44-1.82 (m, 4H). LC/MS: Anal. Calcd. for [M+H]$^+$ C$_{21}$H$_{20}$N$_3$O: 330.16. found: 330.23.

Example M57

When a mixture of alkyne M57b and an arylhalide (such as 2-iodopyridine) was subjected to Sonogashira coupling conditions similar to the one employed in the preparation of M47g, the homocoupled product (Example M57) was produced as a minor component. A clean sample of Example M57 (TFA salt) was isolated after a reverse phase HPLC purification (MeOH/H$_2$O/TFA). $^1$H NMR (DMSO-d$_6$, δ=2.5 ppm, 500 MHz): 7.89 (br s, 1.5H), 7.83 (br s, 0.5H), 7.67-7.44 (m, 4H), 7.31-7.01 (m, 10H), 5.44 (d, J=8.5, 0.5H), 5.23 (d, J=6.7, 1.5H), 3.91-3.83 (m, 2H), 3.82-3.50 (m, 6H), 2.38-2.29 (m, 2H), 2.17-1.86 (m, 6H); LC (M-Cond. 2): RT=2.03 min. LC/MS: Anal. Calcd. for [M+H]$^+$ C$_{24}$H$_{37}$N$_6$O$_2$: 657.30. found: 657.43.

Example M57.1

Methyl((1S)-1-(((2S)-2-(5-(4-(2-((2S)-1-((2S)-2-((methoxycarbonyl)amino)-3-methylbutanoyl)-2-pyrrolidinyl)-1H-benzimidazol-5-yl)-1,3-butadiyn-1-yl)-1H-benzimidazol-2-yl)-1-pyrrolidinyl)carbonyl)-2-methylpropyl)carbamate

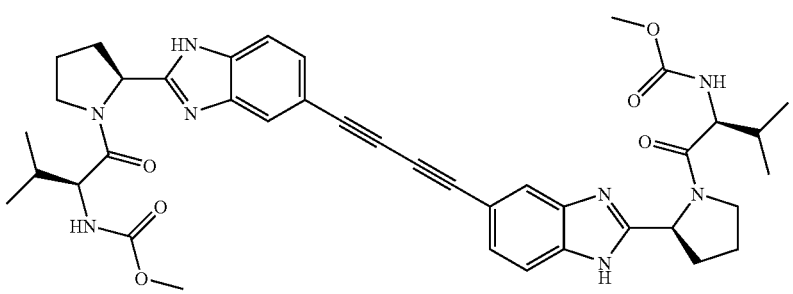

Example M57.1

Step a

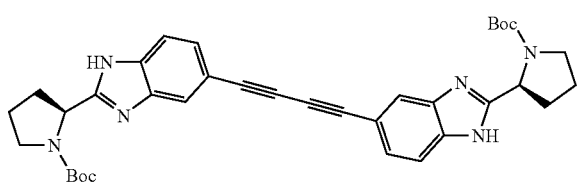

During the Sonogashira coupling step employed in the preparation of carbamate M47g, an impure sample of carbamate M57.1a was also isolated as a side product.

Example M57.1

By employing the procedure described in the synthesis of Example 1 from carbamate M1b, carbamate M57.1a was first deprotected and then coupled with (S)-2-(methoxycarbonylamino)-3-methylbutanoic acid to afford the TFA salt of Example 57.1. $^1$H NMR (DMSO-d$_6$, δ=2.5 ppm, 500 MHz): 7.93 (s, 2H), 7.70 (d, J=8.6, 2H), 7.57 (d, J=8.6, 2H), 5.59-5.53 (m, 0.2H), 5.24-5.14 (m, 1.8H), 4.11 (d, J=7.6, 2H), 3.93-3.77 (m, 4H), 3.54 (s, 6H), 2.41-2.29 (m, 2H), 2.27-2.14 (m, 2H), 2.13-1.75 (m, 6H), 0.89-0.77 (m, 12H). LC (M-Cond. 3): RT=1.98 min; >95% homogeneity index. LC/MS: Anal. Calcd. for [M+H]$^+$ C$_{40}$H$_{47}$N$_5$O$_6$: 735.36. found: 735.43.

Example M57.2

Methyl((1S)-1-(((1R,3S,5R)-3-(5-(4-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-1,3-butadiyn-1-yl)-1H-benzimidazol-2-yl)-2-azabicyclo[3.1.0]hex-2-yl)carbonyl)-2-methylpropyl)carbamate

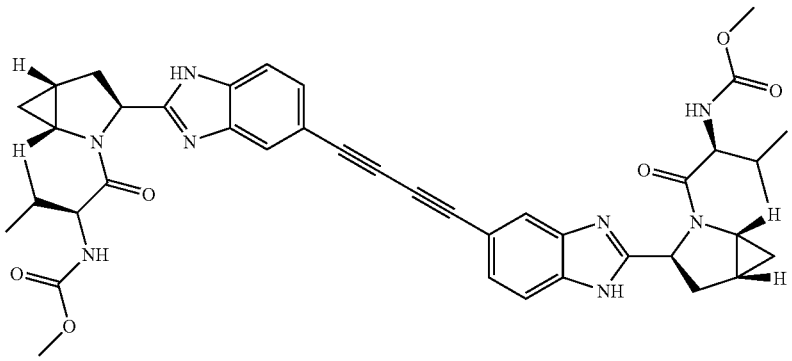

Example M57.2

Step a

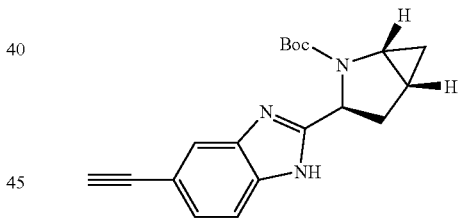

Bromide M46g was subject to Sonogashira coupling conditions similar to the one employed in the preparation of intermediate M47c. Desilylation, as in step M47d gave example M57.2a $^1$H NMR (CDCl$_3$, δ ppm, 500 MHz): 10.5 (br s, 1H), 7.89 (s, 0.5H), 7.65 (dd, J=8.2, 0.5H), 7.56 (s, 0.5H), 7.37-7.32 (m, 1.5H), 4.98 (s, 1H), 3.29 (br s, 1H), 3.02 (d, J=13 Hz, 1H), 2.41 (app t. J=10 Hz, 1H), 1.80 (br s, 1H), 1.59 (s, 1H), 1.48 (s, 9H), 0.92-0.88 (m, 1H), 0.50 (s, 1H).

Example M57.2

Step b

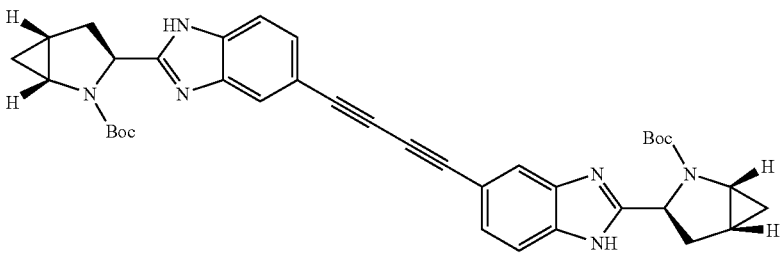

Tetrakis(triphenylphosphine)palladium (45.6 mg, 0.040 mmol) was added to a nitrogen purged solution of an aryl bromide (0.395 mmol), M57.2a (168 mg, 0.519 mmol), copper(I) iodide (7.52 mg, 0.040 mmol), and triethylamine (120 mg, 1.185 mmol) in DMF (2.5 mL) and stirred for 48 h at 24 C. The DMF was removed by rotary evaporation under high vacuum. The residue was applied to a 25 g Thomson™ silica gel column and eluted with 15-100% B over 750 mL (A/B: $CH_2Cl_2$/EtOAc). Under these conditions M57.2b was obtained as a side product (44 mg). $^1$H NMR ($CDCl_3$, δ ppm, 500 MHz): 10.5 (br s, 2H), 7.93 (s, 1H), 7.66 (d, J=8.5, 1 H), 7.59 (d, J=8.5, 1 H), 7.39 (d, J=6.4, 2), 7.33 (d, J=6.4, 1H), 4.99 (br s, 2H), 3.25 (br s, 2H), 2.41 (app t, J=10, 2H), 1.80 (br s, 2H), 1.56/1.48 (s, 18H), 1.24 (s, 4H), 0.93-0.868 (m, 3H), 0.50 (s, 2H). LC (J-Cond. 2): RT=1.5 mm. LC/MS Anal. Calcd. for $[M+H]^+$ $C_{38}H_{41}N_6O_4$: 645.32. found: 645.49.

Example M57.2

M57.2b was subjected to deprotection conditions similar to those described for J6.c (vide infra). In a subsequent coupling step similar to the procedure described for Example M1, the HCl salt obtained upon deprotection was coupled with Cap-51 to give Example M57.2. $^1$H NMR (MeOH-$d_4$, δ ppm, 500 MHz). 7.71 (br s, 2H), 7.54 (br s, 2H), 7.40 (d, J=8.2, 2H), 5.24 (t, J=7.0, 2H), 4.61 (d, J=6.7, 2H), 3.74-3.71 (m, 2H), 3.68 (s, 6H), 2.52-2.50 (m, 4H), 2.20-2.13 (m, 2H), 2.09-2.04 (m, 2H), 1.18-1.14 (m, 2H), 1.00 (d, J=6.7, 6H), 0.92 (d, J=6.7, 6H), 0.88-0.86 (m, 2H). LC (J-Cond. 2): RT=1.38 min. LC/MS: Anal. Calcd. for $[M+H]^+$ $C_{42}H_{47}N_8O_6$: 759.36. found: 759.59.

Example V1

Methyl((1S)-1-(((1R,3S,5R)-3-(5-(3-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate Example V1

Step a

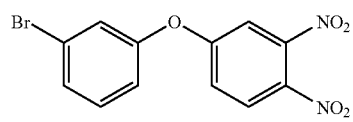

To a solution of 3-bromophenol (5 g, 28.9 mmol) in DMF (147 mL) was added 4-fluoro-1,2-dinitrobenzene (5.49 g, 29.5 mmol) followed by the addition of triethylamine (6.17 mL, 44.2 mmol) dropwise. The reaction was heated at 50° C. under nitrogen for 16 h. All the volatile component was removed in vacuo, and the residue was taken up in ethyl acetate (250 ml) and washed with water (3×50 ml), followed by brine (50 ml), dried over $MgSO_4$, filtered, and concentrated in vacuo. The residue was taken up in $CHCl_3$ (6 ml) and loaded onto a Thomson's silica gel column and eluted with 10% ethyl acetate/hexanes to afford a light yellow viscous oil which solidified upon standing. $^1$H NMR indicated the presence of some 3-bromophenol. The product was recrystallized from hexanes/ethyl acetate to afford bromide V1a as a light yellow solid (5.76 g, 57.6%). $^1$H NMR (DMSO-$d_6$, δ=2.5 ppm, 500 MHz): 8.29 (d, J=9.1, 1H), 7.90 (d, J=2.8, 1H), 7.59-7.55 (m, 1H), 7.49 (t, J=8.1, 1H), 7.42 (dd, J=8.8, 2.50, 1H), 7.31 (dd, J=8.3, 2.2, 1H). LC (M-Cond. 3): RT=4.45 min; >95% homogeneity index. LC/MS: Anal. Calcd. for $[M+H]^+$ $C_{12}H_7^{81}BrN_2O_5$: 340.96. found: 341.04.

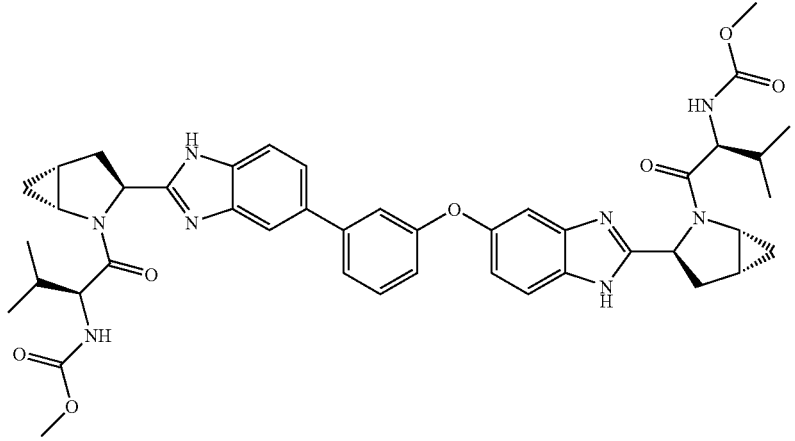

Example V1

Step b

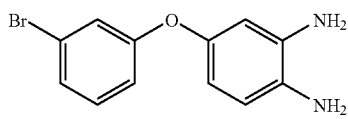

To tin(II) chloride (16.78 g, 89 mmol) was added 12N HCl (40 mL) with stirring. The solution was lowered into an oil bath at 65° C., and bromide V1a (4.618 g, 13.62 mmol) in ethanol (40 ml) was slowly added to it. A condenser was put on top of the flask and heating continued at 65° C. for 3 h. The reaction was allowed to cool to ~25° C. and placed in the freezer for 16 h. The mixture was filtered and the precipitate was collected, which was then added to water (50 ml) and chilled with an ice/water bath. A solution of NaOH (aq) (3.8 g NaOH in 15 ml water) was added dropwise over 45 min while continuously stirring the mixture, and then mixture was filtered and the retrieved solid was dried in vacuo to afford diamine V1b as an off-white solid (3.1 g, 82%). $^1$H NMR (DMSO-d$_6$, δ=2.5 ppm, 500 MHz): 7.27 (t, J=8.2, 1H), 7.20 (d, J=8, 1H), 6.99 (t, J=1.9, 1H), 6.91 (dd, J=8.3, 2.4, 1H), 6.59 (d, J=8.6, 1H), 6.30 (d, J=2.7, 1H), 6.16 (dd, J=8.3, 2.4, 1H), 5.20-4.83 (s, 4H). LC (M-Cond. 3): RT=2.66 min; >95% homogeneity index. LC/MS: Anal. Calcd. for [M+H]$^+$ C$_{12}$H$_7$$^{79}$BrN$_2$O$_5$: 279.01. found: 279.03.

Example V1

Step c

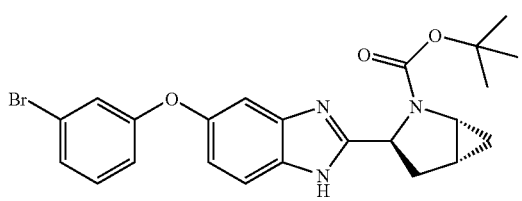

Benzimidazole V1c was prepared from diamine V1b and trans-acid M46f-1 according to the procedure described for the synthesis of benzimidazole M1a. $^1$H NMR (DMSO-d$_6$, δ=2.5 ppm, 500 MHz): 12.49-12.13 (two overlapping br s, 1H), 7.58 (d, J=8.8, 0.5H), 7.48 (d, J=8.5, 0.5H), 7.37-7.23 (m, 2.5H), 7.13 (d, J=2.1, 0.5H), 7.11-7.00 (two overlapping app. bs, 1H), 6.99-6.92 (m, 1.5H), 6.90 (dd, J=8.7, 2.5, 0.5H), 4.88-4.64 (app. bs, 1H), 3.57-3.37 (app. bs, 1H), 2.48-2.40 (m, 1H), 2.34-2.22 (app. bs, 1H), 1.72-1.63 (m, 1H), 1.59-0.87 (two overlapping app. bs, 9H), 0.85-075 (m, 1H), 0.67-0.58 (app. bs, 1H). LC (M-Cond. 3): RT=2.87 min; >95% homogeneity index. LC/MS: Anal. Calcd. for [M+H]$^+$ C$_{12}$H$_7$$^{81}$BrN$_2$O$_5$: 472.11. found: 472.01.

Example V1

Step d

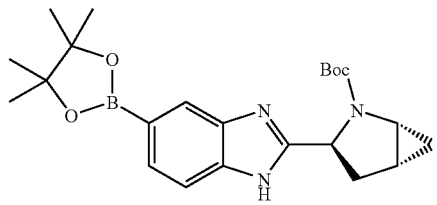

To a mixture of benzimidazole V1c (1 g, 2.64 mmol), 4,4,4',4',5,5,5',5'-octamethyl-2,2'-bi(1,3,2-dioxaborolane) (1.343 g, 5.29 mmol), and potassium acetate (0.649 g, 6.61 mmol) in a 20 ml microwave reaction vessel containing dioxane (15 mL) was added tetrakis(triphenylphosphine)palladium (0) (0.153 g, 0.132 mmol). The mixture was flushed with nitrogen thoroughly, sealed, and heated at 80° C. for 16 h. After it was allowed to cool to ambient condition, the volatile component was removed in vacuo. The residue was dissolved in CH$_2$Cl$_2$ (150 ml), washed with water (25 ml), followed by NaHCO$_3$ (aq) (25 ml), dried over MgSO$_4$, filtered, and concentrated in vacuo. The residue was taken up in CHCl$_3$ (4 ml) and loaded onto a Thomson's silica gel cartridge and eluted with 50% ethyl acetate/hexanes to afford boronate V1d as an off-white foam (928.1 mg). LC/MS indicated a mixture of boronate ester as well as the corresponding boronic acid, albeit it was not apparent if the boronic acid is a result of hydrolysis on the LC column. The product was used for the next step without further purification. $^1$H NMR (DMSO-d$_6$, δ=2.5 ppm, 500 MHz): 12.40-12.20 (two overlapping br s, 1H), 7.79 (d, J=43, 1H), 7.52-7.41 (m, 2H), 4.86-4.66 (app. bs, 1H), 3.60-3.39 (app. bs, 1H), 2.49-2.41 (m, 1H), 2.33-2.13 (app. bs, 1H), 1.72-1.62 (m, 1H), 1.55-0.87 (br m and a singlet, 21H), 0.84-0.74 (m, 1H), 0.69-0.60 (app. bs, 1H). LC/MS: Anal. Calcd. for [M+H]$^+$ C$_{23}$H$_{33}$BN$_3$O$_4$: 426.26. found: 426.21.

Example V1

Step e

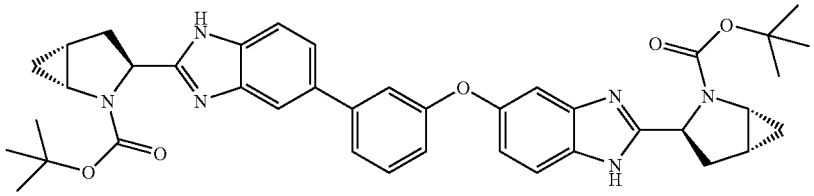

To a microwave reaction vessel containing boronate V1d (0.300 g, 0.705 mmol), bromide V1c (0.332 g, 0.705 mmol), sodium bicarbonate (0.178 g, 2.116 mmol), 1,2-dimethoxyethane (5 mL) and water (1.7 mL) was added Pd (Ph$_3$P)$_4$ (0.082 g, 0.071 mmol). The mixture was flushed thoroughly with nitrogen, capped, and heated at 85° C. for 16.5 h. After it was allowed to cool to ambient temperature, the volatile component was removed in vacuo. The residue was taken up in CH$_2$Cl$_2$ (150 ml), washed sequentially with water (25 ml), saturated NaHCO$_3$ (aq) (25 ml), and brine (25 ml), and dried over MgSO$_4$, filtered, and concentrated in vacuo. The residue was dissolved in CHCl$_3$ (4 ml) and loaded onto a Thomson's silica gel column and eluted with 75-100% ethyl acetate/hexanes over 1296 ml to afford benzimidazole V1e as a light yellow foam (281.4 mg, 57.9%). $^1$H NMR (DMSO-d$_6$, δ=2.5 ppm, 500 MHz): 12.42-12.10 (m, 2H), 7.79-7.56 (m, 2H), 7.48-7.32 (m, 4H), 7.28-7.10 (m, 2H), 6.98-6.78 (m, 2H), 4.91-4.60 (br s, 2H), 3.60-3.35 (bs, 2H), 2.47-2.34 (m, 2H), 2.35-2.14 (br s, 2H), 1.77-1.62 (m, 2H), 1.59-0.87 (two overlapping bs, 18H), 0.86-0.73 (m, 2H), 0.69-0.54 (br s, 2H). LC/MS: Anal. Calcd. for [M+H]$^+$ C$_{40}$H$_{45}$N$_6$O$_5$: 689.35. found: 689.40.

Example V1

Step f

Pyrrolidine V1f was prepared from benzimidazole V1e according to the procedure described for the synthesis of pyrrolidine M1c. $^1$H NMR (DMSO-d$_6$, δ=2.5 ppm, 500 MHz): 12.30-11.98 (m, 2H), 7.79-7.44 (m, 3H), 7.43-7.31 (m, 3H), 7.29-7.07 (m, 2H), 6.96-6.91 (m, 1H), 6.91-6.85 (m, 1H), 4.17-4.07 (m, 2H), 3.28-3.04 (br s and m, 2H), 2.90-2.83 (m, 2H), 2.30-2.23 (m, 2H), 2.00-1.90 (m, 2H), 1.49-1.44 (m, 2H), 0.72-0.66 (m, 2H), 0.41-0.35 (m, 2H). LC/MS: Anal. Calcd. for [M+H]$^+$ C$_{30}$H$_{29}$N$_6$O: 489.24. found: 489.21.

Example V1

Example V1 (TFA salt) was prepared from pyrrolidine V1f according to the procedure described for the synthesis of Example M1. $^1$H NMR (DMSO-d$_6$, δ=2.5 ppm, 500 MHz): 7.91-7.84 (app. bs, 1H), 7.75-7.65 (m, 3H), 7.52-7.46 (m, 2H), 7.39-7.32 (app. bs, 2H), 7.27-7.12 (m, 3H), 7.05-6.91 (m, 1H), 5.20 5.12 (m, 2H), 4.47-4.30 (m, 2H), 3.76-3.64 (m, 2H), 3.56 (s, 6H), 2.48-2.34 (m, 4H), 2.14-2.03 (m, 2H), 2.01-1.88 (m, 2H), 1.06-0.96 (m, 2H), 0.95-0.88 (m, 6H), 0.87-0.74 (m, 8H). LC (M-Cond. 3): RT=1.96 min; >95% homogeneity index; LC/MS: Anal. Calcd. for [M+H]$^+$ C$_{44}$H$_{51}$N$_8$O$_7$: 803.39. found: 803.36.

Example V2-V5

Example V2-V3 were prepared from pyrrolidine V1f and appropriate acids according to the procedure described for Example V1. When (R)-2-(methoxycarbonylamino)-2-phenylacetic acid was used as a coupling partner, two diastereomers (Example V4 and V5) were isolated, presumably a result of partial epimerization during the HATU-assisted coupling step. Example V2-V5 were isolated as TFA salts.

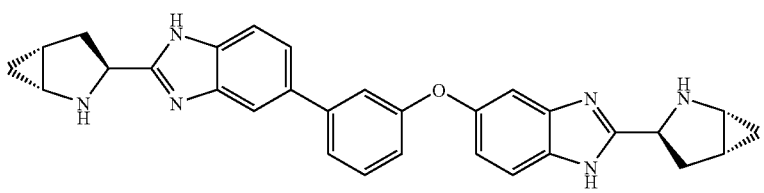

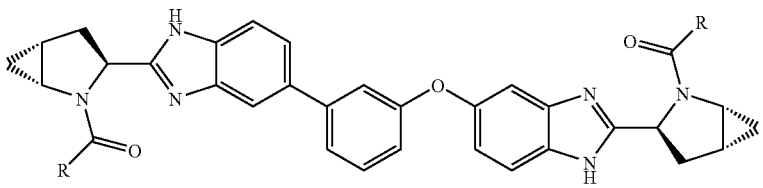

| Example | Compound Name | R (structure) | RT (LC-Cond.); % homogeneity index; MS data |
|---|---|---|---|
| V2 | methyl ((1S)-2-((1R,3S,5R)-3-(5-(3-((2-((1R,3S,5R)-2-(N-(methoxycarbonyl)-L-alanyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-1-methyl-2-oxoethyl)carbamate | methyl carbamate-Ala | 1.68 min (M- Cond. 3); >95%; LC/MS: Anal. Calcd. for [M + H]⁺ $C_{40}H_{43}N_8O_7$: 747.33; found: 747.38. |
| V3 | methyl ((1R)-1-(((1R,3S,5R)-3-(5-(3-(2-((1R,3S,5R)-2-((2R)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate | methyl carbamate-Val | 1.93 min (M-Cond. 3); >95%; LC/MS: Anal. Calcd. for [M + H]⁺ $C_{44}H_{51}N_8O_7$: 803.39; found: 803.43. |
| V4 (diastereomer-1) | methyl (2-((1R,3S,5R)-3-(5-(3-((2-((1R,3S,5R)-2-(((methoxycarbonyl)amino)(phenyl)acetyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-2-oxo-1-phenylethyl)carbamate | methyl carbamate-Ph | 2.01 min (M-Cond. 3); >95%; LC/MS: Anal. Calcd. for [M + H]⁺ $C_{50}H_{47}N_8O_7$: 871.36; found: 871.36. |

| Example | Compound Name | R | RT (LC-Cond.); % homogeneity index; MS data |
|---|---|---|---|
| V5 (diastereomer-2) | methyl (2-((1R,3S,5R)-3-(5-(3-((2-((1R,3S,5R)-2-(((methoxycarobnyl)amino)phenyl)acetyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-2-oxo-1-phenylethyl)carbamate | (structure: MeO-C(=O)-NH-CH(Ph)-C(=O)-) | 2.00 min (M-Cond. 3); >95%; LC/MS: Anal. Calcd. for [M + H]+ $C_{50}H_{47}N_8O_7$: 871.36; found: 871.43. |

Example V6

Methyl((1S)-1-(((1R,3S,5R)-3-(4-(4-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate

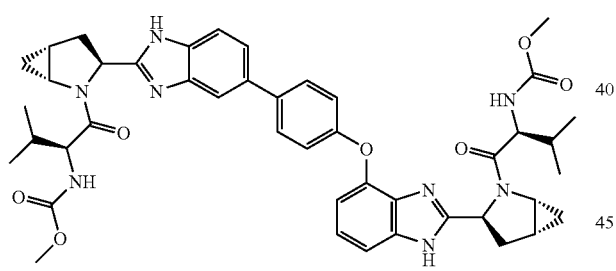

Example V6

Step a

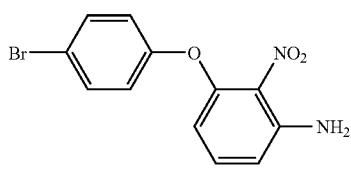

To a solution of 4-bromophenol (5 g, 28.9 mmol) and 3-chloro-2-nitroaniline (4.99 g, 28.9 mmol) in DMF (145 mL) was added potassium carbonate (7.99 g, 57.8 mmol), and the mixture was heated at 160° C. under nitrogen for 48 h. After the mixture was allowed to cool to ambient condition, the volatile component was removed in vacuo. The residue was taken up in ethyl acetate (400 ml) and washed with water (3×50 ml), followed by brine (50 ml), dried over MgSO₄, filtered, and concentrated in vacuo. The residue was dissolved in CHCl₃ (6 ml) and loaded onto a Thomson's silica gel column and eluted with 5-15% ethyl acetate/hexanes to afford bromide V6a as a red/brown oil (3.4956 g, 39.1%). ¹H NMR (DMSO-d₆, δ=2.5 ppm, 500 MHz): 7.56 (d, J=8.9, 2H), 7.23 (t, J=8.3, 1H), 6.98 (d, J=9.2, 2H), 6.74 (dd, J=8.5, 0.9, 1H), 6.47 (s, 2H), 6.19 (dd, J=8.0, 1.0, 1H). LC/MS: Anal. Calcd. for [M+H]+ $C_{12}H_{10}^{81}BrN_2O_3$: 310.99. found: 311.00.

Example V6

Step b

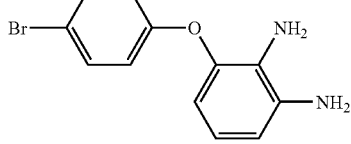

To tin(II) chloride (8.46 g, 44.6 mmol) was added 12 N HCl (40 mL) with stirring. The solution was lowered into an oil bath at 65° C. A solution of nitroaniline V6a (3.939 g, 12.74 mmol) in EtOH (10 ml) was added dropwise into the tin(II) chloride solution at 65° C. The reaction flask was equipped with a condenser and heating continued for 4.5 h. The reaction mixture was allowed to cool to ambient temperature and placed in the freezer overnight. The reaction was filtered and the precipitate collected. The solid was suspended in water (50 ml), chilled with an ice/water bath, and a solution of NaOH (aq) (3.8 g NaOH in 15 ml water) was added dropwise. The mixture was stirred for 45 min, and the mixture was filtered and the solid was dried in vacuo to afford a tan solid. The solid was taken up in CH₂Cl₂ (150 ml) and washed with a solution of NaOH (2.8 g in 25 ml of water), dried over MgSO₄, filtered, and concentrated in vacuo to afford diamine V6b as a reddish oil (2.98 g, 84%). $^1$H NMR (DMSO-$d_6$, δ=2.5 ppm, 300 MHz): 7.50-7.43 (m, 2H), 6.90-6.82 (m, 2H), 6.52-6.39 (m, 2H), 6.24-6.13 (m, 1H), 5.01-4.91 (bs, 0.2H), 4.72-4.51 (bs, 1.8H), 4.36-4.25 (bs, 0.2H), 4.24-4.03 (bs, 1.82H). LC/MS: Anal. Calcd. for [M+H]$^+$ $C_{12}H_7{}^{81}BrN_2O_5$: 472.11. found: 472.01.

Example V6

Step c

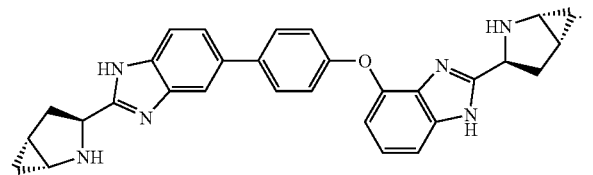

Pyrrolidine V6c was prepared from diamine V6b according to the procedure described for the preparation of pyrrolidine V1f from diamine V1b, with the exception that the free-basing step after Boc-deprotection was conducted with an MCX resin. $^1$H NMR (DMSO-$d_6$, δ=2.5 ppm, 500 MHz): 12.51-11.99 (two overlapping br s, 2H), 7.84-7.44 (m, 4H), 7.43-7.19 (m, 2H), 7.13 (t, J=8, 1H), 7.07-6.93 (m, 2H), 6.83-6.69 (m, 1H), 4.21-4.03 (m, 2H), 3.47-3.15 (br s, 2H), 2.91-2.83 (m, 2H), 2.32-2.17 (m, 2H), 2.02-1.90 (m, 2H), 1.52-1.42 (m, 2H), 0.73-0.63 (m, 2H), 0.42-0.32 (m, 2H). LC/MS: Anal. Calcd. for [M+H]$^+$ $C_{30}H_{29}N_6O$: 489.24. found: 489.28.

Example V6

Example V6 (TFA salt) was prepared from pyrrolidine V6c according to the procedure described for the synthesis of Example M1. $^1$H NMR (DMSO-$d_6$, δ=2.5 ppm, 500 MHz). 7.93 (s, 1H), 7.82 (d, J=8.5, 1H), 7.78-7.75 (m, 3H), 7.46 (d, J=8.3, 1H), 7.33 (t, J=7.9, 1H), 7.26 (d, J=8.5, 1H), 7.22-7.19 (m, 3H), 6.89 (d, J=7.9, 1H), 5.18 (dd, J=6.6, 6.4, 1H), 5.13 (dd, J=6.1, 6.1, 1H), 4.44 (q, J=8.5, 2H), 3.80-3.73 (m, 1H), 3.73-3.67 (m, 1H), 3.56 (s, 3H), 3.55 (s, 3H), 2.56-2.37 (m, 4H), 2.14-2.05 (m, 2H), 2.01-1.92 (m, 2H), 1.0-0.97 (m, 2H), 0.93-0.79 (m, 16H). LC (M-Cond. 3): RT=1.91 min; >95% homogeneity index. LC/MS: Anal. Calcd. for [M+H]$^+$ $C_{44}H_{51}N_8O_7$: 803.39. found: 803.43.

Example V7-V10

Example V7-V8 (TFA salt) were prepared from pyrrolidine V6c and appropriate acids according to the procedure described for Example V1. When (R)-2-(methoxycarbonylamino)-2-phenylacetic acid was used as a coupling partner, two diastereomers (Example V9 and V10) were isolated as TFA salts, presumably a result of partial epimerization during the HATU-assisted coupling step.

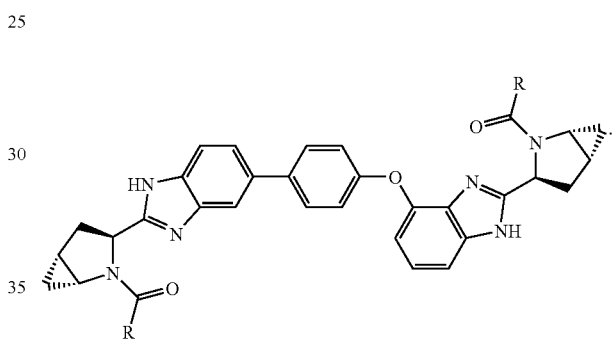

| Example | Compound Name | | RT (LC-Cond.); % homogeneity index; MS data |
|---|---|---|---|
| V7 | methyl ((1R)-1-(((1R,3S,5R)-3-(4-(4-(2-((1R,3S,5R)-2-((2R)-2-(methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate | | 1.95 min (M-Cond. 3); >95%; LC/MS: Anal. Calcd. for [M + H]$^+$ $C_{44}H_{51}N_8O_7$: 803.39; found: 803.36. |

| Example | Compound Name | R | RT (LC-Cond.); % homogeneity index; MS data |
|---|---|---|---|
| V8 | methyl ((1S)-2-((1R,3S,5R)-3-(5-(4-((2-((1R,3S,5R)-2-(N-(methoxycarbonyl)-L-alanyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-1-methyl-2-oxoethyl) carbamate | | 1.68 min (M. Cond. 3); >95%; LC/MS: Anal. Calcd. for [M + H]$^+$ C$_{40}$H$_{43}$N$_8$O$_7$: 747.33; found: 747.32. |
| V9 (diastereomer-1) | methyl (2-((1R,3S,5R)-3-(5-(4-((2-((1R,3S,5R)-2-(((methoxycarbonyl)amino)(phenyl)acetyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-2-oxo-1-phenylethyl) carbamate | | 1.99 min (M-Cond. 3); >95%; LC/MS: Anal. Calcd. for [M + H]$^+$ C$_{50}$H$_{47}$N$_8$O$_7$: 871.36; found: 871.36. |
| V10 (diastereomer-2) | methyl (2-((1R,3S,5R)-3-(5-(4-((2-((1R,3S,5R)-2-(((methoxycarbonyl)amino)(phenyl)acetyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-2-oxo-1-phenylethyl) carbamate | | 1.98 min (M-Cond. 3); >95%; LC/MS: Anal. Calcd. for [M + H]$^+$ C$_{50}$H$_{47}$N$_8$O$_7$: 871.36; found: 871.43. |

Example V11

Methyl((1S)-1-(((2S)-2-(4-(4-(2-((2S)-1-((2S)-2-((methoxycarbonyl)amino)-3-methylbutanoyl)-2-pyrrolidinyl)-1H-benzimidazol-5-yl)phenoxy)-1H-benzimidazol-2-yl)-1-pyrrolidinyl)carbonyl)-2-methylpropyl)carbamate

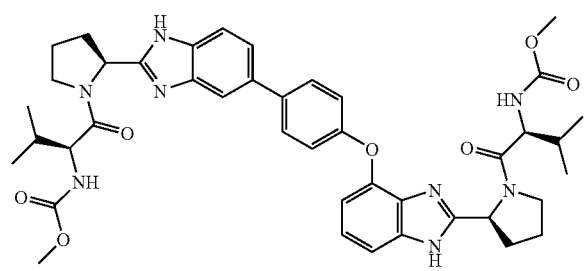

Example V11 (TFA salt) was prepared from Boc-L-proline according to the procedure described for the preparation of Example V6. $^1$H NMR (DMSO-d$_6$, δ=2.5 ppm, 500 MHz): 7.96 (s, 1H), 7.84 (d, J=8.5, 1H), 7.80-7.78 (m, 3H), 7.48 (d, J=8.3, 1H), 7.38 (t, J=7.9, 1H), 7.24 (d, J=8.9, 2H), 6.91 (d, J=8, 1H), 6.25 (dd, J=5.9, 5.8, 1H), 5.20 (dd, J=5.8, 5.5, 1H), 4.14 (d, J=7.3, 1H), 4.11 (d, J=7.3, 1H), 3.90-3.84 (m, 5H), 3.55 (s, 3H), 3.54 (s, 3H), 2.49-2.36 (m, 2H), 2.24-1.94 (m, 9H), 0.90-0.74 (m, 14H). LC (M-Cond. 3): RT=1.85 min; >95% homogeneity index. LC/MS: Anal. Calcd. for [M+H]$^+$ C$_{42}$H$_{51}$N$_8$O$_7$: 779.39. found: 779.49.

Example V12

Methyl((1S)-1-(((2S)-2-(5-(4-(2-((2S)-1-((2S)-2-((methoxycarbonyl)amino)-3-methylbutanoyl)-2-pyrrolidinyl)-1H-benzimidazol-5-yl)phenoxy)-1H-benzimidazol-2-yl)-1-pyrrolidinyl)carbonyl)-2-methylpropyl)carbamate

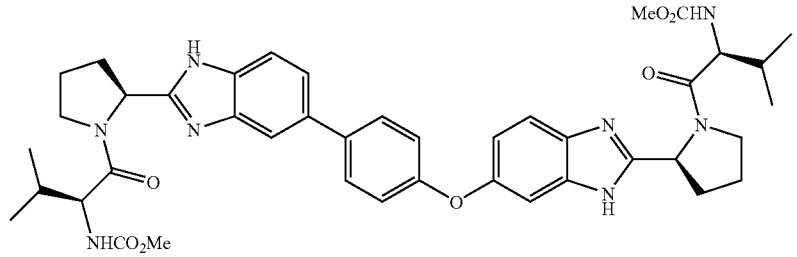

Example V12 (TFA salt) was prepared from appropriate precursors by employing the procedure described for the synthesis its regioisomer, Example V1, with the following modifications: alternate protocols were utilized for the amidation (V12b to V12c) and Suzuki steps as highlighted in the Scheme below. Note that the corresponding coupling procedures described for Example V1 were not tried in the current case. $^1$H NMR (400 MHz, d$_4$-MeOH, d=7.33); δ 7.92 (s, 1H), 7.85-7.83 (m, 2H), 7.77-7.73 (m, 3H), 7.37-7.27 (m, 2H), 7.19 (d, J=8.7, 2H), 5.38-5.30 (m, 2H), 4.28 (m, 2H), 4.16-4.12 (m, 2H), 3.99-3.90 (m, 2H), 3.68 (s, 6H), 2.63-2.57 (m, 2H), 2.37-2.20 (m, 6H), 2.11-2.05 (m, 2H), 1.0-0.9 (m, 12H). RT=1.54 min under the LC condition noted below; >95% homogeneity index. LC/MS: Anal. Calcd. for [M+H]$^+$ C$_{42}$H$_{51}$N$_8$O$_7$: 779.4. found: 779.2.

Column=Chromolith SpeedROD C18, 4.6×30 mm, 5 µM; Start % B=0; Final % B=100; Gradient time=2 min; Stop time=3 min; Flow Rate=5 mL/min; Wavelength=220 nm; Solvent A=0.1% TFA in 10% methanol/90% H$_2$O; Solvent B=0.1% TFA in 90% methanol/10% H$_2$O.

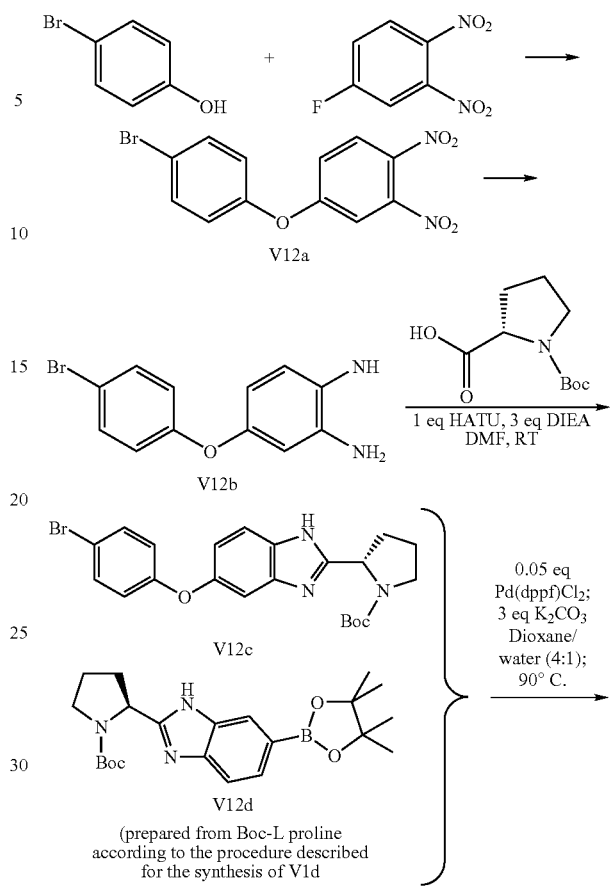

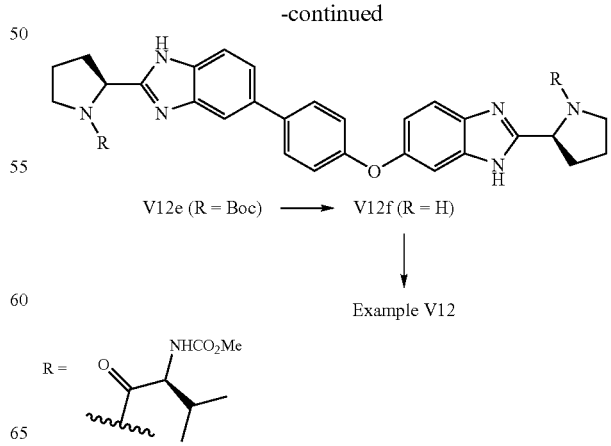

Example F1

(1R,1'R)-2,2'-(1H,1'H-5,5'-bibenzimidazole-2,2'-diyldi(2S)-2,1-pyrrolidinediyl)bis(N,N-dimethyl-2-oxo-1-phenylethanamine)

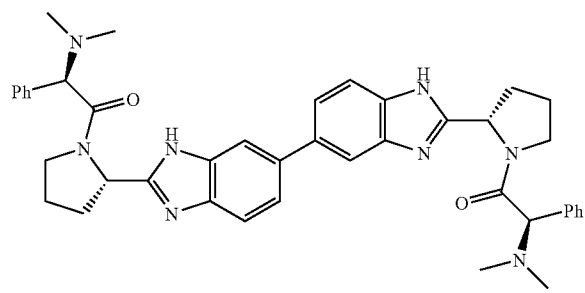

Example F1

Step a

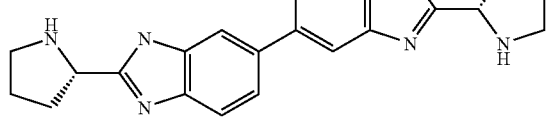

A mixture of TFA salt of Example M40 (90 mg, 0.104 mmol) and 10% Pd/C (20 mg) in MeOH (15 mL) was stirred under a balloon of hydrogen for 3 hr. The reaction mixture was filtered through 0.45 µM filter and the volatile component was removed in vacuo. The residue was treated with HCl/dixane (4N, 3 mL) and stirred for five min, and then the volatile component was removed in vacuo. The resultant crude material was used to prepare Example F1 without purification.

Example F1

HATU (45.4 mg, 0.119 mmol) was added to a DMF (1 mL) solution of the HCl salt of pyrrolidine F1a (30 mg, 0.058 mmol), Cap-1 (19.9 mg, 0.092 mmol) and DIEA (0.081 mL, 0.46 mmol), and the mixture was stirred at ambient condition for 3 hr and directly submitted to a reverse phase HPLC purification (MeOH/H$_2$O/TFA) to provide the TFA salt of Example F1 as white powder. LC (M-Cond. 1b): RT=0.99 min; >95% homogeneity index. LC/MS: Anal. Calcd. for [M+H]$^+$ C$_{42}$H$_{47}$N$_8$O$_2$: 695.38. found: 895.44.

Example F2 dimethyl(1H,1'H-5,5'-bibenzimidazole-2,2'-diylbis((2S)-2,1-pyrrolidinediyl((1R)-2-oxo-1-phenyl-2,1-ethanediyl)))biscarbamate

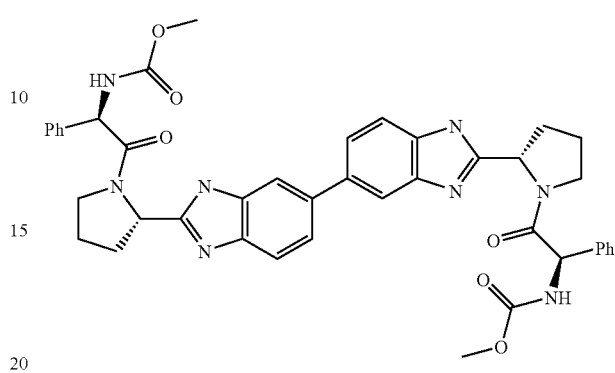

The TFA salt of Example F2 was prepared from pyrrolidine F1a and (R)-2-(methoxycarbonylamino)-2-phenylacetic acid according to the procedure described for the synthesis of Example F1. LC (M-Cond. 1b): RT=1.27 min; >95% homogeneity index. LC/MS: Anal. Calcd. for [M+H]$^+$ C$_{42}$H$_{43}$N$_8$O$_6$: 755.33. found: 755.37.

Example F3

5,5'-(1,2-ethanediyl)bis(2-((2S)-1-(phenylacetyl)-2-piperidinyl)-1H-benzimidazole)

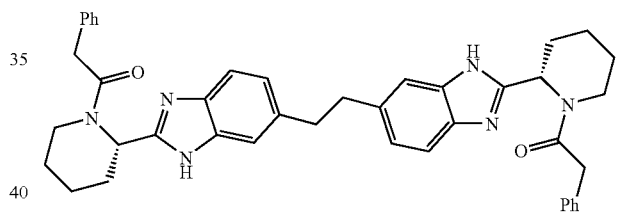

Example F3

Step a

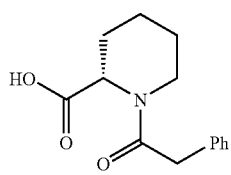

Acid F3a was prepared from L-pipecolic acid in analogous fashion to a procedure described in Gudasheva, et al. *Eur. J. Med. Chem. Chim. Ther.* 1996, 31, 151.

Example F3

The TFA salt of Example F3 was prepared from acid F3a and intermediate OL1c according to the procedure described for the synthesis of Example OL1, vide infra. LC (F-Cond. 1): RT=1.31 min; 94% homogeneity index. LC/MS: Anal. Calcd. for [M+H]$^+$ C$_{42}$H$_{45}$N$_6$O$_2$: 665.36. found: 665.24.

Example F4-F6

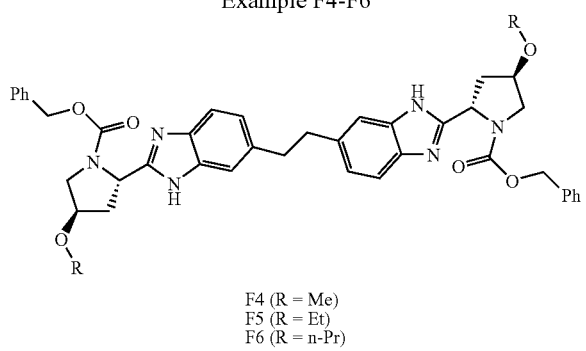

F4 (R = Me)
F5 (R = Et)
F6 (R = n-Pr)

Example F4-F6

Step a

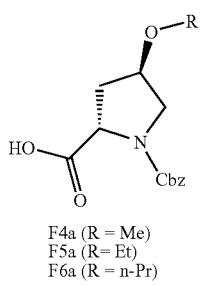

F4a (R = Me)
F5a (R = Et)
F6a (R = n-Pr)

NaH (60%; 158 mg, 3.95 mmol) was added to a THF (10 mL) solution of (2S,4R)-1-(benzyloxycarbonyl)-4-hydroxy-pyrrolidine-2-carboxylic acid (500 mg, 1.88 mmol), and stirred at room temperature for 45 min. Methyl iodide (0.240 mL, 3.86 mmol) was added, and the reaction mixture was refluxed for 3 hr. Then the volatile component was removed in vacuo and the residue was partitioned between water and $CH_2Cl_2$. The aqueous phase was acidified with dilute HCl, and extracted with $CH_2Cl_2$. The organic phase was dried ($MgSO_4$), filtered, and concentrated in vacuo to provide acid F4a as a yellow oil (237 mg), which was used as such for subsequent steps. Acids F5a and F6a were prepared in analogous fashion by employing ethyl iodide and propyl iodide, respectively, and the crude products were employed as such for subsequent steps.

Example F4-F6

The TFA salt of Example F4-F6 was prepared from acids F4a-F6a and intermediate OL1c according to the procedure described for the synthesis of Example OL1, vide infra.

Example F7

N,N'-(1H,1'H-5,5'-bibenzimidazole-2,2'-diylbis((2S)-2,1-pyrrolidinediyl((1R)-2-oxo-1-phenyl-2,1-ethanediyl)))diacetamide

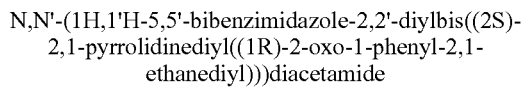

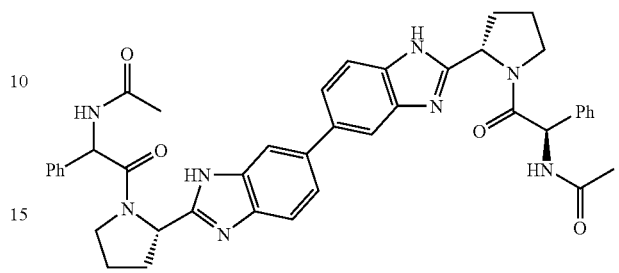

Example F7

Step a

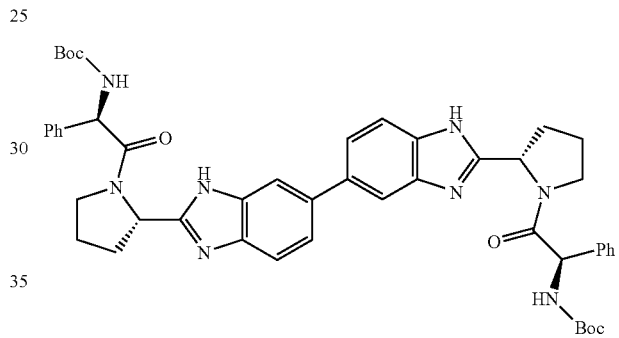

HATU (304 mg, 0.80 mmol) was added to a DMF (4 mL) solution of the HCl salt of pyrrolidine F1a (190 mg, 0.37 mmol), Boc-D-Phenylglycine (205 mg, 0.8 mmol) and DIEA (0.7 mL, 4 mmol), and the mixture was stirred at ambient condition for 3 h and directly submitted to a reverse phase HPLC purification (MeOH/$H_2O$/TFA) to provide the TFA salt of carbamate F7a as white solid. LC (G-Cond.1): RT=3.75 min; >95% homogeneity index. LC/MS: Anal. Calcd. for $[M+H]^+$ $C_{48}H_{55}N_8O_6$: 839.42. found: 839.66.

| Example | Compound Name | RT (LC-Cond.); % homogeneity index; MS data |
|---|---|---|
| F4 | benzyl (2S,4R)-2-(5-(2-(2-((2S,4R)-1-((benzyloxy)carbonyl)-4-methoxy-2-pyrrolidinyl)-1H-benzimidazol-6-yl)ethyl)-1H-benzimidazol-2-yl)-4-methoxy-1-pyrrolidinecarboxylate | 1.30 min (F-Cond. 1); 99%; LC/MS: Anal. Calcd. for $[M + H]^+$ $C_{42}H_{45}N_6O_6$: 729.35; found: 729.30. |
| F5 | benzyl (2S,4R)-2-(5-(2-(2-((2S,4R)-1-((benzyloxy)carbonyl)-4-ethoxy-2-pyrrolidinyl)-1H-benzimidazol-6-yl)ethyl)-1H-benzimidazol-2-yl)-4-ethoxy-1-pyrrolidinecarboxylate | 1.39 min (F-Cond. 1); 95%; LC/MS: Anal. Calcd. for $[M + H]^+$ $C_{44}H_{49}N_6O_6$: 757.37; found: 757.35. |
| F6 | benzyl (2S,4R)-2-(5-(2-(2-((2S,4R)-1-((benzyloxy)carbonyl)-4-propoxy-2-pyrrolidinyl)-1H-benzimidazol-6-yl)ethyl)-1H-benzimidazol-2-yl)-4-propoxy-1-pyrrolidinecarboxylate | 1.53 min (F-Cond. 1); 99%; LC/MS: Anal. Calcd. for $[M + H]^+$ $C_{46}H_{53}N_6O_6$: 785.40; found: 785.36. |

Example F7

Step b

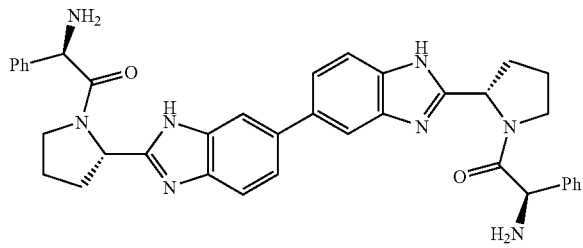

The TFA salt of carbamate F7a was treated with 50% TFA/CH$_2$Cl$_2$ (3 mL) and stirred for 1 hr, and then the volatile component was removed in vacuo. The resultant crude material was used in the next step without purification.

Example F7

To the TFA salt of pyrrolidine F7b (60 mg, 0.055 mmol) was added 1N NaOH solution (5 mL) followed by acetic anhydride (300 mg, 3.3 mmol). The reaction was stirred at ambient condition for 2 h and directly submitted to a reverse phase HPLC purification (MeOH/H$_2$O/TFA) to provide the TFA salt of Example F7 as white powder. LC (G-Cond.2): RT=2.74 min; >95% homogeneity index. LC/MS: Anal. Calcd. for [M+H]$^+$ C$_{42}$H$_{43}$N$_8$O$_4$: 723.34. found: 723.45.

Example F8, F9 and F10 were prepared as TFA salts from acids F4a, F5a, and the t-Bu ether analog of F4a (obtained from a commercial source), respectively, by employing the procedure described for the preparation of Example OL1 (vide infra).

| Example | Compound Name | R | RT (LC-Cond.); % homogeneity index; MS data |
|---|---|---|---|
| F8 | benzyl (2S,4R)-2-(5-((2-((2S,4R)-1-((benzyloxy)carbonyl)-4-methoxy-2-pyrrolidinyl)-1H-benzimidazol-6-yl)ethynyl)-1H-benzimidazol-2-yl)-4-methoxy-1-pyrrolidinecarboxylate | Me | 2.06 min (M-Cond. 2); >95%; LC/MS: Anal. Calcd. for [M + H]$^+$ C$_{42}$H$_{41}$N$_6$O$_6$: 725.31; found: 725.66. |
| F9 | benzyl (2S,4R)-2-(5-((2-((2S,4R)-1-((benzyloxy)carbonyl)-4-ethoxy-2-pyrrolidinyl)-1H-benzimidazol-6-yl)ethynyl)-1H-benzimidazol-2-yl)-4-ethoxy-1-pyrrolidinecarboxylate | Et | 2.15 min (M-Cond. 2); >95%; LC/MS: Anal. Calcd. for [M + H]$^+$ C$_{44}$H$_{45}$N$_6$O$_6$: 753.34; found: 753.69. |
| F10 | benzyl (2S,4R)-2-(5-((2-((2S,4R)-1-((benzyloxy)carbonyl)-4-tert-butoxy-2-pyrrolidinyl)-1H-benzimidazol-6-yl)ethynyl)-1H-benzimidazol-2-yl)-4-tert-butoxy-1-pyrrolidinecarboxylate | t-Bu | 2.63 min (D-Cond. 1b); LC/MS: Anal. Calcd. for [M + H]$^+$ C$_{48}$H$_{53}$N$_6$O$_6$: 809.40; found: 809.59. HRMS: Anal. Calcd. for [M + H]$^+$ C$_{48}$H$_{53}$N$_6$O$_6$: 809.4027; found 809.4032. |

Example F8-F10

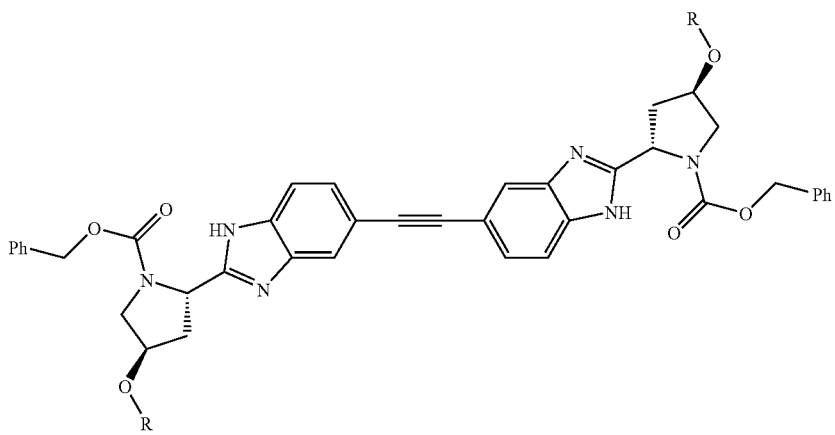

Example F11 benzyl(2S,4R)-2-(5-((2-((2S,4R)-1-((benzyloxy)carbonyl)-4-hydroxy-2-pyrrolidinyl)-1H-benzimidazol-6-yl)ethynyl-1H-benzimidazol-2-yl)-4-hydroxy-1-pyrrolidinecarboxylate

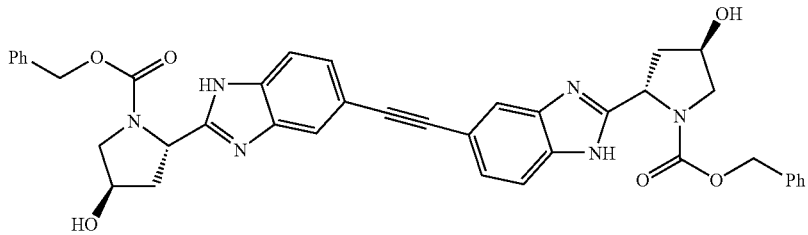

Example F11 was prepared from Example F10 according to the procedure described for the preparation of pyrrolidine M1c. LC (D-Cond. 1a): 1.80 min; LC/MS: Anal. Calcd. for [M+H]$^+$ C$_{40}$H$_{37}$N$_6$O$_6$: 697.28. found: 697.37. HRMS: Anal. Calcd. for [M+H]$^+$ C$_{40}$H$_{37}$N$_6$O$_6$: 697.2775. found 697.2779.

Example OL1 benzyl((1S)-1-(5-(2-(2-((1)-1-(((benzyloxy)carbonyl)amino)ethyl)-1H-benzimidazol-6-yl)ethyl)-1H-benzimidazol-2-yl)ethyl)carbamate

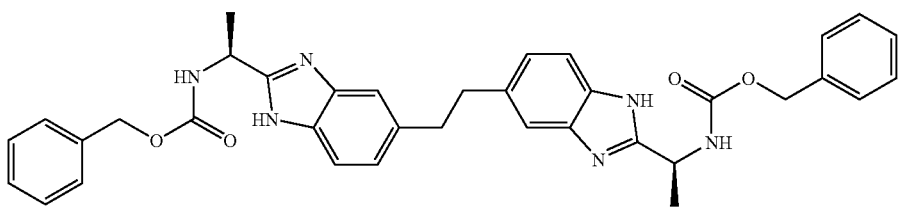

Example OL1

Step a

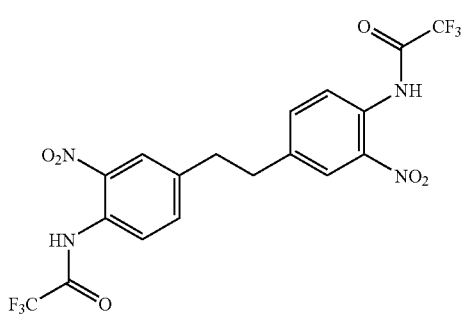

4,4'-Ethylenedianiline (2.5 g, 11.78 mmol) was suspended in trifluoroacetic acid (20 mL) and cooled to 0° C. (ice-water bath). Trifluoroacetic anhydride (10 mL, 31.23 mmol) was added dropwise, followed by addition of KNO$_3$ (2.38 g, 23.56 mmol). The mixture was stirred at 0° C. for 2 h and then poured onto ice-cooled water. The solid was filtered off and dissolved in EtOAc. The organic layer was washed with water and brine, dried (MgSO$_4$), filtered and concentrated in vacuo. A brownish solid corresponding to bis nitro trifluoroacetamide OL1a was recovered (4.96 g) and used without further purification. $^1$H NMR (500 MHz, DMSO-d$_6$) δ ppm 11.62 (s, 2H), 8.02 (d, J=1.53 Hz, 2H), 7.70 (dd, J=8.09, 1.68 Hz, 2H), 7.54 (d, J=8.24 Hz, 2H), 3.05 (s, 4H). LC (OL-Cond. 1a): RT=2.06 min; >95% homogeneity index. LC/MS: Anal. Calcd. for [M+Na]$^+$ C$_{18}$H$_{12}$F$_6$N$_4$NaO$_6$: 517.05. found: 517.04.

Example OL1

Step b

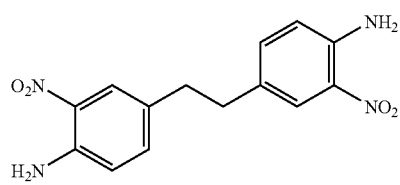

A solution of K$_2$CO$_3$ (1.73 g, 12.6 mmol) in water (25 mL) was added to a solution of bis-nitrotrifluoroacetamide OL1a (2.5 g, 5.03 mmol) in MeOH (75 mL) and the resulting mixture was stirred at rt for 4 h. Volatiles were removed under reduced pressure and the remaining orange residue was taken up in EtOAc (50 ml). The organic layer was then washed with water and brine, dried (MgSO$_4$), filtered and concentrated in vacuo. A bright orange solid corresponding to the bis nitro aniline OL 1b was recovered (1.48 g) and it was used without further purification. $^1$H NMR (500 MHz, DMSO-d$_6$) δ ppm 7.73 (d, J=2.14 Hz, 2H), 7.27 (d, J=2.14 Hz, 1H), 7.26 (s, 5H), 6.91 (d, J=8.85 Hz, 2H), 2.70 (s, 4H) LC/MS: Anal. Calcd. for [M+H]$^+$ C$_{14}$H$_{15}$N$_4$O$_4$: 303.11. found: 303.12.

Example OL1

Step c

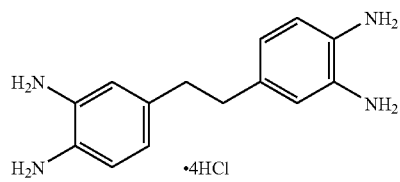

Nitroaniline OL1b (0.26 g, 0.87 mmol) was suspended in EtOAc (20 mL) and MeOH (15 mL) and the mixture was charged with Pd(OH)$_2$ (150 mg). After flushing the flask with N$_2$ three times, the reaction was placed under 1 atm. of H$_2$ (balloon) and stirred at rt for 4 h. The black suspension was filtered through a pad of diatomaceous earth (Celite®) and the filtrate was treated with 4N HCl in Ether (2N, 2 mL). Volatiles were removed under vacuo and the residue was triturated with Et$_2$O. The resulting tan solid (0.26 g) was filtered, washed with Et$_2$O and dried under vacuo. Used without further purification. $^1$H NMR (500 MHz, DMSO-d$_6$) δ ppm 8.57 (br. s., 12H), 7.00 (d, J=7.93 Hz, 2H), 6.80 (s, 2H), 6.66 (d, J=7.93 Hz, 2H), 2.70 (s, 4H). LC/MS: Anal. Calcd. for [M+H]$^+$ C$_{14}$H$_{19}$N$_4$: 243.16. found: 243.17.

Example OL1

EDCI.HCl (77.2 mg, 0.4 mmol) was added to a mixture of 3,3',4,4'-bibenzyltetramine OL 1e (71 mg, 0.183 mmol), N-Cbz-L-alanine (86 mg, 0.38 mmol), 1-hydroxybenzotriazole (59 mg, 0.44 mmol) and Et$_3$N (0.13 mL, 0.91 mmol) in DMF (3 mL), and stirred at rt overnight. The mixture was then diluted with EtOAc, washed with water (2×) and brine, dried (MgSO$_4$), filtered and concentrated in vacuo to provide an off white solid. Acetic acid (10 mL) was added to the residue, and the mixture was heated at 65° C. for 30 min. The volatile component was removed in vacuo, and the residue was dissolved in EtOAc and washed with saturated NaHCO$_3$ solution (2×), and the organic phase was dried (MgSO$_4$), filtered and concentrated in vacuo. The residue was purified with a reverse phase HPLC (MeOH/H$_2$O/TFA) to provide the TFA salt of Example OL1 as an off-white solid (21 mg). $^1$H NMR (500 MHz, DMSO-d$_6$) δ ppm 14.57 (br. s., 2H), 8.19 (br. s., 2H), 7.60 (d, J=7.93 Hz, 2H), 7.52 (br. s., 2H), 7.29-7.41 (m, 12H), 4.97-5.14 (m, 6H), 3.12 (s, 4H), 1.58 (d, J=7.02 Hz, 6H). LC (OL-Cond. 1): RT=2.38 min; >95% homogeneity index. LC/MS: Anal. Calcd. for [M+H]$^+$ C$_{36}$H$_{37}$N$_6$O$_4$: 617.29. found: 617.24.

Example OL2-OL10

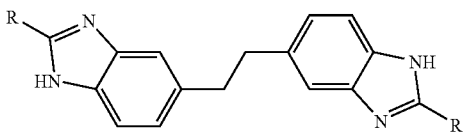

Examples OL2-OL12 were prepared from intermediate OL1c and appropriate acids by employing the EDCI-coupling condition described and a reverse phase HPLC (H$_2$O/MeOH/TFA) purification system. Final products were isolated as TFA salts. The Cbz protected amino acid coupling partners were obtained from commercial sources unless noted otherwise.

| Example | Compound Name | R | RT (LC-Cond.); % homogeneity index; MS data |
|---|---|---|---|
| OL2 | benzyl ((1R)-1-(5-(2-(2-((1R)-1-(((benzyloxy)carbonyl)amino)-2-tert-butoxyethyl)-1H-benzimidazol-6-yl)ethyl)-1H-benzimidazol-2-yl)-2-tert-butoxyethyl)carbamate | | 1.67 min (OL-Cond. 1a); >95%; LC/MS: Anal. Calcd. for [M +H]$^+$ C$_{44}$H$_{53}$N$_6$O$_6$: 761.40; found: 761.42. HRMS: Anal. Calcd. for [M +H]$^+$ C$_{44}$H$_{53}$N$_6$O$_6$: 761.4027; found 761.4019 |
| OL3 | benzyl (2S)-2-(5-(2-(2-((2S)-1-(((benzyloxy)carbonyl)-5-oxo-2-pyrrolidinyl)-1H-benzimidazol-6-yl)ethyl)-1H-benzimidazol-2-yl)-5-oxo-1-pyrrolidinecarboxylate | | 1.44 min (OL-Cond. 1a); >95%; LC/MS: Anal. Calcd. for [M +Na]$^+$ C$_{40}$H$_{36}$N$_6$NaO$_6$: 719.26; found: 719.32. HRMS: Anal. Calcd. for [M +H]$^+$ C$_{40}$H$_{36}$N$_6$O$_6$: 697.2775; found 697.2770 |
| OL4 | benzyl ((1S)-1-(5-(2-(2-((1S)-1-(((benzyloxy)carbonyl)amino)-3-(methylsulfanyl)propyl)-1H-benzimidazol-6-yl)ethyl)-1H-benzimidazol-2-yl)-3-(methylsulfanyl)propyl)carbamate | | 1.60 min (OL-Cond. 1a); >95%; LC/MS: Anal. Calcd. for [M +H]$^+$ C$_{40}$H$_{45}$N$_6$O$_4$S$_2$: 737.29; found: 737.36. HRMS: Anal. Calcd. for [M +H]$^+$ C$_{40}$H$_{45}$N$_6$O$_4$S$_2$: 737.2944; found 737.2949 |

-continued

| Example | Compound Name | R group | RT (LC-Cond.); % homogeneity index; MS data |
|---|---|---|---|
| OL5 | benzyl (2S,4R)-2-(5-(2-(2-((2S,4R)-1-((benzyloxy)carbonyl)-4-tert-butoxy-2-pyrrolidinyl)-1H-benzimidazol-6-yl)ethyl)-1H-benzimidazol-2-yl)-4-tert-butoxy-1-pyrrolidinecarboxylate | (structure: 4-tert-butoxy pyrrolidine with N-CBz) | 1.68 min (OL-Cond. 1a); >95%; LC/MS: Anal. Calcd. for [M +H]$^+$ C$_{48}$H$_{57}$N$_6$O$_6$: 813.43; found: 813.52. HRMS: Anal. Calcd. for [M +H]$^+$ C$_{48}$H$_{57}$N$_6$O$_6$: 813.4340; found 813.4316 |
| OL6 | benzyl ((1R)-1-(5-(2-(2-(1R)-1-(((benzyloxy)carbonyl)amino)ethyl-1H-benzimidazol-6-yl)ethyl)-1H-benzimidazol-2-yl)ethyl)carbamate | (structure: Cbz-NH-CH(CH$_3$)-) | 1.47 min (OL-Cond. 1a); >95%; LC/MS: Anal. Calcd. for [M +H]$^+$ C$_{36}$H$_{37}$N$_6$O$_4$: 617.29; found: 617.20. HRMS: Anal. Calcd. for [M +H]$^+$ C$_{36}$H$_{37}$N$_6$O$_4$: 617.2876; found 617.2868 |
| OL7 | benzyl ((1S)-1-(5-(2-(2-((1S)-1-(((benzyloxy)carbonyl)amino)propyl)-1H-benzimidazol-6-yl)ethyl)-1H-benzimidazol-2-yl)propyl)carbamate | (structure: Cbz-NH-CH(Et)-) | 1.49 min (OL-Cond. 1a); >95%; LC/MS: Anal. Calcd. for [M +H]$^+$ C$_{38}$H$_{41}$N$_6$O$_4$: 645.32; found: 645.20. HRMS: Anal. Calcd. for [M +H]$^+$ C$_{38}$H$_{41}$N$_6$O$_4$: 645.3189; found 645.3194 |
| OL8 | 1-benzyl 4-tert-butyl 2-(5-(2-(2-(1-((benzyloxy)carbonyl)-4-(tert-butoxycarbonyl)-2-piperazinyl)-1H-benzimidazol-6-yl)ethyl)-1H-benzimidazol-2-yl)-1,4-piperazinedicarboxylate | (structure: piperazine with N-Boc and N-Cbz) | 1.77 min (OL-Cond. 1a); >95%; LC/MS: Anal. Calcd. for [M +H]$^+$ C$_{50}$H$_{59}$N$_8$O$_8$: 899.44; found: 899.28. HRMS: Anal. Calcd. for [M +H]$^+$ C$_{50}$H$_{59}$N$_8$O$_8$: 899.4456; found 899.4447 |
| OL9 | tert-butyl (3S)-3-(((benzyloxy)carbonyl)amino)-3-(5-(2-(2-((1S)-1-(((benzyloxy)carbonyl)amino)-3-tert-butoxy-3-oxopropyl)-1H-benzimidazol-6-yl)ethyl)-1H-benzimidazol-2-yl)propanoate | (structure: Cbz-NH-CH(CH$_2$CO$_2$tBu)-) | 1.75 min (OL-Cond. 1a); >95%; LC/MS: Anal. Calcd. for [M +H]$^+$ C$_{46}$H$_{53}$N$_6$O$_8$: 817.39; found: 817.20. HRMS: Anal. Calcd. for [M +H]$^+$ C$_{46}$H$_{53}$N$_6$O$_8$: 817.3925; found 817.3909 |
| OL10 | tert-butyl (4S)-4-(((benzyloxy)carbonyl)amino)-4-(5-(2-(2-((1S)-1-(((benzyloxy)carbonyl)amino)-4-tert-butoxy-4-oxobutyl)-1H-benzimidazol-6-yl)ethyl)-1H-benzimidazol-2-yl)butanoate | (structure: Cbz-NH-CH(CH$_2$CH$_2$CO$_2$tBu)-) | 1.76 min (OL-Cond. 1a); >95%; LC/MS: Anal. Calcd. for [M +H]$^+$ C$_{48}$H$_{57}$N$_6$O$_8$: 845.42; found: 845.31. HRMS: Anal. Calcd. for [M +H]$^+$ C$_{48}$H$_{57}$N$_6$O$_8$: 845.4238; found 845.4238 |

Example OL11 benzyl 4-acetyl-2-(5-(2-(2-(4-acetyl-1-((benzyloxy)carbonyl)-2-piperazinyl)-1H-benzimidazol-6-yl)ethyl)-1H-benzimidazol-2-yl)-1-piperazinecarboxylate (br. s., 1H), 4.23 (d, J=11.90 Hz, 1H), 3.75-4.07 (m, 3H), 3.61 (dd, J=13.58, 3.20 Hz, 2H), 3.26 (t, J=11.90 Hz, 2H), 3.00 (d, J=6.41 Hz, 4H), 2.68-2.81 (m, 1H), 1.84-2.03 (m, 6H). LC (OL-Cond. 1a): RT=1.51 min; >90% homogeneity index. LC/MS: Anal. Calcd. for [M+H]+ $C_{44}H_{47}N_8O_6$: 783.36. found: 783.27.

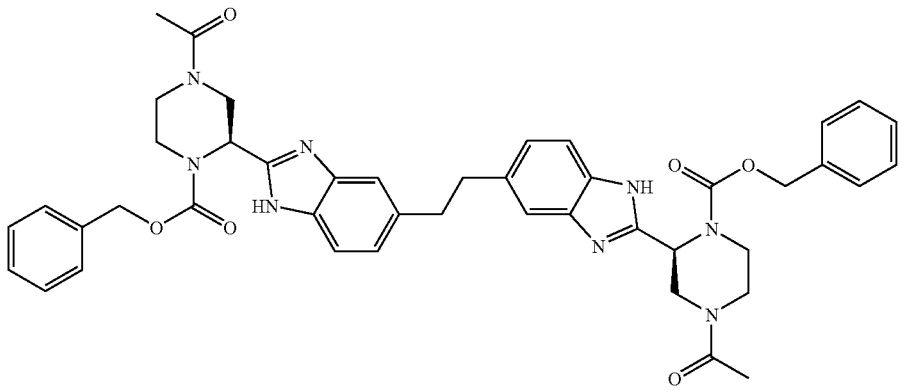

Example OL11

Step a

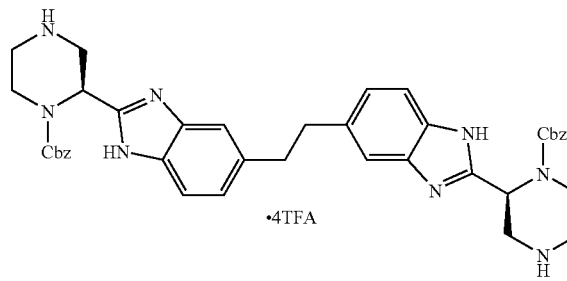

Example OL12-OL13

A solution of bispiperazine OL8 (0.23 g, 0.268 mmol) in 20% TFA/CH$_2$Cl$_2$ (5 mL) was stirred at room temperature until the deprotection was complete (~1 h). The volatile component was removed in vacuo and the resultant residue was triturated with hexanes. The sample was used in the next step without further purification. $^1$H NMR (500 MHz, DMSO-d$_6$) δ ppm 9.40 (br. s., 2H), 7.51 (d, J=7.93 Hz, 2H), 7.24-7.47 (m, 12H), 7.15 (d, J=7.93 Hz, 2H), 5.78 (br. s., 2H), 5.20 (br. s., 4H), 4.16 (d, J=13.12 Hz, 2H), 3.98 (d, J=12.51 Hz, 2H), 3.52 (d, J=12.21 Hz, 2H), 3.19 (br. s., 6H), 2.98-3.09 (m, 4H), 2.88 (br. s., 2H). LC (OL-Cond. 1a): RT=1.48 min; >95% homogeneity index. LC/MS: Anal. Calcd. for [M+H]+ $C_{40}H_{43}N_8O_4$: 699.34. found: 699.24.

Example OL11

Acetyl chloride (24 μL, 0.34 mmol) was added to a solution of bisamine OL-11a (40 mg, 0.035 mmol) and Et$_3$N (50 μL, 0.35 mmol) in THF (3 mL). The resulting mixture was stirred at rt for 3 h followed by addition of 2N NH$_3$ in MeOH (1 mL). Stirring continued for 0.5 h and the volatiles were removed under vacuo. Residue was taken up in EtOAc and the organic layer was washed with water, dried (MgSO$_4$), filtered and concentrated under vacuo to provide the TFA salt of Example OL11 as an off-white solid (20.1 mg). $^1$H NMR (500 MHz, DMSO-d$_6$) δ ppm 12.11-12.45 (m, 2H), 6.97-7.58 (m, 17H), 5.30-5.57 (m, 2H), 5.01-5.27 (m, 4H), 4.81 (br. s., 1H), 4.50

Example OL12-OL13 were prepared from intermediate OL11a and appropriate acids chlorides, and products were purified by a reverse phase HPLC (H$_2$O/MeOH/TFA). Final products were isolated as TFA salts. The acid chlorides were obtained from commercial sources unless noted otherwise.

| Example | Compound Name | R | RT (LC-Cond.); % homogeneity index; MS data |
|---|---|---|---|
| OL12 | benzyl 2-(5-(2-(2-(1-((benzyloxy)carbonyl)-4-(cyclopropylcarbonyl)-2-piperazinyl)-1H-benzimidazol-6-yl)ethyl)-1H-benzimidazol-2-yl)-4-(cyclopropylcarbonyl)-1-piperazinecarboxylate | cyclopropyl | 1.57 min (OL-Cond. 1a); >95%; LC/MS: Anal. Calcd. for [M+H]+ $C_{48}H_{51}N_8O_6$: 835.39; found: 835.40. HRMS: Anal. Calcd. for [M+H]+ $C_{48}H_{51}N_8O_6$: 835.3917; found 835.3956 |

-continued

| Example | Compound Name | R | RT (LC-Cond.); % homogeneity index; MS data |
|---|---|---|---|
| OL13 | benzyl 2-(5-(2-(2-(1-((benzyloxy)carbonyl)-4-isonicotinoyl-2-piperazinyl)-1H-benzimidazol-6-yl)ethyl)-1H-benzimidazol-2-yl)-4-isonicotinoyl-1-piperazinecarboxylate | (4-pyridyl) | 1.57 min (OL-Cond. 1a); >95%; LC/MS: Anal. Calcd. for $[M+H]^+$ $C_{52}H_{49}N_{10}O_6$: 909.38; found: 909.40. HRMS: Anal. Calcd. for $[M+H]^+$ $C_{52}H_{49}N_{10}O_6$: 909.3837; found 909.3837 |

Example OL14 benzyl(((1S)-1-(5-(2-(2-(((1S)-1-((((benzyloxy)carbonyl)amino)-3-(dimethylamino)-3-oxopropyl)-1H-benzimidazol-6-yl)ethyl)-1H-benzimidazol-2-yl)-3-(dimethylamino)-3-oxopropyl)carbamate A solution of OL9 (0.34 g, 0.42 mmol) in 20% TFA/CH$_2$Cl$_2$ (10 mL) was stirred at room temperature until the deprotection was complete (~1 h). The volatile component was removed in vacuo and the resultant residue was triturated with hexanes. The sample was used in the next step without further purification. $^1$H NMR (500 MHz, DMSO-d$_6$) δ ppm 13.48 (br. s. 2H), 8.17 (br. s., 2H), 7.53 (d, J=7.63 Hz, 2H) 7.45 (br. s., 2H), 7.36 (br. s., 6H), 7.29-7.34 (m, 3H), 7.06-7.27 (m, 3H), 5.25 (q, J=7.02 Hz, 2H), 5.09 (d, J=12.51 Hz, 2H), 5.01 (d, J=12.51 Hz, 2H), 3.07-3.16 (m, 2H), 3.07 (s, 4H), 2.92 (dd, J=16.48, 7.63 Hz, 2H). LC (OL-Cond. 1a): RT=1.48 min; >95% homogeneity index. LC/MS: Anal. Calcd. for $[M+H]^+$ $C_{38}H_{37}N_6O_8$: 705.27. found: 705.19.

Example OL14

EDCI.HCl (25 mg, 0.129 mmol) was added to a mixture of OL14a (58 mg, 0.062 mmol), N,N-dimethyl amine hydrochloride (13 mg, 0.155 mmol), 1-hydroxy-benzotriazole (18 mg, 0.137 mmol) and Et$_3$N (24.5 μL, 0.248 mmol) in CH$_2$Cl$_2$ (5 mL), and stirred at rt for 24 h. The volatile component was removed in vacuo, and the residue was purified with a reverse phase HPLC (MeOH/H$_2$O/TFA) to provide the TFA salt of Example OL14 as an off-white solid (17 mg). $^1$H NMR (500

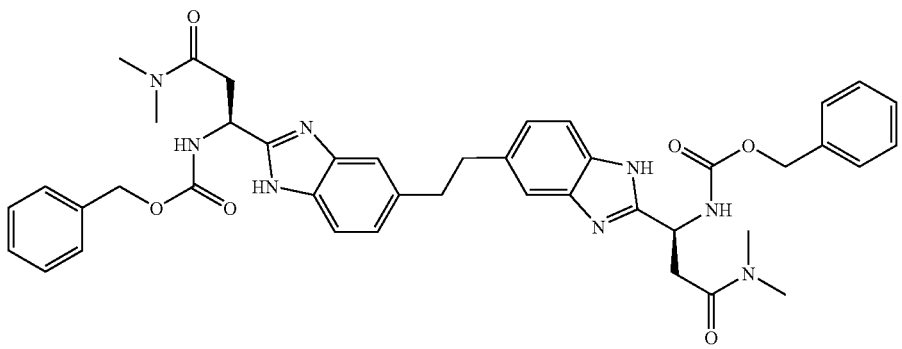

Example OL14

Step a

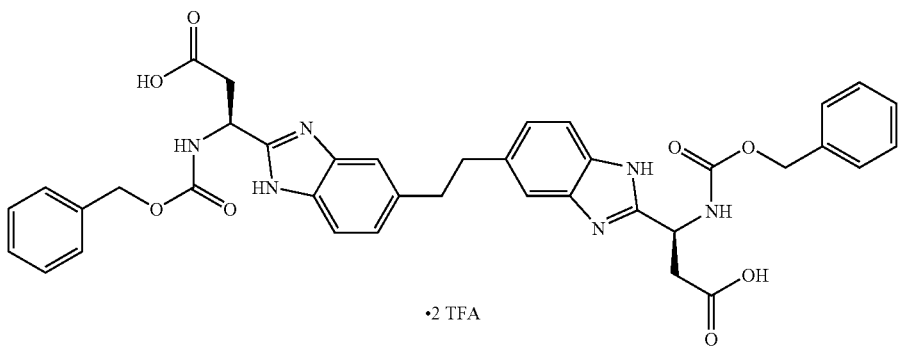

MHz, DMSO-d$_6$) δ ppm 8.10 (br. s., 2H), 7.59 (d, J=6.71 Hz, 2H), 7.51 (br. s., 2H), 7.36 (d, J=3.66 Hz, 8H), 7.27-7.34 (m, 6H), 5.27-5.39 (m, 2H), 5.07 (d, J=12.21 Hz, 2H), 5.00 (d, J=12.21 Hz, 2H), 3.16 (br. s., 4H), 3.03-3.12 (m, 6H), 2.94 (s, 6H), 2.78 (s, 6H). LC (OL-Cond. 1a): RT=1.51 min; >95% homogeneity index. LC/MS: Anal. Calcd. for [M+H]+ $C_{42}H_{47}N_8O_6$: 759.36. found: 759.65.

Example OL15

(2R,2'R)—N,N'-(1,2-ethanediylbis(1H-benzimidazole-5,2-diyl(1S)-1,1-ethanediyl))ditetrahydro-2-furancarboxamide

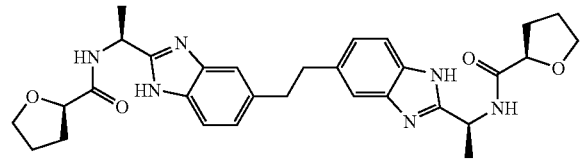

Example OL15

Step a

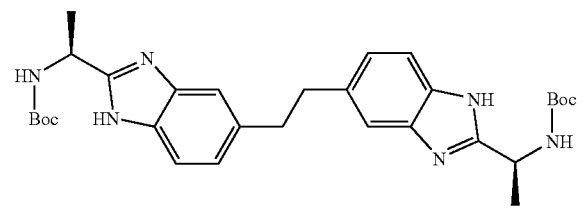

Intermediate OL15a was prepared according to the procedure described for Example OL1 with the exception that (L)-Boc-alanine was used instead of the (L)-Cbz-alanine. $^1$H NMR (500 MHz, DMSO-$d_6$) δ ppm 11.96 (d, 2H), 7.42 (d, J=7.93 Hz, 1H), 7.36 (br. s., 1H), 7.30 (t, J=8.24 Hz, 3H), 7.21 (d, J=5.49 Hz, 1H), 7.00 (d, J=7.32 Hz, 2H), 4.73-4.88 (m, 2H), 2.99 (br. s., 4H), 1.45 (d, J=7.02 Hz, 6H), 1.40 (br. s., 18H). LC (OL-Cond. 1a): RT=1.38 min; >95% homogeneity index. LC/MS: Anal. Calcd. for [M+H]+ $C_{30}H_{41}N_6O_4$: 549.32. found: 549.74.

Example OL15

Step b

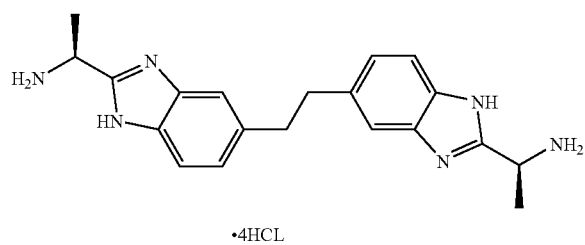

•4HCL

A solution of OL15a (0.40 g, 0.73 mmol) and a 4M solution of HCl in dioxanes (10 mL) were combined in $CH_2Cl_2$ (50 mL) and stirred at room temperature until the deprotection was complete (~2 h). The volatile component was removed in vacuo and the resultant residue was triturated with $Et_2O$. The recovered tan solid was used in the next step without further purification. $^1$H NMR (500 MHz, DMSO-$d_6$) δ ppm 9.40 (br. s., 2H), 7.51 (d, J=7.93 Hz, 2H), 7.24-7.47 (m, 12H), 7.15 (d, J=7.93 Hz, 2H), 5.78 (br. s., 2H), 5.20 (br. s., 4H), 4.16 (d, J=13.12 Hz, 2H), 3.98 (d, J=12.51 Hz, 2H), 3.52 (d, J=12.21 Hz, 2H), 3.19 (br. s., 6H), 2.98-3.09 (m, 4H), 2.88 (br. s., 2H). LC (OL-Cond. 1a): RT=0.88 min; >95% homogeneity index. LC/MS: Anal. Calcd. for [M+H]+ $C_{20}H_{25}N_6$: 349.21. found: 349.70.

Example OL15

EDCI.HCl (44 mg, 0.23 mmol) was added to a mixture of OL15b (50 mg, 0.104 mmol), (R)-tetrahydrofuran-2-carboxylic acid (21 μL, 0.218 mmol) and $Et_3N$ (72.5 μL, 0.52 mmol) in DMF (3 mL), and stirred at rt for 15 h. The volatile component was removed in vacuo, and the residue was purified with a reverse phase HPLC (MeOH/$H_2O$/TFA) to provide the TFA salt of Example OL15 as a white solid (22 mg). $^1$H NMR (500 MHz, DMSO-$d_6$) δ ppm 8.51 (d, 2H), 7.60 (d, J=8.24 Hz, 2H), 7.51 (s, 2H), 7.32 (d, J=7.93 Hz, 2H), 5.25 (quin, J=6.94 Hz, 2H), 4.29 (dd, J=8.09, 5.65 Hz, 2H), 3.87-3.95 (m, 2H), 3.79 (q, J=7.02 Hz, 2H), 3.11 (s, 4H), 2.08-2.18 (m, 2H), 1.77-1.96 (m, 6H), 1.60 (d, J=7.02 Hz, 6H) (note: imidazole proton signals were too broad to be able to assign a chemical shift). LC (OL-Cond. 1a): RT=1.27 min; >95% homogeneity index. LC/MS: Anal. Calcd. for [M+H]+ $C_{30}H_{37}N_6O_4$: 545.29. found: 545.26.

Example JG1

(2R,2'R)-1,1'-(2,5-furandiylbis(1H-benzimidazole-5,2-diyl(2S)-2,1-pyrrolidinediyl))bis(1-oxo-2-phenyl-2-propanol)

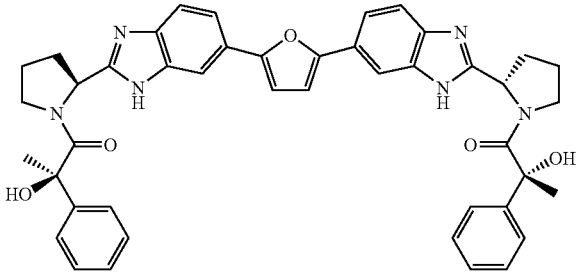

Example JG1

Step a

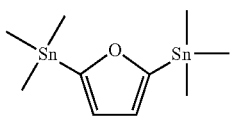

Sec-butyllithium (107 mL, 150 mmol) was added dropwise to a solution of furan (4.4 mL, 60 mmol) and tetramethylethylenediamine (22.60 mL, 150 mmol) in hexanes (150 mL) at 0° C. After 1 hour, the reaction mixture was warmed to room temperature and stirred for four hours. The mixture was cooled to 0° C. and trimethyltin chloride (32.3 g, 162 mmol) in hexanes (50 mL) was added dropwise. The mixture was warmed to room temperature and stirred overnight (17 h). Saturated ammonium chloride (150 mL) was added and the layers separated. Organic phase was washed with saturated aqueous copper sulfate, dried over anhydrous sodium sulfate, filtered, and concentrated under reduced pressure to give JG1a as an orange oil. The material was used for the next step without further purification. $^1$H NMR (500 MHz, DMSO-$d_6$) δ ppm 6.65 (s, 2H), 0.30 (s, 18H).

Example JG1

Step b

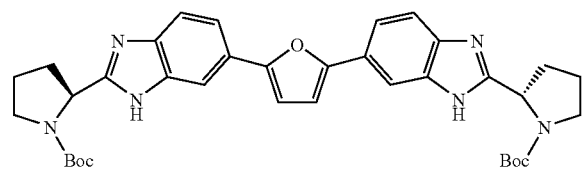

A solution of furyl stannane JG1a (0.35 g, 0.91 mmol) in THF (4 mL) was added to a suspension of Pd$_2$(dba)$_3$ (0.033 g, 0.180 mmol), triphenyl arsine (0.044 g, 0.13 mmol), and iodide M47b (0.75 g, 1.81 mmol) in THF (14 mL) and heated at 50° C. for 20 h. The volatile component was removed in vacuo, and a silica gel mesh was prepared directly from the resultant residue and submitted to flash chromatography (silica gel; 0-100% EtOAc/CH$_2$Cl$_2$) to provide 1.05 g of furan JG1b as a tan solid. $^1$H NMR (500 MHz, DMSO-$d_6$) δ ppm: 7.92 (br. s., 2H), 7.64 (d, J=8.24 Hz, 2H), 7.62-7.54 (m, 2H), 7.00 (s, 2H), 5.04-4.94 (m, 2H), 3.63 (br. s., 2H), 3.50-3.40 (m, 2H), 2.37 (m, 2H), 2.06-1.93 (m 6H), 1.43 (s, 8H), 1.10 (s, 10H). LC: (JG-Cond.1): RT=2.52 min; >95% homogeneity index. LC/MS: Anal. Calcd. for [M+H]$^+$ C$_{36}$H$_{43}$N$_6$O$_5$: 639.32. found 639.69.

Example JG1

Step c

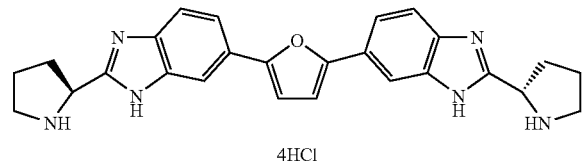

4HCl 4.0 M HCl in dioxanes (1.64 mL, 6.56 mmol) was added to a suspension of furan JG1b (1.05 g, 1.64 mmol) in dioxanes (3.2 mL) and stirred for 4 h at rt. The volatile component was removed in vacuo and the HCl salt of furan JG1c was isolated as a brown solid. Material was used for next steps without further purification. LC: (JG-Cond. 1): RT=0.09 min; >95% homogeneity index. LC/MS: Anal. Calcd. for [M+H]$^+$ C$_{26}$H$_{27}$N$_6$O: 439.22. found 439.19.

Example JG1

HATU (42.0 mg, 0.108 mmol) was added to a mixture of furan JG1c (30.0 mg, 0.051 mmol), (R)-2-hydroxy-2-phenyl-propanoic acid (18.0 mg, 0.108 mmol) and DIEA (54 μL, 0.308 mmol) in DMF (1.5 mL), and the mixture was stirred for 3 h at rt. The volatile component was removed in vacuo and the residue was purified with a reverse phase HPLC (MeOH/H$_2$O/TFA) to provide the TFA salt of Example JG 1 as an off-white solid (12.9 mg). $^1$H NMR (500 MHz, DMSO-$d_6$) δ ppm 8.12 (br. s., 1H), 8.11-7.98 (m, 2H), 7.82-7.95 (m, 2H), 7.45 (d, J=4.27 Hz, 4.5H), 7.40-7.21 (m, 7.5H), 6.08 (br. s., 1H), 5.25 (d, J=7.32 Hz, 2H), 3.87 (br. s., 2H), 3.55 (br. s., 1H), 3.06 (br. s., 0.7H), 2.66 (br. s., 0.3H), 2.39-2.21, (m, 1H), 2.07 (br. s., 3H), 1.88 (br. s., 3H), 1.71 (br. s., 1H), 1.53 (d, J=18.31 Hz, 6H). LC: (JG-Cond. 2): RT=2.59 min; >95% homogeneity index. LRMS: Anal. Calcd. for [M+H]$^+$ C$_{44}$H$_{43}$N$_6$O$_5$: 735.32. found: 735.71. HRMS: Anal. Calcd. for [M+H]$^+$ C$_{44}$H$_{43}$N$_6$O$_5$: 735.3295. found 735.3275.

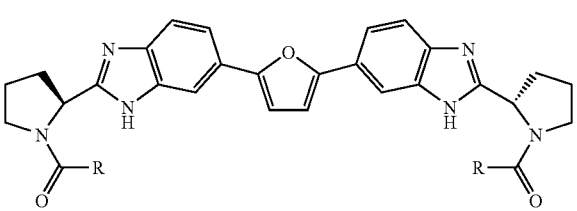

Example JG2-JG4

Example JG2-JG4 were prepared from intermediate JG1c and appropriate acids by employing HATU coupling conditions, and products were purified by a reverse phase HPLC (H$_2$O/MeOH/TFA).

| Example | Compound Name | Coupling protocol; RCO$_2$H source | (Form status of final product) 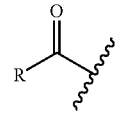 | MS data |
|---|---|---|---|---|
| JG2 | (1R,1'R)-2,2'-(2,5-furandiylbis(1H-benzimidazole-5,2-diyl(2S)-2,1-pyrrolidinediyl))bis(2-oxo-1-phenylethanol) | HATU, DIEA | (structure shown) TFA Salt | 2.28 min (JG-Cond. 2); >95%; LRMS: Anal. Calcd. for [M +H]$^+$ C$_{42}$H$_{39}$N$_6$O$_5$: 707.29; found: 707.55. |

-continued

| Example | Compound Name | Coupling protocol; RCO₂H source | (Form status of final product) | MS data |
|---|---|---|---|---|
| JG3 | (1S,1'S)-2,2'-(2,5-furandiylbis(1H-benzimidazole-5,2-diyl(2S)-2,1-pyrrolidinediyl))bis(2-oxo-1-phenylethanol) | HATU, DIEA | Ph, OH; TFA Salt | 2.33 min (JG-Cond. 2); >95%; LRMS: Anal. Calcd. for [M +H]⁺ C₄₂H₃₉N₆O₅: 707.30; found: 707.67. HRMS: Anal. Calcd. for [M +H]⁺ C₄₂H₃₉N₆O₅: 707.2982; found 707.2995 |
| JG4 | (1R)-2-((2S)-2-(5-(5-(2-((2S)-1-((2R)-2-(dimethylamino)-2-phenylacetyl)-2-pyrrolidinyl)-1H-benzimidazol-6-yl)-2-furyl)-1H-benzimidazol-2-yl)-1-pyrrolidinyl)-N,N-dimethyl-2-oxo-1-phenylethanamine | HATU, DIEA | Me₂N, Ph; TFA Salt | 1.85 min (JG-Cond. 2); >95%; LRMS: Anal. Calcd. for [M +H]⁺ C₄₆H₄₉N₈O₃: 761.39; found: 761.79. HRMS: Anal. Calcd. for [M +H]⁺ C₄₆H₄₉N₈O₃: 761.3927; found 761.3952 |

Example J6-J33

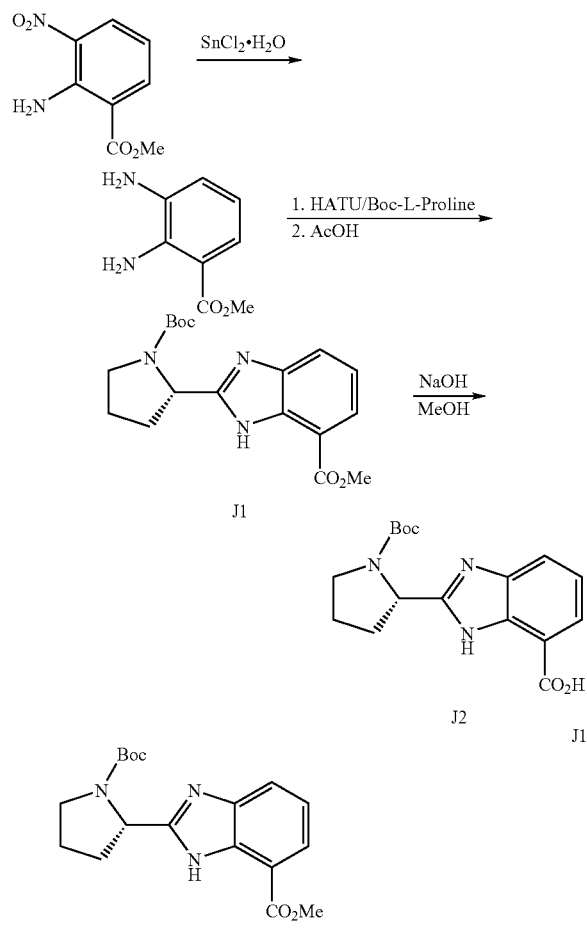

Tin(II)chloride dihydrate (17.25 g, 76.5 mmol) was added in one portion to methyl 2-amino-3-nitrobenzoate (5.0 g, 25.5 mmol) in methanol (100 mL) under nitrogen. The yellow mixture was vigorously stirred at 65° C. for 16 h, and the solvent was removed by rotary evaporation to near dryness. The residue was taken up in EtOAc and the solution was poured into a large beaker containing 1:1 EtOAc/NaHCO₃ soln (300 mL) and stirred 15 min. The precipitates were removed by filtration and the organic layer was separated. The aqueous layer was extracted twice more with EtOAc, and the combined organic layer was washed with saturated NaHCO₃ solution, brine, dried (Na₂SO₄), and filtered. Concentration of the filtrate gave methyl 2,3-diaminobenzoate as a deep red viscous oil (4.1 g, 97%).

HATU (10.66 g, 28.0 mmol) was added in one portion to a stirred solution of methyl 2,3-diaminobenzoate (4.1 g, 24.7 mmol), N-Boc-L-proline (5.49 g, 25.5 mmol), and Hunig's base (4.9 mL, 28.0 mmol) in DMF (50 mL). The reaction mixture was stirred 3 h and solvent removed in vacuo, and the residue was diluted with EtOAc, washed with 0.1N HCl, sat'd NaHCO₃, brine, dried (Na₂SO₄), and filtered. Concentration gave a reddish brown viscous oil which was taken up in glacial acetic acid (60 mL) and heated at 60° C. for 16 h. The solvent was removed in vacuo, and the residue was diluted with EtOAc, washed with sat'd NaHCO₃ soln, brine, dried (Na₂SO₄), and filtered. Concentration gave a residue that was divided into two lots, and each lot was pre-adsorbed onto SiO₂ (CH₂Cl₂), applied to a 40 M Biotage SiO₂ column, and eluted by gradient 10%-100% B (1440 mL); A=Hex; B=EtOAc to give J1, (S)-methyl 2-(1-(tert-butoxycarbonyl)pyrrolidin-2-yl)-1H-benzo[d]imidazole-7-carboxylate (7.05 g, 83%) as a reddish oil. $^1$H NMR (500 MHz, DMSO-$d_6$) δ: 7.86 (d, J=7.9 Hz, 1H), 7.78 (t, J=5 Hz, 1H), 7.28-7.24 (m, 1H), 5.20-5.11 (m, 1H), 3.95 (s, 3H), 3.60-3.52 (m, 1H), 3.43-3.38 (m, 1H), 2.33-2.22 (m, 1H), 2.15-2.0 (m, 2H), 1.91-1.86 (m, 1H), 1.40/1.05 (s, 9H). LC (D-Cond. 2): RT=1.86 min; LC/MS Anal. Calcd. for [M+H]⁺ $C_{18}H_{24}N_3O_4$: 346.18. found 346.26. HRMS: Anal. Calcd. for [M+H]⁺ $C_{18}H_{24}N_3O_4$: 346.1767. found: 346.1776.

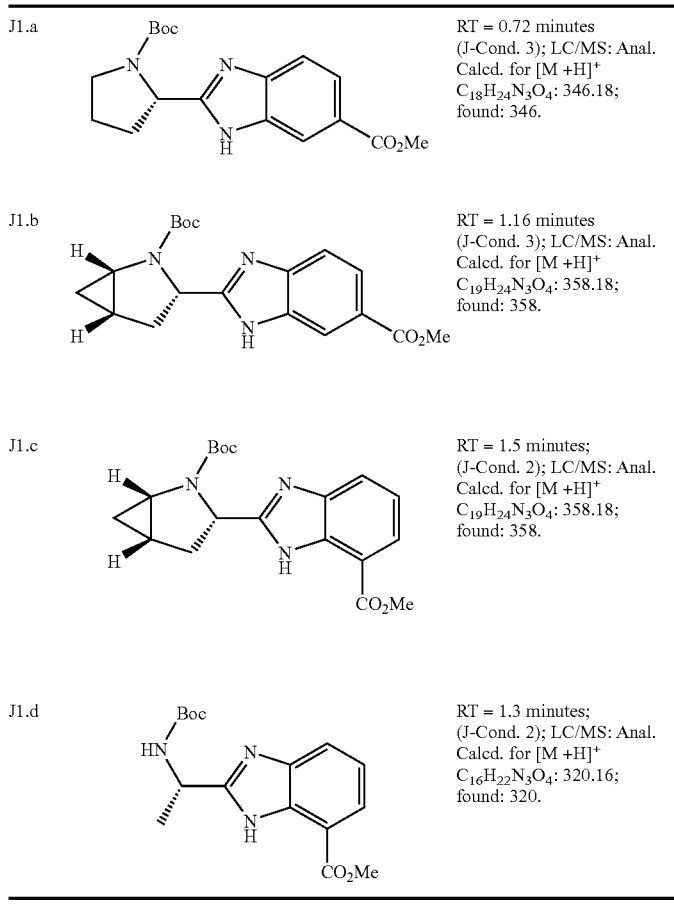

| | | |
|---|---|---|
| J1.a | | RT = 0.72 minutes (J-Cond. 3); LC/MS: Anal. Calcd. for [M +H]$^+$ $C_{18}H_{24}N_3O_4$: 346.18; found: 346. |
| J1.b | | RT = 1.16 minutes (J-Cond. 3); LC/MS: Anal. Calcd. for [M +H]$^+$ $C_{19}H_{24}N_3O_4$: 358.18; found: 358. |
| J1.c | | RT = 1.5 minutes; (J-Cond. 2); LC/MS: Anal. Calcd. for [M +H]$^+$ $C_{19}H_{24}N_3O_4$: 358.18; found: 358. |
| J1.d | | RT = 1.3 minutes; (J-Cond. 2); LC/MS: Anal. Calcd. for [M +H]$^+$ $C_{16}H_{22}N_3O_4$: 320.16; found: 320. |

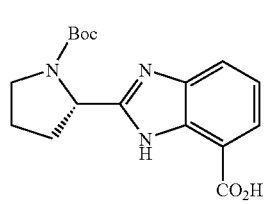

A solution of 5N NaOH (8 mL) was added to methyl ester J1 (7.0 g, 20.3 mmol) in methanol (80 mL) and stirred 8 h. An additional 4 mL 5N NaOH was added and stirring was continued for 18 h, at which time the reaction temperature was raised to 45° C. for a final 8 h to complete the hydrolysis. Most of the methanol was removed by rotary evaporation, and the basic aqueous solution was diluted with EtOAc. A precipitate formed and was isolated by vacuum filtration. The organic layer was separated and washed with brine. Additional lots of precipitate formed during partial concentration to ¼ vol, and the combined lots of J2 (S)-2-(1-(tert-butoxycarbonyl)pyrrolidin-2-yl-1H-benzo[d]imidazole-7-carboxylic acid totaled (5.49 g, 82%). $^1$H NMR (500 MHz, DMSO-d$_6$) δ: 8.04-8.0 (m, 2H), 7.58 (br s, 1H), 5.32 (s, 1H), 3.67-3.63 (m, 1H), 3.47-3.43 (m, 1H), 2.44-2.36 (m, 1H), 2.17-2.11 (m, 1H), 2.05-1.93 (m, 2H), 1.40/1.06 (s, 9H). LC (D-Cond. 2): RT=1.68 min; LC/MS: Anal. Calcd. for [M+H]$^+$ $C_{17}H_{22}N_3O_4$: 332.16. found: 332.25. HRMS: Anal. Calcd. for [M+H]$^+$ $C_{17}H_{22}N_3O_4$: 322.1610. found: 322.1625.

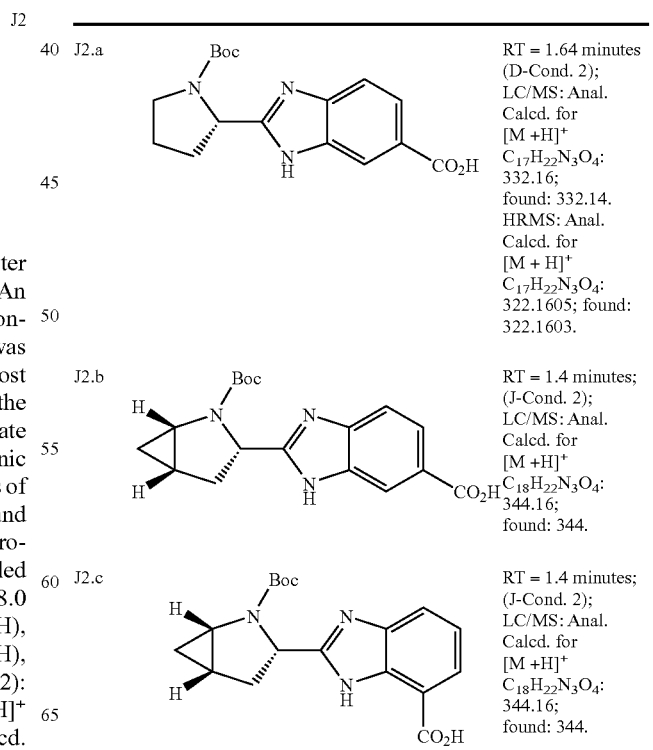

| | | |
|---|---|---|
| J2.a | | RT = 1.64 minutes (D-Cond. 2); LC/MS: Anal. Calcd. for [M +H]$^+$ $C_{17}H_{22}N_3O_4$: 332.16; found: 332.14. HRMS: Anal. Calcd. for [M + H]$^+$ $C_{17}H_{22}N_3O_4$: 322.1605; found: 322.1603. |
| J2.b | | RT = 1.4 minutes; (J-Cond. 2); LC/MS: Anal. Calcd. for [M +H]$^+$ $C_{18}H_{22}N_3O_4$: 344.16; found: 344. |
| J2.c | | RT = 1.4 minutes; (J-Cond. 2); LC/MS: Anal. Calcd. for [M +H]$^+$ $C_{18}H_{22}N_3O_4$: 344.16; found: 344. |

| | | |
|---|---|---|
| J2.d | 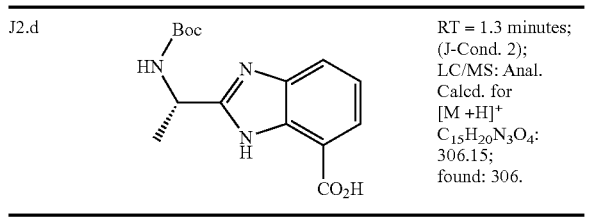 | RT = 1.3 minutes; (J-Cond. 2); LC/MS: Anal. Calcd. for [M+H]$^+$ C$_{15}$H$_{20}$N$_3$O$_4$: 306.15; found: 306. | and the organic layer was separated. The aqueous layer was extracted twice more (EtOAc) and the combined organic layers were washed with brine, dried (Na$_2$SO$_4$), filtered, and concentrated to ¼ volume. 2-Chloro-1-(3,4-diaminophenyl)ethanone, J3, (10.03 g, 59%) was isolated by vacuum filtration as a brick red solid. $^1$H NMR (400 MHz, DMSO-d$_6$) δ: 8.17 (dd, J=8.3, 2.3 Hz, 1H), 7.14 (d, J=2.0 Hz, 1H), 6.51 (d, J=8.0 Hz, 1H), 5.57 (br s, 2H), 4.85 (s, 2H), 4.78 (br. s, 2H). LC (D-Cond. 1a): RT=0.55 min; LC/MS: Anal. Calcd. for [M+H]$^+$ C$_8$H$_{10}$ClN$_2$O: 185.05. found: 185.02. HRMS: Anal.

Synthetic Scheme 2

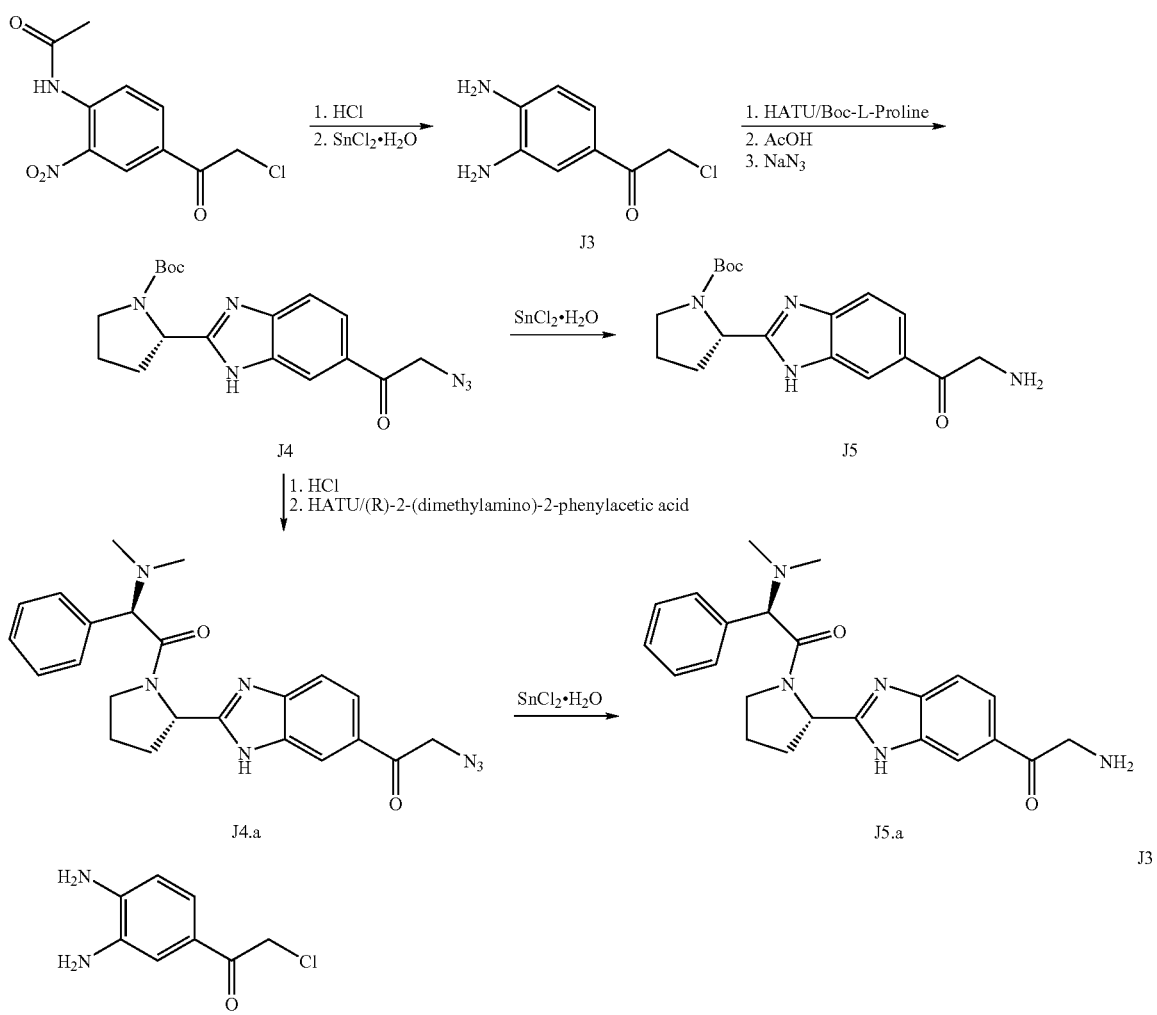

N-(4-(2-Chloroacetyl)-2-nitrophenyl)acetamide (25.7 g, 0.1 mol) was suspended in 250 mL of 3N HCl and heated at 80° C. in a 1 L pressure vessel for 20 h. After being cooled to room temperature, 1-(4-amino-3-nitrophenyl)-2-chloroethanone.HCl (23.2 g, 92%) was isolated by vacuum filtration as a bright, yellow solid. The salt (23.2 g, 0.092 mol) was suspended in methanol (600 mL) and SnCl$_2$.2H$_2$O (65 g, 0.29 mol) was added in one portion. The mixture was heated at 70° C. for 14 h while being vigorously stirred. An additional 20 g of SnCl$_2$.2H$_2$O was added and the reaction stirred 8 h. The solvent was removed by rotary evaporation and the residue was taken up in EtOAc/NaHCO$_3$ soln (caution: much CO$_2$ evolution). The precipitated salts were removed by filtration Calcd. for [M+H]$^+$ C$_8$H$_{10}$ClN$_2$O: 185.0482. found: 185.0480. The reaction was repeated to supply more material.

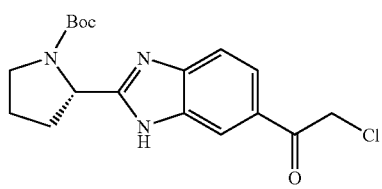

HATU (38.5 g, 101.3 mmol) was added portion wise to a vigorously stirred solution of J3 (17.0 g, 92 mmol), N-Boc-L-proline (19.82 g, 92 mmol), and Hunig's base (17.6 mL, 101.3 mmol) in DMF (200 mL). After 6 h, the reaction mixture was concentrated in vacuo to remove solvent and the residue was taken up in EtOAc, washed with saturated NaHCO$_3$ solution, brine, dried (Na$_2$SO$_4$), and filtered. Concentration yielded a viscous brown oil which was taken up in glacial acetic acid (100 mL) and heated at 60° C. for 20 h. The solvent was removed in vacuo and the residue was taken up in EtOAc, washed with saturated NaHCO$_3$ solution (adjust with 1N NaOH soln until pH=9), brine, and dried (Na$_2$SO$_4$), filtered, and concentrated. The residue obtained upon concentration was pre-adsorbed onto SiO$_2$ (CH$_2$Cl$_2$) and subjected to flash chromatography successively eluting with 50%, 75%, 100% EtOAc/hexanes. (S)-tert-Butyl 2-(6-(2-chloroacetyl)-1H-benzo[d]imidazol-2-yl)pyrrolidine-1-carboxylate (22.37 g, 67%) was obtained as a yellow foam. $^1$H NMR (400 MHz, DMSO-d$_6$) δ: 8.20 (s, 1H), 7.81 (dd, J=8.3, 2.3 Hz, 1H), 7.59 (d, J=8.0 Hz, 1H), 5.24 (s, 2H), 4.99/4.93 (s, 1H), 3.60 (br s, 1H), 3.46-3.41 (m, 1H), 2.36-2.30 (m, 1H), 2.01-1.89 (m, 3H), 1.39/1.06 (s, 9H). LC (D-Cond. 2): RT=1.85 min; LC/MS: Anal. Calcd. for [M+H]$^+$ C$_{18}$H$_{23}$ClN$_3$O$_3$: 364.14. found: 364.20. HRMS: Anal. Calcd. for [M+H]$^+$ C$_{18}$H$_{23}$ClN$_3$O$_3$: 364.1415. found: 364.1428.

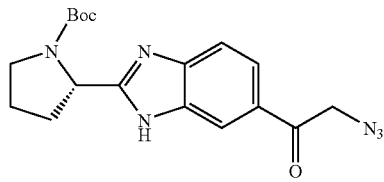

J4

Sodium azide (1.79 g, 27.48 mmol) was added in one portion to a solution of (S)-tert-butyl 2-(6-(2-chloroacetyl)-1H-benzo[d]imidazol-2-yl)pyrrolidine-1-carboxylate (10.0 g, 27.48 mmol) in acetonitrile (200 mL) and stirred at 60° C. for 16 h. The reaction mixture was concentrated to ⅕ volume, diluted with EtOAc, and washed with water and brine prior to being dried (Na$_2$SO$_4$) and filtered. Concentration gave J4 (S)-tert-butyl 2-(6-(2-azidoacetyl)-1H-benzo[d]imidazol-2-yl)pyrrolidine-1-carboxylate (6.8 g, 48%) as a golden orange foam. $^1$H NMR (500 MHz, DMSO-d$_6$) δ: 8.22/8.03 (s, 1H), 7.80-7.75 (m, 1H), 7.65/7.56 (d, J=8.5 Hz, 1H), 4.99-4.93 (m, 3H), 3.60 (br s, 1H), 3.46-3.41 (m, 1H), 2.38-2.27 (m, 1H), 2.01-1.89 (m, 3H), 1.40/1.06 (s, 9H). LC (D-Cond. 2): RT=1.97 min; LC/MS: Anal. Calcd. for [M+H]$^+$ C$_{18}$H$_{23}$N$_6$O$_3$: 371.19. found: 371.32. HRMS: Anal. Calcd. for [M+H]$^+$ C$_{18}$H$_{23}$N$_6$O$_3$: 371.1832. found: 371.1825.

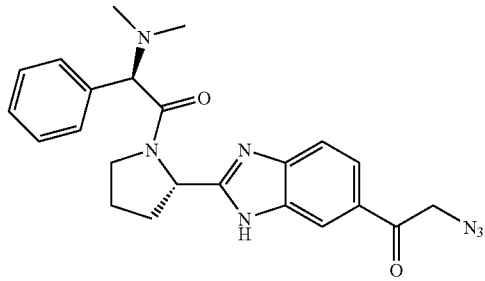

J4.a

To a solution of J4 (1.8 g, 4.86 mmol) in EtOAc (5 mL) was added HCl/Dioxane (10 mL of 4N), and the reaction was stirred 4 hr. The solvents were removed in vacuo, and the HCl salt was exposed to high vacuum for 18 h to give (S)-2-azido-1-(2-pyrrolidin-2-yl)-1H-benzo[d]imidazol-6-yl)ethanone 2HCl as a yellow solid. HATU (1.94 g, 5.10 mmol) was added to the HCl salt of (S)-2-azido-1-(2-(pyrrolidin-2-yl)-1H-benzo[d]imidazol-6-yl)ethanone (1.8 g, 4.86 mmol), (R)-2-(dimethylamino)-2-phenylacetic acid HCl salt (1.05 g, 4.86 mmol), and Hunig's base (3.4 mL, 19.4 mmol) in DMF (50 mL) while being rapidly stirred 6 h. The solvent was removed in vacuo and the reside was partitioned into two lots and separately pre-absorbed onto SiO$_2$ (CH$_2$Cl$_2$), and subjected to flash chromatography on a 40 M Biotage silica gel column pre-equilibrated 2% B, and eluted with 2% B (150 mL); Segment 2: 2-40% B (1200 mL); Segment 3: 40-80% (600 mL). A=CH$_2$Cl$_2$; B=25% MeOH/CH$_2$Cl$_2$ to give J4.a (R)-1-((S)-2-(6-(2-azidoacetyl)-1H-benzo[d]imidazol-2-yl)pyrrolidin-1-yl)-2-(dimethylamino)-2-phenylethanone (combined lots: (1.05 g, 50%)) as a yellow foam. $^1$H NMR (500 MHz, DMSO-d$_6$) δ: 8.16 (s, 1H), 7.82 (dd, J=8.8, 1.5 Hz, 1H), 7.65 (d, J=8.5 Hz, 1H), 7.60-7.56 (m, 5H), 5.51 (s, 1H), 5.22 (dd, J=8.2, 2.8, 1H), 4.95 (m, 2H), 4.09-4.05 (m, 1H), 3.17-3.12 (m, 1H), 2.90/2.84 (br. s, 6H), 2.23-2.19 (m, 1H), 2.21-1.89 (m, 3H). LC (D-Cond. 2): RT=1.53 min; LC/MS: Anal. Calcd. for [M+H]$^+$ C$_{23}$H$_{26}$N$_7$O$_2$: 432.22. found: 431.93. HRMS Anal. Calcd. for [M+H]$^+$ C$_{23}$H$_{26}$N$_7$O$_2$: 432.2148. found: 432.2127.

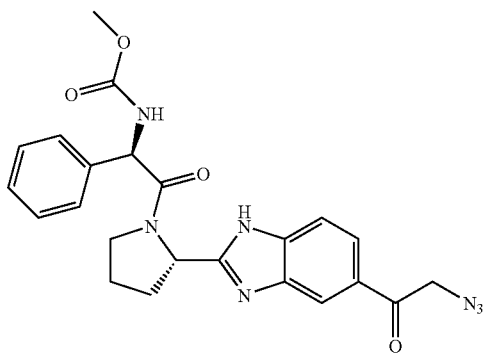

J4.a1

RT = 1.7 minutes (D-Cond. 2);
LR/MS: Anal. Calcd. for [M +H]$^+$ C$_{23}$H$_{24}$N$_7$O$_4$: 462.19; found: 462.44.
HRMS: Anal. Calcd. for [M + H]$^+$ C$_{23}$H$_{24}$N$_7$O$_4$: 462.1890
found: 462.1895.

-continued

| | | |
|---|---|---|
| J4.a2 | 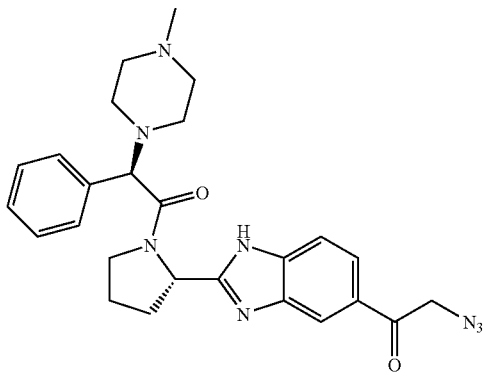 | RT = 1.2 minutes (J-Cond. 2); LR/MS: Anal. Calcd. for [M +H]⁺ $C_{20}H_{31}N_8O_2$: 487.26; found: 487. |

| | | |
|---|---|---|
| J5 |  | Tin(II)dichloride dihydrate (12.24 g, 54.26 mmol) was added to J4 (6.8 g, 18.08 mmol) dissolved in MeOH (200 mL). The reaction mixture was heated at 60° C. for 6 h and concentrated and dried under high vacuum to give J5 (S)-tert-butyl 2-(6-(2-aminoacetyl)-1H-benzo[d]imidazol-2-yl)pyrrolidine-1-carboxylate, 16.6 g which contained tin salts. LC (D-Cond. 2, 5μ particle size): RT=1.21 min; LC/MS: Anal. Calcd. for [M+H]⁺ $C_{18}H_{25}N_4O_3$: 345.19. found: 345.37 The material was used without purification. |

| | | |
|---|---|---|
| J5.a | 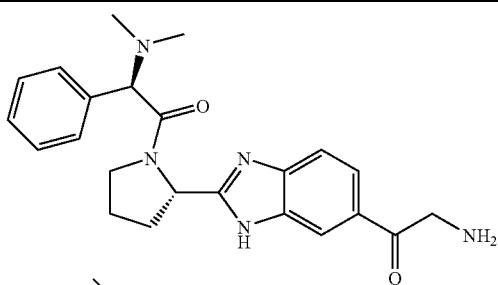 | |
| J5.a1 | 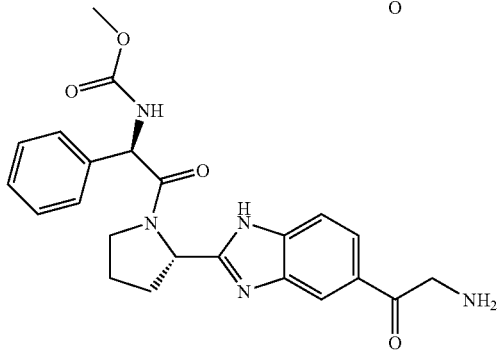 | RT = 1.26 minutes (D-Cond. 2); LC/MS: Anal. Calcd. for [M +H]⁺ $C_{23}H_{26}N_5O_4$: 463.20; found: 436.38. |
| J5.a2 | 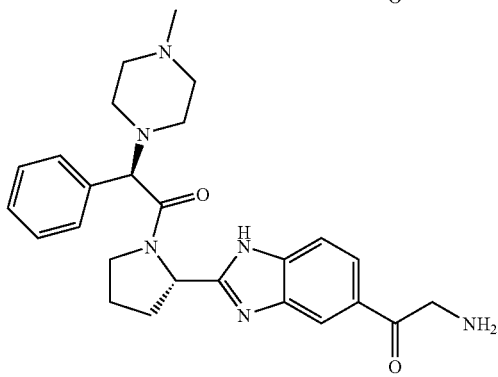 | |

Synthetic Scheme 3

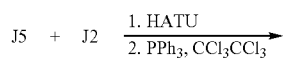

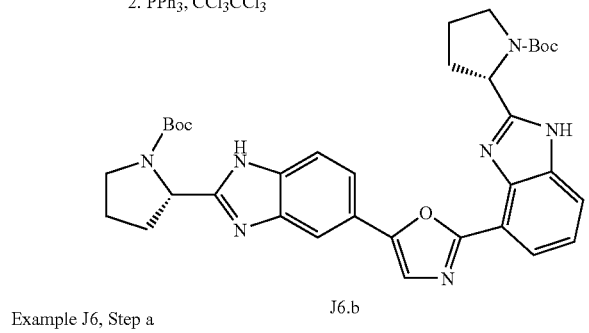

Example J6, Step a

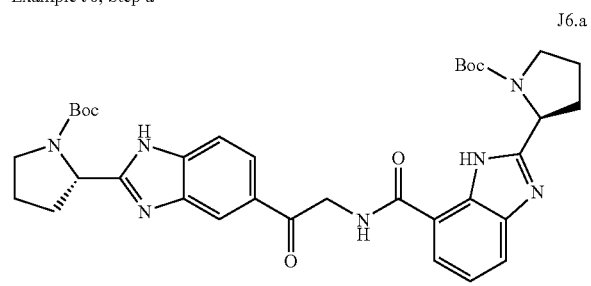

HATU (2.46 g, 6.5 mmol) was added to a solution of J5 (1.86 g, 5.4 mmol), J2 (1.97 g, 5.94 mmol), and Hunig's base (3.76 mL) in DMF (25 mL). The reaction mixture was stirred for 4 h before being diluted with EtOAc. The aqueous phase was extracted twice more with EtOAc and the combined organic layers were washed with saturated NaHCO$_3$, brine, and dried (Na$_2$SO$_4$) and filtered. Concentration gave a residue that was adsorbed onto a 40M Biotage SiO$_2$ column (CH$_2$Cl$_2$), and eluted by gradient 1%-100% B. A=EtOAc; B=10% MeOH/EtOAc to give J6.a (S)-tert-butyl 2-(7-(2-(2-((S)-1-(tert-butoxycarbonyl)pyrrolidin-2-yl)-1H-benzo[d]imidazol-5-yl)-2-oxoethylcarbamoyl)-1H-benzo[d]imidazol-2-yl)pyrrolidine-1-carboxylate (1.43 g, 37%). $^1$H NMR (400 MHz, DMSO-d$_6$) δ: 8.15/7.94 (br s, 3H), 7.78-7.57 (m, 3H), 7.34 (t, J=8.0 Hz, 1H), 5.30-5.23 (m, 2H), 5.0/4.95 (s, 2H), 3.60 (br s, 2H), 3.46-3.41 (m, 2H), 2.36-2.27 (m, 2H), 2.07-1.89 (m, 6H), 1.41/1.08 (s, 18H). LC (D-Cond. 2): RT=2.14 min; LC/MS: Anal. Calcd. for [M+H]$^+$ C$_{35}$H$_{44}$N$_7$O$_6$: 658.34. found: 658.38. HRMS: Anal. Calcd. for [M+H]$^+$ C$_{35}$H$_{44}$N$_7$O$_6$: 658.3353. found: 658.3370.

---

J6.a1

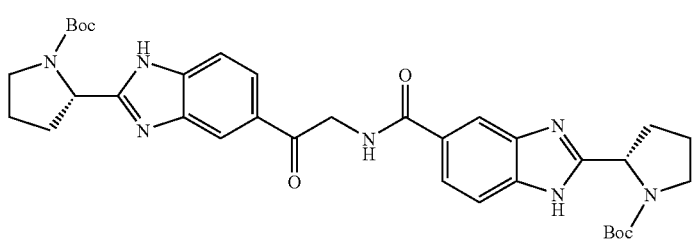

From J5 and J2.a

RT = 1.96 minutes (D-Cond. 2, S5 particle size); LC/MS: Anal. Calcd. for [M +H]$^+$ C$_{35}$H$_{44}$N$_7$O$_6$: 658.34; found: 658.22.

J6.a2

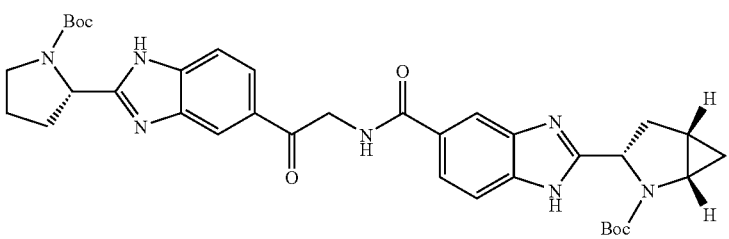

From J5 and J2.b

RT = 1.98 minutes (D-Cond. 2); LC/MS: Anal. Calcd. for [M +H]$^+$ C$_{36}$H$_{44}$N$_7$O$_6$: 670.34; found: 670.40. HRMS: Anal. Calcd. for [M +H]$^+$ C$_{36}$H$_{44}$N$_7$O$_6$: 670.3353; found: 670.3328.

J6.a3

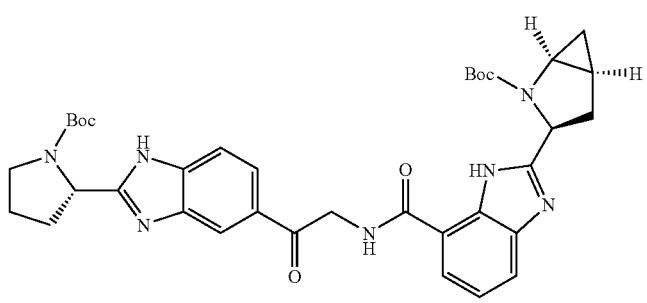

From J5 and J2.c

RT = 2.17 and 2.33 minutes (D-Cond. 2); LC/MS: Anal. Calcd. for [M +H]$^+$ C$_{36}$H$_{44}$N$_7$O$_6$: 670.34; found: 670.33. (Two diastereomers were observed; not separated).

| | | |
|---|---|---|
| J6.a4 | 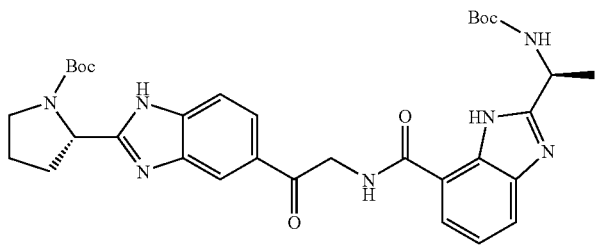<br>From J5 and J2.d | RT = 1.5 minutes (J-Cond. 2); LC/MS: Anal. Calcd. for [M +H]$^+$ C$_{33}$H$_{42}$N$_7$O$_6$: 632.31; found: 632.60. |
| J6.a5 | 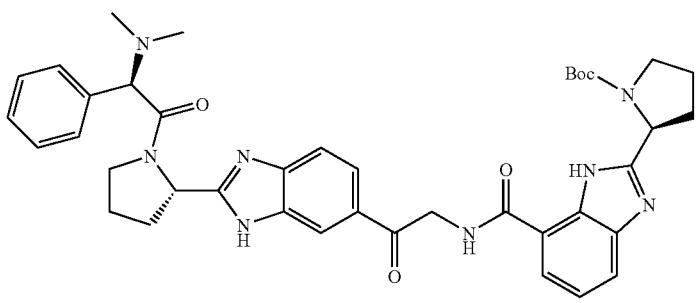<br>From J5.a and J2 | RT = 1.7 minutes (J-Cond. 2); LC/MS: Anal. Calcd. for [M +H]$^+$ C$_{40}$H$_{47}$N$_8$O$_5$: 718.37; found: 718. |
| J6.a6 | 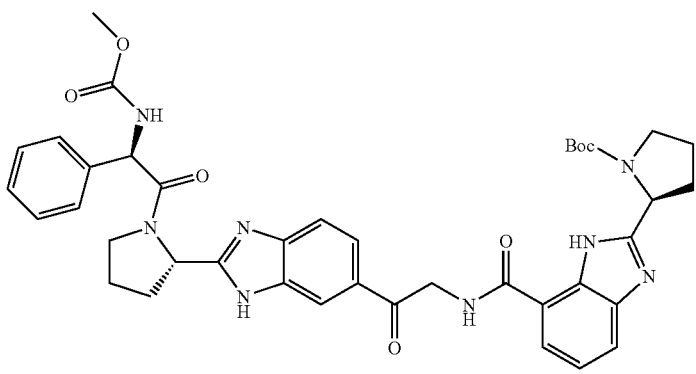<br>From J5.a1 and J2 | RT = 2.09 minutes (D-Cond. 2); LC/MS: Anal. Calcd. for [M +H]$^+$ C$_{40}$H$_{45}$N$_8$O$_7$: 749.34; found: 749.42. HRMS: Anal. Calcd. for [M +H]$^+$ C$_{40}$H$_{45}$N$_8$O$_7$: 749.3411; found: 749.3400. |
| J6.a7 | 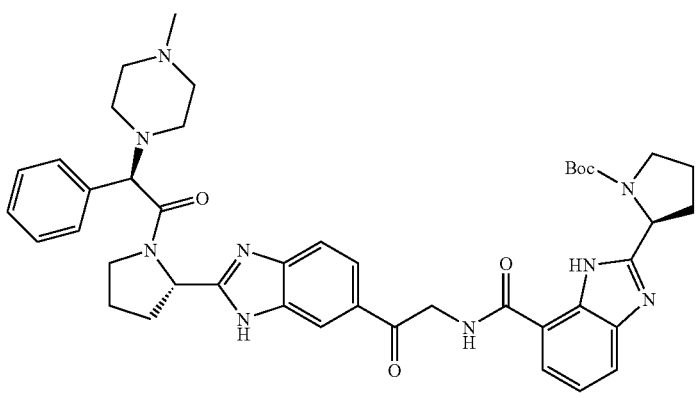<br>From J5.a2 and J2 | RT = 1.4 minutes (J-Cond. 2); LC/MS: Anal. Calcd. for [M +H]$^+$ C$_{43}$H$_{52}$N$_9$O$_5$: 774.41; found: 774. |

Example J6

Step b

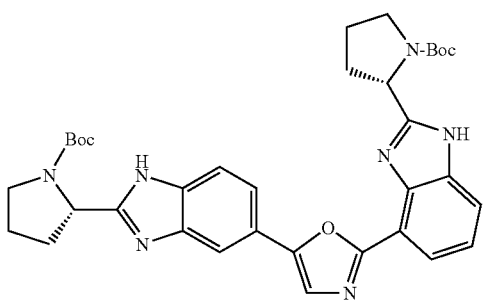

J6.b

A solution of J6.a (1.43 g, 2.17 mmol), triphenylphosphine (0.57 g, 2.17 mmol), and triethylamine (0.61 mL, 4.35 mmol) in dichloromethane (21 mL) was stirred about 5 min under nitrogen atmosphere before addition of hexachloroethane (0.51 g, 2.17 mmol) in one portion. The reaction mixture was stirred 2 h and a second equivalent of reagents added. After 2 h longer, the solution was concentrated on $SiO_2$ (pre-adsorbed), and subjected to flash chromatography on a 40 M Biotage silica gel column and eluted by gradient 1%-100% B. A=EtOAc; B=10% MeOH/EtOAc to give J6.b (S)-tert-butyl 2-(5-(2-(2-((S)-1-(tert-butoxycarbonyl)pyrrolidin-2-yl)-1H-benzo[d]imidazol-4-yl)oxazol-5-yl)-1H-benzo[d]imidazol-2-yl)pyrrolidine-1-carboxylate (1.08 g, 78%) as a yellow foam. $^1$H NMR (400 MHz, DMSO-$d_6$) δ: 8.32/8.15 (br s, 1H), 7.95/7.89 (br s, 1H), 7.86 (d, J=8.0 Hz, 1H), 7.68/7.58 (d, J=8.0 Hz, 2H), 7.31 (t, J=8.0 Hz, 1H), 5.03/4.95 (s, 2H), 3.65-3.58 (m, 2H), 3.49-3.41 (m, 2H), 2.43-2.31 (m, 2H), 2.11-1.90 (m, 6H), 1.41/1.08 (s, 18H). LC (D-Cond. 2): RT=2.37 min; LC/MS: Anal. Calcd. for [M+H]$^+$ $C_{35}H_{42}N_7O_5$: 640.35. found: 640.61. HRMS: Anal. Calcd. for [M+H]$^+$ $C_{35}H_{42}N_7O_5$: 640.3247. found: 640.3246.

---

J6.b1

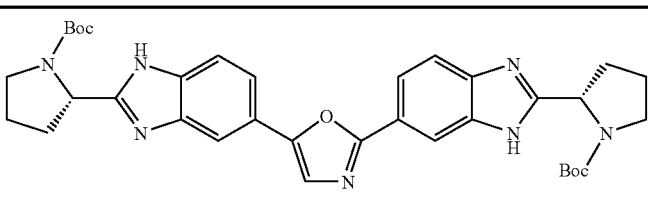

From J6.a1

RT = 2.24 minutes (D-Cond. 2);
LC/MS: Anal. Calcd. for [M +H]$^+$ $C_{35}H_{42}N_7O_5$: 640.32; found: 640.87.
HRMS: Anal. Calcd. for [M +H]$^+$ $C_{35}H_{42}N_7O_5$: 640.3247; found: 640.3231.

J6.b2

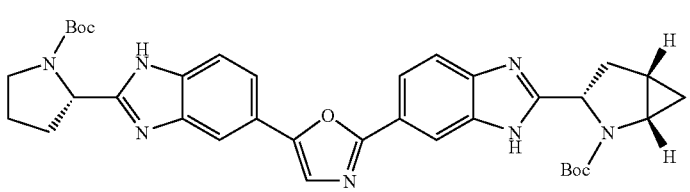

From J6.a2

RT = 2.39 minutes (D-Cond. 2);
LC/MS: Anal. Calcd. for [M +H]$^+$ $C_{36}H_{42}N_7O_5$: 652.32; found: 652.24.

J6.b3.1

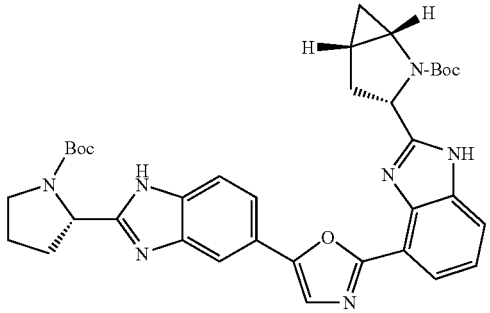

From J6.a3

RT = 2.50 minutes (D-Cond. 2);
LC/MS: Anal. Calcd. for [M +H]$^+$ $C_{36}H_{42}N_7O_5$: 652.32; found: 652.37.
HRMS: Anal. Calcd. for [M +H]$^+$ $C_{36}H_{42}N_7O_5$: 652.3247; found: 652.3232.
(Diasteromer 1; Configuration at methanoproline not assigned).

J6.b3.2

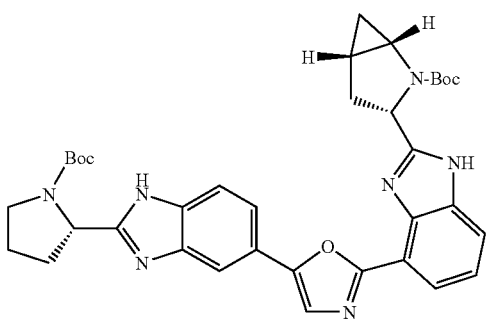

From J6.a3

RT = 2.32 minutes (D-Cond. 2);
LC/MS: Anal. Calcd. for [M +H]$^+$ $C_{36}H_{42}N_7O_5$: 652.32; found: 652.37.
HRMS: Anal. Calcd. for [M +H]$^+$ $C_{36}H_{42}N_7O_5$: 652.3247; found: 652.3259.
(Diasteromer 2; Configuration at methanoproline not assigned).

| | | |
|---|---|---|
| J6.b4 | 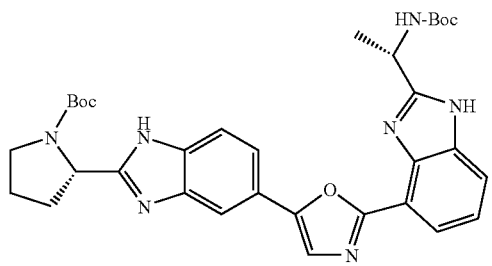
From J6.a4 | RT = 1.89 minutes (D-Cond. 2); LC/MS: Anal. Calcd. for [M +H]$^+$ C$_{43}$H$_{46}$N$_9$O$_3$: 736.37; found: 736.52. HRMS: Anal. Calcd. for [M +H]$^+$ C$_{43}$H$_{46}$N$_9$O$_3$: 736.3724; found: 736.3723. |
| J6.b5 | 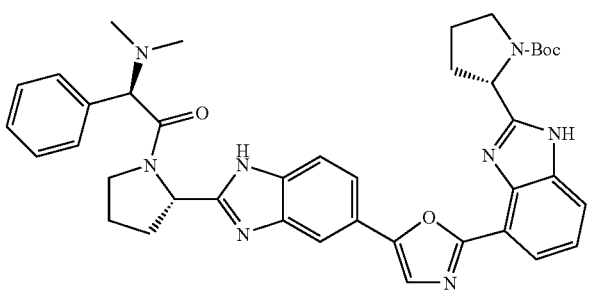
From J6.a5 | RT = 2.10 minutes (D-Cond. 2); LC/MS: Anal. Calcd. for [M +H]$^+$ C$_{40}$H$_{45}$N$_8$O$_4$: 701.36; found: 701.34. |
| J6.b6 | 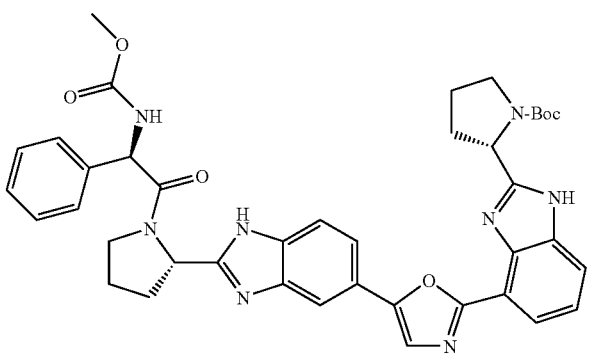
From J6.a6 | |
| J6.b7 | 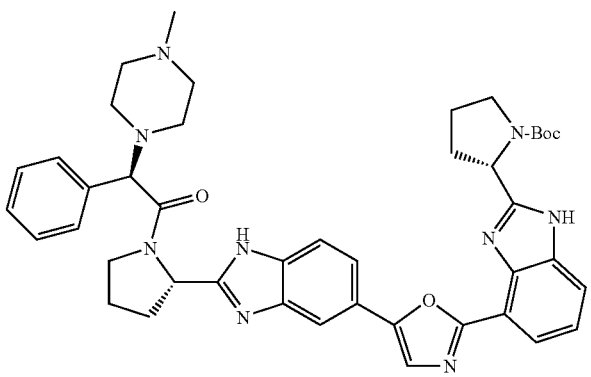
From J6.a7 | RT = 2.11 minutes (D-Cond. 2); LC/MS: Anal. Calcd. for [M +H]$^+$ C$_{43}$H$_{50}$N$_9$O$_4$: 756.40; found: 756.43. |

Synthetic Scheme 4

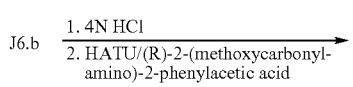

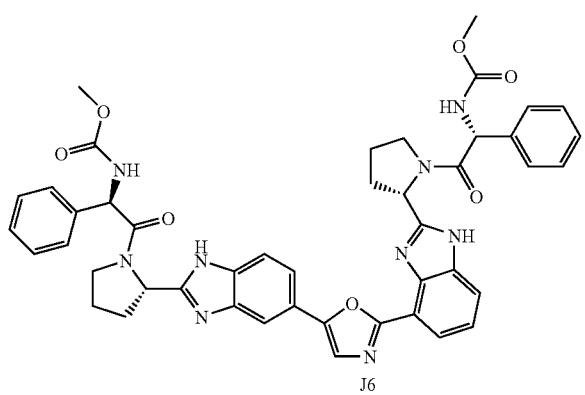

J6

Example J6

Step c

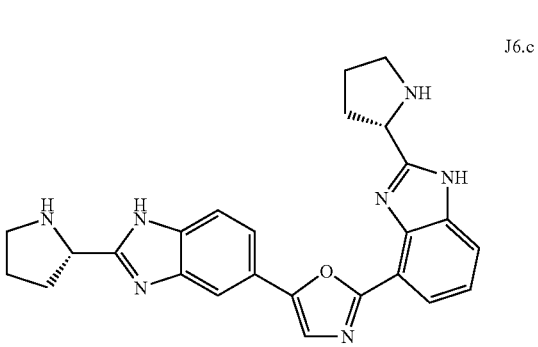

J6.c

To a solution of J6.b (1.04 g, 1.63 mmol) in MeOH (5 mL) was added HCl/Dioxane (16 mL of 4N), and the reaction was stirred 4 h. The solvents were removed in vacuo, and the tetra HCl salt was exposed to high vacuum for 18 h to give J6.c (0.99 g, 103%). LC (D-Cond. 2): RT=1.76 min; LC/MS: Anal. Calcd. for $[M+H]^+$ $C_{25}H_{26}N_7O$: 440.22. found: 440.28. HRMS: Anal. Calcd. for $[M+H]^+$ $C_{25}H_{26}N_7O$: 440.2199. found: 440.2191.

---

J6.c1

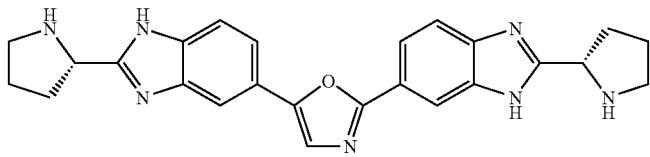

From J6.b1

RT = 1.57 minutes (D-Cond. 1); LC/MS: Anal. Calcd. for $[M+H]^+$ $C_{25}H_{26}N_7O$: 440.22; found: 440.12. HRMS: Anal. Calcd. for $[M+H]^+$ $C_{25}H_{26}N_7O$: 440.2219; found: 440.2218

J6.c2

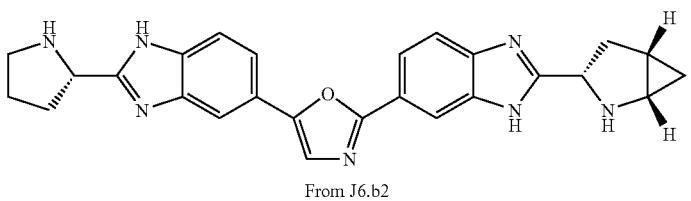

From J6.b2

RT = 1.72 minutes (D-Cond. 2); LRMS: Anal. Calcd. for $[M+H]^+$ $C_{26}H_{26}N_7O$: 452.22; found: 452.17. HRMS: Anal. Calcd. for $[M+H]^+$ $C_{26}H_{26}N_7O$: 452.2199; found: 452.2177

J6.c3.1

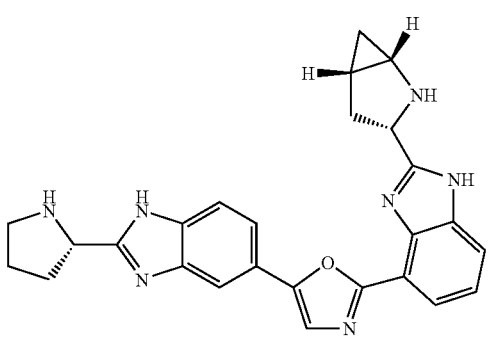

From J6.b3.1
Diastereomer 1

RT = 1.76 minutes (D-Cond. 2); LRMS: Anal. Calcd. for $[M+H]^+$ $C_{26}H_{26}N_7O$: 452.22; found: 452.25. HRMS: Anal. Calcd. for $[M+H]^+$ $C_{26}H_{26}N_7O$: 452.2199; found: 452.2198.

| | | |
|---|---|---|
| J6.c3.2 | 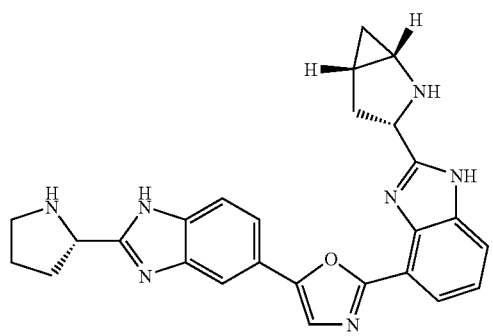<br>From J6.b3.2<br>Diastereomer 2 | RT = 1.69 minutes (D-Cond. 2); LRMS: Anal. Calcd. for [M +H]$^+$ C$_{26}$H$_{26}$N$_7$O: 452.22; found: 452.25. HRMS: Anal. Calcd. for [M +H]$^+$ C$_{26}$H$_{26}$N$_7$O: 452.2199; found: 452.2192. |
| J6.c4 | 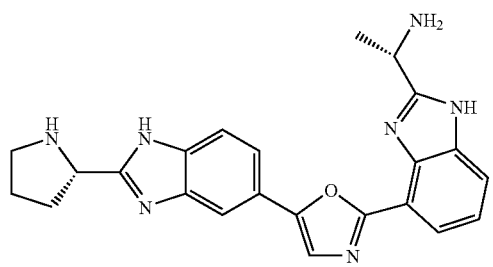<br>From J6.b4 | RT = 1.70 minutes (D-Cond. 2); LRMS: Anal. Calcd. for [M +H]$^+$ C$_{23}$H$_{24}$N$_7$O: 414.20; found: 414.11. |
| J6.c5 | 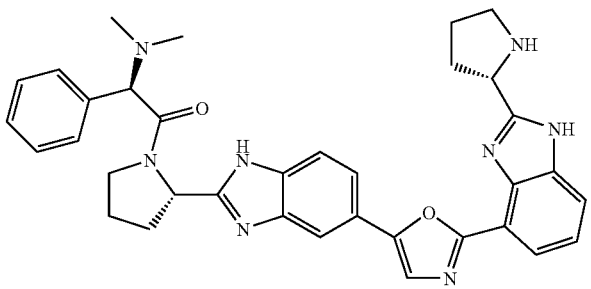<br>From J6.b5 | RT = 1.72 minutes (D-Cond. 2); LC/MS: Anal. Calcd. for [M +H]$^+$ C$_{35}$H$_{37}$N$_8$O$_2$: 601.30; found: 601.87. HRMS: Anal. Calcd. for [M +H]$^+$ C$_{35}$H$_{37}$N$_8$O$_2$: 601.3039; found: 601.3062 |
| J6.c6 | 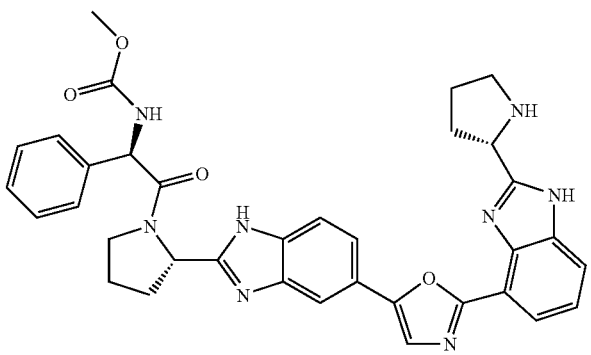<br>From J6.b6 | RT = 1.93 minutes (D-Cond. 2); LC/MS: Anal. Calcd. for [M +H]$^+$ C$_{35}$H$_{35}$N$_8$O$_4$: 631.28; found: 631.41. HRMS: Anal. Calcd. for [M +H]$^+$ C$_{35}$H$_{35}$N$_8$O$_4$: 631.2781; found: 631.2786. |

-continued

| J6.c7 | 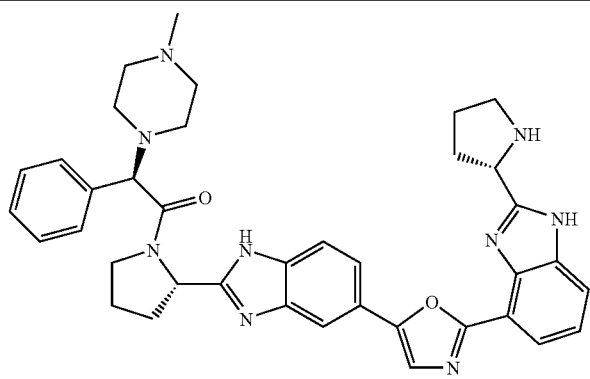<br>From J6.b7 | RT = 1.82 minutes (D-Cond. 2);<br>LC/MS: Anal. Calcd. for [M +H]$^+$ C$_{38}$H$_{42}$N$_9$O$_2$: 656.35; found: 656.17 |
|---|---|---|
| J6.c8 | 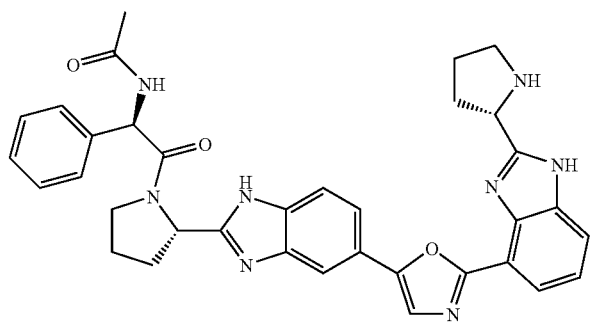<br>From J6.c (mono coupling of cap-location not confirmed)<br>(Diastereomeric mixture at cap) | RT = 1.90 minutes (D-Cond. 2);<br>LC/MS: Anal. Calcd. for [M +H]$^+$ C$_{35}$H$_{35}$N$_8$O$_3$: 615.15; found: 615.62 |

Example J6

Methyl((1R)-2-((2S)-2-(4-(5-(2-((2S)-1-((2R)-2-((methoxycarbonyl)amino)-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate

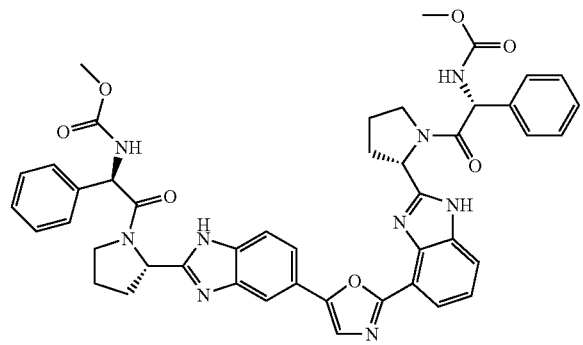

The tetra HCl salt, J6.c (25.0 mg, 0.043 mmol), N-Methoxycarbonyl-L-phenylglycine (19.6 mg, 0.094 mmol), and Hunig's base (0.06 mL, 0.34 mmol) were taken up in DMF (1.5 mL) and HATU (37.4 mg, 0.098 mmol) was added and rapidly stirred for 2 h. The solvent was purged away with nitrogen stream (18 h), and the residue was diluted with MeOH (2 mL, 2×) and directly subjected to prep. HPLC (XTERRA 10%-100% B over 13 min; Flow Rate=40 mL/min; Wavelength=220 nm; Solvent A=0.1% TFA in 10% methanol/90% H$_2$O; Solvent B=0.1% TFA in 90% methanol/10% H$_2$O) gave J6 (23.9 mg, 53%). $^1$H NMR (500 MHz, DMSO-d$_6$) δ: 8.22-7.56 (series m, 8H), 7.45-7.31 (m, 8H), 6.92-6.70 (m, 2H), 5.55-5.27 (s, 4H), 4.0-3.93 (m, 2H), 3.83-3.95 (m, 2H), 3.52/3.46 (s, 6H), 3.26-3.22 (m, 2H), 2.28-1.91 (m, 6H). LC (D-Cond. 2): RT=2.17 min; LC/MS: Anal. Calcd. for [M+H]$^+$ C$_{45}$H$_{44}$N$_9$O$_7$: 822.34. found: 822.59. HRMS: Anal. Calcd. for [M+H]$^+$ C$_{45}$H$_{44}$N$_9$O$_7$: 822.3364. found: 822.3348.

| | | | |
|---|---|---|---|
| J6.1 | methyl ((1R)-2-((2S)-2-(4-(5-(2-((2S)-1-(acetamido(phenyl)acetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate | 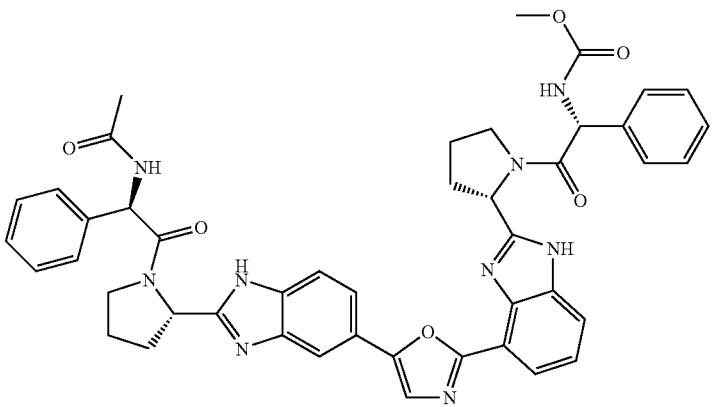<br>From J6.c8 Location of caps not confirmed<br>(Mixture of isomers 2.6:1) | RT = 2.09 min;<br>LC/MS:<br>Anal.<br>Calcd. for<br>$[M +H]^+$<br>$C_{45}H_{44}N_9O_6$:<br>806.34;<br>found:<br>806.42.<br>HRMS:<br>Anal.<br>Calcd. for<br>$[M +H]^+$<br>$C_{45}H_{44}N_9O_6$:<br>806.3415;<br>found:<br>806.3425. |
| J7 | 2-((2S)-1-(phenylacetyl)-2-pyrrolidinyl)-4-(5-(2-((2S)-1-(phenylacetyl)-2-pyrrolidinyl)-1H-benzimidazol-5-yl)-1,3-oxazol-2-yl)-1H-benzimidazole | 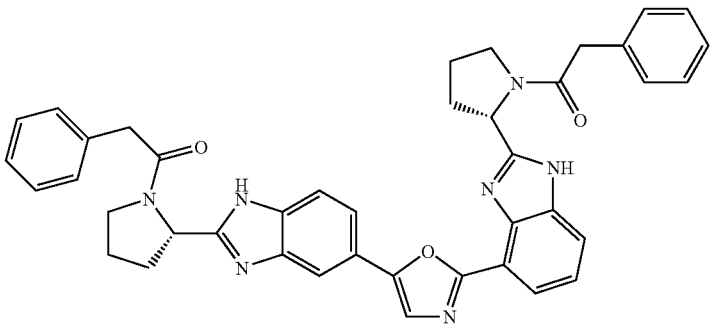<br>From J6.c | RT = 2.27 minutes<br>(D-Cond. 2);<br>LC/MS:<br>Anal.<br>Calcd. for<br>$[M +H]^+$<br>$C_{41}H_{38}N_7O_3$:<br>676.31;<br>found:<br>676.32.<br>HRMS:<br>Anal.<br>Calcd. for<br>$[M +H]^+$<br>$C_{41}H_{38}N_7O_3$:<br>676.3036;<br>found:<br>676.3025. |
| J8 | methyl ((1S)-2-((2S)-2-(5-(2-(2-((2S)-1-(N-(methoxycarbonyl)-L-alanyl)-2-pyrrolidinyl)-1H-benzimidazol-4-yl)-1,3-oxazol-5-yl)-1H-benzimidazol-2-yl)-1-pyrrolidinyl)-1-methyl-2-oxoethyl)carbamate | 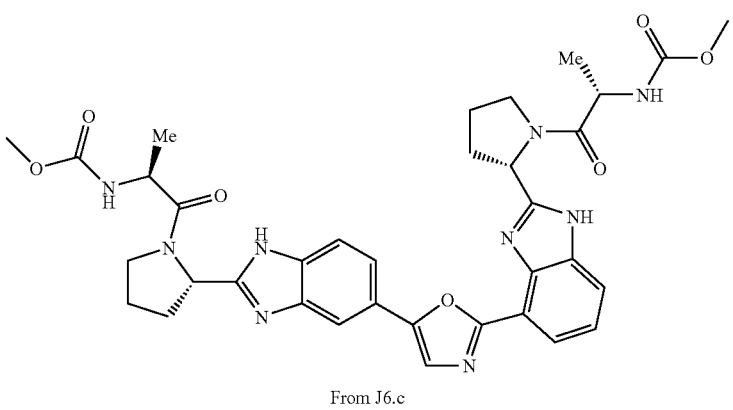<br>From J6.c | RT = 1.8 minutes<br>(D-Cond. 2);<br>LC/MS:<br>Anal.<br>Calcd. for<br>$[M +H]^+$<br>$C_{35}H_{40}N_9O_7$:<br>698.31;<br>found:<br>698.32.<br>HRMS:<br>Anal.<br>Calcd. for<br>$[M + H]^+$<br>$C_{35}H_{40}N_9O_7$:<br>698.3051;<br>found:<br>698.3064. |
| J9 | (1R)-2-((2S)-2-(4-(5-(2-((2S)-1-((2R)-2-hydroxy-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethanol | 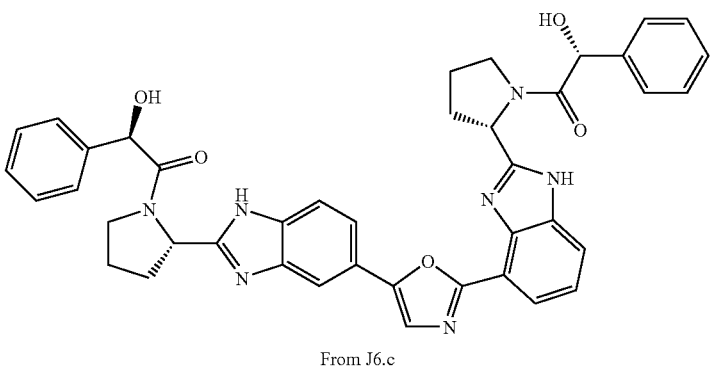<br>From J6.c | RT = 2.02 minutes<br>(D-Cond. 2);<br>LC/MS:<br>Anal.<br>Calcd. for<br>$[M +H]^+$<br>$C_{41}H_{38}N_7O_5$:<br>708.29;<br>found:<br>708.32.<br>HRMS:<br>Anal.<br>Calcd. for<br>$[M + H]^+$<br>$C_{41}H_{38}N_7O_5$:<br>708.2934;<br>found:<br>708.2933. |

| | | | |
|---|---|---|---|
| J10 | methyl ((1S)-1-(((2S)-2-(4-(5-(2-((2S)-1-((2S)-2-(methoxy-carbonyl)amino)-3-methyl-butanoyl)-2-pyrrolidinyl)-1H-benzimidazol-5-yl)-1,3-oxazol-2-yl)-1H-benzimidazol-2-yl)-1-pyrrolidinyl)carbonyl)-2-methylpropyl) carbamate | 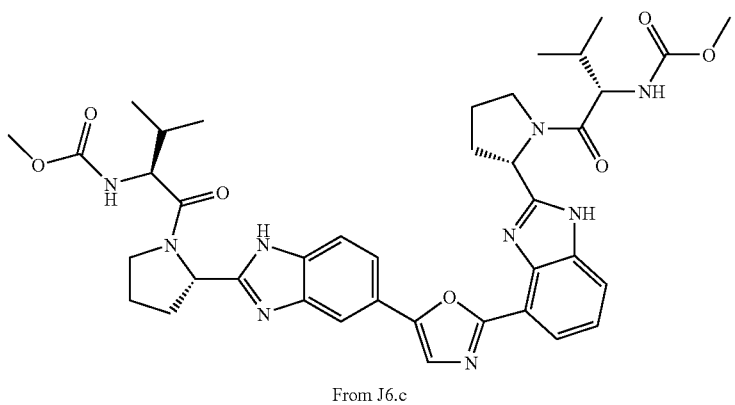<br>From J6.c | RT = 2.0 minutes (D-Cond. 2); LC/MS: Anal. Calcd. for [M +H]$^+$ C$_{39}$H$_{48}$N$_9$O$_7$: 754.37; found: 754.37. HRMS: Anal. Calcd. for [M + H]$^+$ C$_{39}$H$_{48}$N$_9$O$_7$: 754.3677; found: 754.3706. |
| J11 | (1R)-2-((2S)-2-(4-(5-(2-((2S)-1-((2R)-2-(dimethyl-amino)-2-phenylacetyl)-2-pyrrolidinyl)-1H-benzimidazol-5-yl)-1,3-oxazol-2-yl)-1H-benzimidazol-2-yl)-1-pyrrolidinyl)-N,N-dimethyl-2-oxo-1-phenyl-ethanamine | 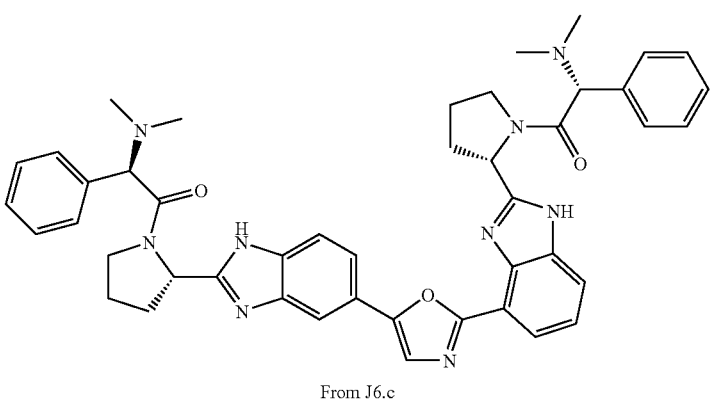<br>From J6.c | RT = 1.88 minutes (D-Cond. 2); LC/MS: Anal. Calcd. for [M +H]$^+$ C$_{45}$H$_{48}$N$_9$O$_3$: 762.39; found: 762.39. HRMS: Anal. Calcd. for [M + H]$^+$ C$_{45}$H$_{48}$N$_9$O$_3$: 762.3880; found: 762.3865. |
| J11.1 | N-((1R)-2-((2S)-2-(5-(2-(2-((2S)-1-((2R)-2-(dimethyl-amino)-2-phenylacetyl)-2-pyrrolidinyl)-1H-benzimidazol-4-yl)-1,3-oxazol-5-yl)-1H-benzimidazol-2-yl)-1-pyrrolidinyl)-2-oxo-1-phenylethyl) acetamide | 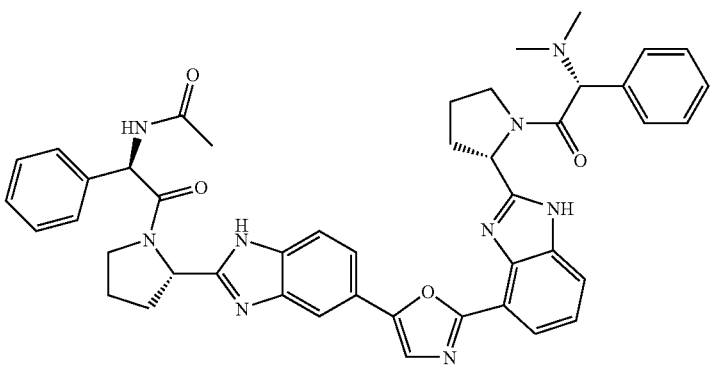<br>From J6.c8-Location of caps not confirmed (Contaminated with 30% J11) | RT = 1.90 minutes (D-Cond. 2); LC/MS: Anal. Calcd. for [M +H]$^+$ C$_{45}$H$_{46}$N$_9$O$_4$: 776.37; found: 776.16. HRMS: Anal. Calcd. for [M − H]$^-$ C$_{45}$H$_{44}$N$_9$O$_4$: 774.3516; found: 774.3503. |

| | | | |
|---|---|---|---|
| J11.2 | N-((1S)-2-((2S)-2-(5-(2-(2-((2S)-1-((2R)-2-(dimethyl-amino)-2-phenylacetyl)-2-pyrrolidinyl)-1H-benzimidazol-4-yl)-1,3-oxazol-5-yl)-1H-benzimidazol-2-yl)-1-pyrrolidinyl)-2-oxo-1-phenylethyl)acetamide | 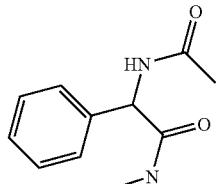 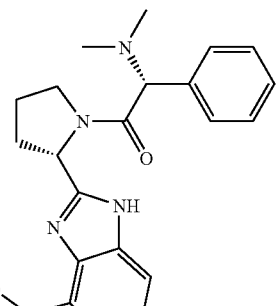<br>From J6.c8-Either a stereoisomer or a regioisomer of J11.1 | RT = 1.96 minutes (D-Cond. 2); LC/MS: Anal. Calcd. for [M +H]$^+$ C$_{45}$H$_{46}$N$_9$O$_4$: 776.37; found: 776.44. HRMS: Anal. Calcd. for [M − H]$^-$ C$_{45}$H$_{44}$N$_9$O$_4$: 774.3503; found: 774.3510. |
| J12 | N-((1R)-2-((2S)-2-(4-(5-(2-((2S)-1-((2R)-2-acetamido-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)acetamide | 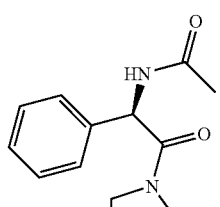 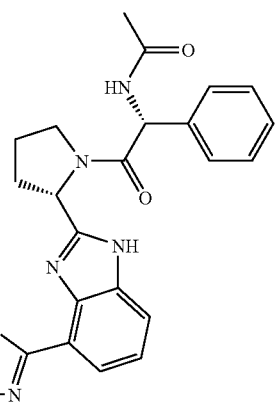<br>From J6.c | RT = 2.03 minutes (D-Cond. 2); LC/MS: Anal. Calcd. for [M +H]$^+$ C$_{45}$H$_{44}$N$_9$O$_5$: 790.34; found: 790.35. HRMS: Anal. Calcd. for [M + H]$^+$ C$_{45}$H$_{44}$N$_9$O$_5$: 790.3465; found: 790.3499. |
| J12.1 | N-((1R)-2-((2S)-2-(4-(5-(2-((2S)-1-((2R)-2-acetamido-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)acetamide | 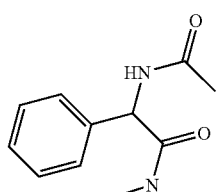 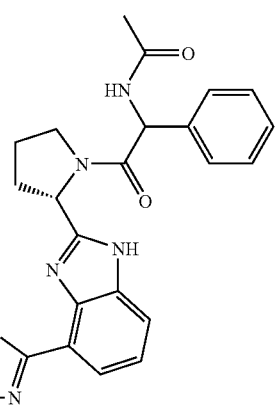<br>From J6.c-1:1 mixture of diastereomers of J12 | RT = 2.09 minutes (D-Cond. 2); LC/MS: Anal. Calcd. for [M +H]$^+$ C$_{45}$H$_{44}$N$_9$O$_5$: 790.34; found: 790.41. HRMS: Anal. Calcd. for [M + H]$^+$ C$_{45}$H$_{44}$N$_9$O$_5$: 790.3465; found: 790.3475. |

| | | | |
|---|---|---|---|
| J13 | 1-(2-((2S)-2-(4-(5-(2-((2S)-1-((4-hydroxy-1-piperidinyl)(phenyl)acetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)-4-piperidinol | 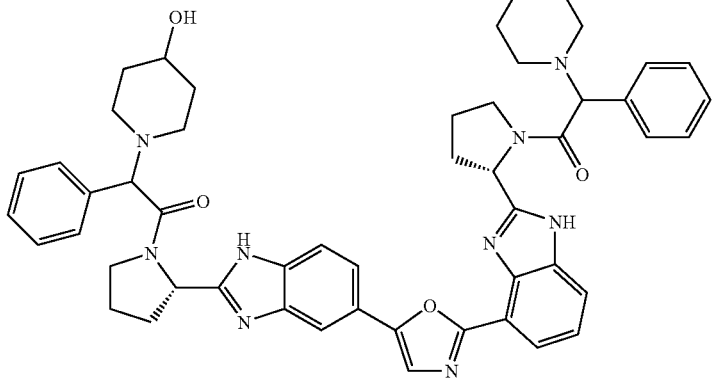<br>From J6.c (A single diastereomer but the absolute stereochemistry of the unspecified center was not determined) | RT = 1.84 minutes (D-Cond. 2); LC/MS: Anal. Calcd. for [M +H]$^+$ $C_{51}H_{56}N_9O_5$: 874.44; found: 874.79. HRMS: Anal. Calcd. for [M + H]$^+$ $C_{51}H_{56}N_9O_5$: 874.4404; found: 874.4419. |
| J14 | 2-((2S)-1-((2R)-2-(4-methyl-1-piperazinyl)-2-phenylacetyl)-2-pyrrolidinyl)-4-(5-(2-((2S)-1-((2R)-2-(4-methyl-1-piperazinyl)-2-phenylacetyl)-2-pyrrolidinyl)-1H-benzimidazol-5-yl)-1,3-oxazol-2-yl)-1H-benzimidazole | 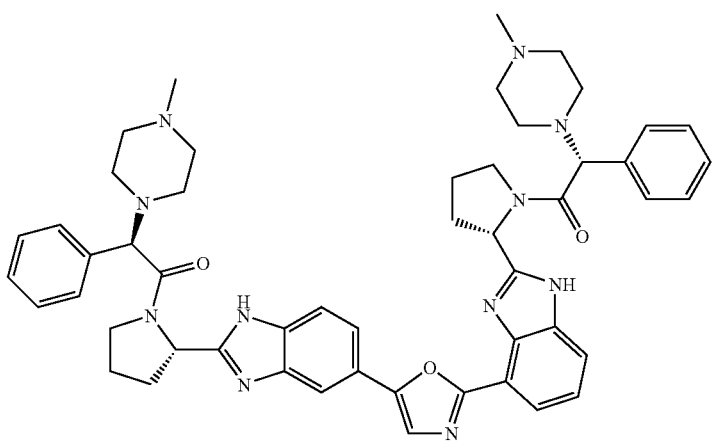<br>From J6.c | RT = 1.87 minutes (D-Cond. 2); LC/MS: Anal. Calcd. for [M +H]$^+$ $C_{51}H_{58}N_{11}O$: 872.47; found: 872.44. HRMS: Anal. Calcd. for [M + H]$^+$ $C_{51}H_{58}N_{11}O_3$: 872.4724; found: 872.4712. |
| J14.1 | 2-((2S)-1-((4-methyl-1-piperazinyl)(phenyl)acetyl)-2-pyrrolidinyl)-4-(5-(2-((2S)-1-((4-methyl-1-piperazinyl)(phenyl)acetyl)-2-pyrrolidinyl)-1H-benzimidazol-5-yl)-1,3-oxazol-2-yl)-1H-benzimidazole | 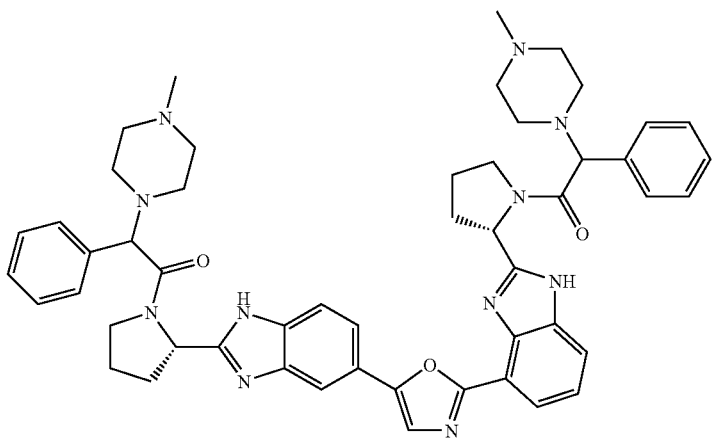<br>From J6.c-Diastereomer of J14 | RT = 1.84 minutes (D-Cond. 2); LC/MS: Anal. Calcd. for [M +H]$^+$ $C_{51}H_{58}N_{11}O$: 872.47; found: 872.58. HRMS: Anal. Calcd. for [M + H]$^+$ $C_{51}H_{58}N_{11}O_3$: 872.4724; found: 872.4720. |

| | | | |
|---|---|---|---|
| J15 | 3-chloro-1-(((2S)-2-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)-1H-benzimidazol-2-yl)-1-pyrrolidinyl)carbonyl)-5-methoxy-isoquinoline | 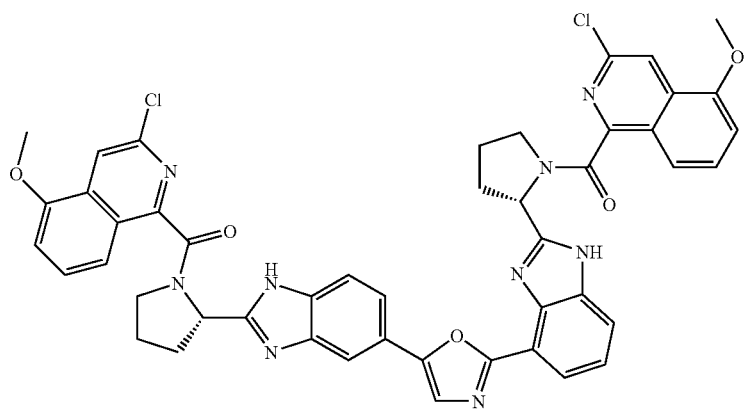<br>From J6.c | RT = 2.87 minutes (D-Cond. 2); LC/MS: Anal. Calcd. for [M +H]$^+$ C$_{47}$H$_{38}$Cl$_2$N$_9$O$_5$: 878.24; found: 878.25. HRMS: Anal. Calcd. for [M + H]$^+$ C$_{47}$H$_{38}$Cl$_2$N$_9$O$_5$: 878.2373; found: 878.2373. |
| J16 | 5,5'-(1,3-oxazole-2,5-diyl)bis(2-((2S)-1-(phenylacetyl)-2-pyrrolidinyl)-1H-benzimidazole | 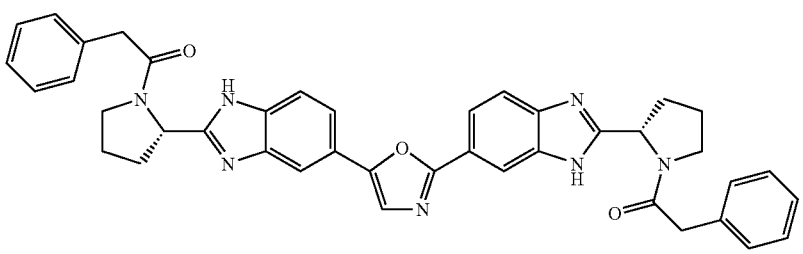<br>From J6.c1 | RT = 2.04 minutes (D-Cond. 2); LC/MS: Anal. Calcd. for [M +H]$^+$ C$_{41}$H$_{38}$N$_7$O$_3$: 676.30; found: 676.24. HRMS: Anal. Calcd. for [M + H]$^+$ C$_{41}$H$_{38}$N$_7$O$_3$: 676.3036; found: 676.3037. |
| J17 | (1R)-2-((2S)-2-(5-(2-(2-((2S)-1-((2R)-2-hydroxy-2-phenylacetyl)-2-pyrrolidinyl)-1H-benzimidazol-6-yl)-1,3-oxazol-5-yl)-1H-benzimidazol-2-yl)-1-pyrrolidinyl)-2-oxo-1-phenylethanol | 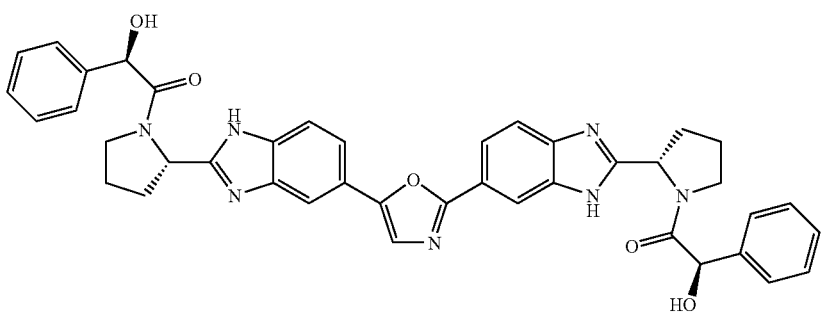<br>From J6.c1 | RT = 1.84 minutes (D-Cond. 1); LC/MS: Anal. Calcd. for [M +H]$^+$ C$_{41}$H$_{38}$N$_7$O$_5$: 708.29; found: 708.26. HRMS: Anal. Calcd. for [M + H]$^+$ C$_{41}$H$_{38}$N$_7$O$_5$: 708.2934; found: 708.2966. |

| | | | |
|---|---|---|---|
| J18 | (2S)-1-((2S)-2-(5-(2-(2-((2S)-1-((2S)-2-hydroxy-2-phenyl-propanoyl)-2-pyrrolidinyl)-1H-benzimidazol-6-yl)-1,3-oxazol-5-yl)-1H-benzimidazol-2-yl)-1-pyrrolidinyl)-1-oxo-2-phenyl-2-propanol | 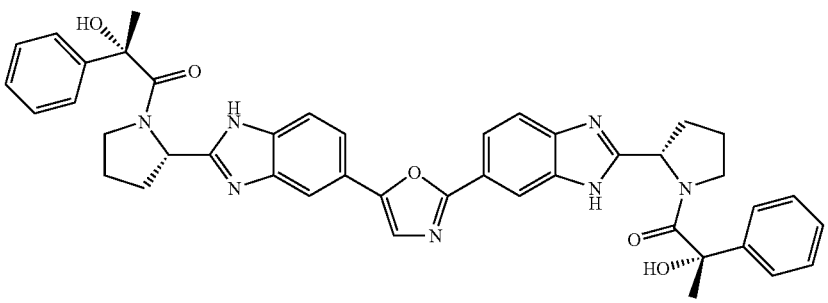<br>From J6.c1 | RT = 2.14 minutes (D-Cond. 1); LC/MS: Anal. Calcd. for [M +H]$^+$ C$_{43}$H$_{42}$N$_7$O$_5$: 736.32; found: 736.26. HRMS: Anal. Calcd. for [M + H]$^+$ C$_{43}$H$_{42}$N$_7$O$_5$: 736.3247; found: 736.3240. |
| J19 | methyl ((1S)-1-(((2S)-2-(5-(2-(2-((2S)-1-((2S)-2-((methoxy-carbonyl)amino)-3-methyl-butanoyl)-2-pyrrolidinyl)-1H-benzimidazol-5-yl)-1,3-oxazol-5-yl)-1H-benzimidazol-2-yl)-1-pyrrolidinyl)carbonyl)-2-methylpropyl)carbamate | 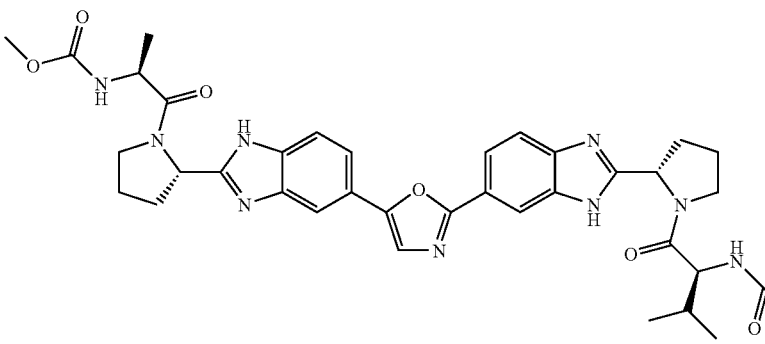<br>From J6.c1 | RT = 2.07 minutes (D-Cond. 1); LC/MS: Anal. Calcd. for [M +H]$^+$ C$_{39}$H$_{48}$N$_9$O$_7$: 754.37; found: 754.38. HRMS: Anal. Calcd. for [M + H]$^+$ C$_{39}$H$_{48}$N$_9$O$_7$: 754.3677; found: 754.3673. |
| J20 | (1R)-2-((2S)-2-(5-(2-(2-((2S)-1-((2R)-2-(dimethyl-amino)-2-phenylacetyl)-2-pyrrolidinyl)-1H-benzimidazol-6-yl)-1,3-oxazol-5-yl)-1H-benzimidazol-2-yl)-1-pyrrolidinyl)-N,N-dimethyl-2-oxo-1-phenyl-ethanamine | 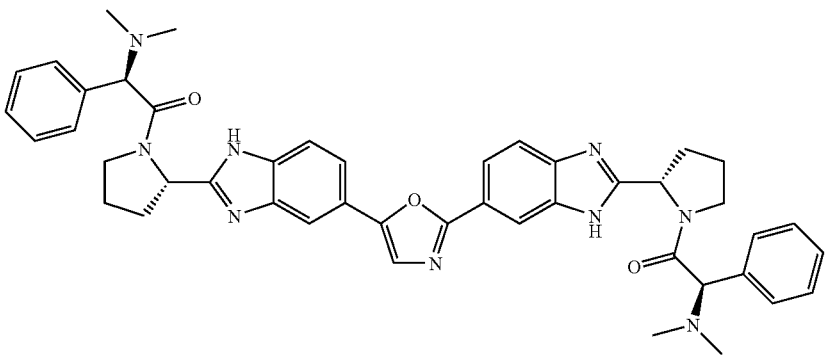<br>From J6.c1 | RT = 1.73 minutes (D-Cond. 1); LC/MS: Anal. Calcd. for [M +H]$^+$ C$_{45}$H$_{48}$N$_9$O$_3$: 762.39; found: 762.31. HRMS: Anal. Calcd. for [M + H]$^+$ C$_{45}$H$_{48}$N$_9$O$_3$: 762.3880; found: 762.3906. |

| | | | |
|---|---|---|---|
| J20.1 | (1R)-N,N-dimethyl-2-oxo-1-phenyl-2-((2S)-2-(5-(2-(2-((2S)-1-(phenylacetyl)-2-pyrrolidinyl)-1H-benzimidazol-5-yl)-1,3-oxazol-5-yl)-1H-benzimidazol-2-yl)-1-pyrrolidinyl) ethanamine | 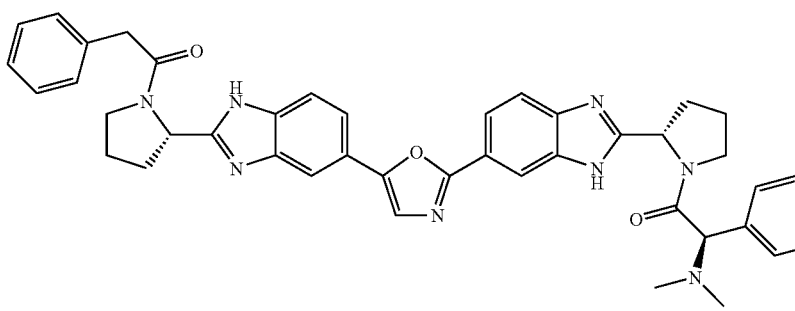<br>From J6.c1-Location of caps not confirmed | RT = 1.88 minutes (D-Cond. 1); LC/MS: Anal. Calcd. for [M +H]$^+$ C$_{43}$H$_{43}$N$_8$O$_3$: 719.35; found: 719.52. HRMS: Anal. Calcd. for [M + H]$^+$ C$_{43}$H$_{43}$N$_8$O$_3$: 719.3458; found: 719.3452. |
| J21 | N-((1R)-2-((2S)-2-(5-(2-(2-((2S)-1-((2R)-2-acetamido-2-phenylacetyl)-2-pyrrolidinyl)-1H-benzimidazol-6-yl)-1,3-oxazol-5-yl)-1H-benzimidazol-2-yl)-1-pyrrolidinyl)-2-oxo-1-phenylethyl) acetamide | 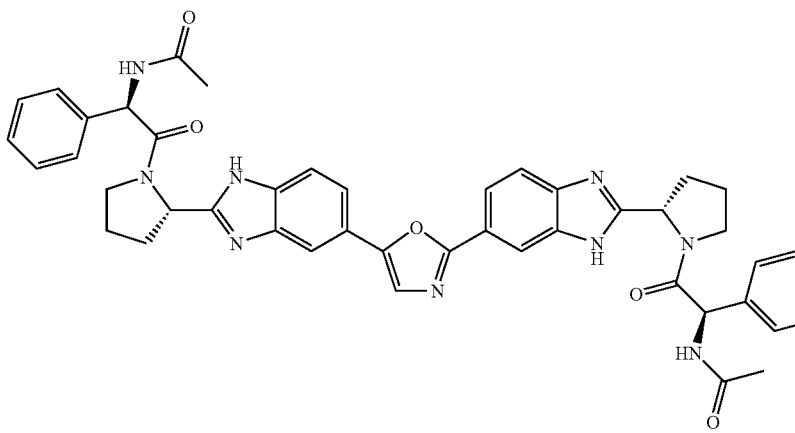<br>From J6.c1 | RT = 1.86 minutes (D-Cond. 1); LC/MS: Anal. Calcd. for [M +H]$^+$ C$_{45}$H$_{44}$N$_9$O$_5$: 790.35; found: 790.33. HRMS: Anal. Calcd. for [M + H]$^+$ C$_{45}$H$_{44}$N$_9$O$_5$: 790.3465; found: 790.3489. |
| J22 | 3-chloro-1-(((2S)-2-(5-(2-(2-((2S)-1-((3-chloro-5-methoxy-1-isoquinolinyl)carbonyl)-2-pyrrolidinyl)-1H-benzimidazol-6-yl)-1,3-oxazol-5-yl)-1H-benzimidazol-2-yl)-1-pyrrolidinyl)carbonyl)-5-methoxy-isoquinoline | 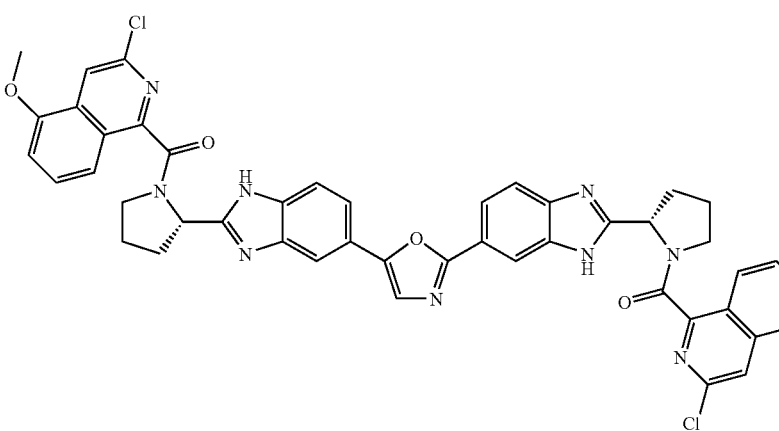<br>From J6.c1 | RT = 2.63 minutes (D-Cond. 1); LC/MS: Anal. Calcd. for [M +H]$^+$ C$_{47}$H$_{38}$Cl$_2$N$_9$O$_5$: 878.24; found: 878.19. HRMS: Anal. Calcd. for [M + H]$^+$ C$_{47}$H$_{38}$Cl$_2$N$_9$O$_5$: 878.2373; found: 878.2377. |

-continued

| | | | |
|---|---|---|---|
| J23 | (1R)-2-((2S)-2-(5-(2-(2-((1S,3S,5S)-2-((2R)-2-(dimethyl-amino)-2-phenylacetyl)-2-azabicyclo[3.1.0]hex-3-yl)-1H-benzimidazol-5-yl)-1,3-oxazol-5-yl)-1H-benzimidazol-2-yl)-1-pyrrolidinyl)-N,N-dimethyl-2-oxo-1-phenyl-ethanamine | 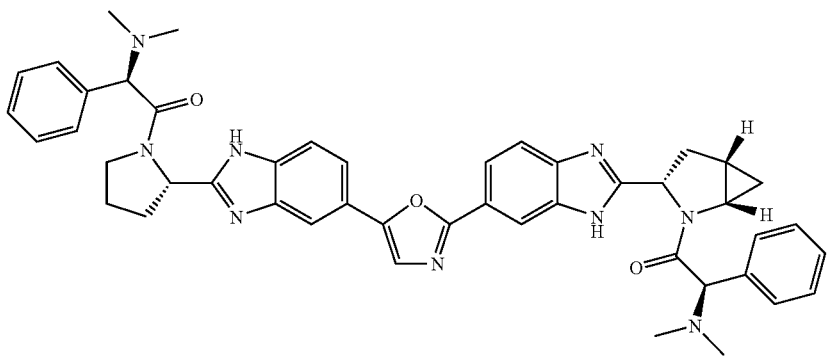<br>From J6.c2 | RT = 1.90 minutes (D-Cond. 2); LC/MS: Anal. Calcd. for [M +H]$^+$ C$_{46}$H$_{48}$N$_9$O$_3$: 774.39; found: 774.64. HRMS: Anal. Calcd. for [M + H]$^+$ C$_{46}$H$_{48}$N$_9$O$_3$: 774.3880; found: 774.3854. |
| J24 | N-((1R)-2-((2S)-2-(5-(2-(2-((1S,3S,5S)-2-((2R)-2-acetamido-2-phenylacetyl)-2-azabicyclo[3.1.0]hex-3-yl)-1H-benzimidazol-5-yl)-1,3-oxazol-5-yl)-1H-benzimidazol-2-yl)-1-pyrrolidinyl)-2-oxo-1-phenylethyl)acetamide | 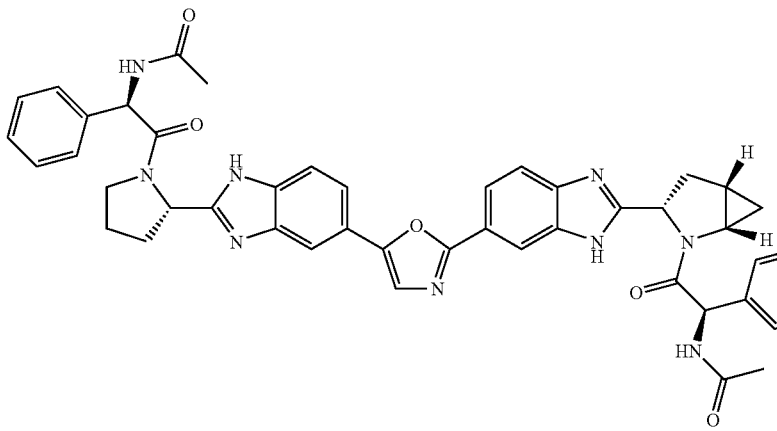<br>From J6.c2 | RT = 2.13 minutes (D-Cond. 2); LC/MS: Anal. Calcd. for [M +H]$^+$ C$_{46}$H$_{44}$N$_9$O$_5$: 802.33; found: 802.49. HRMS: Anal. Calcd. for [M − H]$^-$ C$_{46}$H$_{42}$N$_9$O$_5$: 800.3309; found: 800.3328. |
| J25 | (1R)-2-((2S)-2-(5-(2-(2-((1S,3S,5S)-2-((2R)-2-(dimethyl-amino)-2-phenylacetyl)-2-azabicyclo[3.1.0]hex-3-yl)-1H-benzimidazol-4-yl)-1,3-oxazol-5-yl)-1H-benzimidazol-2-yl)-1-pyrrolidinyl)-N,N-dimethyl-2-oxo-1-phenyl-ethanamine | 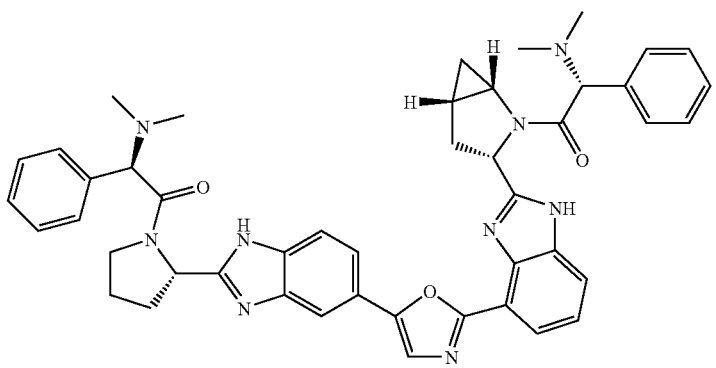<br>From J6.c3.1<br>Diastereomer 1 | RT = 2.03 minutes (D-Cond. 2); LC/MS: Anal. Calcd. for [M +H]$^+$ C$_{46}$H$_{48}$N$_9$O$_3$: 774.39; found: 774.91. HRMS: Anal. Calcd. for [M + H]$^+$ C$_{46}$H$_{48}$N$_9$O$_3$: 774.3880 found: 774.3893. |

| | | | |
|---|---|---|---|
| J25.a | (1R)-2-((2S)-2-(5-(2-(2-((1S,3S,5S)-2-((2R)-2-(dimethyl-amino)-2-phenylacetyl)-2-azabicyclo[3.1.0]hex-3-yl)-1H-benzimidazol-4-yl)-1,3-oxazol-5-yl)-1H-benzimidazol-2-yl)-1-pyrrolidinyl)-N,N-dimethyl-2-oxo-1-phenyl-ethanamine | 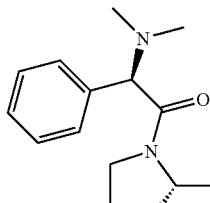 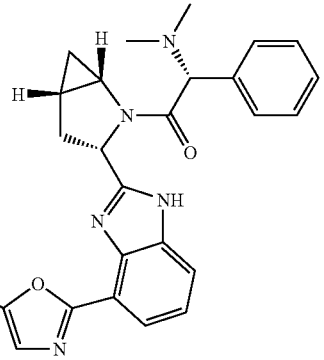<br>From J6.c3.2<br>Diastereomer 2 | RT = 1.92 minutes (D-Cond. 2); LC/MS: Anal. Calcd. for [M +H]$^+$ C$_{46}$H$_{48}$N$_9$O$_3$: 774.39; found: 774.83. HRMS: Anal. Calcd. for [M + H]$^+$ C$_{46}$H$_{48}$N$_9$O$_3$: 774.3880 found: 774.3882. |
| J26 | (2R)-2-(dimethyl-amino)-N-((1S)-1-(4-(5-(2-((2S)-1-((2R)-2-(dimethyl-amino)-2-phenylacetyl)-2-pyrrolidinyl)-1H-benzimidazol-5-yl)-1,3-oxazol-2-yl)-1H-benzimidazol-2-yl)ethyl)-2-phenyl-acetamide | 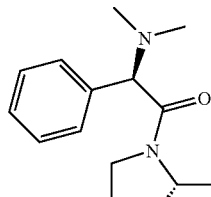 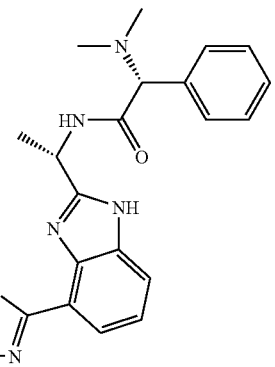<br>From J6.c4 | RT = 1.89 minutes (D-Cond. 2); LC/MS: Anal. Calcd. for [M +H]$^+$ C$_{43}$H$_{46}$N$_9$O$_3$: 736.37; found: 736.52. HRMS: Anal. Calcd. for [M + H]$^+$ C$_{43}$H$_{46}$N$_9$O$_3$: 736.3724 found: 736.3723. |
| J27 | (1R)-2-((2S)-2-(5-(2-(2-((2S)-1-acetyl-2-pyrrolidinyl)-1H-benzimidazol-4-yl)-1,3-oxazol-5-yl)-1H-benzimidazol-2-yl)-1-pyrrolidinyl)-N,N-dimethyl-2-oxo-1-phenyl-ethanamine | 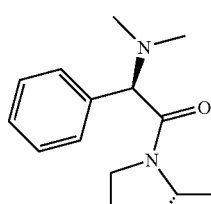 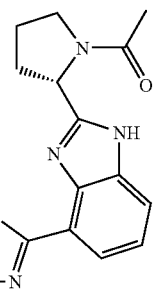<br>From J6.c5 | RT = 1.73 minutes (D-Cond. 2); LC/MS: Anal. Calcd. for [M +H]$^+$ C$_{37}$H$_{39}$N$_8$O$_3$: 643.32; found: 643.35. HRMS: Anal. Calcd. for [M + H]$^+$ C$_{37}$H$_{39}$N$_8$O$_3$: 643.3145 found: 643.3152. |

| | | | |
|---|---|---|---|
| J28 | (1R)-2-((2S)-2-(5-(2-(2-((2S)-1-((dimethyl-amino)acetyl)-2-pyrrolidinyl)-1H-benzimidazol-4-yl)-1,3-oxazol-5-yl)-1H-benzimidazol-2-yl)-1-pyrrolidinyl)-N,N-dimethyl-2-oxo-1-phenyl-ethanamine | 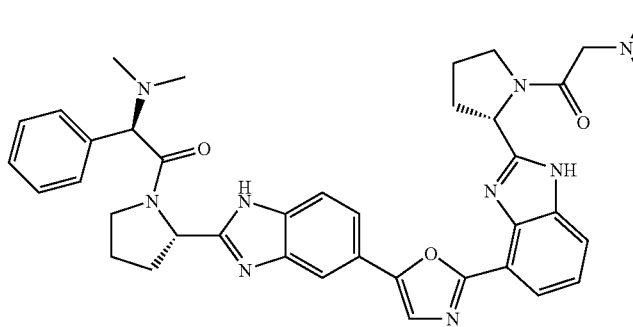<br>From J6.c5 | RT = 1.70 minutes (D-Cond. 2); LC/MS: Anal. Calcd. for [M +H]$^+$ $C_{39}H_{44}N_9O_3$: 686.36; found: 686.41. HRMS: Anal. Calcd. for [M + H]$^+$ $C_{39}H_{44}N_9O_3$: 686.3567 found: 686.3547. |
| J29 | methyl ((1R)-2-(((2S)-2-(5-(2-(2-((2S)-1-((2R)-2-(4-methyl-1-piperazinyl)-2-phenylacetyl)-2-pyrrolidinyl)-1H-benzimidazol-4-yl)-1,3-oxazol-5-yl)-1H-benzimidazol-2-yl)-1-pyrrolidinyl)-2-oxo-1-phenylethyl)carbamate | 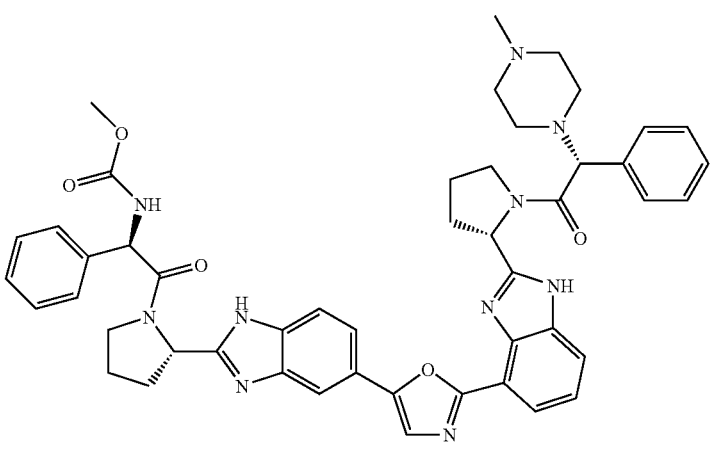<br>From J6.c6 | RT = 2.00 minutes (D-Cond. 2); LC/MS: Anal. Calcd. for [M +H]$^+$ $C_{48}H_{51}N_{10}O_5$: 847.40; found: 847.51. HRMS: Anal. Calcd. for [M + H]$^+$ $C_{48}H_{51}N_{10}O_5$: 847.4044 found: 847.4049. |
| J30 | methyl ((1R)-2-((2S)-2-(4-(5-(2-((2S)-1-((2R)-2-(4-methyl-1-piperazinyl)-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate | 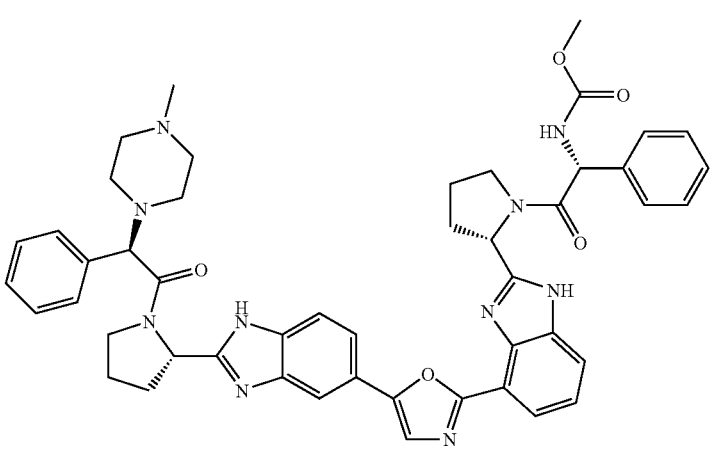<br>From J6.c7 | RT = 1.97 minutes (D-Cond. 2); LC/MS: Anal. Calcd. for [M +H]$^+$ $C_{48}H_{51}N_{10}O_5$: 847.41; found: 847.81. HRMS: Anal. Calcd. for [M + H]$^+$ $C_{48}H_{51}N_{10}O_5$: 847.4044 found: 847.4060. |

Synthetic Scheme 5

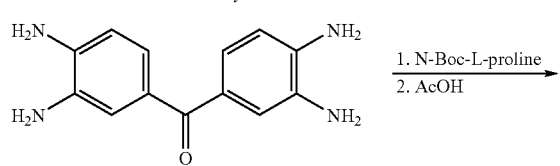

1. N-Boc-L-proline
2. AcOH

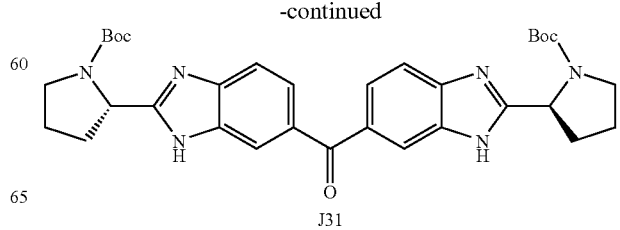

J31 iso-Butyl chloroformate (2.3 mL, 17.8 mmol) was added to a solution of N-Boc-L-proline (3.8 g, 17.8 mmol) and N-methylmorpholine (1.95 mL, 17.8 mmol) in THF (100 mL) under nitrogen cooled to 0° C. After being stirred 30 min, the activated acid was cannulated into a 0° C. suspension of 3,3'-4,4'-tetraaminobenzophenone (2.5 g, 8.89 mmol) and Hunig's base (3 mL, 17.8 mmol) in 1:1 THF/DMF (100 mL). The solvent was removed in vacuo and the residue taken up in acetic acid and heated at 60° C. for 24 h. The solvent was removed in vacuo and the residue taken up in EtOAc and washed with saturated $Na_2CO_3$ solution, brine. Biotage chromatography on a 40 M $SiO_2$ column eluting with 0-100% B (1 L); A=EtOAc; B=MeOH gave J31, 3.7 g (70%). $^1$H NMR (300 MHz, DMSO-$d_6$) δ: 7.99/7.91 (s, 2H), 7.79-7.73 (m, 4H), 5.13-5.04 (m, 2H), 3.60 (br. s, 2H), 3.48-3.41 (m, 2H), 2.45-2.36 (m, 2H), 2.10-1.93 (m, 6H), 1.40/1.09 (s, 18H). LC (J-Cond. 2): RT=1.6 min; LC/MS: Anal. Calcd. for [M+H]$^+$ $C_{33}H_{41}N_6O_5$: 601.32. found: 601.75. LRMS: Anal. Calcd. for [M+H]$^+$ $C_{33}H_{41}N_6O_5$: 601.32. found: 601.28.

vacuum for 18 h to give bis(2-((S)-pyrrolidin-2-yl)-1H-benzo[d]imidazol-6-yl)methanone. HATU (93 mg, 0.25 mmol) was added to a rapidly stirred solution the HCl salt (58 mg, 0.12 mmol), (R)-2-(dimethylamino)-2-phenylacetic acid HCl salt (53 mg, 0.24 mmol), and Hunig's base (0.4 mL, 2.3 mmol) in DMF (3 mL). The reaction was diluted with MeOH (1 vol) and directly subjected to prep. HPLC (Phenonemenex-Luna) 15%-100% B over 8 min; Flow Rate=40 mL/min; Wavelength=220 nm; Solvent A=0.1% TFA in 10% methanol/90% $H_2O$; Solvent B=0.1% TFA in 90% methanol/10% $H_2O$) gave J32 16.75 mg (20%). $^1$H NMR (300 MHz, DMSO-$d_6$) δ: 7.94 (s, 2H), 7.67-7.55 (m, 14H), 6.98-6.75 (m, 2H), 5.26-5.20 (m, 2H), 4.10-4.05 (m, 2H), 3.16-3.05 (m, 2H), 2.90/2.43 (br. s, 12H), 2.33-1.89 (m, 8H). LC (J-Cond. 2): RT=1.2 min; LC/MS: Anal. Calcd. for [M+H]$^+$ $C_{43}H_{47}N_8O_3$: 723.38. found: 723.79. LRMS: Anal. Calcd. for [M+H]$^+$ $C_{33}H_{47}N_8O_3$: 723.38. found: 723.34.

Synthetic Scheme 6

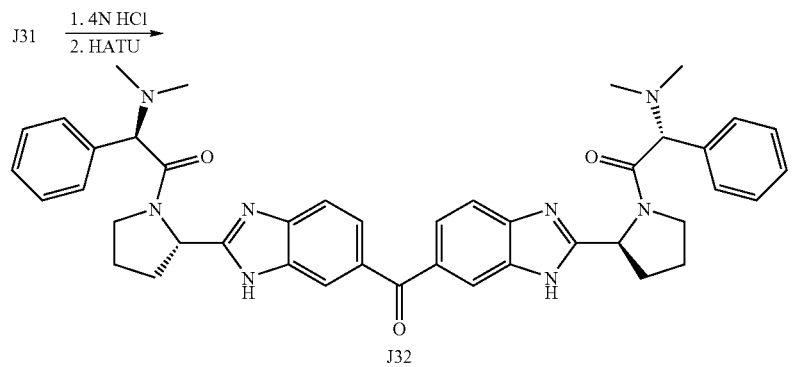

Example J32 bis(2-((2S)-1-((2R)-2-(dimethylamino)-2-phenylacetyl)-2-pyrrolidinyl)-1H-benzimidazol-5-yl)methanone Compound J31 (700 mg, 1.17 mmol) was taken up in 4N HCl/Dioxane (20 mL) and stirred 2.5 hr. The solvent was removed in vacuo, and the HCl salt was exposed to high

| | | |
|---|---|---|
| dimethyl (carbonylbis(1H-benzimidazole-5,2-diyl(2S)-2,1-pyrrolidinediyl((1R)-2-oxo-1-phenyl-2,1-ethanediyl))) biscarbamate | J33 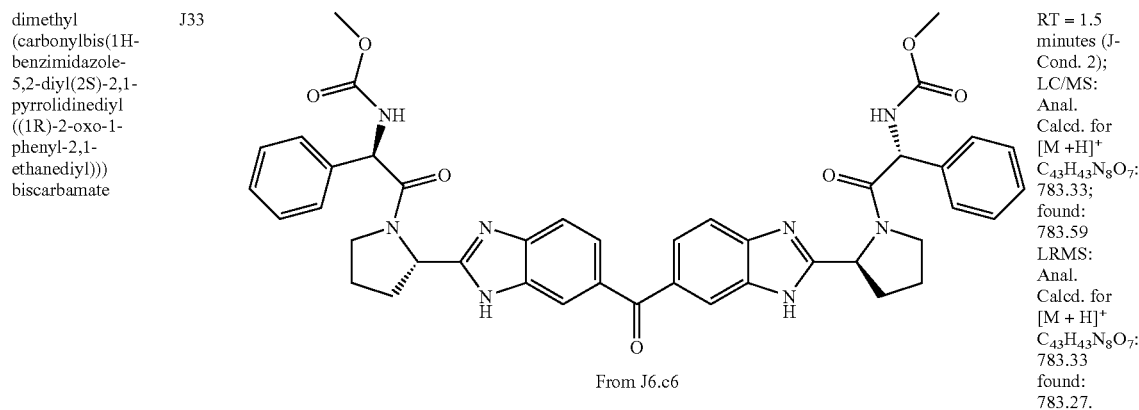 From J6.c6 | RT = 1.5 minutes (J-Cond. 2); LC/MS: Anal. Calcd. for [M +H]$^+$ $C_{43}H_{43}N_8O_7$: 783.33; found: 783.59 LRMS: Anal. Calcd. for [M + H]$^+$ $C_{43}H_{43}N_8O_7$: 783.33 found: 783.27. |

Synthesis of Common Caps

Compound Analysis Conditions

Purity assessment and low resolution mass analysis were conducted on a Shimadzu LC system coupled with Waters Micromass ZQ MS system. It should be noted that retention times may vary slightly between machines. Additional LC conditions applicable to the current section, unless noted otherwise.

| Cond.-MS-W1 | |
|---|---|
| Column = | XTERRA 3.0 × 50 mm S7 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-MS-W2 | |
| Column = | XTERRA 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-MS-W5 | |
| Column = | XTERRA 3.0 × 50 mm S7 |
| Start % B = | 0 |
| Final % B = | 30 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-D1 | |
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-D2 | |
| Column = | Phenomenex-Luna 4.6 × 50 mm S10 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-M3 | |
| Column = | XTERRA C18 3.0 × 50 mm S7 |
| Start % B = | 0 |
| Final % B = | 40 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Condition I | |
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Condition II | |
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Condition III | |
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cap-1

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to $H_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=995 mg/mL in $H_2O$; λ=589 nm]. $^1$H NMR (DMSO-$d_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for [M+H]$^+$ $C_{10}H_{14}NO_2$ 180.10. found 180.17; HRMS: Anal. Calcd. for [M+H]$^+$ $C_{10}H_{14}NO_2$ 180.1025. found 180.1017.

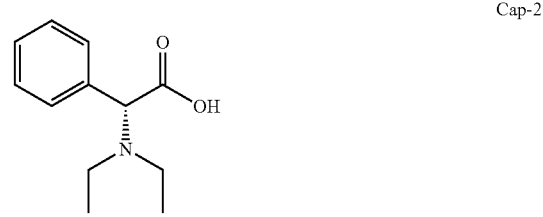

Cap-2

NaBH$_3$CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-d$_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: [α]$^{25}$ −102.21° (c=0.357, H$_2$O); crop-2: [α]$^{25}$ −99.7° (c=0.357, H$_2$O). LC (Cond. I): RT=0.43 min; LC/MS: Anal. Calcd. for [M+H]$^+$ C$_{12}$H$_{18}$NO$_2$: 208.13. found 208.26.

Cap-3

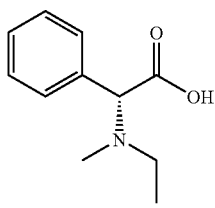

Acetaldehyde (5.0 mL, 89.1 mmol) and a suspension of 10% Pd/C (720 mg) in methanol/H$_2$O (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of H$_2$ for 17 hours. An additional acetaldehyde (10 mL, 178.2 mmol) was added and stirring continued under H$_2$ atmosphere for 24 hours [Note: the supply of H$_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for [M+H]$^+$ C$_{10}$H$_{14}$NO$_2$: 180.10. found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaccous earth (Celite®) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogenieity index; LC/MS: Anal. Calcd. for [M+H]$^+$ C$_{11}$H$_{16}$NO$_2$: 194.12. found 194.18; HRMS: Anal. Calcd. for [M+H]$^+$ C$_{11}$H$_{16}$NO$_2$: 194.1180. found 194.1181.

Cap-4

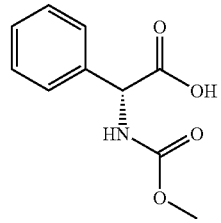

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for [M+Na]$^+$ C$_{14}$H$_{19}$NNaO$_4$: 288.12. found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H$_2$O; λ=589 nm]. $^1$H NMR (DMSO-d$_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homogeneity index; LC/MS: Anal. Calcd. for [M+H]$^+$ C$_{10}$H$_{12}$NO$_4$ 210.08. found 210.17; HRMS: Anal. Calcd. for [M+H]$^+$ C$_{10}$H$_{12}$NO$_4$ 210.0766. found 210.0756.

Cap-5

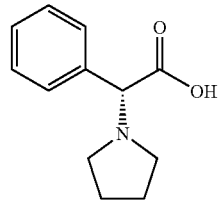

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours.

The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]$^+$ C$_{12}$H$_{16}$NO$_2$: 206.12. found 206.25.

Cap-6

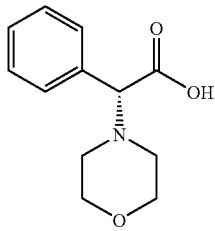

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal. Calcd. for [M+H]$^+$ C$_{12}$H$_{16}$NO$_3$: 222.11. found 222.20; HRMS: Anal. Calcd. for [M+H]$^+$ C$_{12}$H$_{16}$NO$_3$: 222.1130. found 222.1121.

Cap-7

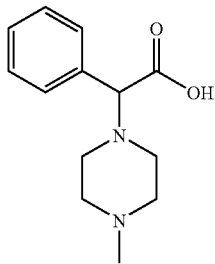

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (−5° C.) CH$_2$Cl$_2$ (200 ml) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]$^+$ C$_{22}$H$_{20}$NaO$_5$S: 419.09. found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Enantiomer-1 (1.474 g) and enantiomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]$^+$ C$_{20}$H$_{25}$N$_2$O$_2$: 325.19. found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Cond. II); >90% homogeneity index; LC/MS: Anal. Calcd. for [M+H]$^+$ C$_{13}$H$_{19}$N$_2$O$_2$: 235.14. found 235.15; HRMS: Anal. Calcd. for [M+H]$^+$ C$_{13}$H$_{19}$N$_2$O$_2$: 235.1447. found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermedites, as described below.

Cap-8

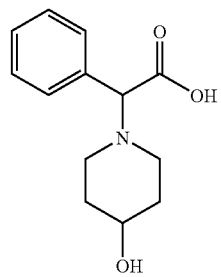

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 µm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-$d_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. II); >98% homogeneity index; LC/MS: Anal. Calcd. for [M+H]$^+$ $C_{13}H_{18}NO_3$: 236.13. found 236.07; HRMS: Calcd. for [M+H]$^+$ $C_{13}H_{18}NO_3$: 236.1287. found 236.1283.

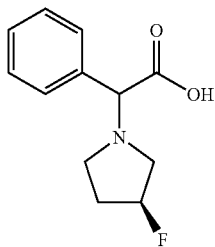

9a: diastereomer-1
9b: diastereomer-2

Cap-9

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 µm) eluting with 95% $CO_2$/5% methanol with 0.1% TFA, at 10 bar pressure, 70 mL/min flow rate, and a temperature of 35° C. The HPLC elute for the respective stereiosmers was concentrated, and the residue was dissolved in $CH_2Cl_2$ (20 mL) and washed with an aqueous medium (10 mL water+1 mL saturated $NaHCO_3$ solution). The organic phase was dried ($MgSO_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using $H_2O$/methanol/TFA solvent): $^1$H NMR (DMSO-$d_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]$^+$ $C_{12}H_{15}FNO_2$: 224.11. found 224.14; Cap-9b (diastereomer-2): $^1$H NMR (DMSO-$d_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]$^+$ $C_{12}H_{15}FNO_2$: 224.11. found 224.14.

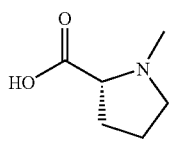

Cap-10

To a solution of D-proline (2.0 g, 17 mmol) and formaldehyde (2.0 mL of 37% wt. in $H_2O$) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-$d_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]$^+$ $C_6H_{12}NO_2$: 130.09. found 129.96.

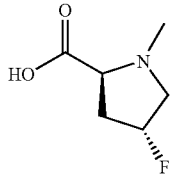

Cap-11

A mixture of (2S,4R)-4-fluoropyrrolidine-2-carboxylic acid (0.50 g, 3.8 mmol), formaldehyde (0.5 mL of 37% wt. in $H_2O$), 12 N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-$d_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]$^+$ $C_6H_{11}FNO_2$: 148.08. found 148.06.

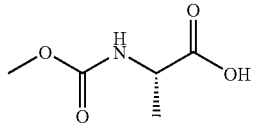

Cap-12 (same as cap 52)

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH~2-3. The resulting solutions was extracted with ethyl acetate (3×100 mL), and the combined organic phase was dried ($Na_2SO_4$), filtered, and concentrated in vacuo to provide a colorless oil (2.58 g). 500 mg of this material was purified by a reverse phase HPLC ($H_2O$/methanol/TFA) to provide 150 mg of Cap-12 as a colorless oil. $^1$H NMR (DMSO-$d_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

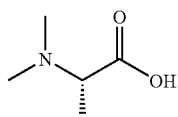

Cap-13

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-$d_6$, δ=2.5, 500 MHz) δ 12.1 (br s, 1H), 4.06 (q, J=7.4, 1H), 2.76 (s, 6H), 1.46 (d, J=7.3, 3H).

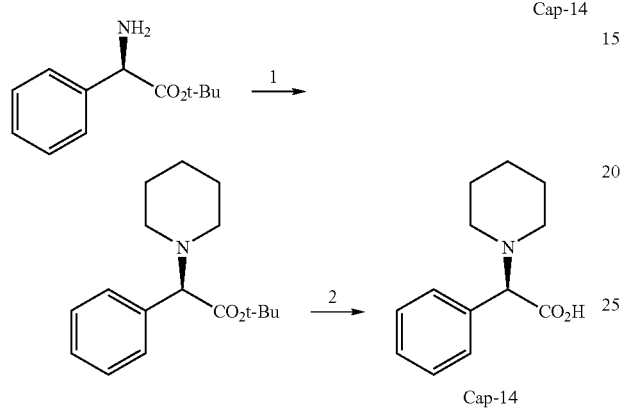

Cap-14

Step 1: A mixture of (R)-(-)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275. found: 276 (M+H)$^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-$d_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{17}$NO$_2$: 219. found: 220 (M+H)$^+$.

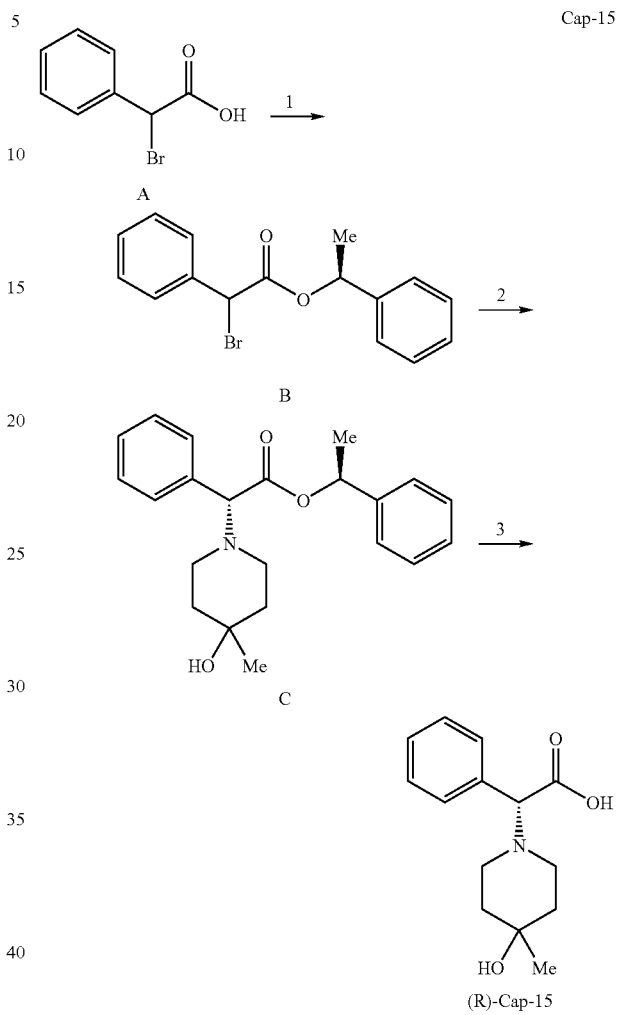

Step 1: (S)-1-Phenylethyl 2-bromo-2-phenylacetate: To a mixture of α-bromophenylacetic acid (10.75 g, 0.050 mol), (S)-(-)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$H NMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 ml) was added. The mixture was stirred for 1 hour at room temperature and then it was heated at 55-60° C. (oil bath temperature) for 4 hours. The cooled reaction mixture was then diluted with ethyl acetate (30 mL), washed (H₂O×2, brine), dried (MgSO₄), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: ¹H NMR (CD₃OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for C₂₂H₂₇NO₃: 353. found: 354 (M+H)⁺. (S,S)-isomer: ¹H NMR (CD₃OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for C₂₂H₂₇NO₃: 353. found: 354 (M+H)⁺.

Step 3: (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH₃CN—H₂O-0.1% TFA) to give the title compound (as TFA salt) as a pale bluish solid (0.128 g, 98%). LCMS: Anal. Calcd. for C₁₄H₁₉NO₃: 249. found: 250 (M+H)⁺.

and concentrated in vacuo. The residue was purified by silica gel chromatography (Biotage/0-20% ethyl acetate-hexane) to provide the title compound as a colorless oil (8.38 g, 92%). ¹H NMR (400 MHz, CD₃OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr₄ (13.5 g, 40.7 mmol) in THF (100 mL) was added and the mixture was allowed to warm to −10° C. and stirred at this temperature for 2 hours. The reaction mixture was quenched with saturated aq. NH₄Cl and the layers were separated. The aqueous layer was back-extracted with ethyl acetate (2×) and the combined organic phases were washed (H₂O, brine), dried (Na₂SO₄), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by ¹H NMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). ¹H NMR (400 MHz, CD₃OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for C₂₁H₂₄FNO₂: 341. found: 342 (M+H)⁺.

Step 3: (R)-2-(2-fluorophenyl)-2-piperidin-1-yl)acetic acid: A mixture of (R)—((S)-1-phenylethyl) 2-(2-fluorophenyl)-2-(piperidin-1-yl)acetate (0.737 g, 2.16 mmol) and 20% Pd(OH)₂/C (0.070 g) in ethanol (30 mL) was hydrogenated at room temperature and atmospheric pressure (H₂ balloon) for 2 hours. The solution was then purged with Ar, filtered through diatomaceous earth (Celite®), and concentrated in vacuo. This provided the title compound as a colorless solid (0.503 g, 98%). ¹H NMR (400 MHz, CD₃OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for C₁₃H₁₆FNO₂: 237. found: 238 (M+H)⁺.

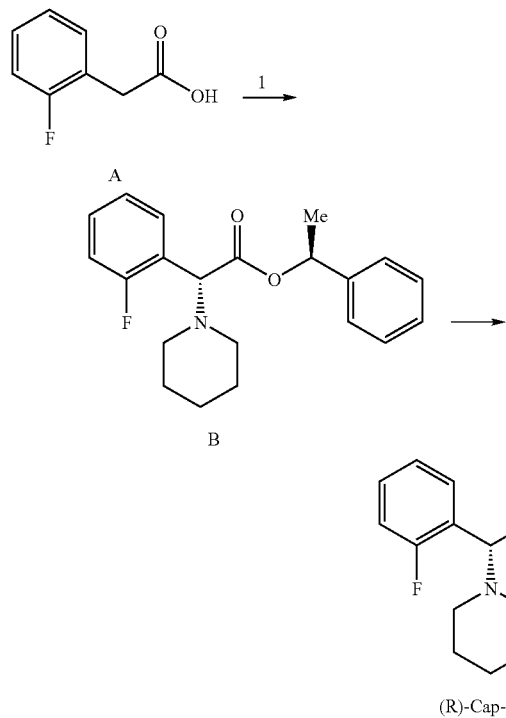

(R)-Cap-16

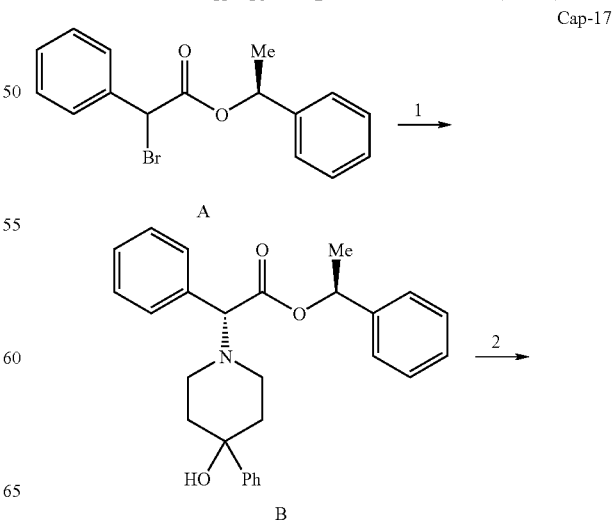

Cap-17

Step 1: (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH₂Cl₂ (100 mL) was stirred at room temperature for 12 hours. The solvent was then concentrated and the residue partitioned with H₂O-ethyl acetate. The phases were separated and the aqueous layer back-extracted with ethyl acetate (2×). The combined organic phases were washed (H₂O, brine), dried (Na₂SO₄), filtered, -continued

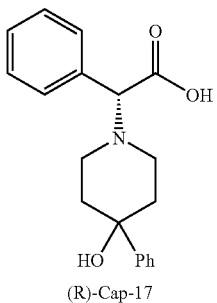

(R)-Cap-17

Step 1: (S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O$ ×2, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (Chiralcel OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415. found: 416 $(M+H)^+$; (S,S)-isomer: $H^1$NMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=1.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415. found: 416 $(M+H)^+$.

The following esters were prepared in similar fashion:

| Intermediate-17a | 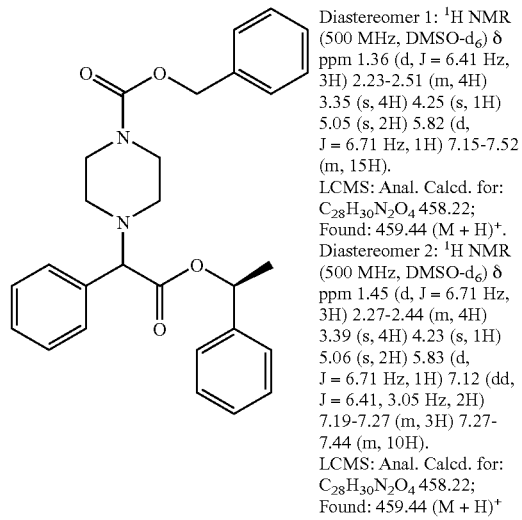 | Diastereomer 1: $^1$H NMR (500 MHz, DMSO-$d_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: $C_{28}H_{30}N_2O_4$ 458.22; Found: 459.44 $(M + H)^+$. Diastereomer 2: $^1$H NMR (500 MHz, DMSO-$d_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LCMS: Anal. Calcd. for: $C_{28}H_{30}N_2O_4$ 458.22; Found: 459.44 $(M + H)^+$ |
|---|---|---|
| Intermediate-17b | 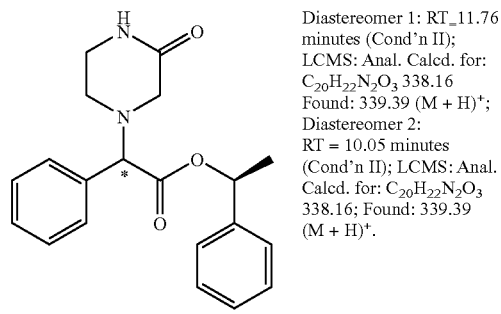 | Diastereomer 1: RT=11.76 minutes (Cond'n II); LCMS: Anal. Calcd. for: $C_{20}H_{22}N_2O_3$ 338.16 Found: 339.39 $(M + H)^+$; Diastereomer 2: RT = 10.05 minutes (Cond'n II); LCMS: Anal. Calcd. for: $C_{20}H_{22}N_2O_3$ 338.16; Found: 339.39 $(M + H)^+$. |

-continued

| | | |
|---|---|---|
| Intermediate-17c | 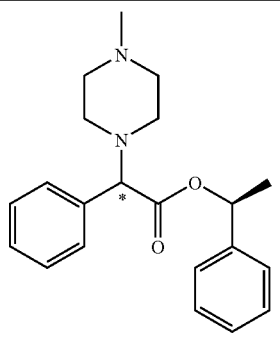 | Diastereomer 1: $T_R$ 4.55 minutes (Cond'n I); LCMS: Anal. Calcd. for: $C_{21}H_{26}N_2O_2$ 338.20 Found: 339.45 (M + H)$^+$; Diastereomer 2: $T_R$ 6.00 minutes (Cond'n I); LCMS: Anal. Calcd. for: $C_{21}H_{26}N_2O_2$ 338.20 Found: 339.45 (M + H)$^+$. |
| Intermediate-17d | 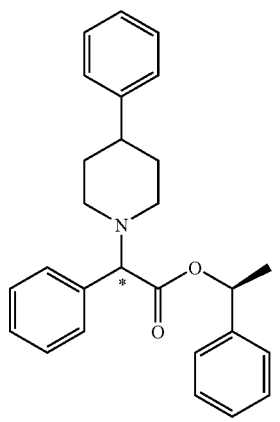 | Diastereomer 1: RT_7.19 minutes (Cond'n I); LCMS: Anal. Calcd. for: $C_{27}H_{29}NO_2$ 399.22 Found: 400.48 (M + H)$^+$; Diastereomer 2: RT = 9.76 minutes (Cond'n I); LCMS: Anal. Calcd. for: $C_{27}H_{29}NO_2$ 399.22 Found: 400.48 (M + H)$^+$. |

Chiral SFC Conditions for Determining Retention Time

Condition I

Column: Chiralpak AD-H Column, 4.62×50 mm, 5 μm

Solvents: 90% CO2-10% methanol with 0.1% DEA

Temp: 35° C.

Pressure: 150 bar

Flow rate: 2.0 mL/min.

UV monitored @220 nm

Injection: 1.0 mg/3 mL methanol

Condition II

Column: Chiralcel OD-H Column, 4.62×50 mm, 5 μm

Solvents: 90% CO2-10% methanol with 0.1% DEA

Temp: 35° C.

Pressure: 150 bar

Flow rate: 2.0 mL/min.

UV monitored @220 nm

Injection: 1.0 mg/mL methanol

Cap 17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH$_3$CN—H$_2$O-0.1% TFA) to give the title compound (as TFA salt) as a white solid (0.230 g, 88%). LCMS: Anal. Calcd. for C$_{19}$H$_{21}$NO$_3$: 311.15. found: 312 (M+H)$^+$.

The following carboxylic acids were prepared in optically pure form in a similar fashion:

| | | |
|---|---|---|
| Cap-17a | 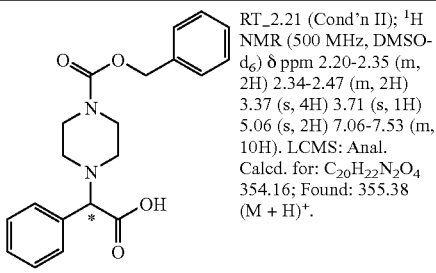 | RT_2.21 (Cond'n II); $^1$H NMR (500 MHz, DMSO-d$_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 (M + H)$^+$. |
| Cap-17b | 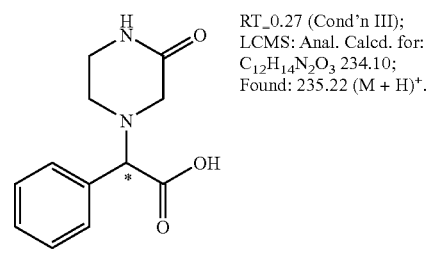 | RT_0.27 (Cond'n III); LCMS: Anal. Calcd. for: $C_{12}H_{14}N_2O_3$ 234.10; Found: 235.22 (M + H)$^+$. |
| Cap-17c | 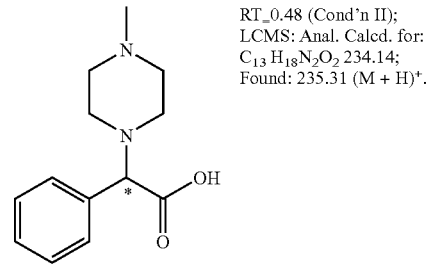 | RT_0.48 (Cond'n II); LCMS: Anal. Calcd. for: $C_{13}H_{18}N_2O_2$ 234.14; Found: 235.31 (M + H)$^+$. |

| | | |
|---|---|---|
| Cap-17d | 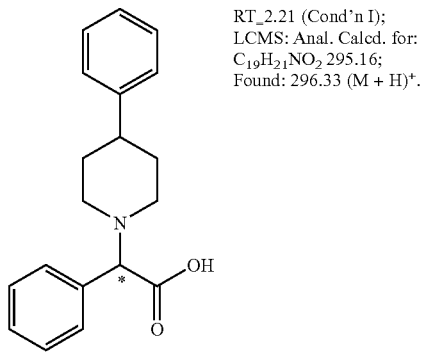 | RT_2.21 (Cond'n I); LCMS: Anal. Calcd. for: $C_{19}H_{21}NO_2$ 295.16; Found: 296.33 (M + H)⁺. |

LCMS Conditions for Determining Retention Time
Condition I
Column: Phenomenex-Luna 4.6×50 mm S10
Start % B=0
Fianl % B=100
Gradient Time=4 min
Flow Rate=4 mL/min
Wavelength=220
Solvent A=10% methanol—90% H₂O—0.1% TFA
Solvent B=90% methanol—10% H₂O—0.1% TFA
Condition II
Column: Waters-Sunfire 4.6×50 mm S5
Start % A=0
Fianl % B=100
Gradient Time=2 min
Flow Rate=4 mL/min
Wavelength=220
Solvent A=10% methanol—90% H₂O—0.1% TFA
Solvent B=90% methanol—10% H₂O—0.1% TFA
Condition III
Column: Phenomenex 10µ 3.0×50 mm
Start % B=0
Fianl % B=100
Gradient Time=2 min
Flow Rate=4 mL/min
Wavelength=220
Solvent A=10% methanol—90% H₂O—0.1% TFA
Solvent B=90% methanol—10% H₂O—0.1% TFA

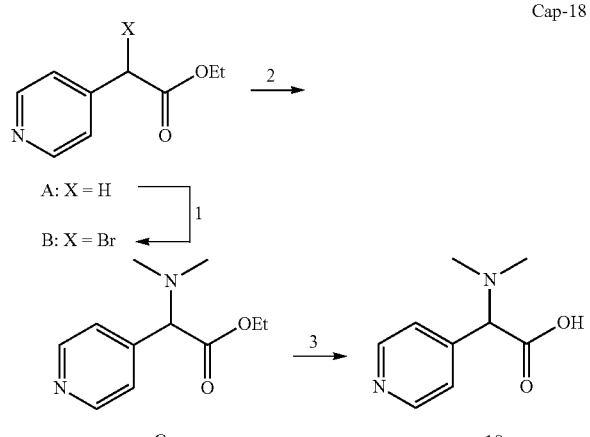

Cap-18

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr₄ (2.21 g, 6.66 mmol) and stirring was continued at −78° C. for 2 hours. The reaction mixture was then quenched with sat. aq. NH₄Cl and the phases were separated. The organic phase was washed (brine), dried (Na₂SO₄), filtered, and concentrated in vacuo. The resulting yellow oil was immediately purified by flash chromatography (SiO₂/hexane-ethyl acetate, 1:1) to provide the title compound (1.40 g, 95%) as a somewhat unstable yellow oil. ¹H NMR (400 MHz, CDCl₃) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244. found: 243, 245 (M+H)⁺.

Step 2; (R,S)-Ethyl 2-(4-pyridyl)-2-N,N-dimethylamino)acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (Biotage, 40+M SiO₂ column; 50%-100% ethyl acetate-hexane) to provide the title compound (0.539 g, 31%) as a light yellow oil. ¹H NMR (400 MHz, CDCl₃) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for $C_{11}H_{16}N_2O_2$: 208. found: 209 (M+H)⁺.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H₂O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. ¹H NMR (400 MHz, DMSO-d₆) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

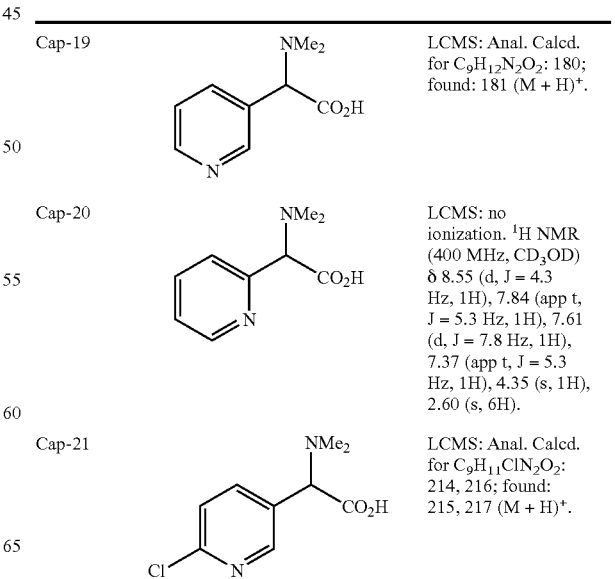

| | | |
|---|---|---|
| Cap-19 | | LCMS: Anal. Calcd. for $C_9H_{12}N_2O_2$: 180; found: 181 (M + H)⁺. |
| Cap-20 | | LCMS: no ionization. ¹H NMR (400 MHz, CD₃OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | | LCMS: Anal. Calcd. for $C_9H_{11}ClN_2O_2$: 214, 216; found: 215, 217 (M + H)⁺. |

201
-continued

| Cap-22 | 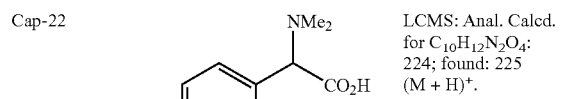 | LCMS: Anal. Calcd. for $C_{10}H_{12}N_2O_4$: 224; found: 225 $(M + H)^+$ |
|---|---|---|
| Cap-23 | 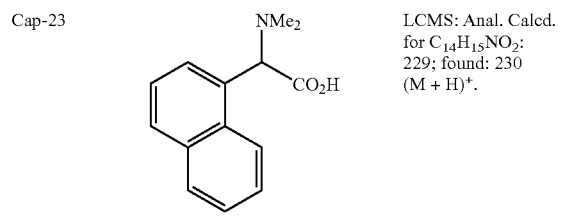 | LCMS: Anal. Calcd. for $C_{14}H_{15}NO_2$: 229; found: 230 $(M + H)^+$ |
| Cap-24 | 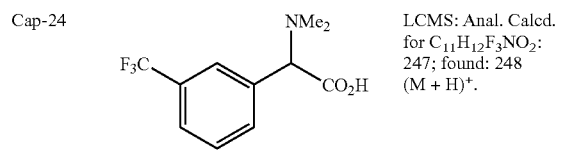 | LCMS: Anal. Calcd. for $C_{11}H_{12}F_3NO_2$: 247; found: 248 $(M + H)^+$ |
| Cap-25 | 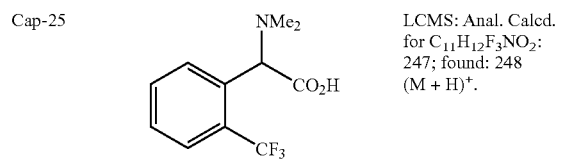 | LCMS: Anal. Calcd. for $C_{11}H_{12}F_3NO_2$: 247; found: 248 $(M + H)^+$ |
| Cap-26 | 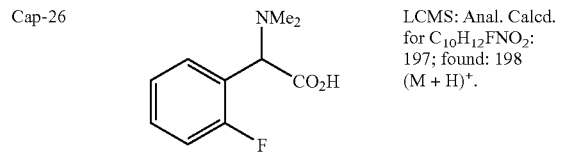 | LCMS: Anal. Calcd. for $C_{10}H_{12}FNO_2$: 197; found: 198 $(M + H)^+$ |
| Cap-27 | 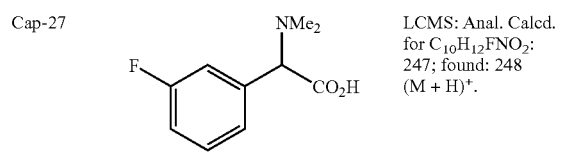 | LCMS: Anal. Calcd. for $C_{10}H_{12}FNO_2$: 247; found: 248 $(M + H)^+$ |
| Cap-28 | 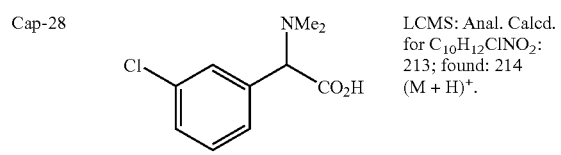 | LCMS: Anal. Calcd. for $C_{10}H_{12}ClNO_2$: 213; found: 214 $(M + H)^+$ |
| Cap-29 | 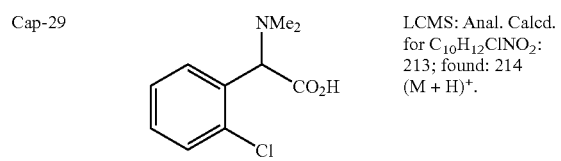 | LCMS: Anal. Calcd. for $C_{10}H_{12}ClNO_2$: 213; found: 214 $(M + H)^+$ |
| Cap-30 | 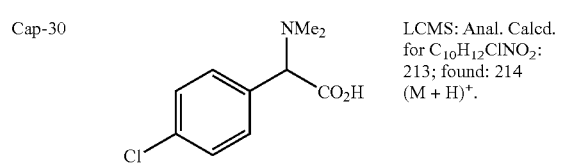 | LCMS: Anal. Calcd. for $C_{10}H_{12}ClNO_2$: 213; found: 214 $(M + H)^+$ |

202
-continued

| Cap-31 | 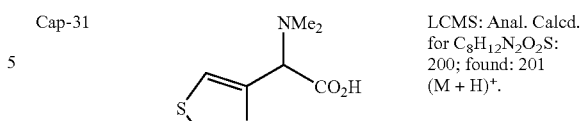 | LCMS: Anal. Calcd. for $C_8H_{12}N_2O_2S$: 200; found: 201 $(M + H)^+$ |
|---|---|---|
| Cap-32 | 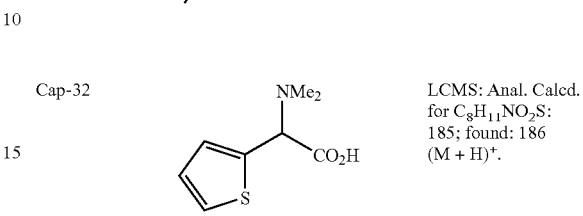 | LCMS: Anal. Calcd. for $C_8H_{11}NO_2S$: 185; found: 186 $(M + H)^+$ |
| Cap-33 | 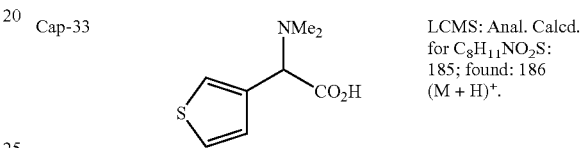 | LCMS: Anal. Calcd. for $C_8H_{11}NO_2S$: 185; found: 186 $(M + H)^+$ |
| Cap-34 | 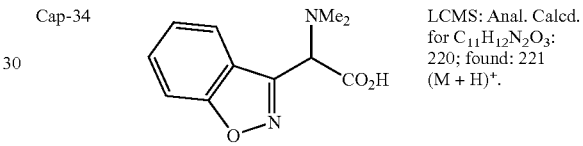 | LCMS: Anal. Calcd. for $C_{11}H_{12}N_2O_3$: 220; found: 221 $(M + H)^+$ |
| Cap-35 | 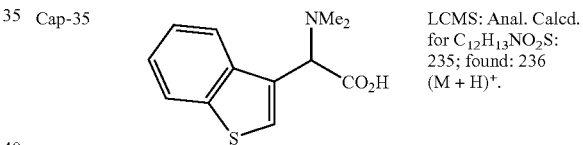 | LCMS: Anal. Calcd. for $C_{12}H_{13}NO_2S$: 235; found: 236 $(M + H)^+$ |
| Cap-36 | 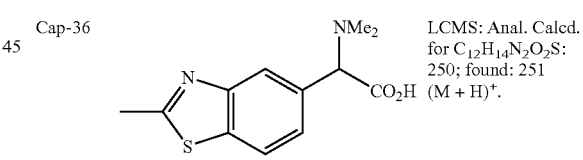 | LCMS: Anal. Calcd. for $C_{12}H_{14}N_2O_2S$: 250; found: 251 $(M + H)^+$ |

Cap-37

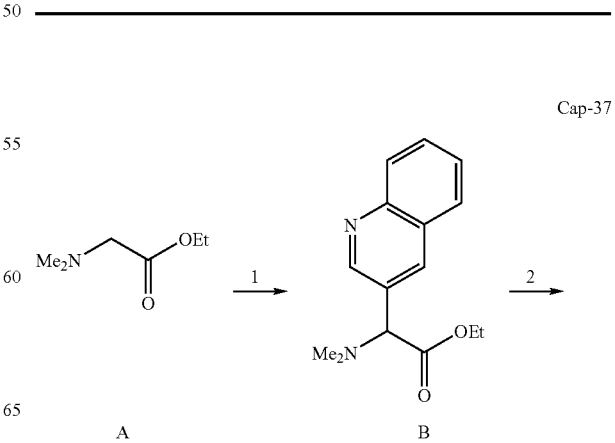

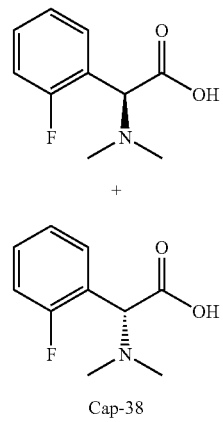

cap-37

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1H$ NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258. found: 259 $(M+H)^+$.

Step 2; (R,S) 2-(Quinolin-3-yl)-2-(N,N-dimethylamino) acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230. found: 231 $(M+H)^+$.

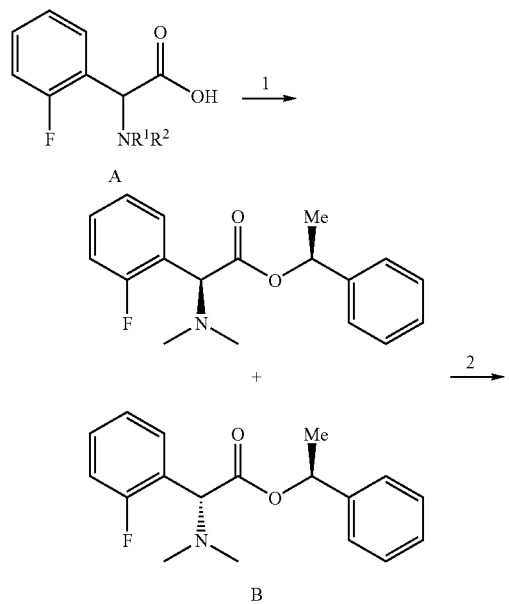

Cap-38

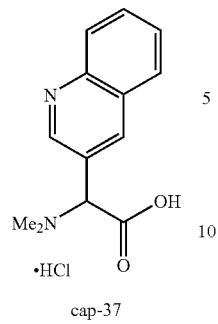

Cap-38

Step 1; (R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried $Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g, 18%), both as their TFA salts. (S,R)-isomer: $^1H$ NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for $C_{18}H_{20}FNO_2$: 301. found: 302 $(M+H)^+$; (S,S)-isomer: $^1H$: NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301. found: 302 $(M+H)^+$.

Step 2; (R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% $Pd(OH)_2/C$ (0.125 g) in ethanol (30 mL) was hydrogenated at room temperature and atmospheric pressure ($H_2$ balloon) for 4 hours. The solution was then purged with Ar, filtered through diatomaceous earth (Celite®), and concentrated in vacuo. This gave the title compound as a colorless solid (0.503 g, 98%). $^1H$ NMR (400 MHz, $CD_3OD$) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197. found: 198 $(M+H)^+$.

The S-isomer could be obtained from (S)—((S)-1-phenylethyl) 2-(dimethylamino)-2-(2-fluorophenyl)acetate TFA salt in similar fashion.

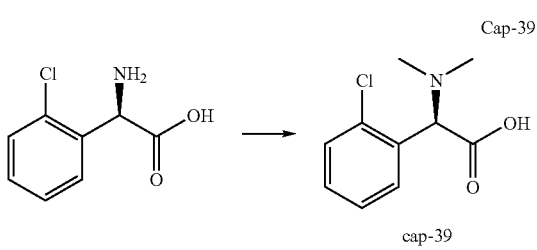

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH$_3$CN—H$_2$O—0.1% TFA) to give the TFA salt of the title compound (R)-2-(dimethylamino)-2-(2-chlorophenyl)acetic acid as a colorless oil (0.290 g, 55%). $^1$H NMR (400 MHz, CD$_3$OD) δ 7.59-7.65 (m, 2H), 7.45-7.53 (m, 2H), 5.40 (s, 1H), 2.87 (s, 6H). LCMS: Anal. Calcd. for C$_{10}$H$_{12}$ClNO$_2$: 213. found: 214 (M+H)$^+$.

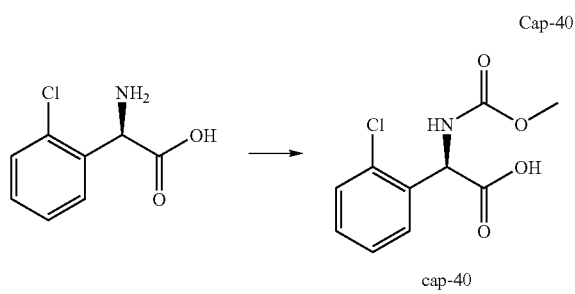

cap-40

To an ice-cold solution of (R)-(2-chlorophenyl)glycine (1.00 g, 5.38 mmol) and NaOH (0.862 g, 21.6 mmol) in H$_2$O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H$_2$O, brine), dried (Na$_2$SO$_4$), filtered, and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LCMS: Anal. Calcd. for C$_{10}$H$_{10}$ClNO$_4$: 243. found: 244 (M+H)$^+$.

To a suspension of 2-(2-(chloromethyl)phenyl)acetic acid (2.00 g, 10.8 mmol) in THF (20 ml) was added morpholine (1.89 g, 21.7 mmol) and the solution was stirred at room temperature for 3 hours. The reaction mixture was then diluted with ethyl acetate and extracted with H$_2$O (2×). The aqueous phase was lyophilized and the residue was purified by silica gel chromatography (Biotage/0-10% methanol-CH$_2$Cl$_2$) to give the title compound 2-(2-(Morpholinomethyl)phenyl)acetic acid as a colorless solid (2.22 g, 87%). $^1$H NMR (400 MHz, CD$_3$OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for C$_{13}$H$_{17}$NO$_3$: 235. found: 236 (M+H)$^+$.

The following examples were similarly prepared using the method described for Cap-41:

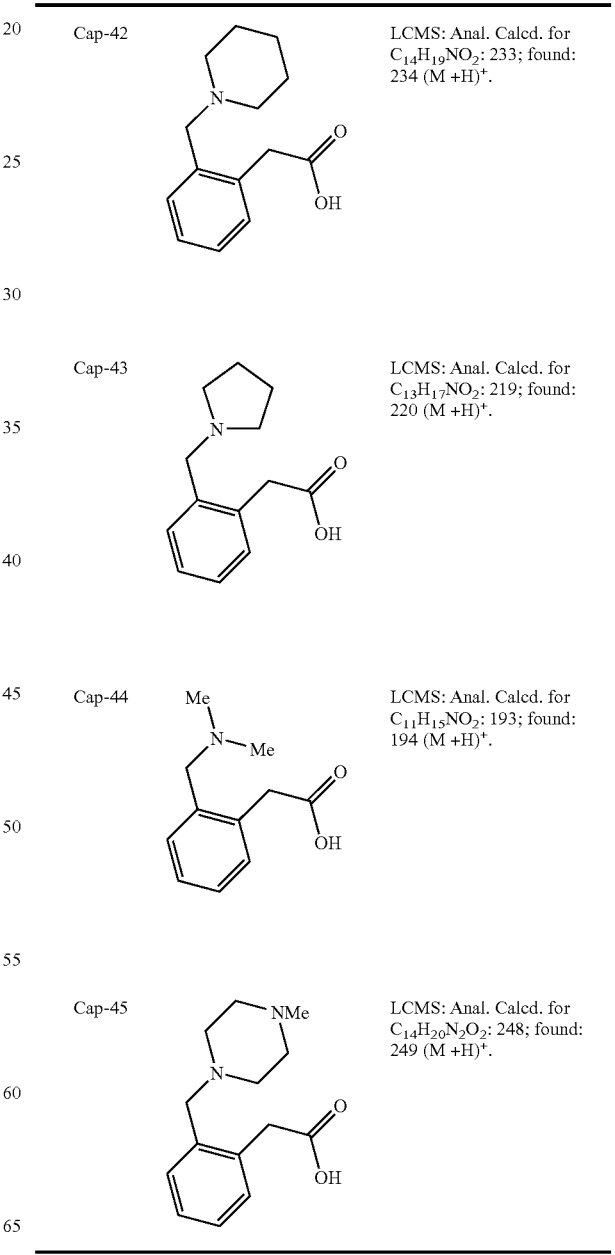

Cap-45a

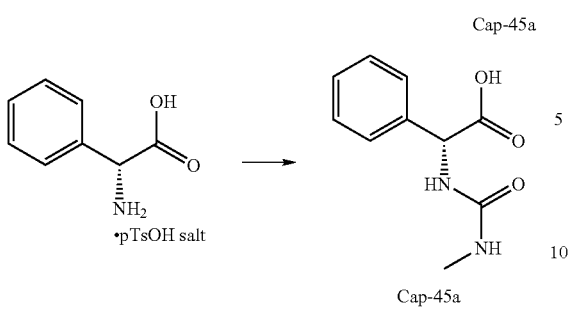

HMDS (1.85 mL, 8.77 mmol) was added to a suspension of (R)-2-amino-2-phenylacetic acid p-toluenesulfonate (2.83 g, 8.77 mmol) in $CH_2Cl_2$ (10 mL) and the mixture was stirred at room temperature for 30 minutes. Methyl isocyanate (0.5 g, 8.77 mmol) was added in one portion stirring continued for 30 minutes. The reaction was quenched by addition of $H_2O$ (5 mL) and the resulting precipitate was filtered, washed with $H_2O$ and n-hexanes, and dried under vacuum. (R)-2-(3-methylureido)-2-phenylacetic acid (1.5 g; 82%). was recovered as a white solid and it was used without further purification. $^1H$ NMR (500 MHz, DMSO-$d_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for $C_{10}H_{12}N_2O_3$ 208.08 found 209.121 (M+H)$^+$; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

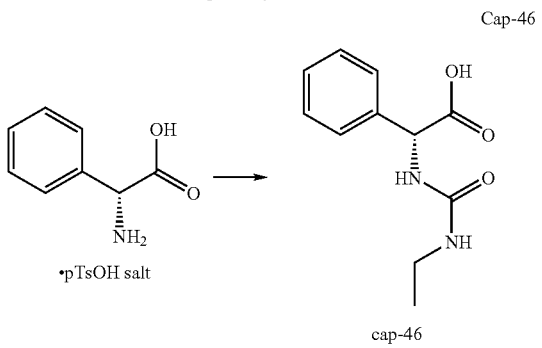

The desired product was prepared according to the method described for Cap-45a. $^1H$ NMR (500 MHz, DMSO-$d_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for $C_{11}H_{14}N_2O_3$ 222.10 found 223.15 (M+H)$^+$. HPLC XTERRA C-18 3.0×506 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.87 min, 90% homogeneity index.

Cap-47

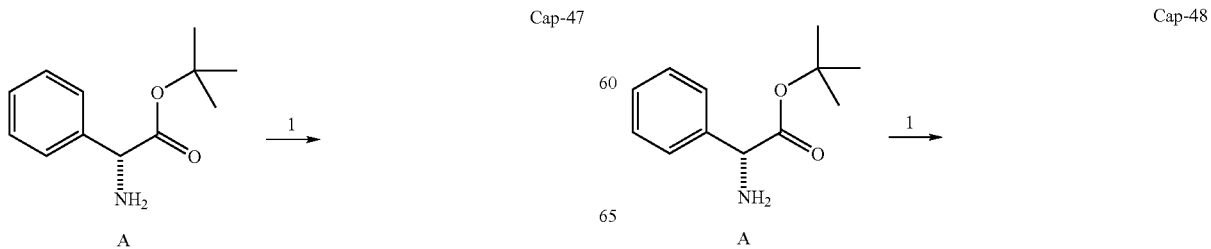

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with $H_2O$, 1N aq. HCl and brine, dried (MgSO$_4$), filtered and concentrated under reduced pressure. (R)-tert-butyl 2-(3,3-dimethylureido)-2-phenylacetate was obtained as a white solid (0.86 g; 75%) and used without further purification. $^1H$ NMR (500 MHz, DMSO-$d_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)$^+$; HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in $CH_2Cl_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1H$ NMR (500 MHz, DMSO-$d_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=17.32 Hz, 2H) 7.38-7.43 (m, 2H) 12.65 (s, 1H). LCMS: Anal. Calcd. for $C_{11}H_{14}N_2O_3$: 222.24. found: 223.21 (M+H)$^+$. HPLC XTERRA C-18 3.0× 50 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.75 min, 93% homogeneity index.

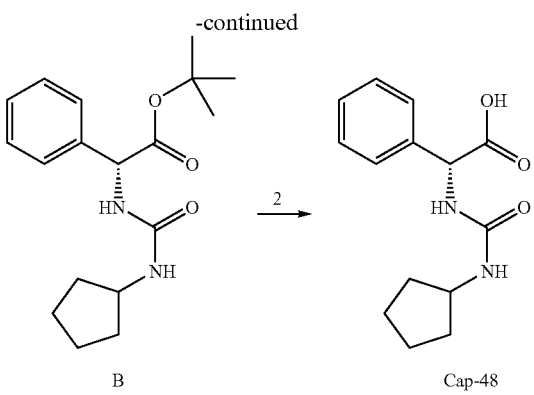

Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with $H_2O$ and brine, dried ($MgSO_4$), filtered, and concentrated under reduced pressure. (R)-tert-butyl 2-(3-cyclopentylureido)-2-phenylacetate was obtained as an opaque oil (1.32 g; 100%) and used without further purification. $^1H$ NMR (500 MHz, $CD_3Cl$-D) δ ppm 1.50-1.57 (m, 2H) 1.58-1.66 (m, 2H) 1.87-1.97 (m, 2H) 2.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)+; HPLC XTERRA C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in $CH_2Cl_2$ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1H$ NMR (500 MHz, DMSO-$d_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31. found: 263.15 (M+H)+. HPLC XTERRA C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=1.24 min, 100% homogeneity index.

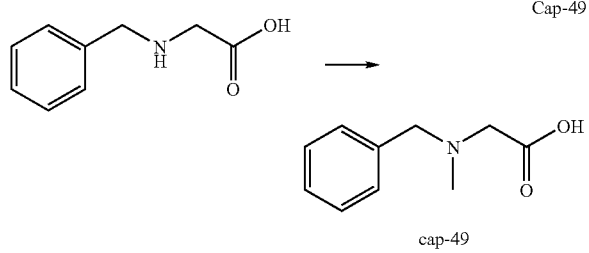

To a stirred solution of 2-(benizylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1H$ NMR (300 MHz, DMSO-$d_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 179.09. Found: 180.20 (M+H)+.

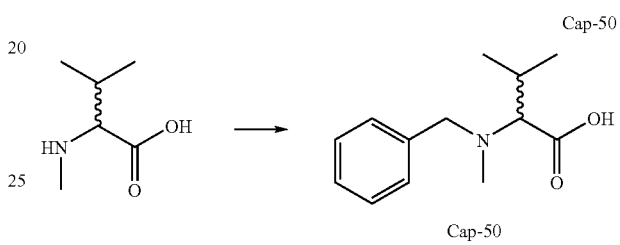

Cap-50

To a stirred solution of 3-methyl-2-(methylamino)butanoic acid (0.50 g, 3.81 mmol) in water (30 mL) was added $K_2CO_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1H$ NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 24) 7.29-7.65 (m, 5H), LCMS: Anal. Calcd. for: $C_{13}H_{19}NO_2$ 221.14. Found: 222.28 (M+H)+.

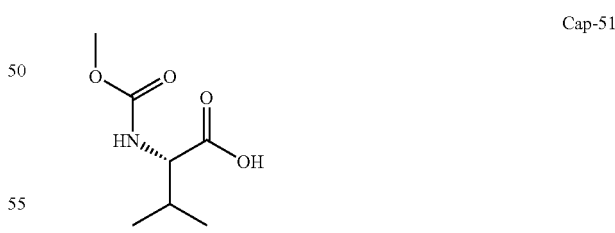

$Na_2CO_3$ (1.83 g, 17.2 mmol) was added to NaOH (33 mL of 1M/$H_2O$, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with $CH_2Cl_2$ (50 mL, 3×). The organic phase was dried (MgSO$_4$) and evaporated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ C$_7$H$_{14}$NO$_4$: 176.0923. found 176.0922.

Cap-52 (Same as Cap-12)

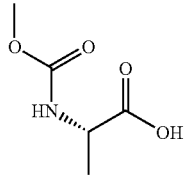

Cap-52 was synthesized from L-alanine according to the procedure described for the synthesis of Cap-51. For characterization purposes, a portion of the crude material was purified by a reverse phase HPLC (H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R) Cap-53b: (S) | 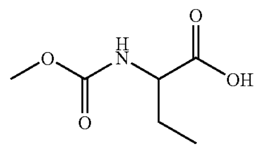 | $^1$H NMR (DMSO-d$_6$, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) | 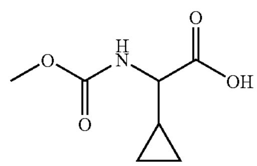 | $^1$H NMR (DMSO-d$_6$, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M +H]$^+$ C$_7$H$_{12}$NO$_4$: 174.0766; found 174.0771 |
| Cap-55 | 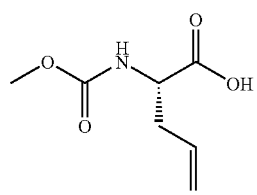 | $^1$H NMR (DMSO-d$_6$, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 | 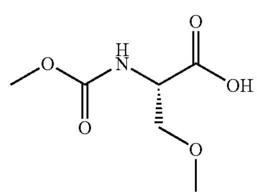 | $^1$H NMR (DMSO-d$_6$, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 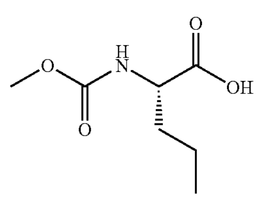 | $^1$H NMR (DMSO-d$_6$, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M +H]$^+$ C$_7$H$_{14}$NO$_4$: 176.09; found 176.06. |
| Cap-58 | 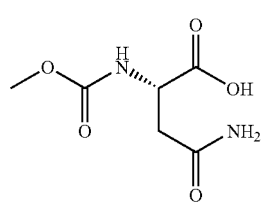 | $^1$H NMR (DMSO-d$_6$, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC/MS: Anal. Calcd. for [M +H]$^+$ C$_6$H$_{11}$N$_2$O$_5$: 191.07; found 191.14. |

| Cap | Structure | Data |
|---|---|---|
| Cap-59a: (R) Cap-59b: (S) | 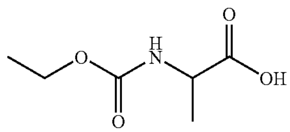 | $^1$H NMR (DMSO-d$_6$, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M +H]$^+$ C$_6$H$_{12}$NO$_4$: 162.0766; found 162.0771. |
| Cap-60 | 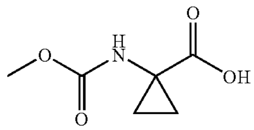 | The crude material was purified with a reverse phaseHPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M +H]$^+$ C$_6$H$_{10}$NO$_4$: 160.0610; found 160.0604. |
| Cap-61 | 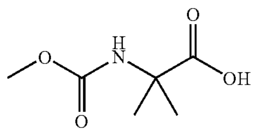 | $^1$H NMR (DMSO-d$_6$, δ = 2.5 ppm, 400 MHz): δ 12.27 (br s, 1H), 7.40 (br s, 1H), 3.50 (s, 3H), 1.32 (s, 6H). HRMS: Anal. Calcd. for [M +H]$^+$ C$_6$H$_{12}$NO$_4$: 162.0766; found 162.0765. |
| Cap-62 | 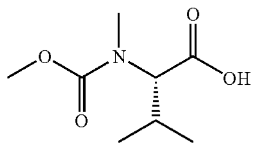 | $^1$H NMR (DMSO-d$_6$, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC/MS: Anal. Calcd. for [M − H]$^-$ C$_8$H$_{14}$NO$_4$: 188.09; found 188.05. |
| Cap-63 | 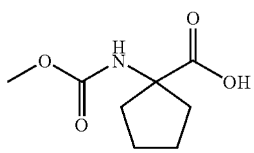 | [Note: the reaction was allowed to run for longer than what was noted for the general procedure.] $^1$H NMR (DMSO-d$_6$, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC/MS: Anal. Calcd. for [M +H]$^+$ C$_8$H$_{14}$NO$_4$: 188.09; found 188.19. |
| Cap-64 | 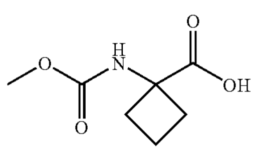 | [Note: the reaction was allowed to run for longer than what was noted for the general procedure.] $^1$H NMR (DMSO-d$_6$, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

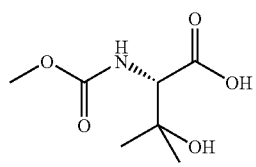

Cap-65

Methyl chloroformate (0.65 mL, 8.39 mmol) was added dropwise over 5 min to a cooled (ice-water) mixture of Na$_2$CO$_3$ (0.449 g, 4.23 mmol), NaOH (8.2 mL of 1M/H$_2$O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH$_2$Cl$_2$, and the aqueous phase was cooled with ice-water bath and acidified with concentrated HCl to a pH region of 1-2. The volatile component was removed in vacuo and the residue was taken up in a 2:1 mixture of MeOH/CH$_2$Cl$_2$ (15 mL) and filtered, and the filtrate was rotervaped to afford Cap-65 as a white semi-viscous foam (1.236 g). $^1$H NMR (DMSO-d$_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

Cap-66

$^1$H NMR (DMSO-d$_6$, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

Cap-67

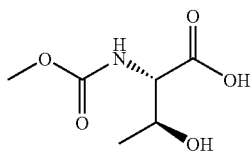

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

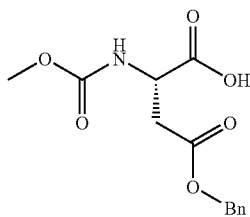

Methyl chloroformate (0.38 ml, 4.9 mmol) was added drop-wise to a mixture of 1N NaOH (aq) (9.0 ml, 9.0 mmol), 1M NaHCO₃ (aq) (9.0 ml, 9.0 mol), L-aspartic acid β-benzyl ester (1.0 g, 4.5 mmol) and Dioxane (9 ml). The reaction mixture was stirred at ambient conditions for 3 h, and then washed with Ethyl acetate (50 ml, 3×). The aqueous layer was acidified with 12N HCl to a pH~1-2, and extracted with ethyl acetate (3×50 ml). The combined organic layers were washed with brine, dried Na₂SO₄), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ C₁₃H₁₆NO₆: 282.10. found 282.12.

Cap-69a and -69b

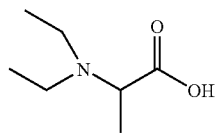

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. ¹H NMR (DMSO-d₆, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R)<br>Cap-70b: (S) | 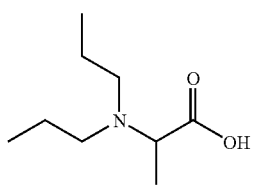 | ¹H NMR (DMSO-d₆, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M +H]⁺ C₉H₂₀NO₂: 174.15; found 174.13. |
| Cap-71a: (R)<br>Cap-71b: (S) | 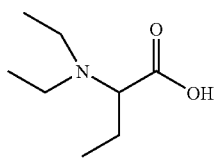 | ¹H NMR (DMSO-d₆, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M +H]⁺ C₈H₁₈NO₂: 160.13; found 160.06. |
| Cap-72 | 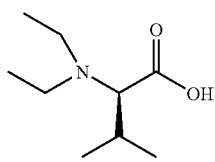 | ¹H NMR (DMSO-d₆, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M +H]⁺ C₉H₂₀NO₂: 174.15; found 174.15. |

-continued

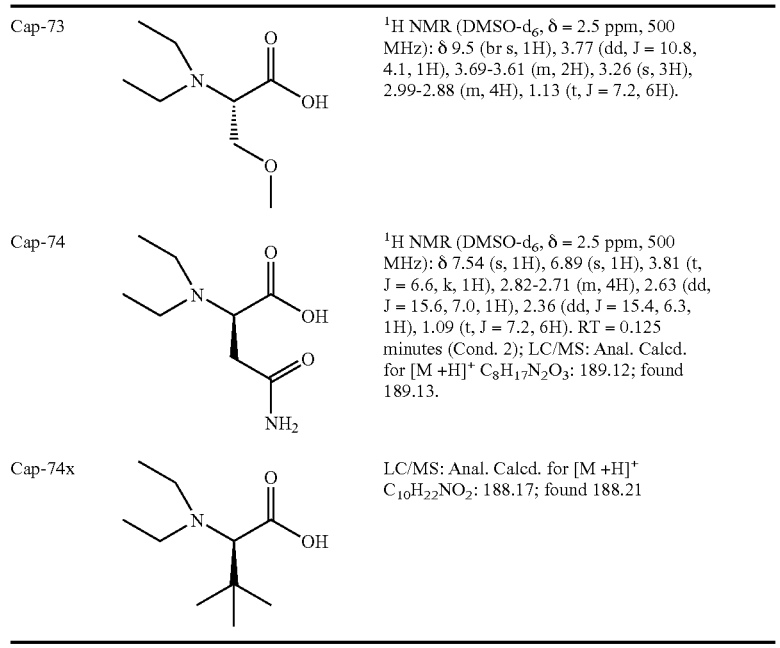

| | | |
|---|---|---|
| Cap-73 | | $^1$H NMR (DMSO-$d_6$, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |
| Cap-74 | | $^1$H NMR (DMSO-$d_6$, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4, 6.3, 1H), 1.09 (t, J = 7.2, 6H). RT = 0.125 minutes (Cond. 2); LC/MS: Anal. Calcd. for [M +H]$^+$ $C_8H_{17}N_2O_3$: 189.12; found 189.13. |
| Cap-74x | | LC/MS: Anal. Calcd. for [M +H]$^+$ $C_{10}H_{22}NO_2$: 188.17; found 188.21 |

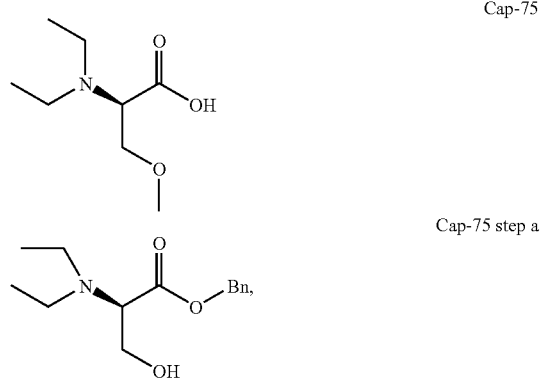

Cap-75

Cap-75 step a

NaBH$_3$CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H$_2$O/TFA) to afford the TFA salt of (R)-benzyl 2-(diethylamino)-3-hydroxypropanoate as a colorless viscous oil (1.9 g). $^1$H NMR (DMSO-$d_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]$^+$ $C_{14}H_{22}NO_3$: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH$_3$/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

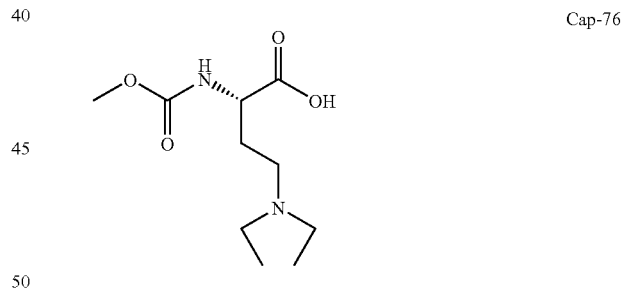

Cap-76

NaCNBH$_3$ (1.60 g, 24.2 mmol) was added in batches to a chilled (~15° C.) water/MeOH (12 mL each) solution of (S)-4-amino-2-(tert-butoxycatonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute NH$_4$OH, prepared from 18 ml of NH$_4$OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na$_2$CO$_3$ (0.243 g, 2.29 mmol), NaOH (4.6 mL of 1M/H$_2$O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH$_2$Cl$_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH$_3$/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ C$_{10}$H$_{21}$N$_2$O$_4$: 233.15. found 233.24.

Cap-77a and -77b

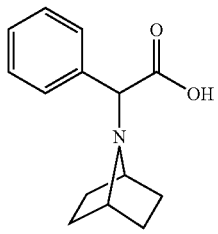

Cap-77a: enantiomer-1
Cap-77b: enantiomer-2

The synthesis of Cap-77 was conducted according to the procedure described for Cap-7 by using 7-azabicyclo[2.2.1] heptane for the SN$_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO$_2$-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ C$_{14}$H$_{18}$NO$_2$: 232.13. found 232.18. HRMS: Anal. Calcd. for [M+H]$^+$ C$_{14}$H$_{18}$NO$_2$: 232.1338. found 232.1340.

Cap-78

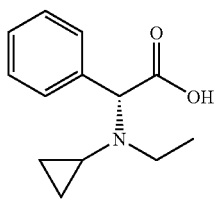

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H$_2$O/MeOH/TFA) to afford the TFA salt of Cap-78 as a colorless viscous oil (353 mg). $^1$H NMR (DMSO-d$_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ C$_{13}$H$_{18}$NO$_2$: 220.13. found 220.21. HRMS: Anal. Calcd. for [M+H]$^+$ C$_{13}$H$_{18}$NO$_2$: 220.1338. found 220.1343.

Cap-79

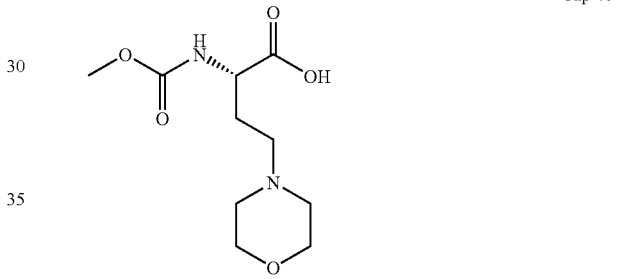

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC (H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

Cap-80a and -80b

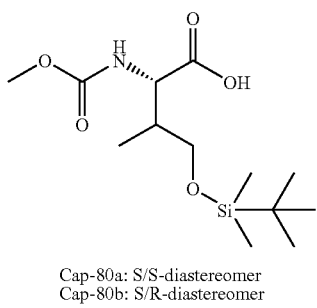

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11. found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20. found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S, 3S) isomer elutes before the (2S,3R) isomer under the above condition]. (2S, 3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45. found 464.22. (2S, 3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45. found 464.52.

The relative stereochemical assignments of the DIBAL-reduction products were made based on NOE studies conducted on lactone derivatives prepared from each isomer by employing the following protocol: LiHMDS (50 µL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for

[M+Na]⁺ C₂₄H₂₁NNaO₂: 378.15. found 378.42. (3S,4R)-lactone isomer: ¹H NMR (DMSO-d₆, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]⁺ C₂₄H₂₁NNaO₂: 378.15. found 378.49.

TBDMS-Cl (48 mg, 0.312 mmol) followed by imidazole (28.8 mg, 0.423 mmol) were added to a CH₂Cl₂ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH₂Cl₂ (30 mL) and washed with water (15 mL), and the organic layer was dried (MgSO₄), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: ¹H NMR (DMSO-d₆, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]⁺ C₃₇H₄₄NO₃Si: 578.31. found 578.40. (2S,3R)-silyl ether isomer: ¹H NMR (DMSO-d₆, δ=2.5 ppm, 400 MHz), 7.82 (d, J=3.0, 1H), 7.80 (d, J13.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S, 3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H₂ as necessary. The reaction mixture was diluted with CH₂Cl₂ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H₂O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: ¹H NMR (Methanol-d₄, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]⁺ C₁₁H₂₆NO₃Si: 248.17. found 248.44. (2S,3R)-amino acid isomer: ¹H NMR (Methanol-d₄, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]⁺ C₁₁H₂₆NO₃Si: 248.17. found 248.44.

Water (1 mL) and NaOH (0.18 mL of 1.0 M/H₂O, 0.18 mmol) were added to a mixture of (2S,3S)-2-amino-4-(tert-butyldimethylsilyloxy)-3-methylbutanoic acid (41.9 mg, 0.169 mmol) and Na₂CO₃ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH₂Cl₂ (15 mL, 2×). The combined organic phase was dried (MgSO₄), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: ¹H NMR (DMSO-d₆, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]⁺ C₁₃H₂₇NNaO₅Si: 328.16. found 328.46. Cap-80b: ¹H NMR (CDCl₃, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]⁺ C₁₃H₂₇NNaO₅Si: 328.16. found 328.53. The crude products were utilized without further purification.

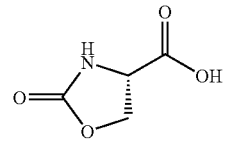

Cap-81

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively).

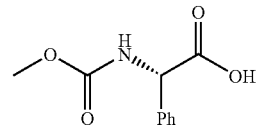

Cap-82

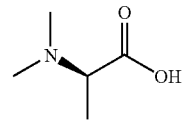

Cap-83

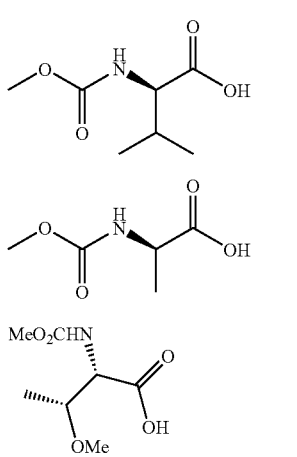

Cap-84

Cap-85

Cap-86

To a mixture of O-methyl-L-threonine (3.0 g, 22.55 mmol), NaOH (0.902 g, 22.55 mmol) in H$_2$O (15 mL) was added ClCO$_2$Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH$_2$Cl$_2$ (250 mL) and the combined organic phases were concentrated under in vacuo to afford a colorless oil (4.18 g, 97%) which was of sufficient purity for use in subsequent steps. $^1$HNMR (400 MHz, CDCl$_3$) δ 4.19 (s, 1H), 3.92-3.97 (m 1H), 3.66 (s, 3H), 1.17 (d, J=7.7 Hz, 3H). LCMS: Anal. Calcd. for C$_7$H$_{13}$NO$_5$: 191. found: 190 (M−H)$^-$.

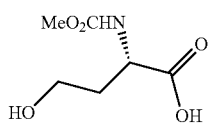

Cap-87

To a mixture of L-homoserine (2.0 g, 9.79 mmol), Na$_2$CO$_3$ (2.08 g, 19.59 mmol) in H$_2$O (15 mL) was added ClCO$_2$Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. $^1$HNMR (400 MHz, CDCl$_3$) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C$_7$H$_{13}$NO$_5$: 191. found: 192 (M+H)$^+$.

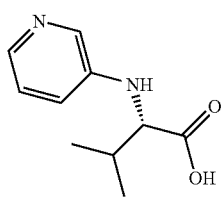

Cap-88

A mixture of L-valine (1.0 g, 8.54 mmol), 3-bromopyridine (1.8 mL, 18.7 mmol), K$_2$CO$_3$ (2.45 g, 17.7 mmol) and CuI (169 mg, 0.887 mmol) in DMSO (10 mL) was heated at 100° C. for 12 h. The reaction mixture was cooled to rt, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$HNMR (400 MHz, DMSO-d$_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C$_{10}$H$_{14}$N$_2$O$_2$: 194. found: 195 (M+H)$^+$.

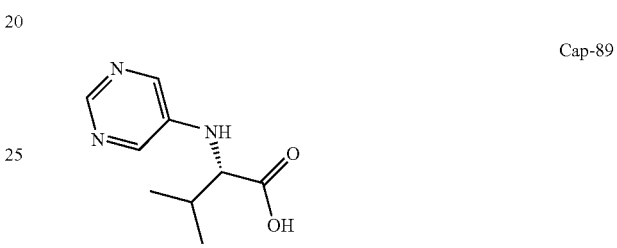

Cap-89

A mixture of L-valine (1.0 g, 8.54 mmol), 5-bromopyrimidine (4.03 g, 17.0 mmol), K$_2$CO$_3$ (2.40 g, 17.4 mmol) and CuI (179 mg, 0.94 mmol) in DMSO (10 mL) was heated at 100° C. for 12 h. The reaction mixture was cooled to RT, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$HNMR (400 MHz, CD$_3$OD) showed the mixture to contain valine and the purity could not be estimated. The material was used as is in subsequent reactions. LCMS: Anal. Calcd. for C$_9$H$_{13}$N$_3$O$_2$: 195. found: 196 (M+H)$^+$.

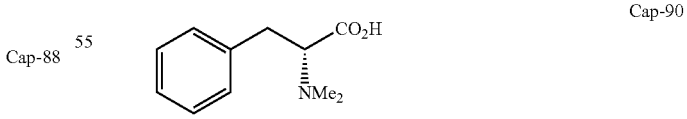

Cap-90

Cap-90 was prepared according to the method described for the preparation of Cap-1. The crude material was used as is in subsequent steps. LCMS: Anal. Calcd. for C$_{11}$H$_{15}$NO$_2$: 193. found: 192 (M−H)$^-$.

The following caps were prepared according to the method used for preparation of cap 51 unless noted otherwise:

| Cap | Structure | LCMS |
|---|---|---|
| Cap-91 | (S)-3-phenyl-3-(NHCO₂Me)propanoic acid; NHCO₂Me, CO₂H, phenyl | LCMS: Anal. Calcd. for $C_{11}H_{13}NO_4$: 223; found: 222 $(M-H)^-$. |
| Cap-92 | (R)-3-phenyl-3-(NHCO₂Me)propanoic acid; NHCO₂Me, CO₂H, phenyl | LCMS: Anal. Calcd. for $C_{11}H_{13}NO_4$: 223; found: 222 $(M-H)^-$. |
| Cap-93 | methyl carbamate-protected 3-(pyridin-2-yl)alanine | LCMS: Anal. Calcd. for $C_{10}H_{12}N_2O_4$: 224; found: 225 $(M+H)^+$. |
| Cap-94 | methyl carbamate-protected L-histidine | LCMS: Anal. Calcd. for $C_8H_{11}N_3O_4$: 213; found: 214 $(M+H)^+$. |
| Cap-95 | methyl carbamate-protected 3-amino-5-phenylpentanoic acid | LCMS: Anal. Calcd. for $C_{13}H_{17}NO_4$: 251; found: 250 $(M-H)^-$. |
| Cap-96 | methyl carbamate-protected 3-amino-4-phenylbutanoic acid | LCMS: Anal. Calcd. for $C_{12}H_{15}NO_4$: 237; found: 236 $(M-H)^-$. |
| Cap-97 | methyl carbamate-protected 2-aminocyclohexanecarboxylic acid | LCMS: Anal. Calcd. for $C_9H_{15}NO_4$: 201; found: 200 $(M-H)^-$. |

-continued

| Cap | Structure | LCMS |
|---|---|---|
| Cap-98 | 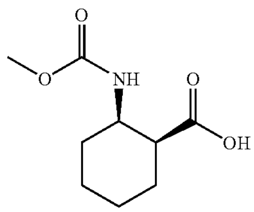 | LCMS: Anal. Calcd. for $C_9H_{15}NO_4$: 201; found: 202 (M +H)$^+$. |
| Cap-99 | 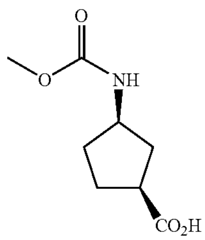 | $^1$HNMR (400 MHz, $CD_3OD$) δ 3.88-3.94 (m, 1H), 3.60, 3.61 (s, 3H), 2.80 (m, 1H), 2.20 (m, 1H), 1.82-1.94 (m, 3H), 1.45-1.71 (m, 2H). |
| Cap-99a | 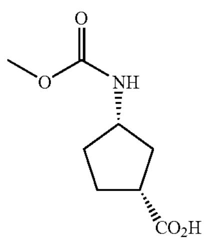 | $^1$HNMR (400 MHz, $CD_3OD$) δ 3.88-3.94 (m, 1H), 3.60, 3.61 (s, 3H), 2.80 (m, 1H), 2.20 (m, 1H), 1.82-1.94 (m, 3H), 1.45-1.71 (m, 2H). |
| Cap-100 | 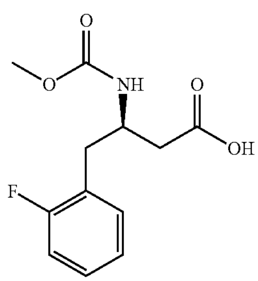 | LCMS: Anal. Calcd. for $C_{12}H_{14}NO_4F$: 255; found: 256 (M +H)$^+$. |
| Cap-101 | 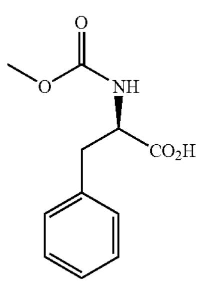 | LCMS: Anal. Calcd. for $C_{11}H_{13}NO_4$: 223; found: 222 (M −H)$^-$. |
| Cap-102 | 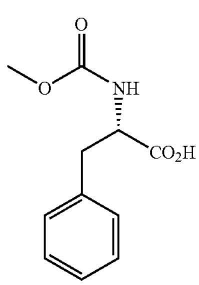 | LCMS: Anal. Calcd. for $C_{11}H_{13}NO_4$: 223; found: 222 (M −H)$^-$. |

| Cap | Structure | LCMS |
|---|---|---|
| Cap-103 | 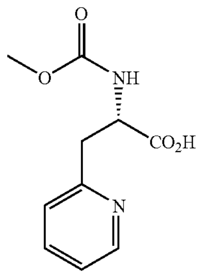 | LCMS: Anal. Calcd. for $C_{10}H_{12}N_2O_4$: 224; found: 225 (M +H)$^+$. |
| Cap-104 | 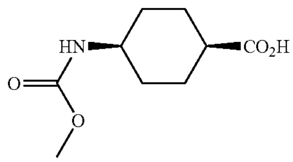 | $^1$HNMR (400 MHz, CD$_3$OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | 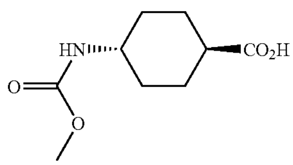 | $^1$HNMR (400 MHz, CD$_3$OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | Prepared from cis-4-aminocyclohexane carboxylic acid and acetaldehyde by employing a similar procedure described for the synthesis of Cap-2. The crude HCl salt was passed through MCX (MeOH/H$_2$O/CH$_2$Cl$_2$ wash; 2 N NH$_3$/MeOH elution) to afford an oil, which was dissolved in CH$_3$CN/H$_2$O and lyophilized to afford a tan solid. | $^1$HNMR (400 MHz, CD$_3$OD) δ 3.16 (q, J = 7.3Hz, 4H), 2.38-2.41 (m, 1H), 2.28-2.31 (m, 2H), 1.79-1.89 (m, 2H), 1.74 (app, ddd J = 3.5, 12.5, 15.9Hz, 2H), 1.46 (app dt J = 4.0, 12.9Hz, 2H), 1.26 (t, J = 7.3Hz, 6H) |
| Cap-107 | 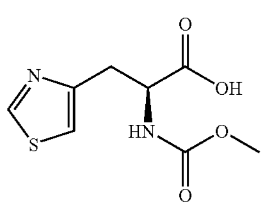 | LCMS: Anal. Calcd. for $C_8H_{10}N_2O_4S$: 230; found: 231 (M +H)$^+$. |
| Cap-108 | 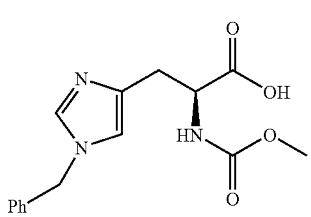 | LCMS: Anal. Calcd. for $C_{15}H_{17}N_3O_4$: 303; found: 304 (M +H)$^+$. |

-continued
| Cap | Structure | LCMS |
|---|---|---|
| Cap-109 | 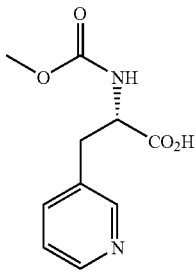 | LCMS: Anal. Calcd. for $C_{10}H_{12}N_2O_4$: 224; found: 225 $(M+H)^+$. |
| Cap-110 | 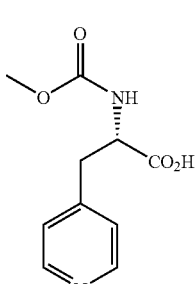 | LCMS: Anal. Calcd. for $C_{10}H_{12}N_2O_4$: 224; found: 225 $(M+H)^+$. |
| Cap-111 | 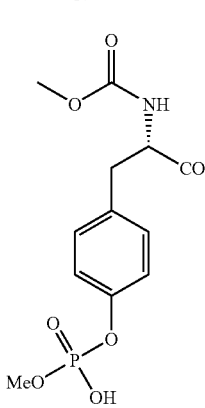 | LCMS: Anal. Calcd. for $C_{12}H_{16}NO_8P$: 333; found: 334 $(M+H)^+$. |
| Cap-112 | 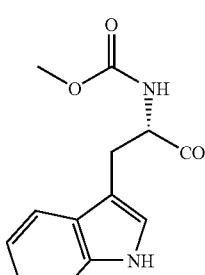 | LCMS: Anal. Calcd. for $C_{13}H_{14}N_2O_4$: 262; found: 263 $(M+H)^+$. |
| Cap-113 | 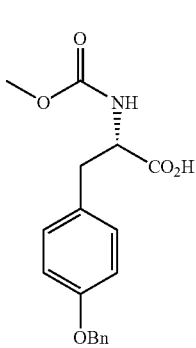 | LCMS: Anal. Calcd. for $C_{18}H_{19}NO_5$: 329; found: 330 $(M+H)^+$. |

| Cap | Structure | LCMS |
|---|---|---|
| Cap-114 | azetidine with CO₂Me on N and CO₂H on C2 | ¹HNMR (400 MHz, CDCl₃) δ 4.82-4.84 (m, 1H), 4.00-4.05 (m, 2H), 3.77 (s, 3H), 2.56 (s, br, 2H) |
| Cap-115 | CH₃-CH(NHCO₂Me)-CH₂-CO₂H | ¹HNMR (400 MHz, CDCl₃) δ 5.13 (s, br, 1H), 4.13 (s, br, 1H), 3.69 (s, 3H), 2.61 (4, J = 5.0Hz, 2H), 1.28 (d, J = 9.1Hz, 3H). |
| Cap-116 | (CH₃)₂CH-CH(NHCO₂Me)-CH₂-CO₂H | ¹HNMR (400 MHz, CDCl₃) δ 5.10 (d, J = 8.6 Hz, 1H), 3.74-3.83 (m, 1H), 3.69 (s, 3H), 2.54-2.61 (m, 2H), 1.88 (sept, J = 7.0Hz, 1H), 0.95 (d, J = 7.0Hz, 6H). |

Cap-117 to Cap-123

For the preparation of Cap-117 to Cap-123 the Boc amino acids were obtained from commercially sources and were deprotected by treatment with 25% TFA in CH₂Cl₂. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | MeO-C(O)-NH-CH(CH₂Ph)-CH₂-CO₂H | LCMS: Anal. Calcd. for C₁₂H₁₅NO₄: 237; found: 238 (M +H)⁺. |
| Cap-118 | MeO-C(O)-NH-CH(CH₂-2-thienyl)-CH₂-CO₂H | LCMS: Anal. Calcd. for C₁₀H₁₃NO₄S: 243; found: 244 (M +H)⁺. |
| Cap-119 | MeO-C(O)-NH-CH(CH₂-2-thienyl)-CH₂-CO₂H (opposite stereochemistry) | LCMS: Anal. Calcd. for C₁₀H₁₃NO₄S: 243; found: 244 (M +H)⁺. |

| Cap | Structure | LCMS |
|---|---|---|
| Cap-120 | 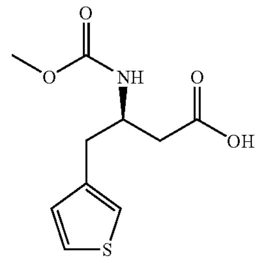 | LCMS: Anal. Calcd. for $C_{10}H_{13}NO_4S$: 243; found: 244 $(M+H)^+$. |
| Cap-121 | 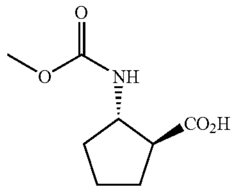 | $^1$HNMR (400 MHz, $CDCl_3$) δ 4.06-4.16 (m, 1H), 3.63 (s, 3H), 3.43 (s, m), 2.82 and 2.66 (s, br, 1H), 1.86-2.10 (m, 3H), 1.64-1.76 (m, 2H), 1.44-1.53 (m, 1H). |
| Cap-122 | 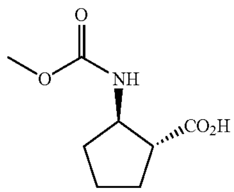 | $^1$HNMR profile is similar to that of its enantiomer, Cap-121. |
| Cap-123 | 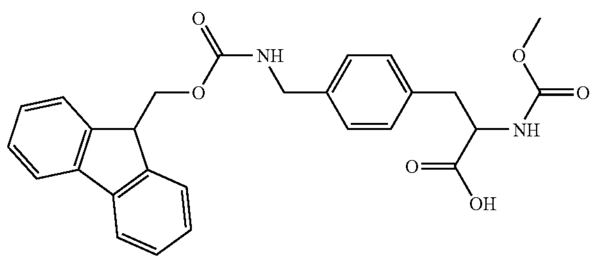 | LCMS: Anal. Calcd. for $C_{27}H_{26}N_2O_6$: 474; found: 475 $(M+H)^+$. |

Cap-124

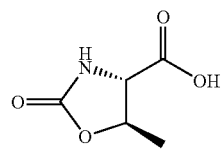

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc—$CH_2Cl_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, $CD_3OD$) δ 4.60 (m, 1H), 4.04 (d, J=5.0 Hz, 1H), 1.49 (d, J=6.3 Hz, 3H). LCMS: Anal. Calcd. for $C_5H_7NO_4$: 145. found: 146 $(M+H)^+$.

Cap-125

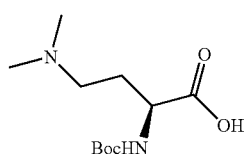

To a suspension of $Pd(OH)_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (Celite®), and the volatile component was removed in vacuo. The resulting crude material was used as is for the next step. LC/MS: Anal. Calcd. for $C_{11}H_{22}N_2O_4$: 246. found: 247 $(M+H)^+$.

Cap-126

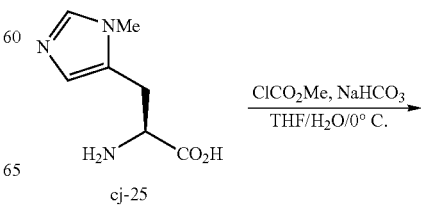

-continued

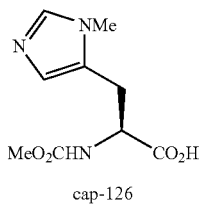
cap-126

This procedure is a modification of that used to prepare Cap-51. To a suspension of 3-methyl-L-histidine (0.80 g, 4.70 mmol) in THF (10 mL) and H₂O (10 mL) at 0° C. was added NaHCO₃ (0.88 g, 10.5 mmol). The resulting mixture was treated with ClCO₂Me (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in CH₂Cl₂. The mixture was filtered and concentrated to give a light yellow foam (1.21 g). LCMS and ¹H NMR showed the material to be a 9:1 mixture of the methyl ester and the desired product. This material was taken up in THF (10 mL) and H₂O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and ¹H NMR confirm the absence of the ester. The title compound was obtained as its HCl salt contaminated with inorganic salts (1.91 g, >100%). The compound was used as is in subsequent steps without further purification. ¹HNMR (400 MHz, CD₃OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for C₉H₁₃N₃O₄: 227.09. found: 228.09 (M+H)⁺.

Cap-127

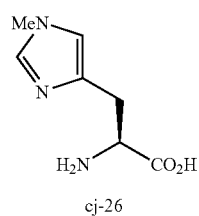
cj-26

ClCO₂Me, NaHCO₃
THF/H₂O/0° C.

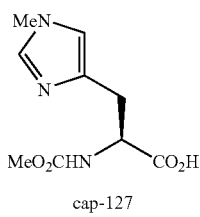
cap-127

Cap-127 was prepared according to the method for Cap-126 above starting from (S)-2-amino-3-(1-methyl-1H-imidazol-4-yl)propanoic acid (1.11 g, 6.56 mmol), NaHCO₃ (1.21 g, 14.4 mmol) and ClCO₂Me (0.56 mL, 7.28 mmol). The title compound was obtained as its HCl salt (1.79 g, >100%) contaminated with inorganic salts. LCMS and ¹H NMR showed the presence of ca. 5% of the methyl ester. The crude mixture was used as is without further purification. ¹HNMR (400 MHz, CD₃OD) δ 8.90 (s, 1H); 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for C₉H₁₃N₃O₄: 227.09. found: 228 (M+H)⁺.

Preparation of Cap-128

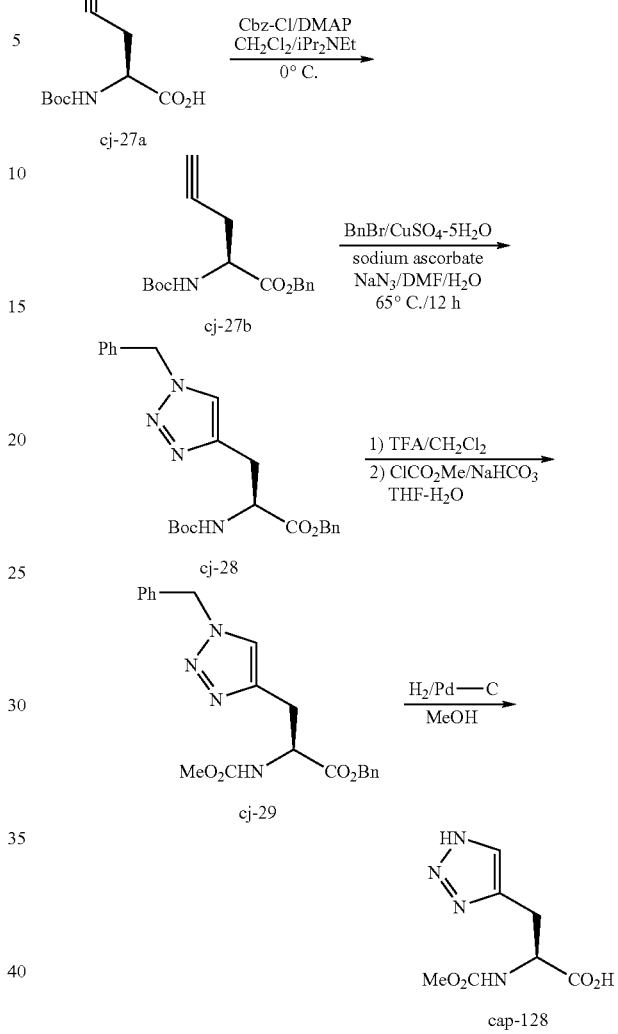

Step 1. Preparation of (S)-benzyl 2-(tert-butoxycarbonylamino)pent-4-ynoate (cj-27b)

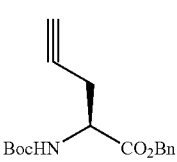
cj-27b

To a solution of cj-27a (1.01 g, 4.74 mmol), DMAP (58 mg, 0.475 mmol) and iPr₂NEt (1.7 mL, 9.8 mmol) in CH₂Cl₂ (100 mL) at 0° C. was added Cbz-Cl (0.68 mL, 4.83 mmol). The solution was allowed to stir for 4 h at 0° C., washed (1N KHSO₄, brine), dried (Na₂SO₄), filtered, and concentrated in vacuo. The residue was purified by flash column chromatography (TLC 6:1 hex:EtOAc) to give the title compound (1.30 g, 91%) as a colorless oil. ¹HNMR (400 MHz, CDCl₃) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303. found: 304 $(M+H)^+$.

Step 2. Preparation of (S)-benzyl 3-(1-benzyl-1H-1,2,3-triazol-4-yl)-2-(tert-butoxycarbonylamino)propanoate (cj-28)

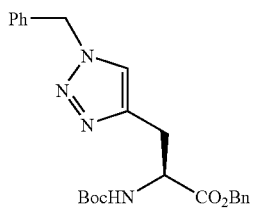

cj-28

To a mixture of (S)-benzyl 2-(tert-butoxycarbonylamino)pent-4-ynoate (0.50 g, 1.65 mmol), sodium ascorbate (0.036 g, 0.18 mmol), $CuSO_4 \cdot 5H_2O$ (0.022 g, 0.09 mmol) and $NaN_3$ (0.13 g, 2.1 mmol) in $DMF-H_2O$ (5 mL, 4:1) at rt was added BnBr (0.24 mL, 2.02 mmol) and the mixture was warmed to 65° C. After 5 h LCMS indicated low conversion. A further portion of $NaN_3$ (100 mg) was added and heating was continued for 12 h. The reaction was poured into EtOAc and $H_2O$ and shaken. The layers were separated and the aqueous layer extracted 3× with EtOAc and the combined organic phases washed ($H_2O$ ×3, brine), dried ($Na_2SO_4$), filtered, and concentrated. The residue was purified by flash (Biotage, 40+M 0-5% MeOH in $CH_2Cl_2$; TLC 3% MeOH in $CH_2Cl_2$) to afford a light yellow oil which solidified on standing (748.3 mg, 104%). The NMR was consistent with the desired product but suggests the presence of DMF. The material was used as is without further purification. $^1$HNMR (400 MHz, DMSO-$d_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H).

LCMS: Anal. Calcd. for $C_{24}H_{28}N_4O_4$: 436. found: 437 $(M+H)^+$.

Step 3. Preparation of (S)-benzyl 3-(1-benzyl-1H-1,2,3-triazol-4-yl)-2-(methoxycarbonylamino)propanoate (cj-29)

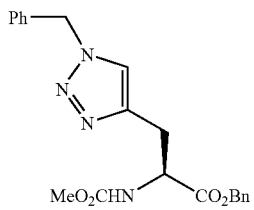

cj-29

A solution of (S)-benzyl 3-(1-benzyl-1H-1,2,3-triazol-4-yl)-2-(tert-butoxycarbonylamino)propanoate (0.52 g, 1.15 mmol) in $CH_2Cl_2$ was added TFA (4 mL). The mixture was allowed to stir at room temperature for 2 h. The mixture was concentrated in vacuo to give a colorless oil which solidified on standing. This material was dissolved in THF—$H_2O$ and cooled to 0° C. Solid $NaHCO_3$ (0.25 g, 3.00 mmol) was added followed by $ClCO_2Me$ (0.25 mL, 3.25 mmol). After stirring for 1.5 h the mixture was acidified to pH~2 with 6N HCl and then poured into $H_2O$-EtOAc. The layers were separated and the aq phase extracted 2× with EtOAc. The combined org layers were washed ($H_2O$, brine), dried ($Na_2SO_4$), filtered, and concentrated in vacuo to give a colorless oil (505.8 mg, 111%, NMR suggested the presence of an unidentified impurity) which solidified while standing on the pump. The material was used as is without further purification. $^1$HNMR (400 MHz, DMSO-$d_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for $C_{21}H_{22}N_4O_4$: 394. found: 395 $(M+H)^+$.

Step 4. Preparation of (S)-2-(methoxycarbonylamino)-3-(1H-1,2,3-triazol-4-yl)propanoic acid (Cap-128)

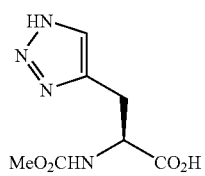

Cap-128

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$HNMR (400 MHz, DMSO-$d_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for $C_7H_{10}N_4O_4$: 214. found: 215 $(M+H)^+$.

Preparation of Cap-129

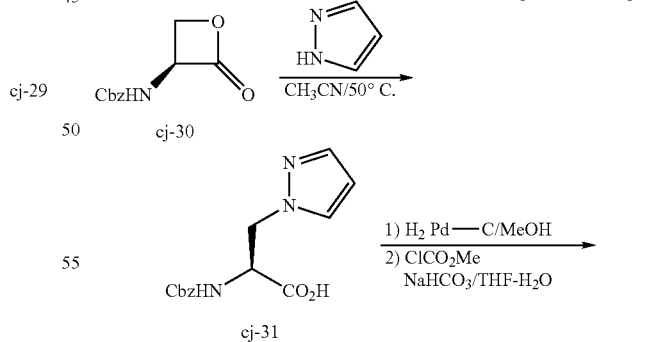

cj-30 cj-31

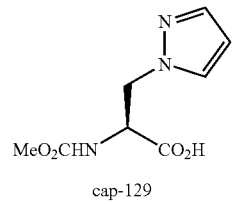

cap-129

Step 1. Preparation of (S)-2-(benzyloxycarbonylamino)-3-(1H-pyrazol-1-yl)propanoic acid (cj-31)

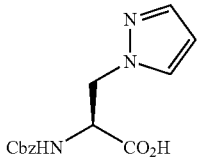
cj-31

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%). m.p. 165.5-168° C. lit m.p. 168.5-169.5 [Vederas et al. *J. Am. Chem. Soc.* 1985, 107, 7105]. $^1$HNMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289. found: 290 (M+H)$^+$.

Step 2. Preparation of (S)-2-(methoxycarbonylamino)-3-(1H-pyrazol-1-yl)propanoic acid (Cap-129)

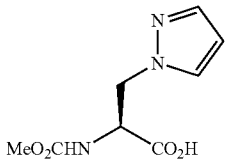
Cap-129

(S)-2-(benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL H$_2$O and a few drops of 6N HCl. The homogeneous solution was filtered through diatomaceous earth (Celite®), and the MeOH removed in vacuo. The remaining solution was frozen and lyophyllized to give a yellow foam (188.9 mg). This material was suspended in THF—H$_2$O (1:1, 10 mL) and then cooled to 0° C. To the cold mixture was added NaHCO$_3$ (146.0 mg, 1.74 mmol) carefully (evolution of CO$_2$). After gas evolution had ceased (ca. 15 Min) ClCO$_2$Me (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried (Na$_2$SO$_4$), filtered, and concentrated to give the title compound as a colorless solid (117.8 mg, 79%). $^1$HNMR (400 MHz, DMSO-d$_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213. found: 214 (M+H)$^+$.

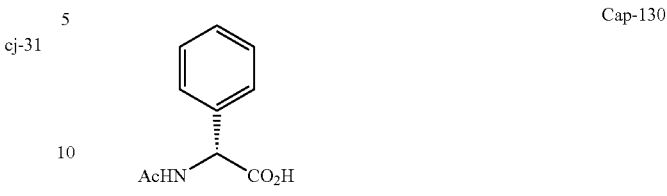
Cap-130

Cap-130 was prepared by acylation of commercially available (R)-phenylglycine analgous to the procedure given in: Calmes, M.; Daunis, J.; Jacquier, R.; Verducci, J. *Tetrahedron*, 1987, 43(10), 2285.

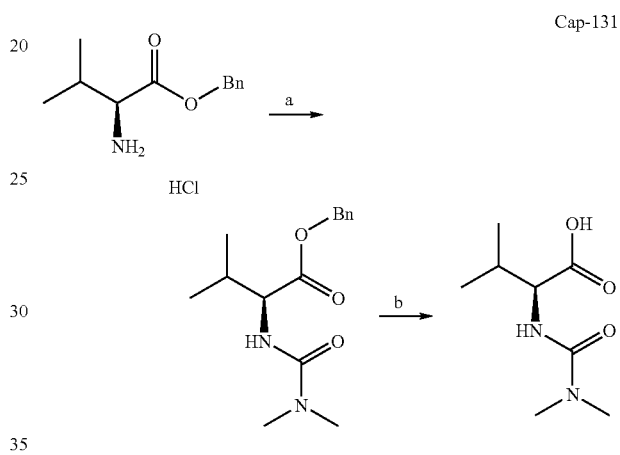
Cap-131

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO$_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-d$_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]$^+$ C$_{16}$H$_{22}$N$_2$O$_3$: 279.17. found 279.03.

Step b: To a MeOH (50 mL) solution of the intermediate prepared above (2.35 g; 8.45 mmol) was added Pd/C (10%; 200 mg) and the resulting black suspension was flushed with N$_2$ (3×) and placed under 1 atm of H$_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-d$_6$) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]$^+$ C$_8$H$_{17}$N$_2$O$_3$: 189.12. found 189.04.

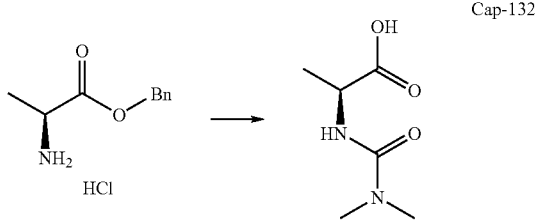
Cap-132

Cap-132 was prepared from (S)-benzyl 2-aminopropanoate hydrochloride according to the method described for Cap-131. $^1$H NMR (500 MHz, DMSO-d$_6$) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]$^+$ C$_6$H$_{13}$N$_2$O$_3$: 161.09. found 161.00.

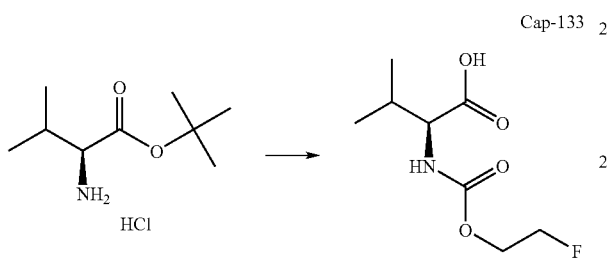
Cap-133

Cap-133 was prepared from (S)-tert-butyl 2-amino-3-methylbutanoate hydrochloride and 2-fluoroethyl chloroformate according to the method described for Cap-47. $^1$H NMR (500 MHz, DMSO-d$_6$) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

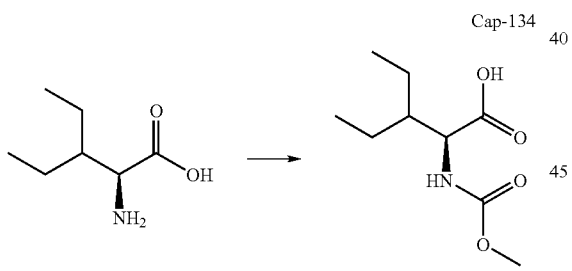
Cap-134

Cap-134 was prepared from (S)-diethyl alanine and methyl chloroformate according to the method described for Cap-51. $^1$H NMR (500 MHz, DMSO-d$_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for [M+H]$^+$ C$_9$H$_{18}$NO$_4$: 204.12. found 204.02.

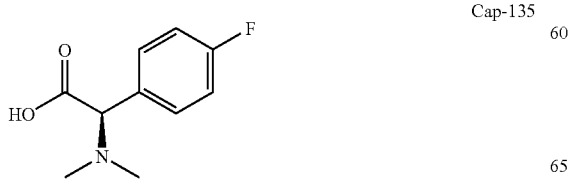
Cap-135

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through Celite to afford the HCl salt of Cap-135 as a white foam (316 mg, 80%). $^1$H NMR (300 MHz, MeOH-d$_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); R$_t$=0.19 min (Cond.-MS-W5); 95% homogenity index; LRMS: Anal. Calcd. for [M+H]$^+$ C$_{10}$H$_{13}$FNO$_2$: 198.09. found: 198.10.

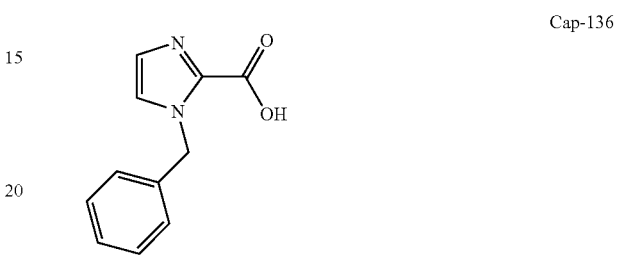
Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization, of the residue from water (5 mL) afforded the HCl salt of Cap-136 as a white solid (817 mg, 40%). $^1$H NMR (300 MHz, DMSO-d$_6$) δ 7.94 (d, J=1.5 Hz, 1H), 7.71 (d, J=1.5 Hz, 1H), 7.50-7.31 (m, 5H), 5.77 (s, 2H); R$_t$=0.51 min (Cond.-MS-W5); 95% homogenity index; LRMS: Anal. Calc. for [M+H]$^+$ C$_{11}$H$_{12}$N$_2$O$_2$: 203.08. found: 203.11.

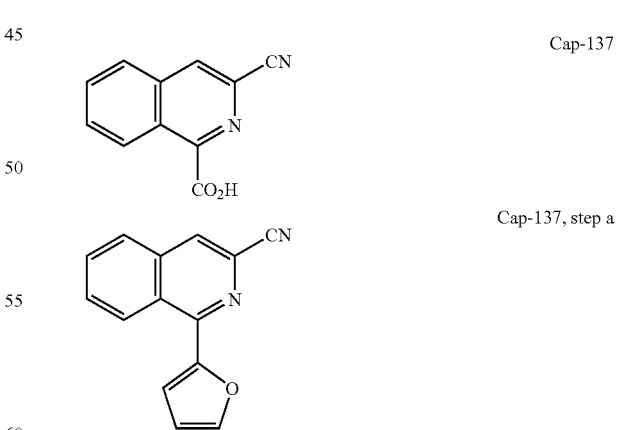
Cap-137

Cap-137, step a

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 μL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over $Na_2SO_4$, filtered and concentrated. Purification of the residue on silica gel (elution with 0% to 30% ethyl acetate/hexanes) afforded Cap-137, step a as a white solid which was used as is (230 mg, 105%). $R_t$=1.95 min (Cond.-MS-W2); 90% homogeneity index; LRMS: Anal. Calc. for $[M+H]^+$ $C_{14}H_8N_2O$: 221.07. found: 221.12.

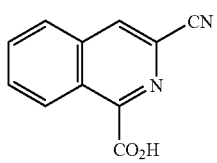

Cap-137

To a suspension of Cap 137, step a, (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over $Na_2SO_4$, filtered and concentrated. Trituration of the residue with hexanes afforded Cap-137 (55 mg, 55%) as a grayish-colored solid. $R_t$=1.10 min (Cond.-MS-W2); 90% homogeneity index; LCMS: Anal. Calc. for $[M+H]^+$ $C_{11}H_8N_2O_2$: 200.08. found: 200.08.

Caps 138 to 158

Synthetic Strategy. Method A.

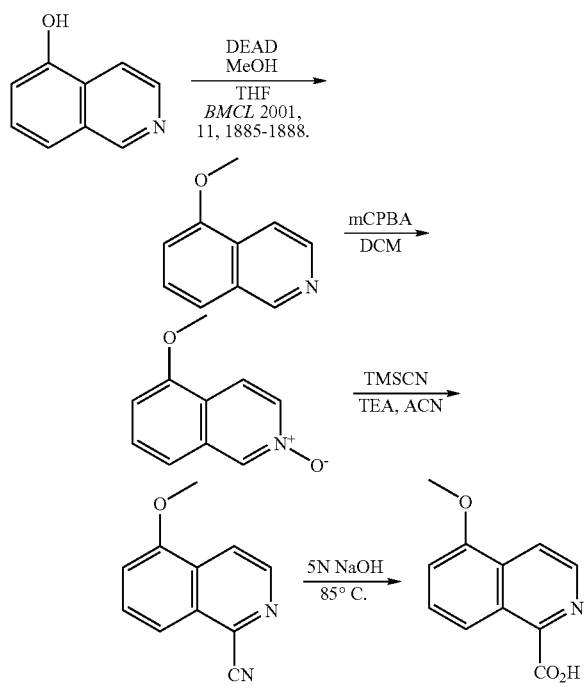

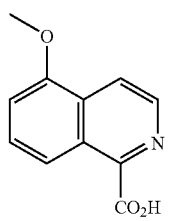

Cap-138

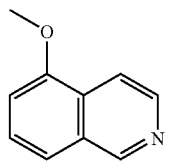

Cap-138, step a

To a stirred suspension of 5-hydroxisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and purified (elution with 40% ethyl acetate/hexanes) to afford Cap-138, step a as a light yellow solid (1.00 g, 45%). $^1$H NMR ($CDCl_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_t$=0.66 min (Cond. D2); 95% homogeneity index; LCMS: Anal. Calc. for $[M+H]^+$ $C_{10}H_{10}NO$: 160.08. found 160.10.

Cap-138, step b

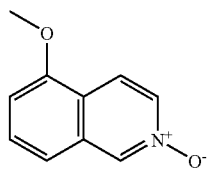

To a stirred solution of Cap 138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated to afford Cap-138, step b as a pale, yellow solid which was sufficiently pure to carry forward (2.15 g, 83.3%). $^1$H NMR ($CDCl_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_t$=0.92 min, (Cond.-D1); 90% homogenity index; LCMS: Anal. Calc. for $[M+H]^+$ $C_{10}H_{10}N_2$: 176.07. found: 176.0.

Cap-138, step c

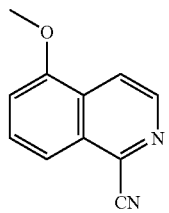

To a stirred solution of Cap 138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over $Na_2SO_4$ and solvent concentration. The residue was flash chromatographed on silica gel (elution with 5% ethyl acetate/hexanes) to 25% ethyl acetate/hexanes to afford Cap-138, step c (498.7 mg) as a white, crystalline solid along with 223 mg of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); R$_t$=1.75 min, (Cond.-D1); 90% homogeneity index; LCMS: Anal. Calc. for [M+H]$^+$ C$_{11}$H$_9$N$_2$O: 185.07. found: 185.10.

Cap-138

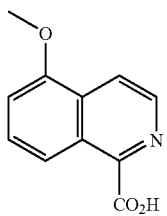

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 as a yellow solid (0.44 g, 88.9%). $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); R$_t$=0.70 min (Cond.-D1); 95% homogenity index; LCMS: Anal. Calc. for [M+H]$^+$ C$_{11}$H$_{10}$NO$_3$: 204.07. found: 204.05.

Synthetic Strategy. Method B (Derived from *Tetrahedron Letters*, 2001, 42, 6707).

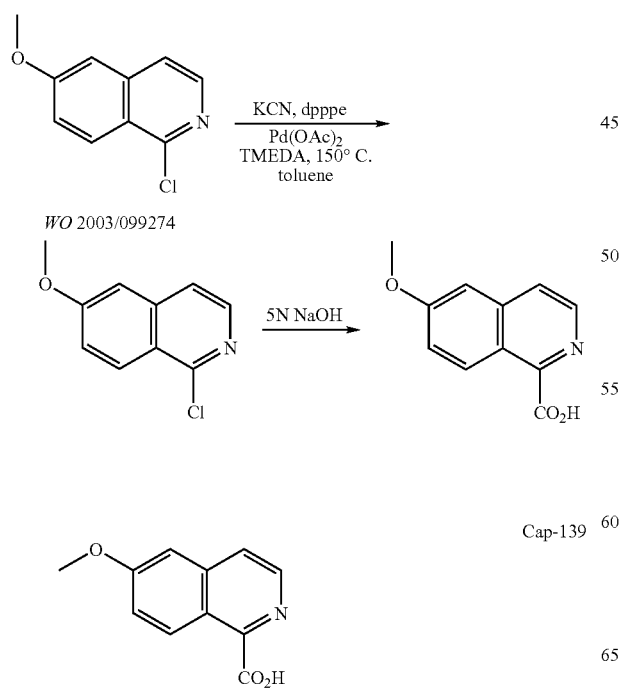

Cap-139 step a

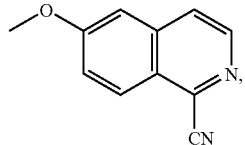

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis (diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over Na$_2$SO$_4$, filtered and concentrated. The residue was purified on silica gel eluting with 5% ethyl acetate/hexanes to 25% ethyl acetate/hexanes to afford Cap-139, step a as a white solid (669.7 mg). $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); R$_t$=1.66 min (Cond.-D1); 90% homogenity index; LCMS: Anal. Calc. for [M+H]$^+$ C$_{11}$H$_9$N$_2$O: 185.07. found: 185.20.

Cap-139

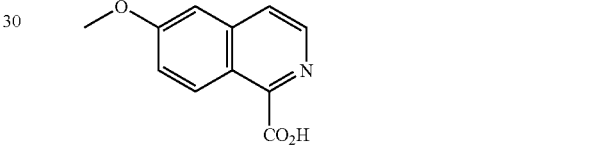

Cap-139 was prepared from the basic hydrolysis of Cap-139, step a with 5N NaOH according to the procedure described for Cap 138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); R$_t$=0.64 min (Cond.-D1); 90% homogenity index; LCMS: Anal. Calc. for [M+H]$^+$ C$_{11}$H$_{10}$NO$_3$: 204.07. found: 204.05.

Cap-140

Cap-140, step a

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 μL of acetone cyanohydrin in 4.34 mL DMA) was added in 1 mL portions over 18 h using a syringe pump. The mixture was then partitioned between ethyl acetate and water and the organic layer was separated, washed with brine, dried over $Na_2SO_4$, filtered and concentrated. The residue was purified on silica gel eluting with 10% ethyl acetate/hexanes to 40% ethyl acetate/hexanes to afford Cap-140, step a as a yellow solid (160 mg, 34%). $R_t$=2.46 min (Cond.-MS-W2); 90% homogenity index; LCMS: Anal. Calc. for $[M+H]^+$ $C_{12}H_9ClN_2O$: 233.05. found: 233.08.

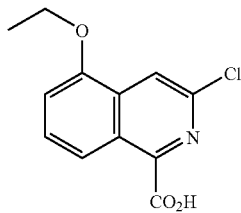

Cap-140

Cap-140 was prepared by the acid hydrolysis of Cap-140, step a with 12N HCl as described in the procedure for the preparation of Cap 141, described below. $R_t$=2.24 mm (Cond.-MS-W2); 90% homogenity index; LCMS: Anal. Calc. for $[M+H]^+$ $C_{12}H_{11}ClNO_3$: 252.04. found: 252.02.

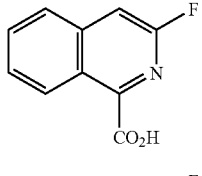

Cap-141

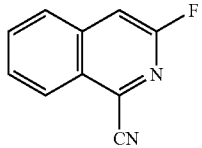

Cap-141, step a

Cap-141, step a was prepared from 1-bromo-3-fluoroisoquinoline (prepared from 3-amino-1-bromoisoquinoline using the procedure outlined in *J. Med. Chem.* 1970, 13, 613) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); $R_t$=1.60 min (Cond.-D1); 90% homogenity index; LCMS: Anal. Calc. for $[M+H]^+$ $C_{10}H_6FN_2$: 173.05. found: 172.99.

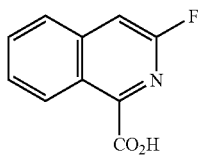

Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 as an off-white solid (44.1 mg, 47.8%). The filtrate was diluted with dichloromethane and washed with brine, dried over $Na_2SO_4$, and concentrated to afford additional Cap-141 which was sufficiently pure to be carried forward directly (29.30 mg, 31.8%). $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); $R_t$=1.33 min (Cond.-D1); 90% homogenity index; LCMS: Anal. Calc. for $[M+H]^+$ $C_{10}H_7FNO_2$: 192.05. found: 191.97.

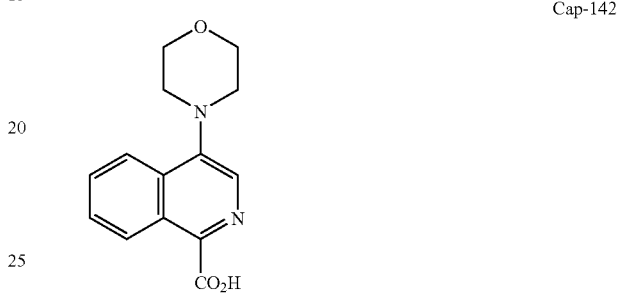

Cap-142

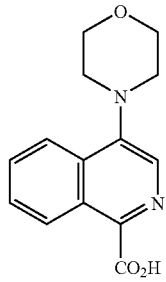

Cap-142, step a

Cap-142, step a was prepared from 4-bromoisoquinoline N-oxide as described in the two-step procedure for the preparation of Cap-138, steps b and c. $R_t$=1.45 min (Cond.-MS-W1); 90% homogenity index; LCMS: Anal. Calc. for $[M+H]^+$ $C_{10}H_6BrN_2$: 232.97. found: 233.00.

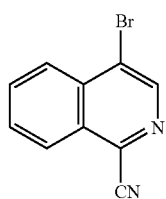

Cap-142, step b

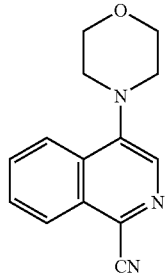

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C. and filtered through diatomaceous earth (Celite®). Purification of the residue on silica gel, eluting with 10% to 70% ethyl acetate/hexanes afforded Cap-142, step b (38 mg, 32%) as a yellow solid, which was carried forward directly. $R_t$=1.26 min (Cond.-MS-W1); 90% homogenity index; LCMS: Anal. Calc. for $[M+H]^+$ $C_{14}H_{14}N_3O$: 240.11. found: 240.13.

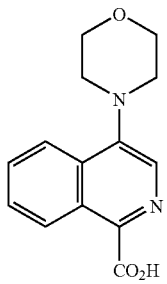

Cap-142

Cap-142 was prepared from Cap-142, step b with 5N sodium hydroxide as described in the procedure for Cap 138. $R_t$=0.72 min (Cond.-MS-W1); 90% homogenity index; LCMS: Anal. Calc. for [M+H]$^+$ $C_{14}H_{15}N_2O_3$: 259.11. found: 259.08.

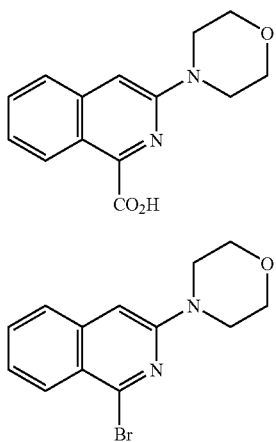

Cap-143

Cap-143, step a

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 µL, 2.00 mmol) was added. The mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over Na$_2$SO$_4$, filtered and concentrated. Purification of the residue on silica gel eluting with 0% to 70% ethyl acetate/hexanes afforded Cap-143, step a as a yellow solid (180 mg, 31%). $R_t$=1.75 min (Cond.-MS-W1); 90% homogenity index; LCMS: Anal. Calc. for [M+H]$^+$ $C_{13}H_{14}BrN_2O$: 293.03. found: 293.04.

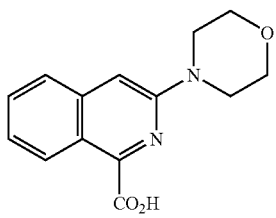

Cap-143

To a cold (–60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by a reverse phase HPLC (MeOH/water/TFA) afforded Cap-143 (16 mg, 12%). $R_t$=1.10 min (Cond.-MS-W1); 90% homogenity index; LCMS: Anal. Calc. for [M+H]$^+$ $C_{14}H_{15}N_2O_3$: 259.11. found: 259.08.

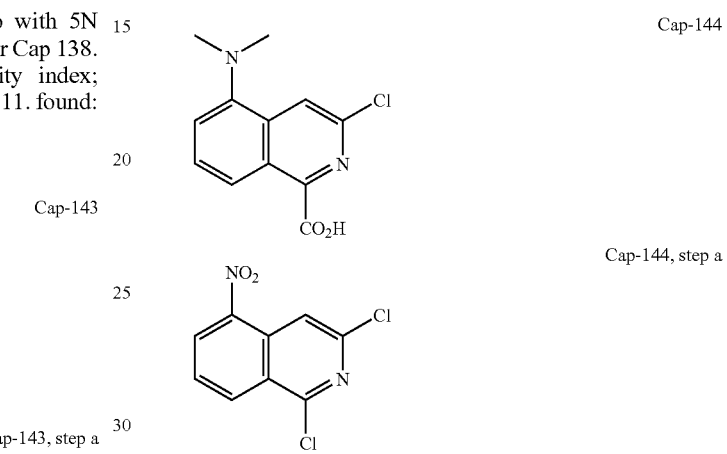

Cap-144

Cap-144, step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_t$=2.01 min. (Cond.-D1); 95% homogenity index; LCMS: Anal. Calc. for [M+H]$^+$ $C_9H_5Cl_2N_2O_2$: 242.97. found: 242.92.

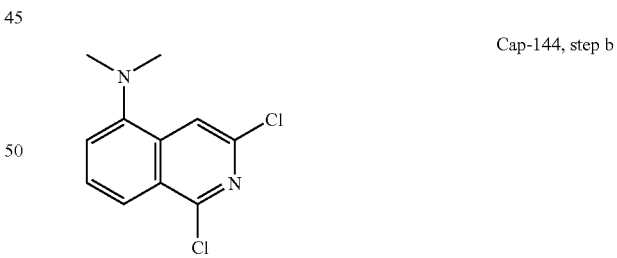

Cap-144, step b

Cap-144, step a (0.30 g, 1.23 mmol) was taken up in methanol (60 mL) and treated with platinum oxide (30 mg), and the suspension was subjected to Parr hydrogenation at 7 psi H$_2$ for 1.5 h. Then formalin (5 mL) and additional platinum oxide (30 mg) were added, and the suspension was resubjected to Parr hydrogenation at 45 psi H$_2$ for 13 h. It was then suction-filtered through diatomaceous earth (Celite®) and concentrated down to ¼ volume. Suction-filtration of the ensuing precipitate afforded the title compound as a yellow solid which was flash chromatographed on silica gel eluting with 5% ethyl acetate in hexanes to 25% ethyl acetate in hexanes to afford Cap-144, step b (231 mg, 78%) as a pale yellow solid.

$R_t$=2.36 min (Cond.-D1); 95% homogenity index; $^1$H NMR (400 MHz, CDCl$_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for [M+H]$^+$ C$_{11}$H$_{11}$Cl$_2$N$_2$: 241.03. found: 241.02. HRMS: Anal Calc. for [M+H]$^+$ C$_{11}$H$_{11}$Cl$_2$N$_2$: 241.0299. found: 241.0296.

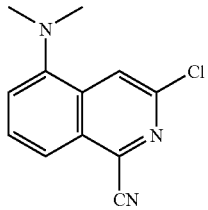

Cap-144, step c

Cap-144, step c was prepared from Cap-144, step b according to the procedure described for the preparation of Cap-139, step a. $R_t$=2.19 min (Cond.-D1); 95% homogenity index; LCMS: Anal. Calc. for [M+H]$^+$ C$_{12}$H$_{11}$ClN$_3$: 232.06. found: 232.03. HRMS: Anal. Calc. for [M+H]$^+$ C$_{12}$H$_{11}$ClN$_3$: 232.0642. found: 232.0631.

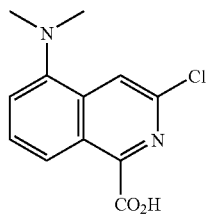

Cap-144

Cap-144 was prepared according to the procedure described for Cap-141. $R_t$=2.36 min (Cond.-D1); 90%; LCMS: Anal. Calc. for [M+H]$^+$ C$_{12}$H$_{12}$ClN$_2$O$_2$: 238.01. found: 238.09.

Caps-145 to 162

Caps-145 to 162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | $R_t$ (LC-Cond.); % homogeneity index; MS data |
|---|---|---|---|---|
| Cap-145 | 3-chloroisoquinoline-1-carboxylic acid structure; Prepared from commercially available 1,3-dichloroisoquinoline | B | 12 N HCl | 1.14 min (Cond.-MS-W1); 90%; LCMS: Anal. Calc. for [M +H]$^+$ C$_{10}$H$_7$ClNO$_2$: 208.02; found: 208.00. |
| Cap-146 | 3-methoxyisoquinoline-1-carboxylic acid structure; Prepared from commercially available 3-hydroxyisoquinoline | A | 5 N NaOH | 1.40 min (Cond.-D1); 95%; LCMS: Anal. Calc. for [M +H]$^+$ C$_{11}$H$_{10}$NO$_3$: 204.07; found: 204.06. |
| Cap-147 | 4-methoxyisoquinoline-1-carboxylic acid structure; Prepared from commercially available 1-chloro-4-hydroxyisoquinoline | B | 5 N NaOH | 0.87 min (Cond.-D1); 95%; LCMS: Anal. Calc. for [M +H]$^+$ C$_{11}$H$_{10}$NO$_3$: 204.07; found: 204.05. |

| Cap # | Cap | Method | Hydrolysis | $R_f$ (LC-Cond.); % homogeneity index; MS data |
|---|---|---|---|---|
| Cap-148 | Prepared from commercially available 7-hydroxyisoquinoline | A | 5 N NaOH | 0.70 min (Cond.-D1); 95%; LCMS: Anal. Calc. for [M+H]$^+$ $C_{11}H_{10}NO_3$: 204.07; found: 204.05. |
| Cap-149 | Prepared from commercially available 5-hydroxyisoquinoline | A | 5 N NaOH | 0.70 min (Cond.-D1); 95%; LCMS: Anal. Calc. for [M+H]$^+$ $C_{11}H_{10}NO_3$: 204.07; found: 204.05. |
| Cap-150 | Prepared from 8-methoxy-1-chloroisoquinoline, which can be synthesized following the procedure in WO 2003/099274 | A | 12 N HCl | 0.26 min (Cond.-D1); 95%; LCMS: Anal. Calc. for [M+H]$^+$ $C_{11}H_{10}NO_3$: 204.07; found: 204.04. |
| Cap-151 | Prepared from 5-methoxy-1,3-dichloroisoquinoline, which can be synthesized following the procedure in WO 2005/051410. | B | 12 N HCl | 1.78 min (Cond.-D1); 90%; LCMS: Anal. Calc. for [M+H]$^+$ $C_{11}H_9ClNO_3$: 238.03; found: 238.09. |
| Cap-152 | Prepared from commercially available 6-methoxy-1,3-dichloroisoquinoline | B | 12 N HCl | 1.65 min (Cond.-D1); 95%; LCMS: Anal. Calc. for [M+H]$^+$ $C_{11}H_9ClNO_3$: 238.00; found: 238.09. |

| Cap # | Cap | Method | Hydrolysis | $R_f$ (LC-Cond.); % homogeneity index; MS data |
|---|---|---|---|---|
| Cap-153 | 4-Bromoisoquinoline-1-carboxylic acid. Prepared from 4-bromoisoquinoline, which can be synthesized following the procedure in WO 2003/062241 | A | 6 N HCl | 1.18 min (Cond.-MS-W1); 95%; LCMS: Anal. Calc. for [M +H]$^+$ $C_{10}H_7BrNO_2$: 251.97; found: 251.95. |
| Cap-154 | 7-Fluoroisoquinoline-1-carboxylic acid. Prepared from 7-fluoro-1-chloroisoquinoline, which can be synthesized following the procedure in WO 2003/099274 | B | 5 N NaOH | 0.28 min (Cond.-MS-W1); 90%; LCMS: Anal. Calc. for [M +H]$^+$ $C_{10}H_7FNO_2$: 192.05; found: 192.03. |
| Cap-155 | 7-Chloroisoquinoline-1-carboxylic acid. Prepared from 1,7-dichloroisoquinoline, which can be synthesized following the procedure in WO 2003/099274 | B | 5 N NaOH | 0.59 min (Cond.-MS-W1); 90%; LCMS: Anal. Calc. for [M +H]$^+$ $C_{10}H_7ClNO_2$: 208.02; found: 208.00. |
| Cap-156 | 6-Chloroisoquinoline-1-carboxylic acid. Prepared from 1,6-dichloroisoquinoline, which can be synthesized following the procedure in WO 2003/099274 | B | 5 N NaOH | 0.60 min (Cond.-MS-W1); 90%; LCMS: Anal. Calc. for [M +H]$^+$ $C_{10}H_7ClNO_2$: 208.02; found: 208.03. |
| Cap-157 | 4-Chloroisoquinoline-1-carboxylic acid. Prepared from 1,4-dichloroisoquinoline, which can be synthesized following the procedure in WO 2003/062241 | B | 12 N HCl | 1.49 min (Cond.-D1); 95%; LCMS: Anal. Calc. for [M +H]$^+$ $C_{10}H_{17}ClNO$: 208.02; found: 208.00. |

-continued

| Cap # | Cap | Method | Hydrolysis | $R_t$ (LC-Cond.); % homogeneity index; MS data |
|---|---|---|---|---|
| Cap-158 | 5-chloro-isoquinoline-1-carboxylic acid. Prepared from 1,5-dichloroisoquinoline, which can be synthesized following the procedure in WO 2003/099274 | B | 5 N NaOH | 0.69 min (Cond.-MS-W1); 90%; LCMS: Anal. Calc. for [M +H]+ $C_{10}H_7ClNO_2$: 208.02; found: 208.01. |
| Cap-159 | 5-fluoro-isoquinoline-1-carboxylic acid. Prepared from 5-fluoro-1-chloroisoquinoline, which can be synthesized following the procedure in WO 2003/099274 | B | 5 N NaOH | 0.41 min (Cond.-MS-W1); 90%; LCMS: Anal. Calc. for [M +H]+ $C_{10}H_7FNO_2$: 192.05; found: 192.03. |
| Cap-160 | 6-fluoro-isoquinoline-1-carboxylic acid. Prepared from 6-fluoro-1-chloroisoquinoline, which can be synthesized following the procedure in WO 2003/099274 | B | 5 N NaOH | 0.30 min (Cond.-MS-W1); 90%; LCMS: Anal. Calc. for [M +H]+ $C_{10}H_7FNO_2$: 192.05; found: 192.03. |
| Cap-161 | 4-(dimethylamino)quinoline-2-carboxylic acid. Prepared from 4-bromoisoquinoline-2-carboxylic acid and dimethylamine (DMSO, 100° C.) | — | — | 0.70 min (Cond. D1); 95%; LCMS: Anal. Calc. for [M +H]+ $C_{12}H_{13}N_2O_2$: 217.10; found: 217.06. |
| Cap-162 | 7-methoxyquinoline-2-carboxylic acid. Prepared from m-anisidine following the procedure described in J. Hetero. Chem. 1993, 17 and Heterocycles, 2003, 60, 953. | — | — | 0.65 min (Cond.-M3); 95%; LCMS: Anal. Calc. for [M +H]+ $C_{11}H_{10}NO_3$: 204.07; found: 203.94. |

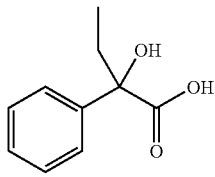

Cap-163

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

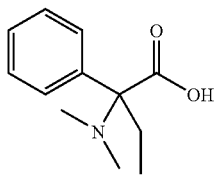

Cap-164

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over Celite and concentrated in vacuo, the residue was taken up in MeOH (36 mL) and the product was purified with a reverse phase HPLC (MeOH/$H_2$O/TFA) to afford the TFA salt of Cap-164 as a white solid (1.7 g). $^1$H NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

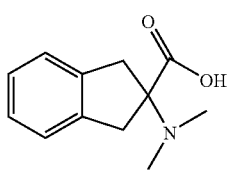

Cap-165

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2$O/TFA) to afford the TFA salt of Cap-165 as a viscous oil (120.2 mg). $^1$H NMR (DMSO-$d_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC/MS: Anal. Calcd. for [M+H]$^+$ $C_{12}H_{16}NO_2$: 206.12. found: 206.07.

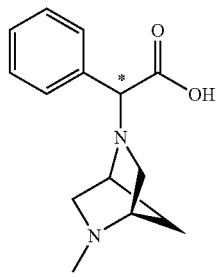

Cap-166a and -166b

Cap-166a: Diastereomer-1
Cap-166b: Diastereomer-2

Caps-166a and -166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 µm eluting with 85:15 heptane/ethanol mixture at 10 mL/min elution rate for 25 min. Cap-166b: $^1$H NMR (DMSO-$d_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J9.8 Hz, 1H), 1.63 (d, J=9.8 Hz, 1H). CC/MS: Anal. Calcd. for [M+H]$^+$ $C_{14}H_{19}N_2O_2$: 247.14. found: 247.11.

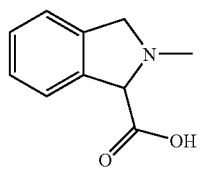

Cap-167

A solution of racemic Boc-1,3-dihydro-2H-isoinidole carboxylic acid (1.0 g, 3.8 mmol) in 20% TFA/$CH_2Cl_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to $H_2$ (40 PSI) in a Parr bottle for 23 h. The reaction mixture was filtered over Celite and concentrated in vacuo to afford Cap-167 as a yellow foam (873.5 mg). $^1$H NMR (DMSO-$d_6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]$^+$ $C_{10}H_{12}NO_2$: 178.09. found: 178.65.

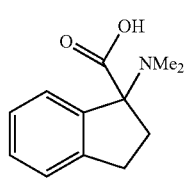

Cap-168

Racemic Cap-168 was prepared from racemic Boc-aminoindane-1-carboxylic acid according to the procedure described for the preparation of Cap-167. The crude material was employed as such.

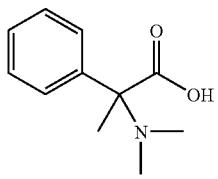
Cap-169

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PST) for 4 days. The reaction mixture was filtered over Celite and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC/MS: Anal. Calcd. for [M+H]$^+$ C$_{11}$H$_{16}$NO$_2$: 194.12. found: 194.12.

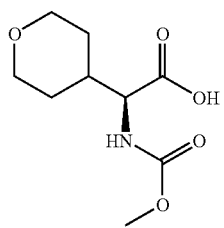
Cap-170

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. $^1$H NMR (500 MHz, DMSO-d$_6$) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC/MS: Anal. Calcd. for [M+H]$^+$ C$_9$H$_{16}$NO$_5$: 218.1. found 218.1.

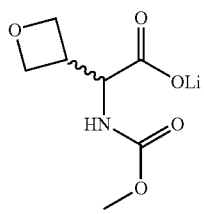
Cap-171

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 CH$_2$Cl$_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through celite and concentrated. The residue was purified via Biotage® (load with dichloromethane on 25 samplet; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. $^1$H NMR (500 MHz, CHLOROFORM-D) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC/MS: Anal. Calcd. for [M+H]$^+$ C$_8$H$_{14}$NO$_5$: 204.2. found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnite at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnite providing 55 mg lithium 2-(methoxycarbonylamino)-2-(oxetan-3-yl)acetate as a colorless solid. $^1$H NMR (500 MHz, MeOD) δ ppm 3.39-3.47 (m, 1H) 3.67 (s, 3H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

Biological Activity

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49 (4):1346-53. Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO/O4014852. Further, the compounds of the present disclosure can be effective against the HCV 1b genotype. It should also be understood that the compounds of the present disclosure can inhibit multiple genotypes of HCV. Table 2 shows the EC$_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. EC$_{50}$ values against HCV 1b are as follows: A (1-10 μM); B (100-999 nM); C (4.57-99 nM); D (<4.57 nM).

TABLE 2

| Example | 1b EC$_{50}$ |
|---|---|
| M1 | D |
| M2 | C |
| M3 | C |
| M4 | C |
| M5 | 0.01 μM |
| M6 | C |
| M7 | D |
| M8 | C |
| M9 | C |
| M10 | 0.01 μM |
| M11 | D |
| M12 | C |
| M13 | D |
| M14 | C |
| M15 | D |
| M16 | D |
| M17 | 0.02 μM |
| M18 | B |
| M19 | D |
| M20 | D |
| M21 | D |
| M22 | D |
| M23 | D |
| M24 | D |
| M25 | C |
| M26 | D |
| M26.1 | B |
| M26.2 | B |
| M26.3 | B |
| M26.4 | C |
| M26.5 | B |
| M26.6 | C |
| M27 | D |
| M28 | D |
| M29 | D |
| M30 | D |
| M31 | 3.3 × 10$^{-5}$ μM |
| M32 | D |
| M33 | D |
| M34 | 0.04 μM |
| M35 | D |
| M36 | 5.00 × 10$^{-6}$ μM |
| M37 | D |
| M37.1 | D |
| M37.2 | D |
| M37.3 | C |
| M38 | D |
| M39 | B |
| M40 | B |
| M41 | 0.46 μM |
| M42 | C |
| M43 | C |
| M44 | B |
| M45 | B |
| M45.1 | B |
| M45.2 | C |
| M46 | 6.00 × 10$^{-6}$ μM |
| M46.1 | D |
| M46.2 | D |
| M46.3 | D |
| M47 | D |
| M47.1 | B |
| M47.2 | 0.61 μM |
| M48 | D |
| M49 | D |
| M50 | D |
| M51 | D |
| M52 | C |
| M53 | D |
| M54 | D |
| M54.1 | C |
| M54.2 | B |
| M54.3 | C |
| M54.4 | D |
| M54.5 | C |
| M54.6 | C |
| M54.7 | C |
| M54.8 | C |
| M54.9 | C |
| M54.10 | C |
| M54.11 | C |
| M54.12 | B |
| M54.13 | B |
| M54.14 | B |
| M54.15 | C |
| M54.16 | C |
| M54.17 | C |
| M54.18 | C |
| M54.19 | B |
| M54.20 | C |
| M54.21 | C |
| M54.22 | B |
| M54.23 | C |
| M54.24 | C |
| M54.25 | B |
| M54.26 | C |
| M54.27 | A |
| M54.28 | B |
| M54.29 | B |
| M54.30 | B |
| M54.31 | C |
| M54.32 | C |
| M54.33 | C |
| M55 | B |
| M56 | D |
| M57 | D |
| M57.1 | D |
| M57.2 | D |
| V1 | D |
| V2 | D |
| V3 | C |
| V4 | D |
| V5 | D |
| V6 | D |
| V7 | C |
| V8 | D |
| V9 | D |
| V10 | D |
| V11 | D |
| V12 | D |
| F1 | D |
| F2 | D |
| F3 | B |
| F4 | D |
| F5 | C |
| F6 | 0.48 μM |
| F7 | C |
| F8 | D |
| F9 | 0.02 μM |
| F10 | C |
| F11 | D |
| OL1 | C |
| OL2 | 0.02 μM |
| OL3 | B |
| OL4 | C |
| OL5 | B |
| OL6 | B |
| OL7 | C |
| OL8 | 2.88 μM |
| OL9 | C |
| OL10 | B |
| OL11 | B |
| OL12 | B |
| OL13 | 8.56 μM |
| OL14 | B |
| OL15 | B |
| JG1 | C |
| JG2 | D |
| JG3 | C |
| JG4 | D |
| J6 | D |
| J6.1 | D |
| J7 | C |
| J8 | D |
| J9 | C |
| J10 | 7.00 × 10$^{-6}$ μM |

TABLE 2-continued

| Example | 1b EC$_{50}$ |
|---|---|
| J11 | D |
| J11.1 | D |
| J11.2 | D |
| J12 | D |
| J12.1 | C |
| J13 | D |
| J14 | D |
| J14.1 | C |
| J15 | >10.00 μM |
| J16 | C |
| J17 | D |
| J18 | D |
| J19 | D |
| J20 | D |
| J20.1 | D |
| J21 | D |
| J22 | A |
| J23 | D |
| J24 | D |
| J25 | D |
| J25.a | C |
| J26 | 2.10 × 10$^{-5}$ μM |
| J27 | D |
| J28 | D |
| J29 | D |
| J30 | 5.80 × 10$^{-5}$ μM |
| J32 | C |
| J33 | D |

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of Formula (I)

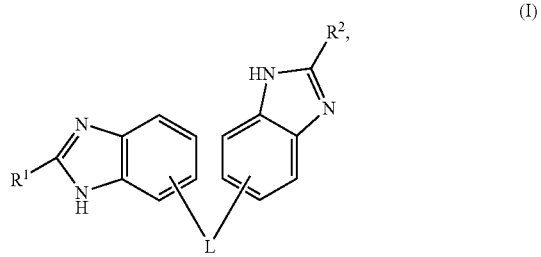

(I)

or a pharmaceutically acceptable salt thereof, wherein
L is a bond or is selected from

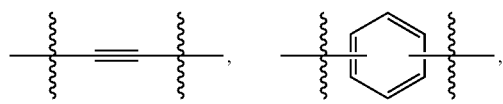

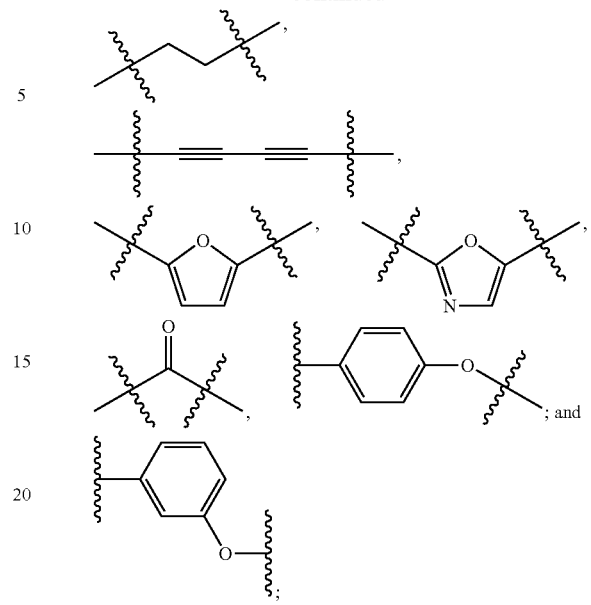

$R^1$ and $R^2$ are independently selected from

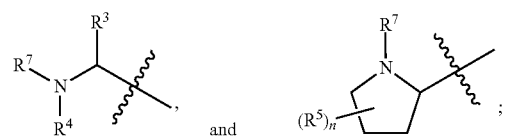

wherein
n is 0, 1, 2, or 3;
$R^3$ is selected from alkoxyalkyl, alkoxycarbonylalkyl, alkyl, alkylsulfanylalkyl, carboxyalkyl, and ($NR^aR^b$)carbonylalkyl;
$R^4$ is selected from hydrogen and alkyl;
each $R^5$ is independently selected from alkoxy, alkyl, hydroxy, —$NR^aR^b$, and oxo, wherein the alkyl can optionally form a fused three- to six-membered ring with an adjacent carbon atom, wherein the three- to six-membered ring is optionally substituted with one or two alkyl groups;
$R^6$ and $R^7$ are independently selected from hydrogen and $R^8$—C(O)—;
each $R^8$ is independently selected from alkoxy, alkyl, aryl, arylalkoxy, arylalkyl, arylcarbonyl, aryloxyalkyl, cycloalkyl, (cycloalkyl)alkyl, heterocyclyl, heterocyclylalkyl, —$NR^cR^d$, ($NR^cR^d$)alkenyl, and ($NR^cR^d$)alkyl, provided that when L is a bond and $R^1$ and $R^2$ are both

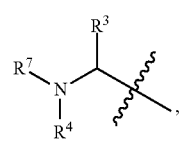

then $R^8$ is other than phenyl;
$R^a$ and $R^b$ are independently selected from hydrogen, alkoxycarbonyl, alkyl, alkylcarbonyl, and formyl; or, $R^a$ and $R^b$, together with the nitrogen atom to which they are attached, form a 5- or 6-membered ring optionally containing one additional heteroatom selected from nitrogen, oxygen, and sulfur;

$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, $(NR^xR^y)$alkyl, and $(NR^xR^y)$carbonyl; and $R^x$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{x'}R^{y'})$carbonyl, wherein $R^{x'}$ and $R^{y'}$ are independently selected from hydrogen and alkyl.

2. A compound of claim 1, or a pharmaceutically acceptable salt thereof, wherein L is selected from

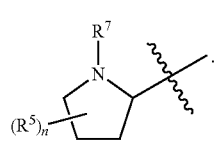

3. A compound of claim 2, or a pharmaceutically acceptable salt thereof, wherein $R^1$ and $R^2$ are each

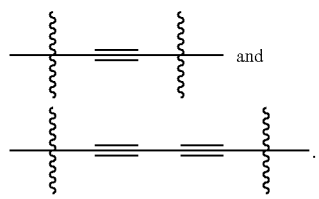

4. A compound of claim 2, or a pharmaceutically acceptable salt thereof, wherein $R^1$ and $R^2$ are each

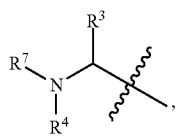

5. A compound of claim 1, or a pharmaceutically acceptable salt thereof, wherein L is

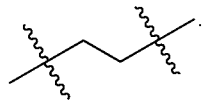

6. A compound of claim 5, or a pharmaceutically acceptable salt thereof, wherein $R^1$ and $R^2$ are each

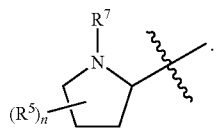

7. A compound of claim 5, or a pharmaceutically acceptable salt thereof, wherein $R^1$ and $R^2$ are each

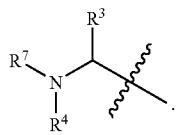

8. A compound of claim 5, or a pharmaceutically acceptable salt thereof, wherein $R^1$ and $R^2$ are each

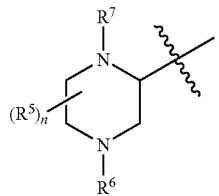

9. A compound of claim 5, or a pharmaceutically acceptable salt thereof, wherein $R^1$ and $R^2$ are each

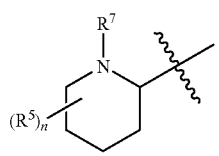

10. A compound of claim 1, or a pharmaceutically acceptable salt thereof, wherein L is selected from

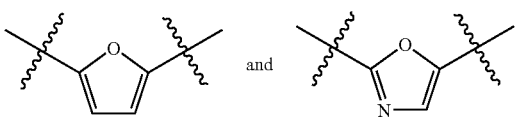 and 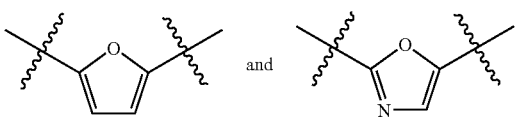.

11. A compound of claim 10, or a pharmaceutically acceptable salt thereof, wherein $R^1$ and $R^2$ are independently selected from

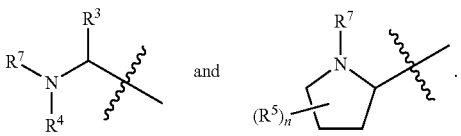

12. A compound of claim 1, or a pharmaceutically acceptable salt thereof, wherein L is selected from a bond,

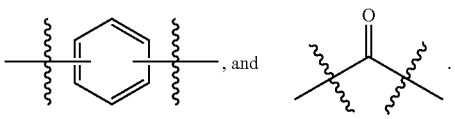

13. A compound of claim 12, or a pharmaceutically acceptable salt thereof, wherein $R^1$ and $R^2$ are

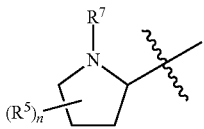

14. A compound of claim 1, or a pharmaceutically acceptable salt thereof, wherein L is selected from

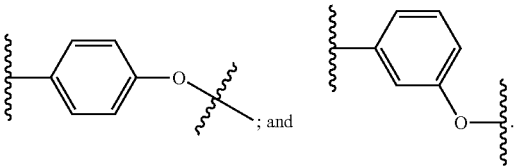

15. A compound of claim 14, or a pharmaceutically acceptable salt thereof, wherein $R^1$ and $R^2$ are each

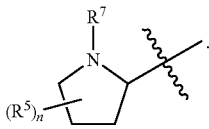

16. A compound selected from
5,5'-(1,2-ethynediyl)bis(2-((2S)-1-((2R)-2-phenylpropanoyl)-2-pyrrolidinyl)-1H-benzimidazole);
5,5'-(1,2-ethynediyl)bis(2-((2S)-1-propionyl-2-pyrrolidinyl)-1H-benzimidazole);
5,5'-(1,2-ethynediyl)bis(2-((2S)-1-isobutyryl-2-pyrrolidinyl)-1H-benzimidazole);
2-((2S)-1-(cyclopropylcarbonyl)-2-pyrrolidinyl)-5-((2-((2S)-1-(cyclopropylcarbonyl)-2-pyrrolidinyl)-1H-benzimidazol-6-yl)ethynyl)-1H-benzimidazole;
5,5'-(1,2-ethynediyl)bis(2-((2S)-1-((2R)-tetrahydro-2-furanylcarbonyl)-2-pyrrolidinyl)-1H-benzimidazole);
2-((2S)-1-benzoyl-2-pyrrolidinyl)-5-((2-((2S)-1-benzoyl-2-pyrrolidinyl)-1H-benzimidazol-6-yl)ethynyl)-1H-benzimidazole;
5,5'-(1,2-ethynediyl)bis(2-((2S)-1-(2-pyridinylacetyl)-2-pyrrolidinyl)-1H-benzimidazole);
2-((2S)-1-(cyclopropylacetyl)-2-pyrrolidinyl)-5-((2-((2S)-1-(cyclopropylacetyl)-2-pyrrolidinyl)-1H-benzimidazol-6-yl)ethynyl)-1H-benzimidazole;
2-((2S)-1-(cyclobutylcarbonyl)-2-pyrrolidinyl)-5-((2-((2S)-1-(cyclobutylcarbonyl)-2-pyrrolidinyl)-1H-benzimidazol-6-yl)ethynyl)-1H-benzimidazole;
5,5'-(1,2-ethynediyl)bis(2-((2S)-1-(2-thienylcarbonyl)-2-pyrrolidinyl)-1H-benzimidazole);
5,5'-(1,2-ethynediyl)bis(2-((2S)-1-(3-pyridinylacetyl)-2-pyrrolidinyl)-1H-benzimidazole);
5,5'-(1,2-ethynediyl)bis(2-((2S)-1-((1-methyl-1H-pyrrol-2-yl)carbonyl)-2-pyrrolidinyl)-1H-benzimidazole);
5,5'-(1,2-ethynediyl)bis(2-((2S)-1-(3-furoyl)-2-pyrrolidinyl)-1H-benzimidazole);
5,5'-(1,2-ethynediyl)bis(2-((2S)-1-(tetrahydro-3-furanylcarbonyl)-2-pyrrolidinyl)-1H-benzimidazole);
(1R,1'R)-2,2'-(1,2-ethynediylbis(1H-benzimidazole-5,2-diyl(2S)-2,1-pyrrolidinediyl))bis(2-oxo-1-phenylethanol);
(2S,2'S)-1,1'-(1,2-ethynediylbis(1H-benzimidazole-5,2-diyl(2S)-2,1-pyrrolidinediyl))bis(1-oxo-2-phenyl-2-propanol);
2,2'-(1,2-ethynediylbis(1H-benzimidazole-5,2-diyl(2S)-2,1-pyrrolidinediylcarbonyl))bis(7-methoxyquinoline);
3-chloro-1-(((2S)-2-(5-((2-((2S)-1-((3-chloro-5-methoxy-1-isoquinolinyl)carbonyl)-2-pyrrolidinyl)-1H-benzimidazol-6-yl)ethynyl)-1H-benzimidazol-2-yl)-1-pyrrolidinyl)carbonyl)-5-methoxyisoquinoline;
(1R)-2-((2S)-2-(5-((2-((2S)-1-((2R)-2-(dimethylamino)-2-phenylacetyl)-2-pyrrolidinyl)-1H-benzimidazol-6-yl)ethynyl)-1H-benzimidazol-2-yl)-1-pyrrolidinyl)-N,N-dimethyl-2-oxo-1-phenylethanamine;
N,N'-(1,2-ethynediylbis(1H-benzimidazole-5,2-diyl(2S)-2,1-pyrrolidinediyl((1R)-2-oxo-1-phenyl-2,1-ethanediyl)))diformamide;
N-((1R)-2-((2S)-2-(5-((2-((2S)-1-((2R)-2-acetamido-2-phenylacetyl)-2-pyrrolidinyl)-1H-benzimidazol-6-yl)ethynyl)-1H-benzimidazol-2-yl)-1-pyrrolidinyl)-2-oxo-1-phenylethyl)acetamide;
5,5'-(1,2-ethynediyl)bis(2-((2S)-1-((2R)-2-(4-morpholinyl)-2-phenylacetyl)-2-pyrrolidinyl)-1H-benzimidazole);
dimethyl(1,2-ethynediylbis(1H-benzimidazole-5,2-diyl(2S)-2,1-pyrrolidinediyl((1R)-2-oxo-1-phenyl-2,1-ethanediyl)))biscarbamate;
methyl((1S)-1-(((2S)-2-(5-((2-((2S)-1-((2S)-2-((methoxycarbonyl)amino)-3-methylbutanoyl)-2-pyrrolidinyl)-1H-benzimidazol-5-yl)ethynyl)-1H-benzimidazol-2-yl)-1-pyrrolidinyl)carbonyl)-2-methylpropyl)carbamate;
methyl((1S)-2-((2S)-2-(5-((2-((2S)-1-(N-(methoxycarbonyl)-L-alanyl)-2-pyrrolidinyl)-1H-benzimidazol-5-yl)ethynyl)-1H-benzimidazol-2-yl)-1-pyrrolidinyl)-1-methyl-2-oxoethyl)carbamate;

methyl((1R)-2-((2S)-2-(5-((2-((2S)-1-(N-(methoxycarbonyl)-D-alanyl)-2-pyrrolidinyl)-1H-benzimidazol-5-yl)ethynyl)-1H-benzimidazol-2-yl)-1-pyrrolidinyl)-1-methyl-2-oxoethyl)carbamate;
5,5'-(1,2-ethynediyl)bis(2-((2S)-1-(3-pyridinylcarbonyl)-2-pyrrolidinyl)-1H-benzimidazole);
3-chloro-1-(((2S)-2-(5-((2-((2S)-1-((3-chloro-1-isoquinolinyl)carbonyl)-2-pyrrolidinyl)-1H-benzimidazol-6-yl)ethynyl)-1H-benzimidazol-2-yl)-1-pyrrolidinyl)carbonyl)isoquinoline;
2,2'-(1,2-ethynediylbis(1H-benzimidazole-5,2-diyl(2S)-2,1-pyrrolidinediyl))bis(2-oxo-1-phenylethanone);
benzyl (2S)-2-(5-((2-((2S)-1-((benzyloxy)carbonyl)-2-pyrrolidinyl)-1H-benzimidazol-6-yl)ethynyl)-1H-benzimidazol-2-yl)-1-pyrrolidinecarboxylate;
5,5'-(1,2-ethynediyl)bis(2-((2S)-1-((2S)-tetrahydro-2-furanylcarbonyl)-2-pyrrolidinyl)-1H-benzimidazole);
5,5'-(1,2-ethynediyl)bis(2-((2S)-1-(2-furoyl)-2-pyrrolidinyl)-1H-benzimidazole);
(2R,2'R)—N,N'-(1,2-ethynediylbis(1H-benzimidazole-5,2-diyl(1S)-1,1-ethanediyl))bis(2-hydroxy-2-phenylacetamide);
(2S,2'S)—N,N'-(1,2-ethynediylbis(1H-benzimidazole-5,2-diyl(1S)-1,1-ethanediyl))bis(2-hydroxy-2-phenylpropanamide);
(2R)-2-(dimethylamino)-N-((1S)-1-(5-((2-((1S)-1-(((2R)-2-(dimethylamino)-2-phenylacetyl)amino)ethyl)-1H-benzimidazol-6-yl)ethynyl)-1H-benzimidazol-2-yl)ethyl)-2-phenylacetamide;
(2R)-2-acetamido-N-((1S)-1-(5-((2-((1S)-1-(((2R)-2-acetamido-2-phenylacetyl)amino)ethyl)-1H-benzimidazol-6-yl)ethynyl)-1H-benzimidazol-2-yl)ethyl)-2-phenylacetamide;
dimethyl (1,2-ethynediylbis(1H-benzimidazole-5,2-diyl(1S)-1,1-ethanediylimino((1R)-2-oxo-1-phenyl-2,1-ethanediyl)))biscarbamate;
N,N'-(1,2-ethynediylbis(1H-benzimidazole-5,2-diyl(1S)-1,1-ethanediyl))bis(N-methyl-2-phenylacetamide);
(2R,2'R)—N,N'-(1,2-ethynediylbis(1H-benzimidazole-5,2-diyl(1S)-1,1-ethanediyl))bis(2-hydroxy-N-methyl-2-phenylacetamide);
(2S,2'S)—N,N'-(1,2-ethynediylbis(1H-benzimidazole-5,2-diyl(1S)-1,1-ethanediyl))bis(2-hydroxy-N-methyl-2-phenylpropanamide);
(2R)-2-(dimethylamino)-N-((1S)-1-(5-((2-((1S)-1-(((2R)-2-(dimethylamino)-2-phenylacetyl)(methyl)amino)ethyl)-1H-benzimidazol-6-yl)ethynyl)-1H-benzimidazol-2-yl)ethyl)-N-methyl-2-phenylacetamide;
dimethyl (1,2-ethynediylbis(1H-benzimidazole-5,2-diyl(1S)-1,1-ethane diyl(methylimino)((1R)-2-oxo-1-phenyl-2,1-ethanediyl)))biscarbamate;
5,5'-(1,2-ethynediyl)bis(2-((2S)-1-(phenylacetyl)-2-pyrrolidinyl)-1H-benzimidazole);
(3R,5S,3'R,5'S)-5,5'-(1,2-ethynediylbis(1H-benzimidazole-5,2-diyl))bis(1-(phenylacetyl)-3-pyrrolidinol);
(3'S,5'S,3'R,5'S)-5,5'-(1,2-ethynediylbis(1H-benzimidazole-5,2-diyl))bis(1'-(phenylacetyl)-1,3'-bipyrrolidine);
5,5'-(1,2-ethynediyl)bis(2-((2S,4S)-4-(4-morpholinyl)-1-(phenylacetyl)-2-pyrrolidinyl)-1H-benzimidazole);
5,5'-(1,2-ethanediyl)bis(2-((2S)-1-(phenylacetyl)-2-pyrrolidinyl)-1H-benzimidazole);
2,2'-bis((2S)-1-(phenylacetyl)-2-pyrrolidinyl)-1H,1'H-5,5'-bibenzimidazole;
dibenzyl (2S,2'S)-2,2'-(1H, 1'H-5,5'-bibenzimidazole-2,2'-diyl)di(1-pyrrolidinecarboxylate);

2-((2S)-1-(cyclopropylcarbonyl)-2-pyrrolidinyl)-5-(2-(2-((2S)-1-(cyclopropylcarbonyl)-2-pyrrolidinyl)-1H-benzimidazol-6-yl)ethyl)-1H-benzimidazole;
5,5'-(1,2-ethanediyl)bis(2-((2S)-1-(2R)-tetrahydro-2-furanylcarbonyl)-2-pyrrolidinyl)-1H-benzimidazole);
5,5'-(1,2-ethanediyl)bis(2-((2S)-1-(2-pyridinylacetyl)-2-pyrrolidinyl)-1H-benzimidazole);
2-((2S)-1-(cyclopropylacetyl)-2-pyrrolidinyl)-5-(2-(2-((2S)-1-(cyclopropylacetyl)-2-pyrrolidinyl)-1H-benzimidazol-6-yl)ethyl)-1H-benzimidazole;
2-((2S)-1-(cyclobutylcarbonyl)-2-pyrrolidinyl)-5-(2-(2-((2S)-1-(cyclobutylcarbonyl)-2-pyrrolidinyl)-1H-benzimidazol-6-yl)ethyl)-1H-benzimidazole;
5,5'-(1,2-ethanediyl)bis(2-((2S)-1-(2-thienylcarbonyl)-2-pyrrolidinyl)-1H-benzimidazole);
5,5'-(1,2-ethanediyl)bis(2-((2S)-1-(3-pyridinylacetyl)-2-pyrrolidinyl)-1H-benzimidazole);
methyl((1S)-1-(((1R,3S,5R)-3-(6-(4-(2-((1R,3S,5R)-2-((2S)-2-((methoxycarbonyl)amino)-3-methylbutanoyl)-2-azabicyclo[3.1.0]hex-3-yl)-1H-benzimidazol-6-yl)phenyl)-1H-benzimidazol-2-yl)-2-azabicyclo[3.1.0]hex-2-yl)carbonyl)-2-methylpropyl)carbamate;
dimethyl(1,4-phenylenebis(1H-benzimidazole-5,2-diyl(1R,3S,5R)-2-azabicyclo[3.1.0]hexane-3,2-diyl(2-oxo-1-phenyl-2,1-ethanediyl)))biscarbamate;
dimethyl(1,4-phenylenebis(1H-benzimidazole-5,2-diyl(1R,3S,5R)-2-azabicyclo[3.1.0]hexane-3,2-diyl(2-oxo-1-phenyl-2,1-ethanediyl)))biscarbamate;
5-((2-((2S)-1-(phenylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
(3R,5S,3'R,5'S)-5,5'-(1,2-ethynediylbis(1H-benzimidazole-5,2-diyl))bis(1-((2R)-tetrahydro-2-furanylcarbonyl)-3-pyrrolidinol);
(3S,5S,3'R,5'S)-5,5'-(1,2-ethynediylbis(1H-benzimidazole-5,2-diyl))bis(N-isobutyl-1-((2R)-tetrahydro-2-furanylcarbonyl)-3-pyrrolidinamine);
5-((2-((2S)-1-(2-pyridinylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
5-((2-((2S)-1-(3-pyridinylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
5-((2-((2S)-1-((2R)-tetrahydro-2-furanylcarbonyl)-2-pyrrolidinyl)-1H-benzimidazol-6-yl)ethynyl)-2-((2S)-1-(2-thienylacetyl)-2-pyrrolidinyl)-1H-benzimidazole;
5-((2-((2S)-1-(2-furoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
5-((2-((2S)-1-(cyclopropylacetyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
(1R)—N,N-dimethyl-2-oxo-1-phenyl-2-((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)ethanamine;
benzyl (2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinecarboxylate;
5-((2-((2S)-1-benzoyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;
5-((2-((2S)-1-(2-ethylbenzoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-(3-pyridinylcarbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-((2R)-tetrahydro-2-furanylcarbonyl)-2-pyrrolidinyl)-1H-benzimidazol-6-yl)ethynyl)-2-((2S)-1-(2-thienylcarbonyl)-2-pyrrolidinyl)-1H-benzimidazole;

5-((2-((2S)-1-(3-furoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-((1-methyl-1H-pyrrol-2-yl)carbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-propionyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-isobutyryl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-(cyclopropylcarbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-(cyclobutylcarbonyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

N-methyl-2-((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)carbonyl)aniline;

5-((2-((2S)-1-(2-propoxybenzoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

N-benzyl-2-((2S)-2-(5-((2-((2S)-1-((2R)-tetrahydro-2-furanylcarbonyl)-2-pyrrolidinyl)-1H-benzimidazol-5-yl)ethynyl)-1H-benzimidazol-2-yl)-1-pyrrolidinyl)carbonyl)aniline;

5-((2-((2S)-1-(2-methoxy-5-methylbenzoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-(3-phenoxypropanoyl)-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(phenylacetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-((3-methoxyphenyl)acetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-benzoyl-2-pyrrolidinyl)-1H-benzimidazole;

5-((2-((2S)-1-acetyl-2-pyrrolidinyl)-1H-benzimidazol-6-yl)ethynyl)-2-((2S)-1-(2-ethylbenzoyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(2-pyridinylacetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(3-pyridinylacetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(3-pyridinylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(2-thienylacetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(2-thienylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-((2R)-tetrahydro-2-furanylcarbonyl)-2-pyrrolidinyl)-1H-benzimidazole;

benzyl (2S)-2-(5-((2-((2S)-1-acetyl-2-pyrrolidinyl)-1H-benzimidazol-5-yl)ethynyl)-1H-benzimidazol-2-yl)-1-pyrrolidinecarboxylate;

5-((2-((2S)-1-acetyl-2-pyrrolidinyl)-1H-benzimidazol-6-yl)ethynyl)-2-((2S)-1-(1-methyl-L-prolyl)-2-pyrrolidinyl)-1H-benzimidazole;

2-((2S)-1-acetyl-2-pyrrolidinyl)-5-((2-((2S)-1-acetyl-2-pyrrolidinyl)-1H-benzimidazol-6-yl)ethynyl)-1H-benzimidazole;

5-((2-((2S)-1-acetyl-2-pyrrolidinyl)-1H-benzimidazol-6-yl)ethynyl)-2-((2S)-1-propionyl-2-pyrrolidinyl)-1H-benzimidazole;

5-((2-((2S)-1-acetyl-2-pyrrolidinyl)-1H-benzimidazol-6-yl)ethynyl)-2-((2S)-1-(cyclopropylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(cyclobutylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(cyclopropylacetyl)-2-pyrrolidinyl)-1H-benzimidazole;

5-((2-((2S)-1-acetyl-2-pyrrolidinyl)-1H-benzimidazol-6-yl)ethynyl)-2-((2S)-1-(4-morpholinylcarbonyl)-2-pyrrolidinyl)-1H-benzimidazole;

5-((2-((2S)-1-acetyl-2-pyrrolidinyl)-1H-benzimidazol-6-yl)ethynyl)-2-((2S)-1-((4-methyl-1-piperazinyl)carbonyl)-2-pyrrolidinyl)-1H-benzimidazole;

(1R)-2-((2S)-2-(5-((2-((2S)-1-acetyl-2-pyrrolidinyl)-1H-benzimidazol-5-yl)ethynyl)-1H-benzimidazol-2-yl)-1-pyrrolidinyl)-N,N-dimethyl-2-oxo-1-phenylethanamine;

methyl((1S)-1-(((1R,3S,5R)-3-(4-(4-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate;

methyl((1S)-2-((1R,3S,5R)-3-(5-(4-((2-((1R,3S,5R)-2-(N-(methoxycarbonyl)-L-alanyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-1-methyl-2-oxoethyl)carbamate;

methyl (2-((1R,3S,5R)-3-(5-(4-((2-((1R,3S,5R)-2-(((methoxycarbonyl)amino)(phenyl)acetyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-2-oxo-1-phenylethyl)carbamate;

methyl (2-((1R,3S,5R)-3-(5-(4-((2-((1R,3S,5R)-2-(((methoxycarbonyl)amino)(phenyl)acetyl)-2-azabicyclo[3.1.0]hex-3-yl)-1H-benzimidazol-4-yl)oxy)phenyl)-1H-benzimidazol-2-yl)-2-azabicyclo[3.1.0]hex-2-yl)-2-oxo-1-phenylethyl)carbamate;

methyl((1S)-1-(((2S)-2-(4-(4-(2-((2S)-1-((2S)-2-((methoxycarbonyl)amino)-3-methylbutanoyl)-2-pyrrolidinyl)-1H-benzimidazol-5-yl)phenoxy)-1H-benzimidazol-2-yl)-1-pyrrolidinyl)carbonyl)-2-methylpropyl)carbamate;

methyl((1S)-1-(((2S)-2-(5-(4-(2-((2S)-1-((2S)-2-((methoxycarbonyl)amino)-3-methylbutanoyl)-2-pyrrolidinyl)-1H-benzimidazol-5-yl)phenoxy)-1H-benzimidazol-2-yl)-1-pyrrolidinyl)carbonyl)-2-methylpropyl)carbamate;

benzyl (2S,4R)-2-(5-((2-((2S,4R)-1-((benzyloxy)carbonyl)-4-methoxy-2-pyrrolidinyl)-1H-benzimidazol-6-yl)ethynyl)-1H-benzimidazol-2-yl)-4-methoxy-1-pyrrolidinecarboxylate;

benzyl (2S,4R)-2-(5-((2-((2S,4R)-1-((benzyloxy)carbonyl)-4-ethoxy-2-pyrrolidinyl)-1H-benzimidazol-6-yl)ethynyl)-1H-benzimidazol-2-yl)-4-ethoxy-1-pyrrolidinecarboxylate;

benzyl (2S,4R)-2-(5-((2-((2S,4R)-1-((benzyloxy)carbonyl)-4-tert-butoxy-2-pyrrolidinyl)-1H-benzimidazol-6-yl)ethynyl)-1H-benzimidazol-2-yl)-4-tert-butoxy-1-pyrrolidinecarboxylate;

benzyl (2S,4R)-2-(5-((2-((2S,4R)-1-((benzyloxy)carbonyl)-4-hydroxy-2-pyrrolidinyl)-1H-benzimidazol-6-yl)ethynyl)-1H-benzimidazol-2-yl)-4-hydroxy-1-pyrrolidinecarboxylate;

5,5'-(1,3-butadiyne-1,4-diyl)bis(2-((2S)-1-(phenylacetyl)-2-pyrrolidinyl)-1H-benzimidazole);

methyl((1S)-1-(((2S)-2-(5-(4-(2-((2S)-1-((2S)-2-((methoxycarbonyl)amino)-3-methylbutanoyl)-2-pyrrolidinyl)-1H-benzimidazol-5-yl)-1,3-butadiyn-1-yl)-1H-benzimidazol-2-yl)-1-pyrrolidinyl)carbonyl)-2-methylpropyl)carbamate;

methyl((1S)-1-(((1R,3S,5R)-3-(5-(4-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-1,3-butadiyn-1-yl)-1H-benzimidazol-2-yl)-2-azabicyclo[3.1.0]hex-2-yl)carbonyl)-2-methylpropyl)carbamate;

methyl((1S)-1-(((1R,3S,5R)-3-(5-(3-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate;

methyl((1S)-2-((1R,3S,5R)-3-(5-(3-((2-((1R,3S,5R)-2-(N-(methoxycarbonyl)-L-alanyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-1-methyl-2-oxoethyl)carbamate;

methyl((1R)-1-(((1R,3S,5R)-3-(5-(3-(2-((1R,3S,5R)-2-((2R)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate;

methyl(2-((1R,3S,5R)-3-(5-(3-((2-((1R,3S,5R)-2-(((methoxycarbonyl)amino)(phenyl)acetyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-2-oxo-1-phenylethyl)carbamate;

methyl(2-((1R,3S,5R)-3-(5-(3-((2-((1R,3S,5R)-2-(((methoxycarbonyl)amino)(phenyl)acetyl)-2-azabicyclo[3.1.0]hex-3-yl)-1H-benzimidazol-5-yl)oxy)phenyl)-1H-benzimidazol-2-yl)-2-azabicyclo[3.1.0]hex-2-yl)-2-oxo-1-phenylethyl)carbamate;

methyl((1S)-1-(((1R,3S,5R)-3-(4-(4-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)phenoxy)-1H-benzimidazol-2-yl)-2-azabicyclo[3.1.0]hex-2-yl)carbonyl)-2-methylpropyl)carbamate;

(1R,1'R)-2,2'-(1H, 1'H-5,5'-bibenzimidazole-2,2'-diyldi(2S)-2,1-pyrrolidinediyl)bis(N,N-dimethyl-2-oxo-1-phenylethanamine);

dimethyl(1H, 1'H-5,5'-bibenzimidazole-2,2'-diylbis((2S)-2,1-pyrrolidinediyl((1R)-2-oxo-1-phenyl-2,1-ethanediyl)))biscarbamate;

benzyl(2S,4R)-2-(5-(2-(2-((2S,4R)-1-((benzyloxy)carbonyl)-4-methoxy-2-pyrrolidinyl)-1H-benzimidazol-6-yl)ethyl)-1H-benzimidazol-2-yl)-4-methoxy-1-pyrrolidinecarboxylate;

benzyl(2S,4R)-2-(5-(2-(2-((2S,4R)-1-((benzyloxy)carbonyl)-4-ethoxy-2-pyrrolidinyl)-1H-benzimidazol-6-yl)ethyl)-1H-benzimidazol-2-yl)-4-ethoxy-1-pyrrolidinecarboxylate;

benzyl (2S,4R)-2-(5-(2-(2-((2S,4R)-1-((benzyloxy)carbonyl)-4-propoxy-2-pyrrolidinyl)-1H-benzimidazol-6-yl)ethyl)-1H-benzimidazol-2-yl)-4-propoxy-1-pyrrolidinecarboxylate;

N,N'-(1H,1'H-5,5'-bibenzimidazole-2,2'-diylbis((2S)-2,1-pyrrolidinediyl((1R)-2-oxo-1-phenyl-2,1-ethanediyl)))diacetamide;

benzyl((1S)-1-(5-(2-(2-((1S)-1-(((benzyloxy)carbonyl)amino)ethyl)-1H-benzimidazol-6-yl)ethyl)-1H-benzimidazol-2-yl)ethyl)carbamate;

benzyl((1R)-1-(5-(2-(2-((1R)-1-(((benzyloxy)carbonyl)amino)-2-tert-butoxyethyl)-1H-benzimidazol-6-yl)ethyl)-1H-benzimidazol-2-yl)-2-tert-butoxyethyl)carbamate;

benzyl(2S)-2-(5-(2-(2-((2S)-1-((benzyloxy)carbonyl)-5-oxo-2-pyrrolidinyl)-1H-benzimidazol-6-yl)ethyl)-1H-benzimidazol-2-yl)-5-oxo-1-pyrrolidinecarboxylate;

benzyl((1S)-1-(5-(2-(2-((1S)-1-(((benzyloxy)carbonyl)amino)-3-(methylsulfanyl)propyl)-1H-benzimidazol-6-yl)ethyl)-1H-benzimidazol-2-yl)-3-(methylsulfanyl)propyl)carbamate;

benzyl(2S,4R)-2-(5-(2-(2-((2S,4R)-1-((benzyloxy)carbonyl)-4-tert-butoxy-2-pyrrolidinyl)-1H-benzimidazol-6-yl)ethyl)-1H-benzimidazol-2-yl)-4-tert-butoxy-1-pyrrolidinecarboxylate;

benzyl((1R)-1-(5-(2-(2-((1R)-1-(((benzyloxy)carbonyl)amino)ethyl)-1H-benzimidazol-6-yl)ethyl)-1H-benzimidazol-2-yl)ethyl)carbamate;

benzyl((1S)-1-(5-(2-(2-((1S)-1-(((benzyloxy)carbonyl)amino)propyl)-1H-benzimidazol-6-yl)ethyl)-1H-benzimidazol-2-yl)propyl)carbamate;

tert-butyl(3S)-3-(((benzyloxy)carbonyl)amino)-3-(5-(2-(2-((1S)-1-(((benzyloxy)carbonyl)amino)-3-tert-butoxy-3-oxopropyl)-1H-benzimidazol-6-yl)ethyl)-1H-benzimidazol-2-yl)propanoate;

tert-butyl(4S)-4-(((benzyloxy)carbonyl)amino)-4-(5-(2-(2-((1S)-1-(((benzyloxy)carbonyl)amino)-4-tert-butoxy-4-oxobutyl)-1H-benzimidazol-6-yl)ethyl)-1H-benzimidazol-2-yl)butanoate;

benzyl((1S)-1-(5-(2-(2-((1S)-1-(((benzyloxy)carbonyl)amino)-3-(dimethylamino)-3-oxopropyl)-1H-benzimidazol-6-yl)ethyl)-1H-benzimidazol-2-yl)-3-(dimethylamino)-3-oxopropyl)carbamate;

(2R,2'R)—N,N'-(1,2-ethanediylbis(1H-benzimidazole-5,2-diyl(1S)-1,1-ethanediyl))ditetrahydro-2-furancarboxamide;

(2R,2'R)-1,1'-(2,5-furandiylbis(1H-benzimidazole-5,2-diyl(2S)-2,1-pyrrolidinediyl))bis(1-oxo-2-phenyl-2-propanol);

(1R,1'R)-2,2'-(2,5-furandiylbis(1H-benzimidazole-5,2-diyl(2S)-2,1-pyrrolidinediyl))bis(2-oxo-1-phenylethanol);

(1S,1'S)-2,2'-(2,5-furandiylbis(1H-benzimidazole-5,2-diyl(2S)-2,1-pyrrolidinediyl))bis(2-oxo-1-phenylethanol);

(1R)-2-((2S)-2-(5-(5-(2-((2S)-1-((2R)-2-(dimethylamino)-2-phenylacetyl)-2-pyrrolidinyl)-1H-benzimidazol-6-yl)-2-furyl)-1H-benzimidazol-2-yl)-1-pyrrolidinyl)-N,N-dimethyl-2-oxo-1-phenylethanamine;

methyl((1R)-2-((2S)-2-(4-(5-(2-((2S)-1-((2R)-2-((methoxycarbonyl)amino)-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate;

methyl((1R)-2-((2S)-2-(4-(5-(2-((2S)-1-(acetamido(phenyl)acetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate;

2-((2S)-1-(phenylacetyl)-2-pyrrolidinyl)-4-(5-(2-((2S)-1-(phenylacetyl)-2-pyrrolidinyl)-1H-benzimidazol-5-yl)-1,3-oxazol-2-yl)-1H-benzimidazole;

methyl((1S)-2-((2S)-2-(5-(2-(2-((2S)-1-(N-(methoxycarbonyl)-L-alanyl)-2-pyrrolidinyl)-1H-benzimidazol-4-yl)-1,3-oxazol-5-yl)-1H-benzimidazol-2-yl)-1-pyrrolidinyl)-1-methyl-2-oxoethyl)carbamate;

(1R)-2-((2S)-2-(4-(5-(2-((2S)-1-((2R)-2-hydroxy-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethanol;

methyl((1S)-1-(((2S)-2-(4-(5-(2-((2S)-1-((2S)-2-((methoxycarbonyl)amino)-3-methylbutanoyl)-2-pyrrolidinyl)-1H-benzimidazol-5-yl)-1,3-oxazol-2-yl)-1H-benzimidazol-2-yl)-1-pyrrolidinyl)carbonyl)-2-methylpropyl)carbamate;

(1R)-2-((2S)-2-(4-(5-(2-((2S)-1-((2R)-2-(dimethylamino)-2-phenylacetyl)-2-pyrrolidinyl)-1H-benzimidazol-5-yl)-1,3-oxazol-2-yl)-1H-benzimidazol-2-yl)-1-pyrrolidinyl)-N,N-dimethyl-2-oxo-1-phenylethanamine;

N-((1R)-2-((2S)-2-(4-(5-(2-((2S)-1-((2R)-2-acetamido-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)acetamide;

N-((1S)-2-((2S)-2-(5-(2-(2-((2S)-1-((2R)-2-(dimethylamino)-2-phenylacetyl)-2-pyrrolidinyl)-1H-benzimidazol-4-yl)-1,3-oxazol-5-yl)-1H-benzimidazol-2-yl)-1-pyrrolidinyl)-2-oxo-1-phenylethyl)acetamide;

N-((1R)-2-((2S)-2-(4-(5-(2-((2S)-1-((2R)-2-acetamido-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)acetamide;

N-((1R)-2-((2S)-2-(4-(5-(2-((2S)-1-((2R)-2-acetamido-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)acetamide;

1-(2-((2S)-2-(4-(5-(2-((2S)-1-((4-hydroxy-1-piperidinyl)(phenyl)acetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)-4-piperidinol;

2-((2S)-1-((2R)-2-(4-methyl-1-piperazinyl)-2-phenylacetyl)-2-pyrrolidinyl)-4-(5-(2-((2S)-1-((2R)-2-(4-methyl-1-piperazinyl)-2-phenylacetyl)-2-pyrrolidinyl)-1H-benzimidazol-5-yl)-1,3-oxazol-2-yl)-1H-benzimidazole;

2-((2S)-1-((4-methyl-1-piperazinyl)(phenyl)acetyl)-2-pyrrolidinyl)-4-(5-(2-((2S)-1-((4-methyl-1-piperazinyl)(phenyl)acetyl)-2-pyrrolidinyl)-1H-benzimidazol-5-yl)-1,3-oxazol-2-yl)-1H-benzimidazole;

3-chloro-1-(((2S)-2-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)-1H-benzimidazol-2-yl)-1-pyrrolidinyl)carbonyl)-5-methoxyisoquinoline;

5,5'-(1,3-oxazole-2,5-diyl)bis(2-((2S)-1-(phenylacetyl)-2-pyrrolidinyl)-1H-benzimidazole);

(1R)-2-((2S)-2-(5-(2-(2-((2S)-1-((2R)-2-hydroxy-2-phenylacetyl)-2-pyrrolidinyl)-1H-benzimidazol-6-yl)-1,3-oxazol-5-yl)-1H-benzimidazol-2-yl)-1-pyrrolidinyl)-2-oxo-1-phenylethanol;

(2S)-1-((2S)-2-(5-(2-(2-((2S)-1-((2S)-2-hydroxy-2-phenylpropanoyl)-2-pyrrolidinyl)-1H-benzimidazol-6-yl)-1,3-oxazol-5-yl)-1H-benzimidazol-2-yl)-1-pyrrolidinyl)-1-oxo-2-phenyl-2-propanol;

methyl((1S)-1-(((2S)-2-(5-(2-(2-((2S)-1-((2S)-2-((methoxycarbonyl)amino)-3-methylbutanoyl)-2-pyrrolidinyl)-1H-benzimidazol-5-yl)-1,3-oxazol-5-yl)-1H-benzimidazol-2-yl)-1-pyrrolidinyl)carbonyl)-2-methylpropyl)carbamate;

(1R)-2-((2S)-2-(5-(2-(2-((2S)-1-((2R)-2-(dimethylamino)-2-phenylacetyl)-2-pyrrolidinyl)-1H-benzimidazol-6-yl)-1,3-oxazol-5-yl)-1H-benzimidazol-2-yl)-1-pyrrolidinyl)-N,N-dimethyl-2-oxo-1-phenylethanamine;

(1R)—N,N-dimethyl-2-oxo-1-phenyl-2-((2S)-2-(5-(2-(2-((2S)-1-(phenylacetyl)-2-pyrrolidinyl)-1H-benzimidazol-5-yl)-1,3-oxazol-5-yl)-1H-benzimidazol-2-yl)-1-pyrrolidinyl)ethanamine;

N-((1R)-2-((2S)-2-(5-(2-(2-((2S)-1-((2R)-2-acetamido-2-phenylacetyl)-2-pyrrolidinyl)-1H-benzimidazol-6-yl)-1,3-oxazol-5-yl)-1H-benzimidazol-2-yl)-1-pyrrolidinyl)-2-oxo-1-phenylethyl)acetamide;

3-chloro-1-(((2S)-2-(5-(2-(2-((2S)-1-((3-chloro-5-methoxy-1-isoquinolinyl)carbonyl)-2-pyrrolidinyl)-1H-benzimidazol-6-yl)-1,3-oxazol-5-yl)-1H-benzimidazol-2-yl)-1-pyrrolidinyl)carbonyl)-5-methoxyisoquinoline;

(1R)-2-((2S)-2-(5-(2-(2-((1S,3S,5S)-2-((2R)-2-(dimethylamino)-2-phenylacetyl)-2-azabicyclo[3.1.0]hex-3-yl)-1H-benzimidazol-5-yl)-1,3-oxazol-5-yl)-1H-benzimidazol-2-yl)-1-pyrrolidinyl)-N,N-dimethyl-2-oxo-1-phenylethanamine;

N-((1R)-2-((2S)-2-(5-(2-(2-((1S,3S,5S)-2-((2R)-2-acetamido-2-phenylacetyl)-2-azabicyclo[3.1.0]hex-3-yl)-1H-benzimidazol-5-yl)-1,3-oxazol-5-yl)-1H-benzimidazol-2-yl)-1-pyrrolidinyl)-2-oxo-1-phenylethyl)acetamide;

(1R)-2-((2S)-2-(5-(2-(2-((1S,3S,5S)-2-((2R)-2-(dimethylamino)-2-phenylacetyl)-2-azabicyclo[3.1.0]hex-3-yl)-1H-benzimidazol-4-yl)-1,3-oxazol-5-yl)-1H-benzimidazol-2-yl)-1-pyrrolidinyl)-N,N-dimethyl-2-oxo-1-phenylethanamine;

(2R)-2-(dimethylamino)-N-((1S)-1-(4-(5-(2-((2S)-1-((2R)-2-(dimethylamino)-2-phenylacetyl)-2-pyrrolidinyl)-1H-benzimidazol-5-yl)-1,3-oxazol-2-yl)-1H-benzimidazol-2-yl)ethyl)-2-phenylacetamide;

(1R)-2-((2S)-2-(5-(2-(2-((2S)-1-acetyl-2-pyrrolidinyl)-1H-benzimidazol-4-yl)-1,3-oxazol-5-yl)-1H-benzimidazol-2-yl)-1-pyrrolidinyl)-N,N-dimethyl-2-oxo-1-phenylethanamine;

(1R)-2-((2S)-2-(5-(2-(2-((2S)-1-((dimethylamino)acetyl)-2-pyrrolidinyl)-1H-benzimidazol-4-yl)-1,3-oxazol-5-yl)-1H-benzimidazol-2-yl)-1-pyrrolidinyl)-N,N-dimethyl-2-oxo-1-phenylethanamine;

methyl((1R)-2-((2S)-2-(5-(2-(2-((2S)-1-((2R)-2-(4-methyl-1-piperazinyl)-2-phenylacetyl)-2-pyrrolidinyl)-

1H-benzimidazol-4-yl)-1,3-oxazol-5-yl)-1H-benzimidazol-2-yl)-1-pyrrolidinyl)-2-oxo-1-phenylethyl)carbamate;

methyl((1R)-2-((2S)-2-(4-(5-(2-((2S)-1-((2R)-2-(4-methyl-1-piperazinyl)-2-phenylacetyl)-2-pyrrolidinyl)-1H-benzimidazol-5-yl)-1,3-oxazol-2-yl)-1H-benzimidazol-2-yl)-1-pyrrolidinyl)-2-oxo-1-phenylethyl)carbamate;

bis(2-((2S)-1-((2R)-2-(dimethylamino)-2-phenylacetyl)-2-pyrrolidinyl)-1H-benzimidazol-5-yl)methanone; and dimethyl(carbonylbis(1H-benzimidazole-5,2-diyl(2S)-2,1-pyrrolidinediyl((1R)-2-oxo-1-phenyl-2,1-ethanediyl)))biscarbamate;

or a pharmaceutically acceptable salt thereof.

17. A composition comprising a compound of claim 1, or a pharmaceutically acceptable salt thereof, and a pharmaceutically acceptable carrier.

18. The composition of claim 17 further comprising at least one additional compound having anti-HCV activity.

19. The composition of claim 18 wherein at least one of the additional compounds is an interferon or a ribavirin.

20. The composition of claim 19 wherein the interferon is selected from interferon alpha 2B, pegylated interferon alpha, consensus interferon, interferon alpha 2A, and lymphoblastiod interferon tau.

21. The composition of claim 18 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

22. The composition of claim 18 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

23. A method of treating an HCV infection in a patient, comprising administering to the patient a therapeutically effective amount of a compound of claim 1, or a pharmaceutically acceptable salt thereof.

24. The method of claim 23 further comprising administering at least one additional compound having anti-HCV activity prior to, after or simultaneously with the compound of claim 1, or a pharmaceutically acceptable salt thereof.

25. The method of claim 24 wherein at least one of the additional compounds is an interferon or a ribavirin.

26. The method of claim 25 wherein the interferon is selected from interferon alpha 2B, pegylated interferon alpha, consensus interferon, interferon alpha 2A, and lymphoblastiod interferon tau.

27. The method of claim 24 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

28. The method of claim 24 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

| | |
|---|---|
| PATENT NO. | : 7,906,655 B2 |
| APPLICATION NO. | : 12/536362 |
| DATED | : March 15, 2011 |
| INVENTOR(S) | : Makonen Belema et al. |

It is certified that error appears in the above-identified patent and that said Letters Patent is hereby corrected as shown below:

In the Specification:

Column 7, line 56, change "lymphoblastiod" to -- lymphoblastoid --.

Column 7, line 65, change "Imiqimod" to -- Imiquimod --.

Column 7, line 66, change "5'-monophospate" to -- 5'-monophosphate --.

Column 8, line 25, change "lymphoblastiod" to -- lymphoblastoid --.

Column 8, line 37, change "Imiqimod" to -- Imiquimod --.

Column 8, line 38, change "5'-monophospate" to -- 5'-monophosphate --.

In the Claims:

Claim 16:

Column 275, line 25, change "diyl(15)" to -- diyl(1S) --.

Column 275, line 52, change "ethane diyl" to -- ethanediyl --.

Column 276, line 4, change "-(2R)-" to -- -((2R)- --.

Column 277, line 30, change "-((2S)-" to -- -(((2S)- --.

Column 277, line 38, change "-((2S)-" to -- -(((2S)- --.

Claim 20:

Column 283, lines 24 and 25, change "lymphoblastiod" to -- lymphoblastoid --.

Claim 21:

Column 283, line 30, change "Imiqimod" to -- Imiquimod --.

Column 283, lines 30 and 31, change "5'-monophospate" to -- 5'-monophosphate --.

Signed and Sealed this
Twenty-seventh Day of December, 2011

David J. Kappos
*Director of the United States Patent and Trademark Office*

CERTIFICATE OF CORRECTION (continued)
U.S. Pat. No. 7,906,655 B2

In the Claims:

Claim 26:

Column 284, lines 17 and 18, change "lymphoblastiod" to -- lymphoblastoid --.

Claim 27:

Column 284, line 23, change "Imiqimod" to -- Imiquimod --.

Column 284, lines 23 and 24, change "5'-monophospate" to -- 5'-monophosphate --.